(12) United States Patent
Bondinell et al.

(10) Patent No.: US 6,403,578 B1
(45) Date of Patent: Jun. 11, 2002

(54) BICYCLIC FIBRINOGEN ANTAGONISTS

(75) Inventors: William Edward Bondinell, Wayne; James Francis Callahan, Philadelphia; William Francis Huffman; Richard McCulloch Keenan, both of Malvern; Thomas Wen-Fu Ku, Dresher; Kenneth Allen Newlander, West Chester; James Martin Samanen, Phoenixville; Irene Nijole Uzinskas, Villanova, all of PA (US)

(73) Assignee: SmithKline Beecham Corporation, Philadelphia, PA (US)

(*) Notice: Subject to any disclaimer, the term of this patent is extended or adjusted under 35 U.S.C. 154(b) by 0 days.

(21) Appl. No.: 08/464,779

(22) PCT Filed: Dec. 21, 1993

(86) PCT No.: PCT/US93/12436

§ 371 (c)(1),
(2), (4) Date: Aug. 4, 1995

(87) PCT Pub. No.: WO94/14776

PCT Pub. Date: Jul. 7, 1994

(51) Int. Cl.$^7$ .................. A61K 31/55; C07D 243/14
(52) U.S. Cl. .................. 514/221; 514/221; 514/215; 514/213; 540/490; 540/500; 540/506; 540/512; 540/513; 540/504; 540/514; 540/523
(58) Field of Search .................. 540/490, 500, 540/506, 512, 513, 514, 504, 523; 544/360, 386, 389, 398, 400, 404; 546/189, 190, 247, 248; 514/215, 221, 213

(56) References Cited

U.S. PATENT DOCUMENTS

| | | | |
|---|---|---|---|
| 4,327,026 A | 4/1982 | Branca et al. | 424/244 |
| 4,361,511 A | 11/1982 | Branca et al. | 424/250 |
| 4,377,522 A | 3/1983 | Branca et al. | 424/244 |
| 4,410,520 A | 10/1983 | Watthey et al. | 424/244 |
| 5,096,900 A | 3/1992 | George et al. | 514/213 |
| 5,250,679 A | 10/1993 | Blackburn et al. | 540/490 |
| 5,403,836 A | 4/1995 | Blackburn et al. | 514/213 |
| 5,438,118 A | 8/1995 | Callahan et al. | 530/330 |
| 5,470,894 A | 11/1995 | Callahan et al. | 514/212 |
| 5,565,449 A | 10/1996 | Blackburn et al. | 514/219 |
| 5,663,166 A | 9/1997 | Blackburn et al. | 514/213 |
| 5,674,863 A | 10/1997 | Blackburn et al. | 514/211 |
| 5,674,865 A | 10/1997 | Blackburn et al. | 514/211 |
| 5,693,636 A | 12/1997 | Bondinell et al. | 514/221 |

FOREIGN PATENT DOCUMENTS

| | | |
|---|---|---|
| DE | 3702755 A1 | 1/1987 |
| EP | 0 048 045 | 8/1981 |
| EP | 0 447 857 A1 | 3/1991 |
| WO | WO92/07568 | 5/1992 |
| WO | WO93/00095 | 1/1993 |

OTHER PUBLICATIONS

Samanen et al. (J. of Med. Chem. vol. 39, No. 25, pp. 4867–4870, (1996).*
Tidwell et al., *Thrombosis Research*, vol. 19, pp. 339–349 (1980).
Tighineanu, E. et al., Double Cyclisation of Phenylglycine–o–Carboxylic Acids, Tetrahedron vol. 36, pp. 1385–1397 (1980).
U. S. application No. 08/179,011, filed Jan. 7, 1994, Bondinell et al.
U. S. application No. 07/923,794, filed Jun. 26, 1992, Bondinell et al.

* cited by examiner

*Primary Examiner*—Sabiha Qazi
(74) *Attorney, Agent, or Firm*—Charles M. Kinzig

(57) ABSTRACT

This invention relates to compounds of the formulae:

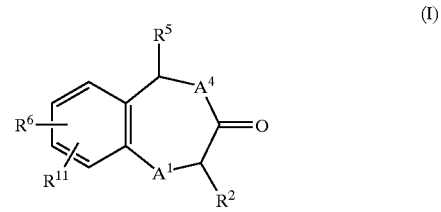

(I)

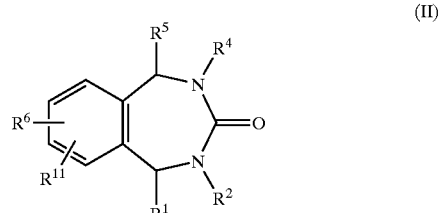

(II)

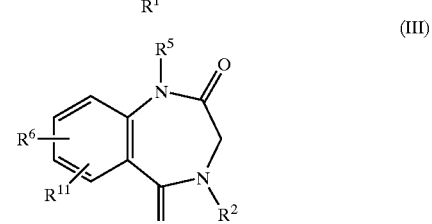

(III)

wherein $A^1$ is O, S, N—$R^1$ or CHR$^1$;

$A^4$ is N—$R^4$ or CHR$^4$;

$R^2$ is a sidechain containing an acid or ester group;

$R^1$, $R^4$ and $R^5$ are substituents such as H, alkyl and aryl alkyl, and $R^6$ is a sidechain containing a nitrogen group; and pharmaceutically acceptable salts thereof, which are effective for inhibiting platelet aggregation, pharmaceutical compositions for effecting such activity, and a method for inhibiting platelet aggregation.

18 Claims, No Drawings

BICYCLIC FIBRINOGEN ANTAGONISTS

This application is a 371 of PCT/US93/12436 filed on Dec. 21, 1993, which claims priority from Ser. No. 07/992,885, filed of Dec. 21, 1992.

FIELD OF THE INVENTION

This invention relates to novel bicyclic compounds which inhibit platelet aggregation, pharmaceutical compositions containing the compounds and methods of using the compounds.

BACKGROUND OF THE INVENTION

Platelet aggregation is believed to be mediated primarily through the fibrinogen receptor, or GPIIb-IIIa platelet receptor complex, which is a member of a family of adhesion receptors referred to as integrins. It has been found that frequently the natural ligands of integrin receptors are proteins which contain an Arg-Gly-Asp sequence. Von Willebrand factor and fibrinogen, which are considered to be natural ligands for the GPIIb-IIIa receptor, possess an Arg-Gly-Asp (RGD in single letter amino acid code) sequence in their primary structure. Functionally, these proteins are able to bind and crosslink GPIIb-IIIa receptors on adjacent platelets and thereby effect aggregation of platelets.

Fibronectin, vitronectin and thromospondin are RGD-containing proteins which have also been demonstrated to bind to GPIIb-IIIa. Fibronectin is found in plasma and as a structural protein in the intracellular matrix. Binding between the structural proteins and GPIIb-IIIa may function to cause platelets to adhere to damaged vessel walls.

Linear and cyclic peptides which bind to vitronectin and contain an RGD sequence are disclosed in WO 89/05150 (PCT US88/04403). EP 0 275 748 discloses linear tetra- to hexapeptides and cyclic hexa- to octapeptides which bind to the GPIIb-IIIa receptor and inhibit platelet aggregation. Other linear and cyclic peptides, the disclosure of which are incorporated herein by reference, are reported in EP-A 0 341 915. However, the peptide like structures of such inhibitors often pose problems, such as in drug delivery, metabolic stability and selectivity. Inhibitors of the fibrinogen receptor which are not constructed of natural amino acid sequences are disclosed in EP-A 0 372,486, EP-A 0 381 033 and EP-A 0 478 363. WO 92/07568 (PCT/US91/08166) discloses fibrinogen receptor antagonists which mimic a conformational γ-turn in the RGD sequence by forming a monocyclic seven-membered ring structure. There remains a need, however, for novel fibrinogen receptor antagonists (e.g. inhibitors of the GPIIb-IIIa protein) which have potent in vivo and in vitro effects and lack the peptide backbone structure of amino acid sequences.

The present invention discloses novel bicyclic compounds including benzazepines and benzodiazepines, which are inhibitors of the GPIIb-IIIa receptor and inhibit platelet aggregation. Certain 5-phenyl-1,4-benzodiazepines are known as a class of drugs which affect the central nervous system, and have been used as anxiolytics. See Sternbach, L. H., *J. Med. Chem.*, 22, 2 (1979). It has also been disclosed that certain 5-phenyl-1,4-benzodiazepines antagonize the effects of cholecystokinin. See Friedinger, *Med. Res. Rev.*, 9, 271 (1989). Certain bicyclic compounds which have fibrinogen antagonist activity are disclosed in WO 93/08174 (PCT/US92/08788) and WO 93/00095 (PCT/US/92/05463).

SUMMARY OF THE INVENTION

In one aspect this invention is a bicyclic compound comprising a substituted six-membered ring fused to a substituted seven-membered ring as described hereinafter in formula (I).

This invention is also a pharmaceutical composition for inhibiting platelet aggregation or clot formation, which comprises a compound of formula (I) and a pharmaceutically acceptable carrier.

This invention further comprises the use of a compound of formula (I) in the manufacture of a medicament for inhibiting platelet aggregation.

In another aspect, this invention provides a method for inhibiting reocclusion of an artery or vein in a mammal following fibrinolytic therapy, which comprises internally administering an effective amount of a fibrinolytic agent and a compound of formula (I). This invention is also a method for treating stroke, transient ischemia attacks, or myocardial infarction.

DETAILED DESCRIPTION OF THE INVENTION

This invention discloses novel bicyclic compounds which inhibit platelet aggregation. The novel bicyclic compounds comprise a seven-membered ring fused to an aromatic six membered ring and having a nitrogen-containing substituent on the six membered ring and an aliphatic substituent, preferably containing an acidic moiety, on the seven membered ring. The fused 6–7 ring system is believed to interact favorably with the GPIIb-IIIa receptor and to orient the substituent sidechains on the six and seven membered rings so that they may also interact favorably with the receptor.

Although not intending to be bound to any specific mechanism of action, these compounds are believed to inhibit the binding of fibrinogen to the platelet-bound fibrinogen receptor GPIIb-IIIa, and may interact with other adhesion proteins via antagonism of a putative RGD binding site.

The compounds of this invention are compounds of formula (I):

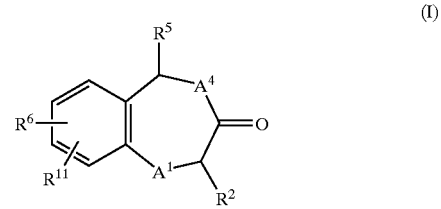

wherein $A^1$ is O, S, N—$R^1$ or CHR$^1$;

$A^4$ is N—$R^4$ or CHR$^4$;

$R^2$ is $R^7$ or Q—$C_{1-4}$alkyl, Q—$C_{2-4}$alkenyl or Q—$C_{2-4}$alkynyl substituted by $R^7$;

$R^1$, $R^4$ and $R^5$ are H, Q—$C_{1-6}$alkyl, Q—$C_{1-6}$oxoalkyl, Q—$C_{2-6}$alkenyl, Q—$C_{3-4}$oxoalkenyl, Q—$C_{3-4}$oxoalkynyl, Q—$C_{2-4}$alkynyl, $C_{3-6}$cycloalkyl, Ar or Het, optionally substituted by one or more of $R^{11}$;

Q is H, $C_{3-6}$cycloalkyl, Het or Ar;

$R^6$ is W—(CR'$_2$)$_q$—Z—(CR'R$^{10}$)$_r$—U—(CR'$_2$)$_s$—V—;

$R^7$ is —COR$^8$, —COCR'$_2$R$^9$, —C(S)R$^8$, —S(O)$_m$OR', —S(O)$_m$NR'R", —PO(OR'), —PO(OR')$_2$, —B(OR')$_2$, —NO$_2$ and Tet;

$R^8$ is —OR', —NR'R", —NR'SO$_2$R', —NR'OR', —OCR'$_2$C(O)OR', —OCR'$_2$OC(O)—R', —OCR'$_2$C(O)NR'$_2$, CH$_3$ or AA;

$R^9$ is —OR', —CN, —S(O)$_r$R', S(O)$_m$NR'$_2$, —C(O)R'C(O)NR'$_2$ or —CO$_2$R';

$R^{10}$ is H, $C_{1-4}$alkyl or —NR'R";

$R^{11}$ is H, halo, —$OR^{12}$, —CN, —$NR'R^{12}$, —$NO_2$, —$CF_3$, $CF_3S(O)_r$—, —$CO_2R'$, —$CONR'_2$, Q—$C_{0-6}$alkyl-, Q—$C_{1-6}$oxoalkyl-, Q—$C_{2-6}$alkenyl-, Q—$C_{2-6}$alkynyl-, Q—$C_{0-6}$alkyloxy-, Q—$C_{0-6}$alkylamino- or Q—$C_{0-6}$alkyl-$S(O)_r$—;

$R^{12}$ is R', —C(O)R', —C(O)$NR'_2$, —C(O)$OR^{15}$, —$S(O)_m$R' or $S(O)_mNR'_2$;

$R^{15}$ is H, $C_{1-6}$alkyl or Ar—$C_{0-4}$alkyl;

R' is H, $C_{1-6}$alkyl, $C_{3-7}$cycloalkyl-$C_{0-4}$alkyl or Ar—$C_{0-4}$alkyl;

R" is R', —C(O)R' or —C(O)$OR^{15}$;

R'" is R" or AA2;

AA1 is an amino acid attached through its amino group and having its carboxyl group optionally protected, and AA2 is an amino acid attached through its carboxyl group, and having its amino group optionally protected;

U and V are absent or CO, $CR'_2$, C(=CR'2), $S(O)_n$, O, NR', CR'OR', CR'(OR")$CR'_2$, $CR'_2CR'(OR")$, C(O)$CR'_2$, $CR'_2C(O)$, CONR', NR'CO, OC(O), C(O)O, C(S)O, OC(S), C(S)NR', NR'C(S), $S(O)_nNR'$, $NR'S(O)_n$, N=N, NR'NR', $NR'CR'_2$, $CR'_2NR'$, $CR'_2O$, $OCR'_2$, C≡C or CR'=CR', provided that U and V are not simultaneously absent;

W is R'R'"N— or 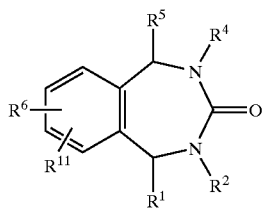;

Z is $(CH_2)_t$ or Het;

m is 1 or 2;

n is 0 to 3;

q is 0 to 3;

r is 0 to 2;

s is 0 to 2; and t is 0 to 2; or pharmaceutically acceptable salts thereof.

In another embodiment, this invention is a compound of formula (II):

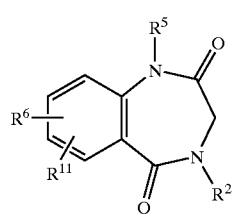

(II)

wherein $R^1$, $R^2$, $R^4$, $R^5$ and $R^{11}$ are as defined in for formula (I) and $R^6$ is W—$(CR'_2)_q$—Z—$(CR'R^{10})_r$—U—$(CR'_2)_s$—V—, where U, V and R' are as defined for formula (I), $R^{10}$ is H, $C_{1-4}$alkyl or —NR'R", W is $R'_2$N, $H_2$NC(=NH), $H_2$NC(=NH)NH or 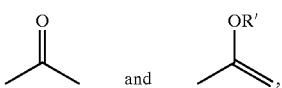; and Z is Ar, $C_{3-7}$cycloalkyl, $(CH_2)_t$ or Het. In particular, compounds of formula (II) where $R^1$ is H, $C_{1-4}$alkyl or C(O)R'; $R^2$ is $CH_2CO_2H$ or $CH_2CH_2CO_2H$, $R^4$ is H, $C_{1-6}$alkyl, $C_{3-6}$cycloalkyl$C_{0-4}$alkyl or Ar—$C_{0-4}$alkyl; and Z is phenyl, a six-membered Het or $(CH_2)_t$, are suitable.

In yet another embodiment of this invention, compounds of formula (III) are provided

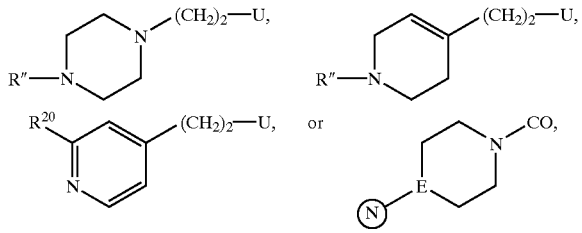

(III)

wherein $R^2$, $R^5$ and $R^{11}$ are as defined for formula (I), and $R^6$ is or

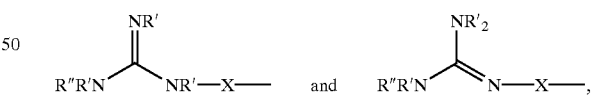

wherein E is N or CH, $R^{20}$ is hydrogen, amino, mono or di-$C_{1-4}$alkylamino, hydroxy or $C_{1-4}$alkyl, and U is NR'CO, CONR', $(CH_2)CO$, CH=CH or C≡C.

Also included in this invention are pharmaceutically acceptable addition salts, complexes or prodrugs of the compounds of this invention. Prodrugs are considered to be any covalently bonded carriers which release the active parent drug according to formula (I) in vivo.

In cases wherein the compounds of this invention may have one or more chiral centers, unless specified, this invention includes each unique nonracemic compound which may be synthesized and resolved by conventional techniques. In cases in which compounds have unsaturated carbon-carbon double bonds, both the cis (Z) and trans (E) isomers are within the scope of this invention. In cases wherein compounds may exist in tautomeric forms, such as keto-enol tautomers, such as $$\underset{}{\overset{O}{\bigwedge}} \quad \text{and} \quad \underset{}{\overset{OR'}{\bigwedge}},$$

and tautomers of guanidine-type groups, such as $$R"R'N \overset{NR'}{\bigwedge} NR'—X— \quad \text{and} \quad R"R'N \overset{NR'_2}{\bigwedge} N—X—,$$

each tautomeric form is contemplated as being included within this invention whether existing in equilibrium or locked in one form by appropriate substitution with R'. The meaning of any substituent at any one occurrence is independent of its meaning, or any other substituent's meaning, at any other occurrence, unless specified otherwise.

Suitably $R^8$ is —OR', —$OCR'_2C(O)OR$, —$OCR'_2C(O)NR'_2$ or $OCR'_2C(O)$—R', preferably —OR'.

Suitably $R^5$, $R^{10}$ and $R^{11}$ are H.

Suitably $(CR'R^{10})_r$—U—$(CR'_2)_s$—V is $(CR'R^{10})_r$—U— or —U—$(CR'_2)_s$.

Suitably U is CO, CONR' or NR'CO.

Preferably, $(CR'R^{10})_r$—U—$(CR'_2)_s$—V is $(CH_2)_{0-2}$NR'CO, $(CH_2)_{0-2}$CONR', $(CH_2)_{0-2}$CO, $(CH_2)_{0-2}$CH=CH, $(CH_2)_{0-2}C\equiv C$, $(CH_2)_{1-3}O$, or $(CH_2)_{1-5}$. More preferably $(CR'R^{10})_r$—U—$(CR'_2)_s$—V is $(CH_2)_{0-2}NR'CO$ or $(CH_2)_{0-2}CONR'$, where R' is H or methyl.

Preferably W is <img/>

Preferably, Z is piperidinyl, piperazinyl or $(CH_2)_t$. Suitably t is 1 or 2.

Particular examples of $R^6$ are:

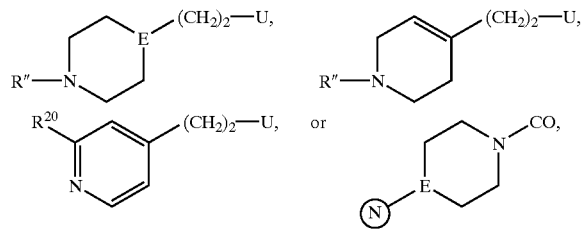

and R"HN—$(CH_2)_5$—U wherein E is N or CH, $R^{20}$ is hydrogen, amino, mono or di-$C_{1-4}$alkylamino, hydroxy or $C_{1-4}$alkyl, and U is NR'CO, CONR', $(CH_2)CO$, CH=CH, C≡C, $CH_2O$, $OCH_2$ and $(CH_2)_2$.

Preferred illustrative examples of $R^6$ are:

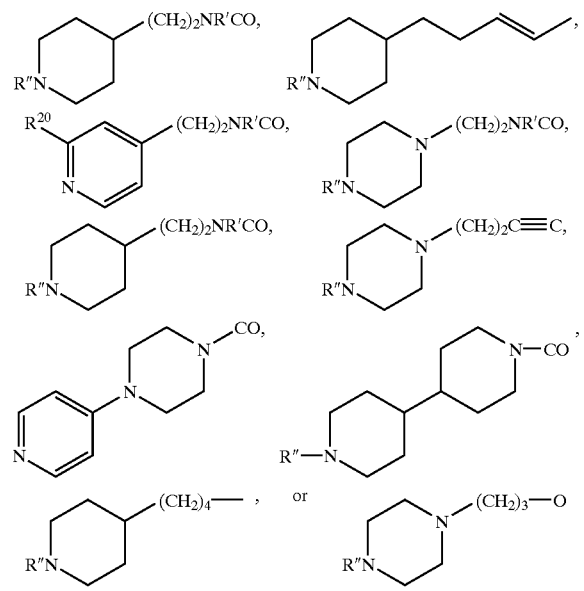

wherein R' and R" are H or $C_{1-4}$alkyl. Preferably R' is methyl and R" is H.

In a preferred embodiment, $A^1$ is $NR^1$, and $A^4$ is NR'.

In another preferred embodiment, $A^1$ is $CHR^1$, and $A^4$ is NR'.

Preferably, $R^2$ is $CH_2$—$R^7$. More preferably, $R^2$ is $CH_2CO_2R'$, particularly $CH_2CO_2H$.

Preferably, $R^1$ and $R^4$ are H, $C_{1-4}$alkyl, Ar—$C_{1-4}$alkyl or $C_{3-6}$cycloalkyl-$C_{1-4}$alkyl. Suitably $R^1$ is H or methyl and $R^4$ is H, methyl, cyclohexylethyl or phenylethyl.

In a more specific preferred embodiment, $A^1$ is NR" or $CH_2$, where R" is H, $C_{1-4}$alkyl or C(O)R'; $R^2$ is $CH_2CO_2H$; $A^4$ is $NR^4$; $R^4$ is H, $C_{1-6}$alkyl, $C_{3-6}$cycloalkyl-$C_{0-4}$alkyl or Ar—$C_{0-4}$alkyl; Z is a six-membered Het or $(CH_2)_t$; W is $R'_2N$, or <img/>; $(CR'R^{10})_r$—U—$(CR'_2)_s$—V is $(CR'R^{10})_r$—U— or —U—$(CR'_2)_s$, (e.g., V is absent and one of s and r are 0) wherein U is NR'CO, CONR', CR'=CR', C≡C, O, CO or $CH_2$. Suitably, $(CR'R^{10})_r$—U—$(CR'_2)_s$—V is $(CH_2)_{0-3}$NR'CO, $(CH_2)_{0-3}$CONR', where R' is H or methyl, or $(CH_2)_{0-3}O$. Preferably R' is methyl.

Specific embodiments of this invention, including useful intermediates and prodrugs, are described in Examples 1–88 inclusive.

In the above description of formula (I), W represents a nitrogen-containing group which is capable of making a hydrogen bond. Preferably W is a basic nitrogen moiety. $R^7$ represents a group with a non-bonding pair of electrons which is capable of forming a hydrogen bond or chelating with a metal cation. Preferably $R^7$ is acidic. It is also preferred that 10–15 (most preferably about 13) intervening covalent bonds via the shortest intramolecular path will exist between the group $R^7$ and a terminal basic nitrogen moiety of W for optimal spacing between these groups, and the moieties T, U, V and Z, and the alkyl spacers represented by q, r, s are chosen accordingly. For instance, by way of illustration, but not limitation, when one of $R^2$ or $R^4$ is $(CH_2)_2CO_2H$, or preferably $CH_2CO_2H$, and $R^6$ is a substituent in the 7- or 8-position of the benzodiazepine ring system and is W—$(CR'_2)_q$—Z—$(CR'R^{10})_r$—U—(e.g., s is 0 and V is absent), then: when W is <img/> (preferably a 4-substituted six-membered nitrogen heterocycle), and Z is $(CH_2)_t$, and U is chosen from NR'CO, CONR', $CH_2O$, $OCH_2$, $CH_2CH_2$, CR'=CR' or C≡C, ('group 1'), suitably q+t+r is 1–3 and preferably q+t+r is 1; when W is <img/> and Z is a six-membered Ar or Het ring (preferably 1,4-disubstituted), and U is O, $CH_2$ or CO, q and r are preferably 0; when W is $H_2N$— and Z is $(CH_2)_t$, and U is chosen from group 1 above, q+r+t is 4–6, preferably 5; when W is $H_2N$— and Z is a six-membered Ar or Het ring, suitably q+t is 0–2, preferably 1.

Abbreviations and symbols commonly used in the peptide and chemical arts are used herein to describe the compounds of this invention. In general, the amino acid abbreviations follow the IUPAC-IUB Joint Commission on Biochemical Nomenclature as described in *Eur. J. Biochem.*, 158, 9 (1984).

Arg refers to arginine, MeArg refers to $N^\alpha$-methylarginine, HArg refers to homoarginine, NArg refers to norarginine, $(Me_2)$Arg refers to N',N"-dimethyl arginine, $(Et_2)$Arg refers to N',N"-diethyl arginine and Orn refers to ornithine. These radicals are suitable components of the substituent $R^6$. $N^\alpha$-Substituted derivatives of these amino acid are also useful in this invention. Representative methods for preparing a-substituted derivatives are disclosed in U.S. Pat. No. 4,687,758; Cheung et al., *Can. J. Chem.*, 55, 906 (1977); Freidinger et al., *J. Org. Chem.*, 48, 77, (1982); and Shuman et al., Peptides: Proceedings of the 7th American Peptide Symposium, Rich, D., Gross, E., Eds, Pierce Chemical Co., Rockford, Ill.,617 (1981), which are incorporated herein by reference.

$C_{1-4}$alkyl as applied herein is meant to include methyl, ethyl, n-propyl, isopropyl, n-butyl, isobutyl and t-butyl. $C_{1-6}$alkyl additionally includes pentyl, n-pentyl, isopentyl, neopentyl and hexyl and the simple aliphatic isomers thereof. $C_{0-4}$alkyl and $C_{0-6}$alkyl additionally indicates that no alkyl group need be present (e.g., that a covalent bond is present).

$C_{2-6}$alkenyl as applied herein means an alkyl group of 2 to 6 carbons wherein a carbon-carbon single bond is replaced by a carbon-carbon double bond. $C_{2-6}$alkenyl includes ethylene, 1-propene, 2-propene, 1-butene, 2-butene, isobutene and the several isomeric pentenes and hexenes. Both cis and trans isomers are included.

$C_{2-6}$ alkynyl means an alkyl group of 2 to 6 carbons wherein one carbon-carbon single bond is replaced by a carbon-carbon triple bond. $C_{2-6}$ alkynyl includes acetylene, 1-propyne, 2-propyne, 1-butyne, 2-butyne, 3-butyne and the simple isomers of pentyne and hexyne.

$C_{1-4}$oxoalkyl refers to an alkyl group of up to four carbons wherein a $CH_2$ group is replaced by a C(O), or carbonyl, group. Substituted formyl, acetyl, 1-propanal, 2-propanone, 3-propanal, 2-butanone, 3-butanone, 1- and 4-butanal groups are representative. $C_{1-6}$oxoalkyl includes additionally the higher analogues and isomers of five and six carbons substituted by a carbonyl group. $C_{3-6}$oxoalkenyl and $C_{3-6}$oxoalkynyl refers to a $C_{3-6}$alkenyl or $C_{3-6}$alkynyl group wherein a $CH_2$ group is replaced by C(O) group. $C_{3-4}$oxoalkenyl includes 1-oxo-2-propenyl, 3-oxo-1-propenyl, 2-oxo-3-butenyl and the like.

A substituent on a $C_{1-6}$alkyl, $C_{2-6}$alkenyl, $C_{2-6}$alkynyl or $C_{1-6}$oxoalkyl group, such as $R^{11}$, may be on any carbon atom which results in a stable structure, and is available by conventional synthetic techniques.

Q—$C_{1-6}$ alkyl refers to a $C_{1-6}$ alkyl group wherein in any position a carbon-hydrogen bond is replaced by a carbon-Q bond. Q—$C_{2-6}$ alkenyl and Q—$C_{2-6}$ alkynyl have a similar meaning with respect to $C_{2-6}$ alkenyl and $C_{2-6}$ alkynyl.

Ar, or aryl, as applied herein, means phenyl or naphthyl, or phenyl or naphthyl substituted by one to three moieties $R^{11}$. In particular, $R^{11}$ may be $C_{1-4}$alkyl, $C_{1-4}$alkoxy, $C_{1-4}$alkylthio, trifluoroalkyl, OH, F, Cl, Br or I.

Het, or heterocycle, indicates an optionally substituted five or six membered monocyclic ring, or a nine or ten-membered bicyclic ring containing one to three heteroatoms chosen from the group of nitrogen, oxygen and sulfur, which are stable and available by conventional chemical synthesis. Illustrative heterocycles are benzofuryl, benzimidazole, benzopyran, benzothiophene, furan, imidazole, indoline, morpholine, piperidine, piperazine, pyrrole, pyrrolidine, tetrahydropyridine, pyridine, thiazole, thiophene, quinoline, isoquinoline, and tetra- and perhydro- quinoline and isoquinoline. A six membered ring heterocycle containing one or two nitrogens, such as piperidine, piperazine, tetrahydropyridine and pyridine, are preferred heterocycles for the moiety Z. Any accessible combination of up to three substituents, such as chosen from $R^{11}$, on the Het ring that is available by chemical synthesis and is stable is within the scope of this invention. A six membered monocyclic ring heterocycle containing one or two nitrogens, such as piperidine, piperazine, tetrahydropyridine and pyridine, are preferred heterocycles for the moiety Z.

$C_{3-7}$cycloalkyl refers to an optionally substituted carbocyclic system of three to seven carbon atoms, which may contain up to two unsaturated carbon-carbon bonds. Typical of $C_{3-7}$cycloalkyl are cyclopropyl, cyclobutyl, cyclopentyl, cyclopentenyl, cyclohexyl, cyclohexenyl and cycloheptyl. Any combination of up to three substituents, such as chosen from $R^{11}$, on the cycloalkyl ring that is available by conventional chemical synthesis and is stable, is within the scope of this invention.

Ⓝ as used herein indicates a nitrogen heterocycle, which may be a saturated or unsaturated stable five-, six- or seven-membered monocyclic ring, or a seven- to ten-membered bicyclic ring containing up to three nitrogen atoms or containing one nitrogen atom and a heteroatom chosen from oxygen and sulfur, and which may be substituted on any atom that results in a stable structure. The nitrogen atom in such ring may be substituted so as to result in a quaternary nitrogen. The nitrogen heterocycle may be substituted in any stable position by $R^{20}$, for instance H, $C_{1-4}$alkoxy, F, Cl, Br, I, $NO_2$, $NR'_2$, OH, $CO_2R'$, CONHR', $CF_3$, Q—$C_{0-4}$alkyl, Q—$C_{1-4}$alkyl-S(O)$_u$ (e.g., where u is 0, 1 or 2) or $C_{1-4}$alkyl substituted by any of the aforementioned substituents. Representative of Ⓝ are pyrroline, pyrrolidine, imidazole, imidazoline, imidazolidine, pyrazole, pyrazoline, pyrazolidine, piperidine, piperazine, morpholine, pyridine, pyridinium, tetrahydropyridine, tetrahydro- and hexahydro-azepine, quinuclidine, quinuclidinium, quinoline, isoquinoline, and tetra- and perhydro-quinoline and isoquinoline. In particular, Ⓝ may be pyridyl, pyrolidinyl, piperidinyl, piperazinyl, azetidinyl, quinuclidinyl or tetrahydropyridinyl. Ⓝ is preferably 4-pyridyl, 4-(2-amino-pyridyl), 4-tetrahydropyridyl, 4-piperidinyl or 4-piperazinyl.

AA1 as referred to herein is an amino acid with its carboxyl group optionally protected, wherein the amino acid may be any of the natural α-amino acids or penicillamine. The unprotected carboxyl group is a free carboxylic acid group. Protecting groups for the carboxyl are esters or amides which are formed, for instance, when the OH of the carboxy group is replaced by $R^8$. AA2 is an amino acid, as above, with its amino group optionally protected. Amino protecting groups are well known in the art, for instance, when the amino group is substituted by $R^{12}$. An unprotected amino group is a free $NH_2$ group.

C(O) indicates a carbon doubly bonded to oxygen (e.g., carbonyl), C(S) indicates a carbon doubly bonded to sulfur (e.g., thiocarbonyl).

t-Bu refers to the tertiary butyl radical, Boc refers to the t-butyloxycarbonyl radical, Fmoc refers to the fluorenyl-methoxycarbonyl radical, Ph refers to the phenyl radical, Cbz refers to the benzyloxycarbonyl radical, BrZ refers to the o-bromobenzyloxycarbonyl radical, ClZ refers to the o-chlorobenzyloxycarbonyl radical, Bzl refers to the benzyl radical, 4-MBzl refers to the 4-methyl benzyl radical, Me refers to methyl, Et refers to ethyl, Ac refers to acetyl, Alk refers to $C_{1-4}$alkyl, Nph refers to 1- or 2-naphthyl and cHex refers to cyclohexyl. Tet refers to 5-tetrazolyl.

DCC refers to dicyclohexylcarbodiimide, DMAP refers to dimethylaminopyridine, DEA refers to diisopropylethyl amine, EDC refers to N-ethyl-N'(dimethylaminopropyl)-carbodiimide.HOBt refers to 1-hydroxybenzotriazole, THF refers to tetrahydrofuran, DIEA refers to diisopropylethylamine, DMF refers to dimethyl formamide, NBS refers to N-bromo-succinimide, Pd/C refers to a palladium on carbon catalyst, PPA refers to 1-propanephosphonic acid cyclic anhydride, DPPA refers to diphenylphosphoryl azide, BOP refers to benzotriazol-1-yloxy-tris(dimethylamino) phosphonium hexafluorophosphate, HF refers to hydrofluoric acid, TEA refers to triethylamine, TFA refers to trifluoroacetic acid, PCC refers to pyridinium chlorochromate.

The compounds of formula (I) are generally prepared by reacting a compound of the formula (XI) with a compound of the formula (XII):

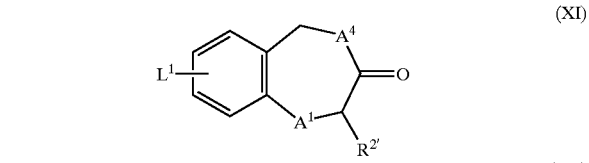

(XI)

(XII)

wherein
A$^1$, A$^4$, U, V, R', R$^{10}$, s and r are as defined in formula (I), with any reactive functional groups protected;
L$^1$ and L$^2$ are functional groups which are capable of reacting to form the linkage —(CR'R$^{10}$)$_r$—U—(CR'$_2$)$_s$—V—;
R$^{6"}$ is W'—(CR'$_2$)$_q$—Z— and any portion of the group —(CR'R$^{10}$)$_r$—U—(CR'$_2$)$_s$—V— which is connected to L$^2$, with any reactive functional groups protected;

R[2'] is R[2] as defined for formula (I) with any reactive group protected; and

W' is W as defined for formula (I) with any basic nitrogen group protected; to form a compound of the formula:

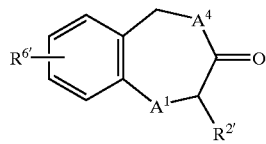

wherein R[6'] is W'—(CR'$_2$)$_q$—Z—(CR'R[10])$_r$—U—(CR'$_2$)$_s$—V—;

and thereafter removing any protecting groups, and optionally forming a pharmaceutically acceptable salt.

It will be apparent that the precise identity of L[1] and L[2] will be dependent upon the site of the linkage being formed. General methods for preparing the linkage —(CR'R[10])$_r$—U—(CR'$_2$)$_s$—V— are described, for example, in EP-A 0 372 486 and EP-A 0 381 033 and EP-A 0 478 363, which are incorporated herein by reference.

For instance, if V is CONH, L[1] may be —NH$_2$, L[2] may be OH (as in an acid) or Cl (as in an acid chloride), and R[6"] may be W—(CR'$_2$)$_q$—Z—(CR'R[10])$_r$—U—(CR'$_2$)$_s$—C(O), with any functional groups optionally protected. For example, R[6"] may be (benzyloxycarbonyl-amidino)benzoyl- or (N[α]Boc,N[guan]-Tos)arginyl-. When L[2] is OH, a coupling agent is used.

Similarly, if V is NHCO, L[1] may be —CO$_2$H or CO—Cl, L[2] may be —NH$_2$, and R[6"] may be W—(CR'$_2$)$_q$—Z—(CR'R[10])$_r$—U—(CR'$_2$)$_s$—. For example, R[6"] may be (benzyloxycarbonylamidino)-phenyl, (benzyloxycarbonylamino)methylbenzyl- or 6-(benzyloxycarbonylamino)hexyl-.

Where V is NHSO$_2$, L[1] may be SO$_2$Cl, L[2] may be —NH$_2$ and R[6"] may be as above. Where V is SO$_2$NH, L[1] may be —NH$_2$ and L[2] may be SO$_2$Cl. Methods to prepare such sulfonyl chlorides are disclosed, for instance, in *J. Org. Chem.*, 23, 1257 (1958).

If V is CH=CH, L[1] may be —CHO, L[2] may be CH=P—Ph$_3$ and R[6"] may be W—(CR'$_2$)$_q$—Z—(CR'R[10])$_r$—U—(CR'$_2$)$_s$—. Alternately, L[1] may be CH=P—Ph$_3$, L[2] may be CHO, e.g., R[6"] may be W—(CR'$_2$)$_q$—Z—(CR'R[10])$_r$—U—(CR'$_2$)$_{s-1}$—CHO.

Where V is CH$_2$CH$_2$, compounds may be obtained by reduction of a suitably protected compound wherein V is CH=CH.

Where V is CH$_2$O, CH$_2$N or C≡C, L[1] may be —OH, —NH or —C≡C H, respectively; L[2] may be —Br, and R[6"] may be W—(CR'$_2$)$_q$—Z—(CR'R[10])$_r$—U—(CR'$_2$)$_s$—. For example, R[6"] may be (benzyloxycarbonylamino)-methylbenzyl- or 2-(N-benzyl-4-piperidinyl)-ethyl. Similarly where U or V is OCH$_2$, NR'CH$_2$ or C≡C, L[1] may be —CH$_2$Br and L[2] may be —OH, —NH or —C≡C H, respectively. Alternately, when U or V is C≡C, L[1] may be Br, I or CF$_3$SO$_3$, L[2] may be C≡C H and the coupling may be catalyzed by palladium and a base.

Compounds wherein V is CHOHCH$_2$ may be prepared from a suitably protected compound where V is CH=CH by the procedure disclosed in *J. Org. Chem.*, 54, 1354 (1989).

Compounds wherein V is CH$_2$CHOH may be obtained from a suitably protected compound where V is CH=CH by hydroboration and basic oxidation as disclosed in *Tet. Lett.*, 31, 231 (1990).

The compounds of formula (XI), are benzodiazepines and benzazepines and are prepared by the general methods illustrated by Schemes 1–9. Representative methods for preparing benzodiazepines are well known in the art (e.g., Hynes, et al., *J. Het. Chem.*, 1988, 25, 1173; Muller, et al., *Helv. Chim. Acta.*, 1982, 65, 2118; Mori, et al., *Heterocycles*, 1981, 16, 1491); and WO 93/00095 which are incorporated herein by reference. Scheme 10 is illustrative of a method to prepare benzothiazepines. Benzoxazepines may be prepared in an analogous manner by starting with the compound wherein S is replaced by O. In the Schemes, R[1"]–R[7"] indicate R[1]–R[7] or a suitable precursor thereof, wherein any functional groups are protected as known in the art.

Scheme 1

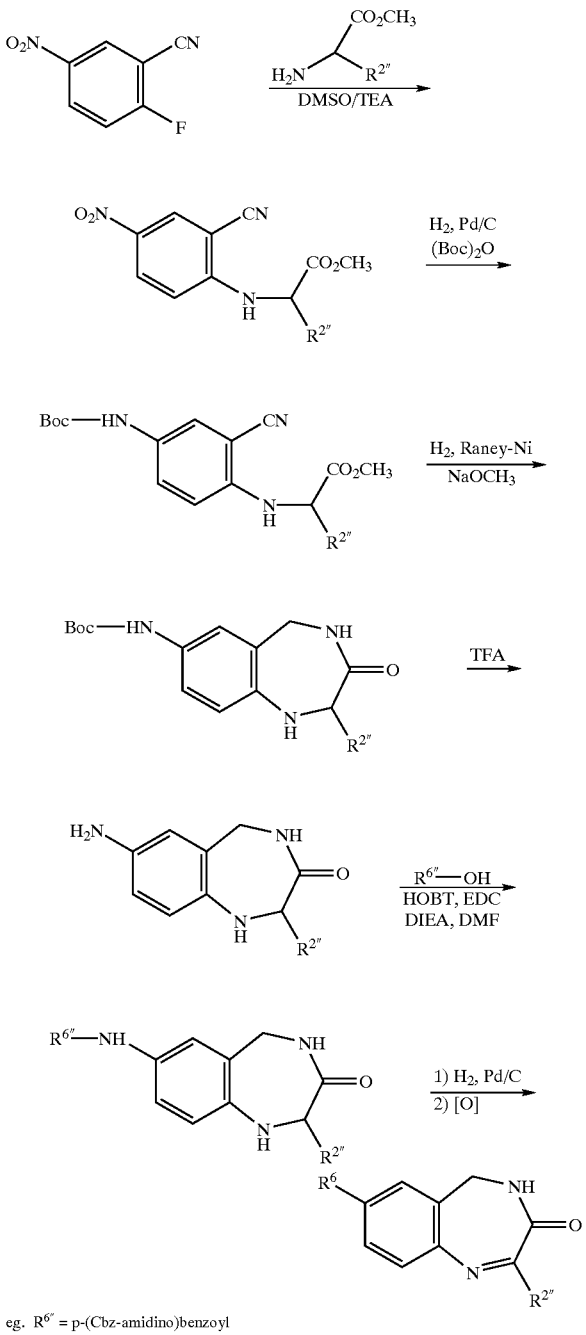

eg. R[6"] = p-(Cbz-amidino)benzoyl
R[6] = p-(amidino)benzoyl amino

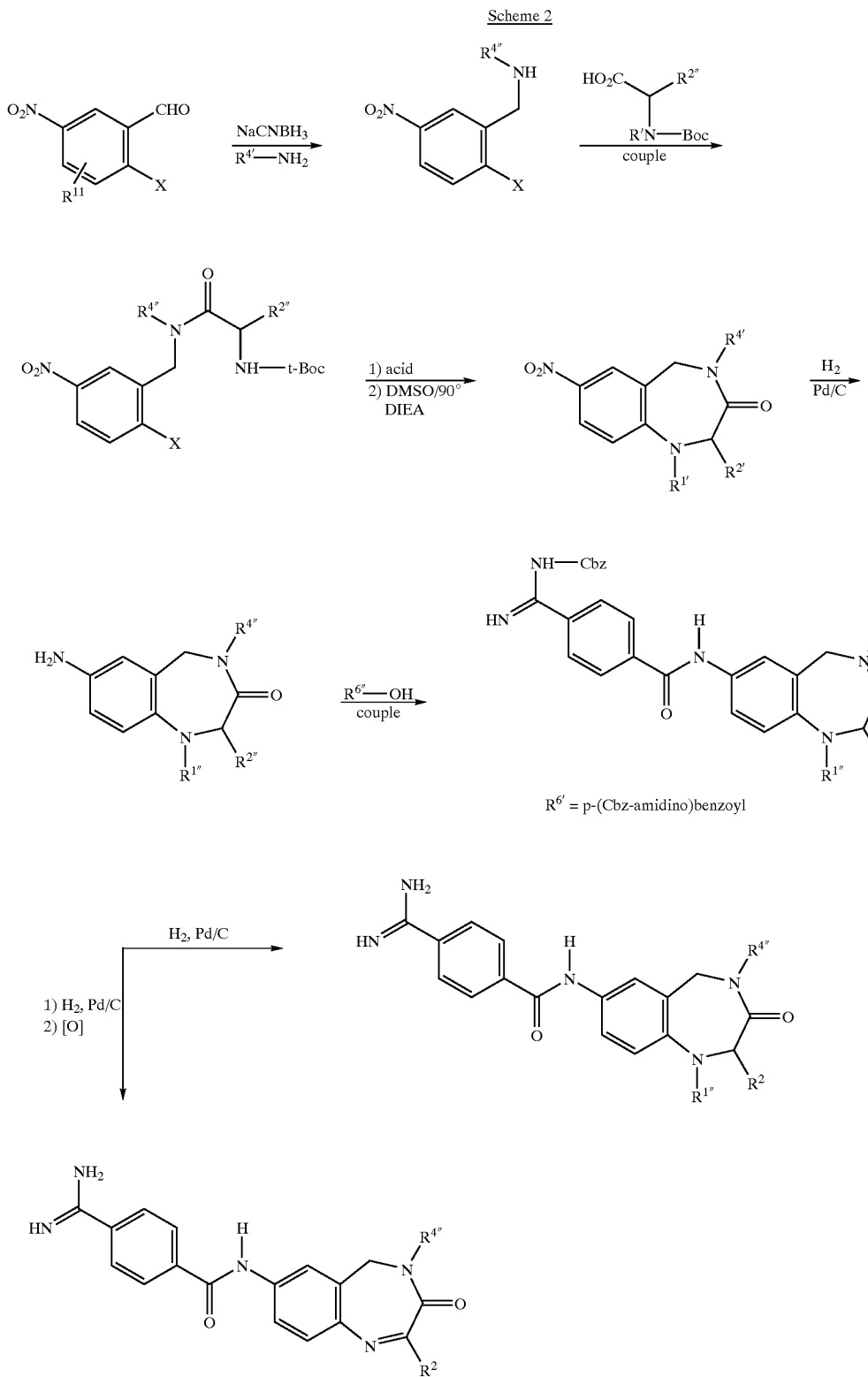

Scheme 3
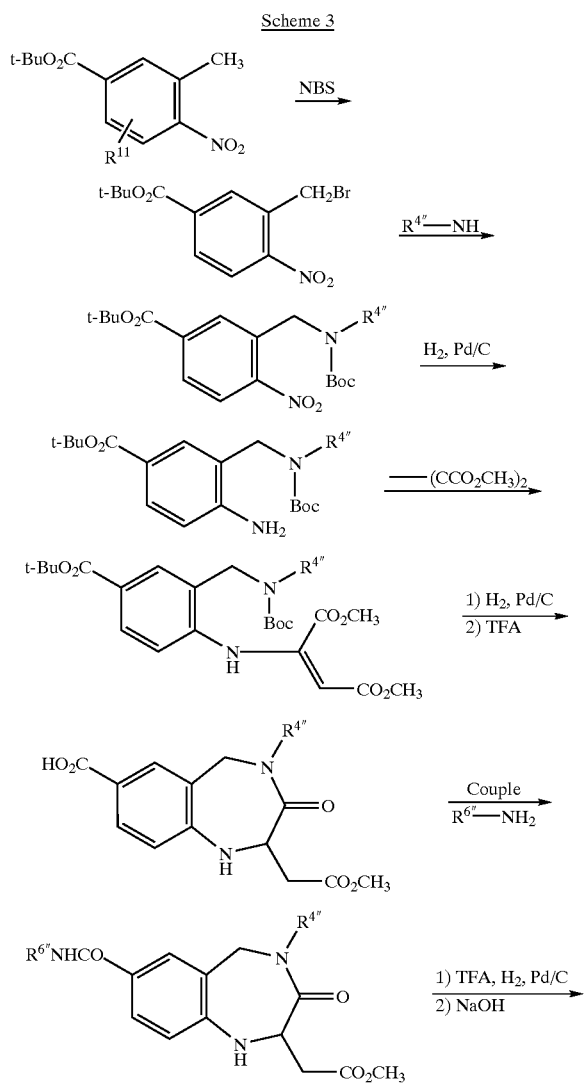
eg. R⁴" = CH₂CH₂Ph
R⁶" = p-(Cbz-amidino)benzyl
R⁶ = p-(amidinobenzyl)aminocarbonyl
R¹¹ = H
Scheme 4
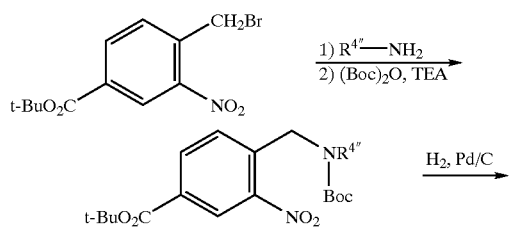
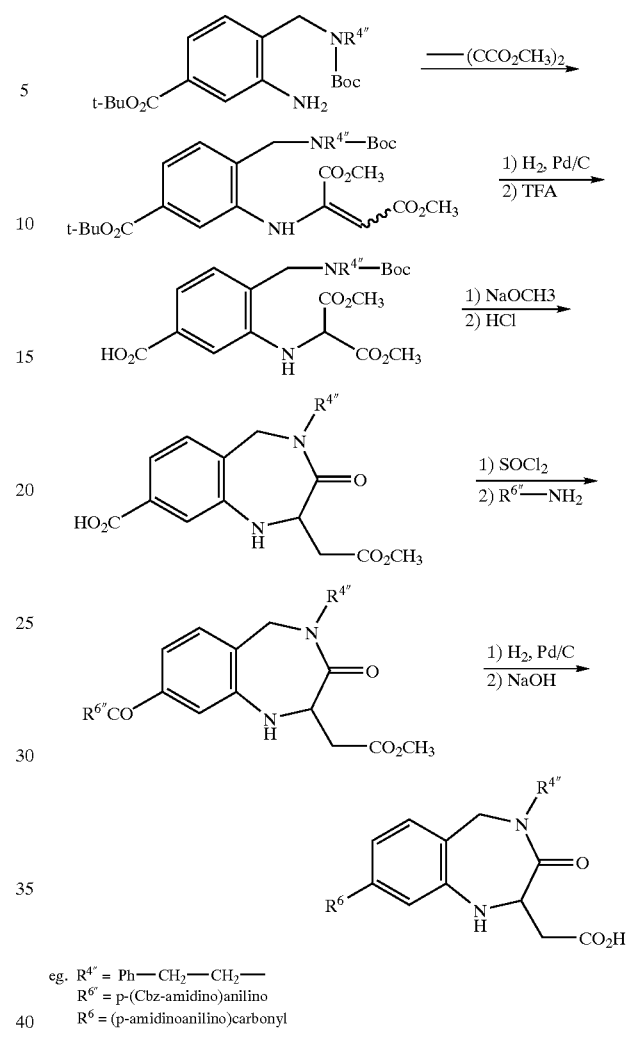
eg. R⁴" = Ph—CH₂—CH₂—
R⁶" = p-(Cbz-amidino)anilino
R⁶ = (p-amidinoanilino)carbonyl
Scheme 5
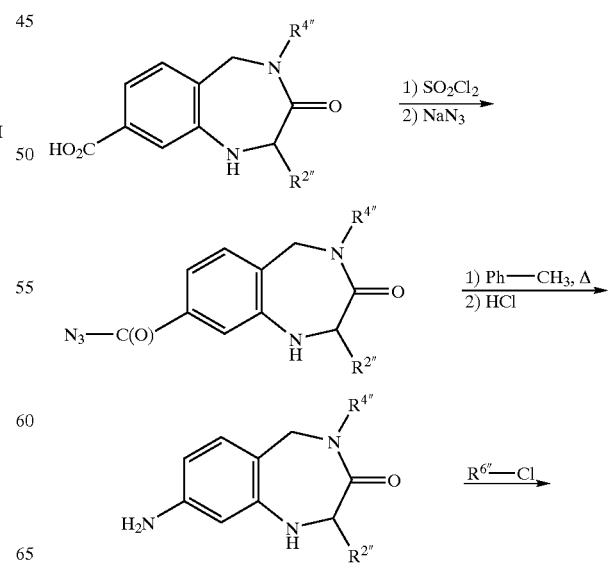

Scheme 7
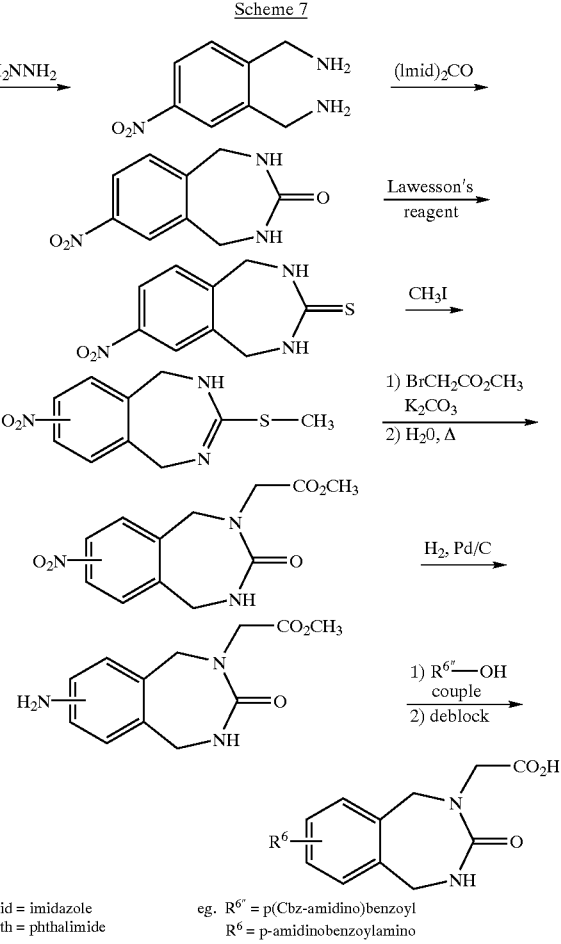
lmid = imidazole
Phth = phthalimide
eg. R6" = p(Cbz-amidino)benzoyl
R6 = p-amidinobenzoylamino
Scheme 6
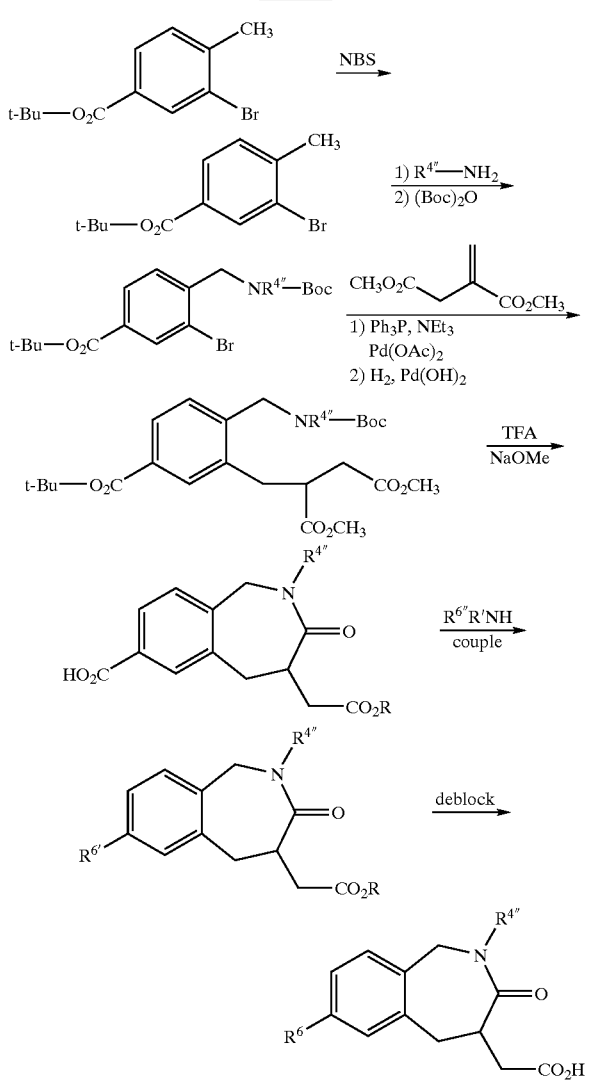
eq. R2" = CH2CO2CH3
R2 = CH2CO2H
R6" = p-(Cbz-amidino)benzoyl
R6 = p-amidino-benzoylamino
eg. R4" = (CH2)2Ph
R6" = p-(Cbz-amidino)anilino
R6 = p-amidinophenylaminocarbonyl
NBS = N-bromosuccinimide
Scheme 8
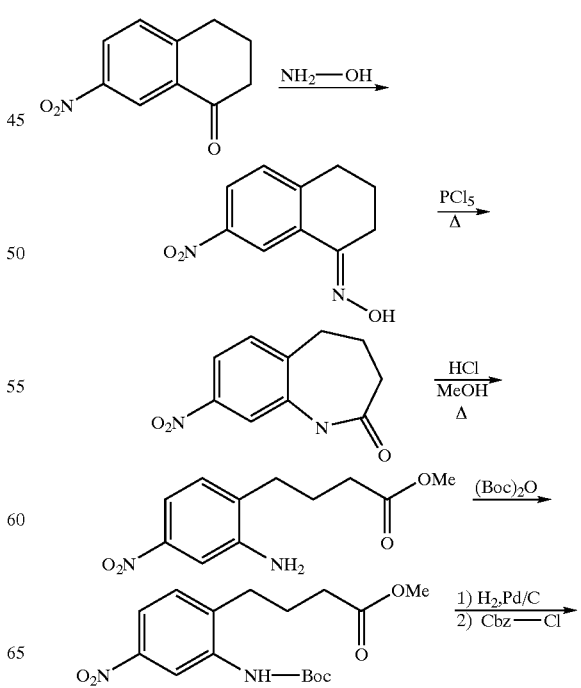

17
-continued
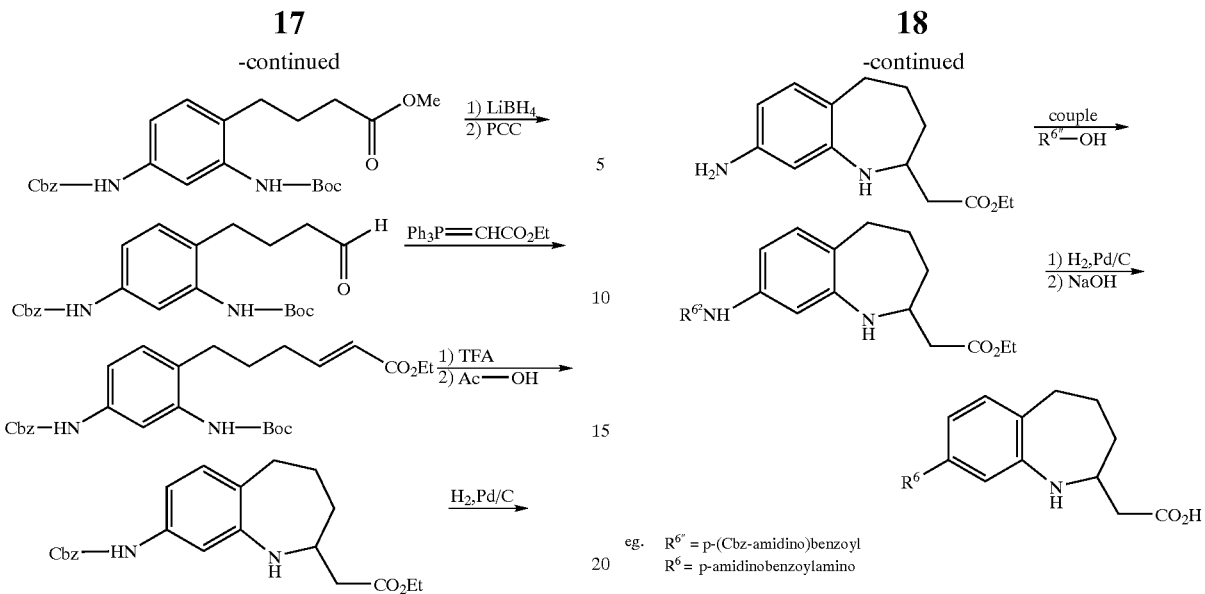
18
-continued
eg. $R^{6''}$ = p-(Cbz-amidino)benzoyl
$R^6$ = p-amidinobenzoylamino
Scheme 9
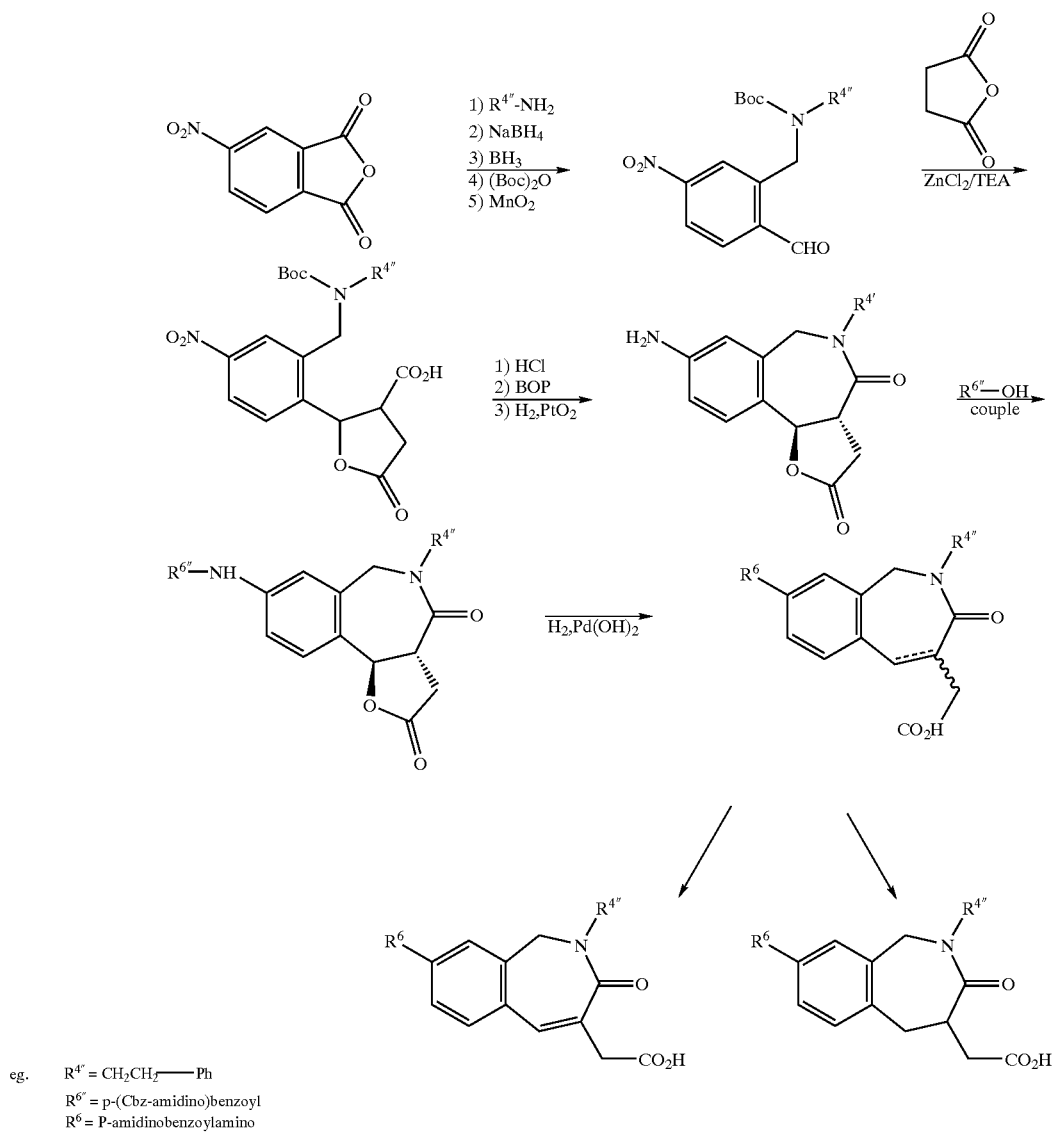
eg. $R^{4''}$ = CH$_2$CH$_2$—Ph
$R^{6''}$ = p-(Cbz-amidino)benzoyl
$R^6$ = P-amidinobenzoylamino

Scheme 10

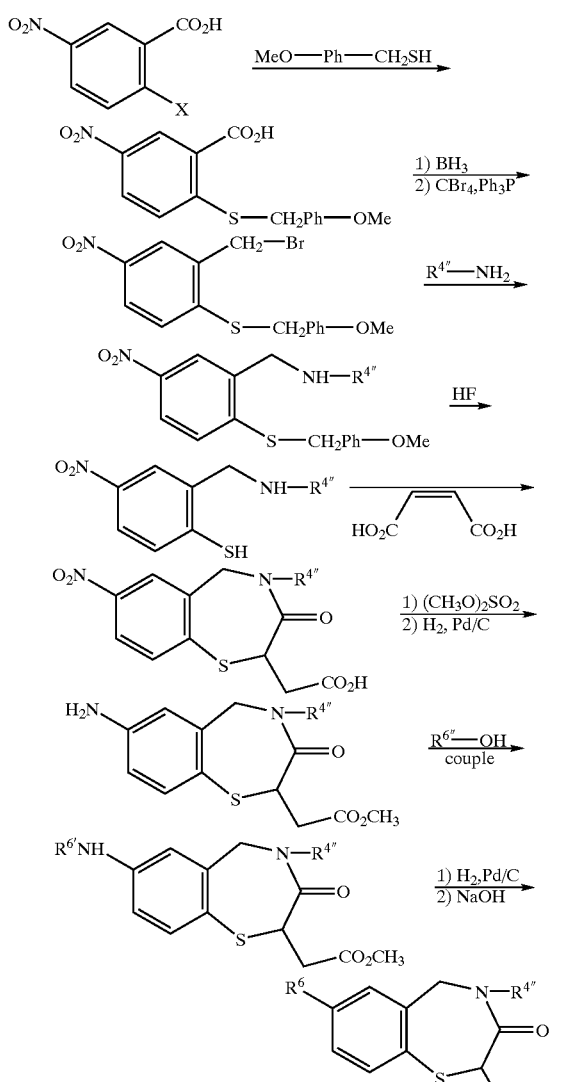

eg. R<sup>4"</sup> = CH₂CH₂Ph
R<sup>6"</sup> = p-(Cbz-amidino)benzoyl
R<sup>6</sup> = p-amidiniobenzoylamino A particularly useful intermediate is the 1,4-benzodiazepine compound of formula (XI), wherein $A^1$ is $NR^1$, $A^4$ is $NR^4$; $L^1$ is CHO, $CO_2R'$, Br, I, OH, $CF_3SO_3$, $CH_2$—T or NR'R", and T is OH, NHR", Cl, Br or I. In particular, compounds wherein $R^1$ is H, $C_{1-4}$alkyl, $C_{1-4}$oxoalkyl; $R^2$ is $CH_2CO_2R'$ and $R^4$ is Q—$C_{1-6}$alkyl are useful. More particularly, compounds wherein $R^4$ is H, $C_{1-4}$alkyl or phenyl$C_{1-4}$alkyl are useful. Other useful intermediates are similarly substituted benzazepine compounds of formula (XI), where $A^1$ is $CHR^1$ and $A^4$ is $NR^4$.

Coupling reagents as used herein denote reagents which may be used to form peptide bonds. Typical coupling methods employ carbodiimides, activated anhydrides and esters and acyl halides. Reagents such as EDC, DCC, DPPA, PPA, BOP reagent, HOBt, N-hydroxysuccinimide and oxalyl chloride are typical.

Coupling methods to form peptide bonds are generally well known to the art The methods of peptide synthesis generally set forth by Bodansky et al., The Practive of Peptide Synthesis, Springer-Verlag, Berlin, 1984, Ali et al. in J. Med. Chem., 29, 984 (1986) and J. Med. Chem., 30, 2291 (1987) are generally illustrative of the technique and are incorporated herein by reference.

Solution synthesis for the formation of amide or peptide bonds is accomplished using conventional methods used to form amide bonds. Typically, the amine or aniline is coupled via its free amino group to an appropriate carboxylic acis substrate using a suitable carbodiimide coupling agent, such as N,N' dicyclohexyl carbodiimide (DCC), optionally in the presence of catalysts such as 1-hydroxybenzotriazole (HOBt) and dimethylamino pyridine (DMAP). Other methods, such as the formation of activated esters, anhydrides or acid halides, of the free carboxyl of a suitably protected acid substrate, and subsequent reaction with the free amine of a suitably protected amine, optionally in the presence of a base, are also suitable. For example, a protected Boc-amino acid or Cbz-amidino benzoic acid is treated in an anhydrous solvent, such as methylene chloride or tetrahydrofuran(THF), in the presence of a base, such as N-methyl morpholine, DMAP or a trialkylamine, with isobutyl chloroformate to form the "activated anhydride", which is subsequently reacted with the free amine of a second protected amino acid or aniline.

Compounds of formula (XII) are prepared by conventional methods known in the art from commercially available materials. W is a generally a basic functional group attached to Z, optionally via an alkyl chain, and is protected during the synthesis of $R^6$ or is introduced into the molecule after the —$(CR'R^{10})_r$—U—$(CR'_2)_s$—V— linkage has been formed. For example, compounds of formula (XII) or formula (I) wherein W is a suitably substituted R'R"N—, R"R'NC(=NR'), R'$_2$N(R$^{13}$)C=N—, R"N=(R$^{13}$)C—NR'—, R'$_2$N(R'$_2$N)C=N— or R"R'N(R'N=)C—NR', are prepared by conventional methods including those disclosed in EP-A 0 372 486, EP-A 0 381 033 or EP-A 0 478 363, which are incorporated herein by reference.

Compounds of formula (XII) wherein W is ⓝ are prepared, inter alia, by methods disclosed in EP-A 0 478 363.

Compounds wherein W is R'$_2$N(R'$_2$N)C=N—X— or R"R'N(R'N=)C—NR'—X—, and X is O are prepared, inter alia, by methods disclosed in J. Org. Chem., 51, 5047 (1986).

Compounds wherein W is R'$_2$N(R'$_2$N)C=N—X— or R"R'N(R'N=)C—NR'—X—, and X is N=CR', are prepared, inter alia, by methods disclosed in U.S. Pat. No. 3,714,253 and Eur. J. Med. Chem.-Chim. Ther., 20, 25 (1985).

Compounds wherein W is R'$_2$N(R'$_2$N)C=N—X— or R"R'N(R'N=)C—NR'—X—, and X is C(O), are prepared, inter alia, by methods disclosed in U.S. Pat. No. 3,714,253 and Can. J. Chem., 43, 3103 (1965).

Compounds wherein W is R'ONR'C(=NR')— may be prepared, inter alia, by methods disclosed in J. Het. Chem., 16, 1063 (1979) or J. Het. Chem., 26, 125 (1989).

Compounds wherein W is R'$_2$NR'NC(=NR')— are prepared by conventional methods including those disclosed in Synthesis, 583 (1974).

Compounds wherein W is R'R"NR'N— are prepared, inter alia, by methods disclosed in J. Prakt. Chem., 36, 29 (1967).

Compounds wherein W is R'R"NR'NCO— are prepared, inter alia, by methods disclosed in Bull. Chem. Soc. Jpn., 43, 2257 (1970).

Compounds wherein W is R"R'NC(=NR')Y, and Y is S, are prepared, inter alia, by methods disclosed in Chem. Lett., 1379 (1986).

Compounds of formula (XII) or formula (I), wherein W is R"R'NC(=NR')Y and Y is O, are prepared by conventional methods including those disclosed in Japanese Patent 2022751.

Useful intermediates of formula (XII) include compounds of the formula W'—(CR'$_2$)$_q$—Z—(CR'R$^{10}$)$_r$—U—(CR'$_2$)$_s$—L$^2$, wherein Z, R', R", R$^{10}$, U, q, r, and s are as defined for formula (I); L$^2$ is CHO, CO$_2$R', C≡C—H, OH, Cl, Br, I, CH$_2$—T or NR'R", and T is CF$_3$SO$_3$, OH, NHR", Cl, Br or I; and W' is W with any reactive basic nitrogen group protected as herein described by R$^P$, a nitrogen protecting group. R'SO$_2$, R'OCO and R'CO (e.g., Tos, Boc, Cbz or acetyl) are typical nitrogen protecting groups. Particular examples of such intermediates are:

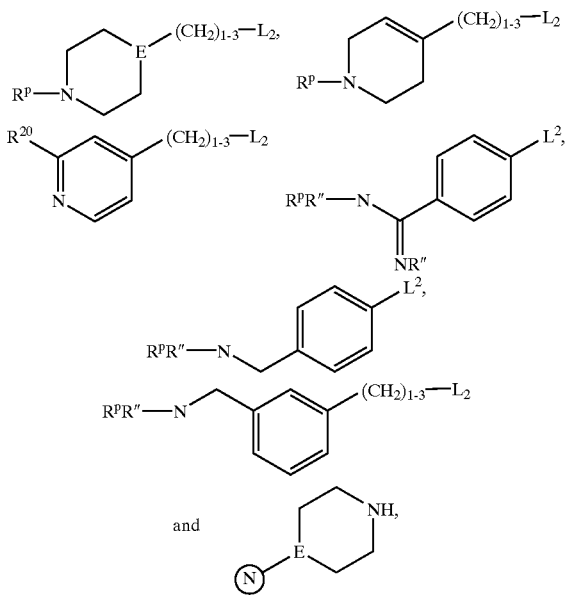

wherein E is N or CH, R$^{20}$ is hydrogen, amino, mono or di-C$_{1-4}$alkylamino, hydroxy or C$_{1-4}$alkyl.

The reactive functional groups of the sidechains of each synthetic fragment are suitably protected as known in the art. Suitable protective groups are disclosed in Greene, Protective Groups in Organic Chemistry, John Wiley and Sons, New York, 1981. For example, the Boc, Cbz, phthaloyl or Fmoc group may be used for protection of an amino or amidino group. The Boc group is generally preferred for protection of an α-amino group. A t-Bu, cHex or benzyl ester may be used for the protection of the side chain carboxyl. A benzyl group or suitably substituted benzyl group (e.g., 4-methoxy-benzyl or 2,4-dimethoxy-benzyl) is used to protect the mercapto group or the hydroxyl group. The tosyl group may be used for protection of the imidazolyl group and tosyl or nitro group for protection of the guanidino group. A suitably substituted carbobenzyloxy group or benzyl group may be also be used for the hydroxyl group or amino group. Suitable substitution of the carbobenzyloxy or benzyl protecting groups is ortho and/or para substitution with chloro, bromo, nitro or methyl, and is used to modify the reactivity of the protective group. Except for the Boc group, the protective groups for the amino moiety are, most conveniently, those which are not removed by mild acid treatment These protective groups are removed by such methods as catalytic hydrogenation, sodium in liquid ammonia or HF treatment, as known in the art.

Modification of amino groups especially on the six-membered ring of the bicyclic system, may be accomplished by alkylation, sulfonylation, cyanation or acylation as is generally known in the art.

Acid addition salts of the peptides are prepared in a standard manner in a suitable solvent from the parent compound and an excess of an acid, such as hydrochloric, hydrobromic, sulfuric, phosphoric, acetic, maleic, succinic or methanesulfonic. The acetate salt form is especially useful. Certain of the compounds form inner salts or zwitterions which may be acceptable. Cationic salts are prepared by treating the parent compound with an excess of an alkaline reagent, such as a hydroxide, carbonate or alkoxide, containing the appropriate cation; or with an appropriate organic amine. Cations such as Li+, Na+, K+, Ca++, Mg++ and NH$_4$+ are specific examples of cations present in pharmaceutically acceptable salts.

This invention provides a pharmaceutical composition which comprises a compound according to formula (I) and a pharmaceutically acceptable carrier. Accordingly, the compounds of formula (I) may be used in the manufacture of a medicament. Pharmaceutical compositions of the compounds of formula (I) prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, these peptides may be encapsulated, tableted or prepared in a emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, the peptides of this invention may also be combined with excipients such as cocoa butter, glycerin, gelatin or polyethylene glycols and molded into a suppository.

The compounds of this invention may be used in vitro to inhibit the aggregation of platelets in blood and blood products, e.g., for storage, or for ex vivo manipulations such as in diagnostic or research use.

This invention also provides a method of inhibiting platelet aggregation and clot formation in a mammal, especially a human, which comprises the internal administration of a peptide of formula (I) and a pharmaceutically acceptable carrier. Indications for such therapy include acute myocardial infarction (AMI), deep vein thrombosis, pulmonary embolism, dissecting anurysm, transient ischemia attack (TIA), stroke and other infarct-related disorders, and unstable angina. Chronic or acute states of hyperaggregability, such as disseminated intravascular coagulation (DIC), septicemia, surgical or infectious shock, postoperative and post-partum trauma, cardiopulmonary bypass surgery, incompatible blood transfusion, abruptio placenta, thrombotic thrombocytopenic purpura (TTP), snake venom and immune diseases, are likely to be responsive to such treatment. In addition, the peptides of this invention may be useful in a method for the prevention of metastatic conditions, the prevention or treatment of fungal or bacterial infection, inducing immunostimulation, treatment of sickle cell disease, and the prevention or treatment of diseases in which bone resorption is a factor.

The peptide is administered either orally or parenterally to the patient, in a manner such that the concentration of drug in the plasma is sufficient to inhibit platelet aggregation, or other such indication. The pharmaceutical composition containing the peptide is administered at a dose between about 0.2 to about 50 mg/kg in a manner consistent with the condition of the patient. For acute therapy, parenteral administration is preferred. For persistent states of hyperaggregability, an intravenous infusion of the peptide in 5% dextrose in water or normal saline is most effective, although an intramuscular bolus injection may be sufficient.

For chronic, but noncritical, states of platelet aggregability, oral administration of a capsule or tablet, or a bolus intramuscular injection is suitable. The peptide is administered one to four times daily at a level of about 0.4 to about 50 mg/kg to achieve a total daily dose of about 0.4 to about 200 mg/kg/day.

This invention further provides a method for inhibiting the reocclusion of an artery or vein following fibrinolytic therapy, which comprises internal administration of a peptide of formula (I) and a fibrinolytic agent. It has been found that administration of an peptide in fibrinolytic therapy either prevents reocclusion completely or prolongs the time to reocclusion.

When used in the context of this invention the term fibrinolytic agent is intended to mean any compound, whether a natural or synthetic product, which directly or indirectly causes the lysis of a fibrin clot. Plasminogen activators are a well known group of fibrinolytic agents. Useful plasminogen activators include, for example, anistreplase, urokinase (UK), pro-urokinase (pUK), streptokinase (SK), tissue plasminogen activator (tPA) and mutants, or variants, thereof, which retain plasminogen activator activity, such as variants which have been chemically modified or in which one or more amino acids have been added, deleted or substituted or in which one or more or functional domains have been added, deleted or altered such as by combining the active site of one plasminogen activator with the fibrin binding domain of another plasminogen activator or fibrin binding molecule. Other illustrative variants include tPA molecules in which one or more glycosylation sites have been altered. Preferred among plasminogen activators are variants of tPA in which the primary amino acid sequence has been altered in the growth factor domain so as to increase the serum half-life of the plasminogen activator. tPA Growth factor variants are disclosed, e.g., by Robinson et al., EP-A 0 297 589 and Browne et al., EP-A 0 240 334. Other variants include hybrid proteins, such as those disclosed in EP 0 028 489, EP 0 155 387 and EP 0 297 882, all of which are incorporated herein by reference. Anistreplase is a preferred hybrid protein for use in this invention. Fibrinolytic agents may be isolated from natural sources, but are commonly produced by traditional methods of genetic engineering.

Useful formulations of tPA, SK, UK and pUK are disclosed, for example, in EP-A 0 211 592, EP-A 0 092 182 and U.S. Pat. No. 4,568,543, all of which are incorporated herein by reference. Typically the fibrinolytic agent may be formulated in an aqueous, buffered, isotonic solution, such as sodium or ammonium acetate or adipate buffered at pH 3.5 to 5.5. Additional excipients such as polyvinyl pyrrolidone, gelatin, hydroxy cellulose, acacia, polyethylene, glycol, mannitol and sodium chloride may also be added. Such a composition can be lyophilized.

The pharmaceutical composition may be formulated with both the compound of formula (I) and fibrinolytic in the same container, but formulation in different containers is preferred. When both agents are provided in solution form they can be contained in an infusion/injection system for simultaneous administration or in a tandem arrangement.

Indications for such therapy include myocardial infarction, deep vein thrombosis, pulmonary embolism, stroke and other infarct-related disorders. The peptide is administered just prior to, at the same time as, or just after parenteral administration of tPA or other fibrinolytic agent. It may prove desirable to continue treatment with the peptide for a period of time well after reperfusion has been established to maximally inhibit post-therapy reocclusion. The effective dose of tPA, SK, UK or pUK may be from 0.5 to 5 mg/kg and the effective dose of the peptide may be from about 0.1 to 25 mg/kg.

For convenient administration of the inhibitor and the fibrinolytic agent at the same or different times, a kit is prepared, comprising, in a single container, such as a box, carton or other container, individual bottles, bags, vials or other containers each having an effective amount of the inhibitor for parenteral administration, as described above, and an effective amount of tPA, or other fibrinolytic agent, for parenteral administration, as described above. Such kit can comprise, for example, both pharmaceutical agents in separate containers or the same container, optionally as lyophilized plugs, and containers of solutions for reconstitution. A variation of this is to include the solution for reconstitution and the lyophilized plug in two chambers of a single container, which can be caused to admix prior to use. With such an arrangement, the fibrinolytic and the peptide may be packaged separately, as in two containers, or lyophilized together as a powder and provided in a single container.

When both agents are provided in solution form, they can be contained in an infusion/injection system for simultaneous administration or in a tandem arrangement. For example, the platelet aggregation inhibitor may be in an i.v. injectable form, or infusion bag linked in series, via tubing, to the fibrinolytic agent in a second infusion bag. Using such a system, a patient can receive an initial bolus-type injection or infusion, of the peptide inhibitor followed by an infusion of the fibrinolytic agent.

The pharmacological activity of the compounds of this invention is assessed by their ability to inhibit the binding of $^3$H-SK&F 107260, a known RGD-fibrinogen antagonist, to the GPIIbIIIa receptor, their ability to inhibit platelet aggregation, in vitro, and their ability to inhibit thrombus formation in vivo.

Inhibition of RGD-mediated GPIIb-IIIa Binding

Inhibition of RGD-mediated GPIIb-IIIa binding was demonstrated by assessing the ability of compounds to inhibit the binding of $^3$H-SK&F 107260, a known RGD-fibrinogen antagonist, to the GPIIbIIIa receptor according to the procedure disclosed in WO 93/00095 (PCT/US/92/05463).

Inhibition of Platelet Aggregation

Inhibition of platelet aggregation was demonstrated following the procedure disclosed in WO 93/00095 (PCT/US/92/05463).

The compounds of this invention inhibit the aggregation of human platelets stimulated with ADP with IC50 of about 0.001 to about 150 μM. Preferred compounds have IC50 of less than 0.1 μM.

To assess the stability of the compounds to plasma proteases, the compounds were incubated for 3 h (rather than 3 min) in the PRP prior to addition of the agonist.

In Vivo Inhibition of Platelet Aggregation

In vivo inhibition of thrombus formation is demonstrated by recording the systemic and hemodynamic effects of infusion of the peptides into anesthetized dogs according to the methods described in Aiken et al., *Prostaglandins*, 19, 629 (1980).

The examples which follow are intended to in no way limit the scope of this invention, but are provided to illustrate how to make and use the compounds of this invention. Many other embodiments will be readily apparent and available to those skilled in the art.

The examples which follow are intended to in no way limit the scope of this invention, but are provided to illustrate how to make and use the compounds of this invention. Many other embodiments will be readily apparent and available to those skilled in the art.

EXAMPLES

In the Examples, all temperatures are in degrees Centigrade. Mass spectra were performed using fast atom bombardment (FAB) or electro-spray (ES) ionization. Melting points were taken on a Thomas-Hoover capillary melting point apparatus and are uncorrected.

NMR were recorded at 250 MHz using a Bruker AM 250 spectrometer, unless otherwise indicated. Chemical shifts are reported in ppm (δ) downfield from tetramethylsilane. Multiplicities for NMR spectra are indicated as: s=singlet, d=doublet, t=triplet, q=quartet, m=multiplet, dd=doublet of doublets, dt=doublet of triplets etc. and br indicates a broad signal. J indicates the NMR coupling constant in Hertz.

Diazald® is N-methyl-N-nitroso-p-toluene sulfonamide, and is a registered trademark of the Alrich Chemical Co., Milwaukee, Wis. Celite® is filter aid composed of acid washed diatomaceous silica, and is a registered trademark of Mansville Corp., Denver, Colo. Florisil® is an activated magnesium silicate chromatographic support and is a registered trademark of Floridon Co., Pittsburgh, Pa. Analtech silica gel GF and EM silica gel thin layer plates were used for thin layer chromatography. Both flash and gravity chromatography were carried out on Merck 60 (230–400 mesh) silica gel. ODS refers to an octadecylsilyl derivatized silica gel chromatographic support AN/W-TFA indicates an isocratic eluant system of the indicated percentage of acetonitrile in water with 0.1% TFA. 5μ L Apex-ODS indicates an octadecylsilane derivatized silica gel support, having a nominal particle size of 5μ, made by Jones Chromatography, Littleton, Colo. YMC ODS-AQ® is an ODS chromatographic support and is a registered trademark of YMC Co. Ltd., Kyoto, Japan. PRP-1® is a polymeric (styrene-divinyl benzene) chromatographic support and is a registered trademark of Hamilton Co., Reno, Nev.

The following methods are illustrative of the manner of making certain useful intermediates for the preparation of the compounds of this invention.

Preparation 1

Preparation of 3-(2-pyrazinyl)propanoic acid a) t-butyl 3-(2-pyrazinyl)propionate A solution of diisopropylamine (4.0 mL, 28.5 mmol) in THF (20 mL) was treated with 2.5M n-butyllithium (11.42 mL, 28.5 mmol) at −78° C. The mixture was warmed to RT for 0.5 h, cooled to −78° C., and 2-methylpyrazine (2.0 mL, 21.9 mmol) was added. The reaction mixture was warmed to RT, stirred for 1 h, cooled to −78° C., and butyl bromoacetate (4.25 mL, 26.3 mmol) was added. The reaction mixture was warmed to RT, stirred for 18 h and quenched with water (1 mL). The mixture was concentrated and the residue was purified by flash chromatography (silica gel, 60% ethyl acetate/hexane) to give the title compound (3.06 g, 67%) as a light yellow oil. MS(ES) m/e 209 [M+H]$^+$; $^1$H NMR (250 MHz) δ8.37–8.57 (m, 3H), 3.10 (t, 2H), 2.74 (t, 2H), 1.43 (s, 9H).

b) 3-(2-pyrazinyl)propanoic Acid

The compound of Preparation 1(a) (0.26 g, 1.2 mmol) was treated with TFA (3 mL) for 30 min and the mixture was concentrated to yield the title compound (0.18 g, 98%) as a light yellow oil. $^1$H NMR (90 MHz) δ8.41–8.56 (m, 3H), 3.24 (t, 2H), 2.77 (t, 2H).

Preparation 2

Preparation of 3-(4-pyridyl)propanamine a) N-[3-(4-pyridyl)propyl]phthalimide

Diethyl azodicarboxylate (4.4 g, 25.4 mmol) was dissolved in dry THF and added dropwise to a solution of 3-(4-pyridyl)propanol (3.18 g, 23.18 mmol), triphenylphosphine (12.3 g, 46.9 mmol) and phthalimide (3.6 g, 24.5 mmol) in dry THF (50 mL). The mixture was stirred at RT for 3.5 h, concentrated and the residue taken up in ether and filtered. The filter cake was taken up in hexane/ethyl acetate/chloroform (40:30:30) and flash chromatographed (silica gel, 30:35:35 hexane:ethyl acetate:chloroform) (3 L) to yield the title compound (3.3 g, 54%). $^1$H NMR (90 MHz, CDCl$_3$) δ8.44 (m, 2H), 7.71 (m, 4H), 7.13 (d, 2H), 3.70 (t, 2H), 2.65 (t, 2H), 2.05 (m, 2H)

b) 3-(4pyridyl)propanamine

The compound of Preparation 2(a) (2.1 g, 7.7 mmol) was dissolved in ethanol, treated with anhydrous hydrazine (0.3 mL, 9.5 mmol), stirred overnight and concentrated. The residue was treated with hydrazine in ethanol overnight, concentrated and the residue taken up in chloroform, filtered and concentrated to give the title compound (1.1 g, quant).

hu 1H NMR (90 MHz, CDCl$_3$) δ8.45 (d, 2H), 7.77 (t, 1H), 7.40 (m, 2H), 7.12 (d, 2H), 3.38 (q, 2H), 2.60(t, 2H), 1.86 (m, 2H).

Preparation 3

Preparation of 5-(benzyloxycarbonylamino) pentanamine

To a suspension of 1,5-diaminopentane dihydrochloride (2.9 g, 16.7 mmol) in THF (100 mL) was added 20% aqueous sodium hydroxide (10.0 g, 50 mmol) at 0° C. A solution of benzyl chloroformate (1.7 g, 10 mmol) in THF (10 mL) was added rapidly dropwise and the resulting mixture stirred at RT. After 1 h, the organic layer was separated and concentrated to give a residue which was dissolved in ethyl acetate (200 mL). This solution was extracted with water (3×50 mL.), dried (sodium sulfate) and concentrated. The residue was redissolved in ether (50 mL) and 1.0 ethereal hydrogen chloride (3.0 mL) was added. The resulting precipitate was filtered, suspended in $CH_2Cl_2$ (75 mL) and shaken with 5% sodium hydroxide (15 mL). The organic layer was washed with water (75 mL), dried (sodium sulfate) and concentrated to give the title compound 0.25 g, 30%): $^1$H NMR (400 MHz, $CDCl_3$) δ7.15–7.4 (m, 5H), 5.15–5.4 (m, 1H), 5.05 (s, 2H), 3.05–3.2 (m, 2H), 2.55–2.7 (m, 2H), 1.2–1.5 (m, 6H).

Preparation 4

Preparation of 4-[N-(t-butoxycarbonyl-N-(propyl)-aminomethyl]aniline a) 4-[N-(t-butoxycarbonyl-N-(propyl)aminomethyl]-1-nitrobenzene A solution of N-(propyl)aminomethyl-1-nitrobenzene (1.8 g, 9.27 mmol), triethylamine (1.41 g, 13.9 mmol) and di-t-butyl dicarbonate (2.8 g, 13 mmol) in THF (60 mL) was stirred for 1 h at RT, concentrated and the residue stirred in water (100 mL) for 1 h. The aqueous phase was decanted and the residue dissolved in ethyl acetate (300 mL). The solution was extracted with water (3×100 mL) and brine (100 mL), dried (sodium sulfate) and concentrated to yield the title compound (2.65 g, 95%). $^1$H NMR (400 MHz, $CDCl_3$) δ8.2 (d, 2H), 7.4 (d, 2H), 4.5 (m, 2H), 3.15 (d, 2H), 1.3–1.6 (m, 9H), 0.9 (t, 3H).

b) 4-[N-(t-butoxycarbonyl)-N-(propyl)aminomethyl] aniline

A solution of the compound of Preparation 4(a) (2.7 g, 9.2 mmol) in ethanol (100 mL) containing 10% palladium on carbon (0.4 g) was hydrogenated at 40 psi. After 30 min, the mixture was filtered and concentrated to give the title compound (2.4 g., 100%).

$^1$H NMR (400 MHz, $CDCl_3$) δ7.0–7.3 (m, 3H), 6.6 (d, 1H), 4.3 (m, 2H), 3.6 (br, 2H), 3.1 (m, 2H), 1.4–1.6 (m, 9H), 0.9 (t, 3H).

Preparation 5

Preparation of 3-[N-(t-butoxycarbonyl) aminomethyl]-benzylamine; and 4-[N-(t-butoxycarbonyl)aminomethyl]benzylamine The title compounds were prepared using the general procedure of *J. Med. Chem.*, 32, 391 (1989).

Preparation 6

Preparation of 3-[4-[N-(t-butoxycarbonyl)piperi-dinyl]]propanamine a) 3-[4-[N-(t-butoxycarbonyl)piperidinyl]]propanol 3-(4-Pyridyl)propanol (10.40 g, 75.8 mmol) was dissolved in glacial acetic acid, platinum oxide (1 g) was added and the mixture was shaken was hydrogenated (50 psi) for 6 h. The mixture was filtered through Celite®, concentrated and concentrated twice from toluene. The residue was dried under reduced pressure, dissolved in $CH_2Cl_2$ (150 mL) and treated with triethylamine (10.2 g, 100.7 mmol) and then with di-t-butyl dicarbonate (18.0 g, 82.5 mmol). The reaction was stirred for 2 h, concentrated and the residue was taken up in ethyl actate and washed sequentially with water, 1N hydrochloric acid (2×), water and 1N sodium bicarbonate (2×). The organic phase was dried (magnesium sulfate), filtered and concentrated and the residue was purified by flash chromatography (silica gel, chloroform; 5:95 methanol:chloroform) to give the title compound (12.87 g, 68.7%): TLC $R_f$ 0.78 (silica 9:1 chloroform:methanol); $^1$H NMR (400 MHz, $CDCl_3$) δ4.08 (m, 2H), 3.65 (t, 2H), 2.64 (t, 2H), 1.80–0.90 (m), 1.43 (s, 9H).

b) N-[3-[4-[N-(t-butoxycarbonyl)piperidinyl]] propyl]-phthalimide

The compound of Preparation 6(a) (2.0 g, 8.22 mmol) was dissolved in dry THF (100 mL) with phthalimide (1.52 g, 10.34 mmol) and triphenylphosphine (2.22 g, 8.46 mmol). Diethyl azidodicarboxylate (1.65 g; 9.53 mmol) was dissolved in dry THF and slowly added to the alcohol reaction mixture. The reaction was left stirring at room temperature for 3 days. The solvents were evaporated under vacuum. The residue was taken up in hexane:ethyl acetate (9:1) and flash chromatographed (silica gel, 10%; 20% ethyl acetate/ hexane) to yield the title compound (2.0 g, 60.6%). $^1$H NMR (90 MHz, $CDCl_3$) δ8.05–7.65 (m, 4H), 4.40 (br. d., 2H), 3.72 (t, 2H), 2.78 (t, 2H), 1.0–2.0 (m), 1.50 (s., 9H)

c) 3-[4-[N-(t-butoxycarbonyl)piperidinyl]] propanamine

The compound of Preparation 6(b) (2.0 g, 5.42 mmol) was dissolved in ethanol (50 mL). Anhydrous hydrazine (excess) was added and the solution was stirred overnight, concentrated and the residue taken into chloroform and filtered. The filtrate was concentrated to yield the title compound (863.5 mg, 65.7%). $^1$H NMR (250 MHz, $CDCl_3$) δ4.05 (br. d., 2H), 3.00 (t, 2H), 2.66 (t, 2H), 2.2–0.90 (m), 1.45 (s, 9H); TLC Rf 0.63 (3:1:1 n-BuOH:HOAc:water).

Preparation 7

Preparation of 2-[1-[4-(benzyloxycarbonyl) piperazinyl]]-ethanamine; and 2-[1-[4-(benzyloxycarbonyl)piperazinyl]]-N-methyl-ethanamine a) 2-[1-[4(benzyloxycarbonyl)piperazinyl]] ethanamine 2-(1-Piperazinyl)ethylamine was protected according to the general procedure of *Tet. Lett.*, 27, 4391 (1986). A solution of t-butylchlorodiphenylsilane (7.8 mL, 30 mmol) in acetonitrile (10 mL) was added dropwise to a solution of 2-(1-piperazinyl)ethylamine (4.0 mL, 31 mmol) and triethylamine (6.3 mL, 45 mmol) in acetonitrile (20 mL) stirred at 10° C. The mixture was stirred 2 h at RT, cooled to 10° C. and treated with triethylamine (6.3 mL, 45 mmol) and a solution of benzyl chloroformate (4.3 mL, 30 mmol) in $CH_2Cl_2$ (10 mL). The mixture was stirred at RT for 2 h, filtered and concentrated. The residue was stirred in 80% acetic acid (100 mL) overnight, poured into brine and washed with ethyl acetate. The aqueous phase was basified with saturated sodium carbonate, extracted with ethyl acetate and the organic phase was dried (magnesium sulfate), filtered and concentrated to give the title compound (1.1 g, 14%). $^1$NMR (400 MHz, $CDCl_3$) δ2.43 (6H, m), 2.80 (2H, m), 3.52 (4H, m), 5.14 (2H, s), 7.38 (5H, s).

b) 2-[1-[4-(benzyloxycarbonyl)piperazinyl]]-N-methyl-ethanamine

Formic acid (0.5 mL, 12.2 mmol) was added dropwise via syringe to acetic anhydride (1.0 mL, 9.8 mmol) at 10° C. The mixture was stirred for 10 min and heated to 50° C. for 2 h. The mixture was cooled to RT, anhydrous THF (10 mL) was added followed by the compound of Preparation 7(a) (1.0 g, 3.8 mmol) dissolved in THF. The mixture was stirred for 2.5 h at RT, concentrated and the residue was dissolved in THF (25 mL) and cooled to 10° C. 1.0M Boron methyl sulfide (1 mL, 10 mmol) dissolved in THF (10 mL) was added dropwise at 10° C. The mixture was stirred until gas evolution ceased and was heated to reflux for 2 h. The mixture was cooled, treated carefully with saturated methanolic hydrogen chloride (20 mL) and heated to reflux for 1 h. The mixture was concentrated to yield the title compound (400 mg, 40%). MS(ES) m/e 278.0 [M+H]$^+$; $^1$NMR (400 MHz, CDCl$_3$) δ2.68–3.92 (15H, m), 5.15(2H, s), 7.37 (5H, s)

Preparation 8

Preparation of 6-(t-butoxycarbonylamino) hexylamine

A solution of 1,6-diaminohexane (14 g, 0.12 mol) in ethanol (500 mL) was mixed with a solution of di-t-butyl carbonate (23 g, 0.1 mol) in ethanol (500 mL) and stirred overnight. The mixture was filtered, concentrated and the residue was shaken with a mixture of ether (200 mL) and water (50 mL). The aqueous phase was extracted twice with ether (50 mL) and the organic phase was extracted sequentially with brine, cold 0.4N hydrochloric acid (150 mL) and water (2×100 mL). The pH of the acidic extract was brought to 12–13 with 1N sodium hydroxide and it was extracted twice with ether (50 mL). The organic phase was washed with brine, dried (sodium sulfate) and concentrated to yield the title compound (13.16 g, 49%). TLC Rf 0.53 (Kieselgel 60 F$_{254}$, 15:3:2 2-butanol:formic acid:water); MS(ES) m/e 217.0; $^1$NMR (400 MHz, CDCl$_3$): δ4.57 (br s, 1H), 3.10–3.12 (m 2H), 2.68–2.71 (m 2H), 1.84 (br s 2H), 1.44–1.48 (br s 9H), 1.32–1.34 (br s 8H).

Preparation 9

Preparation of 4-(t-butoxycarbonylamino) butylamine

Using the procedure of Preparation 8, except substituting 1,4-diaminobutane for 1,6-diaminohexane, gave the title compound (2.5 g, 26%): TLC Rf 0.39 (Kieselgel 60 F$_{254}$, 15:3:2 2-butanol:formic acid:water); MS(ES) m/e 189.0.

Preparation 10

Preparation of 2-(2-pyrazinyl)ethanamine a) 2-[N-(benzyloxycarbonylamino)]ethyl-(2-pyrazine)

A mixture of the compound of Preparation 1(b) (0.49 g, 3.24 mmol), triethylamine (1.02 g, 10.1 mmol) and diphenyl phosphorylazide (1.28 g, 4.5 mmol) in toluene (20 mL) was heated at 105° C. for 0.5 h. The temperature was lowered and the reaction was treated with benzyl alcohol (1.11 g, 10.14 mmol) at 80° C. for 14 h. The mixture was concentrated and the residue was purified by flash chromatagraphy (silica gel, 60% ethyl acetate/hexane) to give the title compound (0.40 g, 48%) of protected amine as a light yellow oil: MS(ES) 258 [M+H]$^+$; $^1$H NMR (250 MHz) δ8.35–8.70 (m, 3H), 7.07–7.51 (m, 5H), 5.42 (b, 1H), 5.11 (s, 2H), 3.62 (t, 2H), 2.99 (t, 2H).

b) 2-(2-pyrazinyl)ethanamine

The compound of Preparation 10(a) (0.15 g, 0.58 mmol) was dissolved in methanol (10 mL) and palladium on carbon (5%, 50 mg) was added. The mixture was hydrogenated for 1 h, filtered through Celite® and concentrated to yield the tide compound (69 mg, 96%) as a light yellow oil.

Preparation 11

Preparation of (S)-4-[N-[N-(t-butoxycarbonyl) alanyl]-aminomethyl]aniline a) (S)-4-[N-[N-(t-butoxycarbonyl)alanyl] aminomethyl]-1-(nitro)benzene A solution of 4-nitrobenzylamine hydrochloride (1.89 g, 10.0 mmol) in DMF (20 mL) was neutralized with 4-methylmorpholine and treated with a solution of N-t-Boc-L-alanine N-hydroxysuccinimide ester (2.86 g, 10.0 mmol) in DMF (14 mL) at RT. The mixture was kept at RT for 72 h, concentrated and the resulting solid was redissolved in ethyl acetate and washed sequentially with water, 1N hydrochloric acid and brine, dried (magnesium sulfate) and concentrated to give the title compound (2.37 g, 73%) as an oil. TLC R$_f$ 0.74 (5:95 methanol:ethyl acetate); $^1$H NMR (CDCl$_3$) δ1.41 (d, J=11.2 Hz, 3H), 1.46 (s, 9H), 4.22 (m, 1H), 4.56 (m, 2H), 4.94 (br s, 1H), 6.90 (br s, 1H), 7.43 (d, J=12.8 Hz, 2H), 8.18 (d, J=12.8 Hz, 2H).

b) (S)-4-[N-[N-(t-butoxycarbonyl)alanyl] aminomethyl]-aniline

A mixture of the compound of Preparation 11(a) (2.37 g, 7.3 mmol), 10% palladium on carbon (0.24 g, 0.23 mmol), and methanol (125 mL) was stirred at RT under H$_2$ (1 atm) for 6.5 h, filtered and the filtrate was concentrated to give the title compound (2.02 g, 98%) as an oil. TLC R$_f$ 0.68 (5% methanol/ethyl acetate); $^1$H NMR (CDCl$_3$) δ1.33 (d, J=7.10 Hz, 3H), 1.39 (s, 9H), 4.12 (m, 1H), 4.27 (d, J=5.0 Hz, 2H), 5.05 (br s, 1H), 6.38 (br s, 1H), 6.60 (d, J=8.3 Hz, 2H), 7.01 (d, J=8.3 Hz, 2H).

Preparation 12

Preparation of 4-[(t-butoxycarbonyl)aminomethyl]-3-chlorobenzoic acid a) methyl 4-(phthalimidomethyl)-3-chlorobenzoate A mixture of methyl 4-bromomethyl-3-chlorobenzoate 10 g, 38 mmol) and potassium phthalimide (9.85 g, 53 mmol) in dimethylformamide (65 mL) was stirred and heated to 85° C. for 2 h. The hot mixture was poured into ice water and the resulting solid was filtered, washed sequentially with water, ethanol and a small amount of ether and dried to give the title compound.

b) 4-(aminomethyl)-3-chlorobenzoic acid

A mixture of the compound of Preparation 12(a) (4.0 g, 12.2 mmol) and hydrazine (1.25 g, 25 mmol) in methanol (55 mL) was heated to reflux for 1 h, concentrated and the residue was treated with concentrated hydrochloric acid (25 mL). The mixture was heated to reflux for 1 h, cooled to 0° C., and filtered. The filtrate was concentrated and the residue was diluted with water and adjusted to pH 7 with 2N sodium hydroxide. The resulting precipitate was filtered and dried to yield the tide compound.

c) 4-[(t-butoxycarbonyl)aminomethyl]-3-chlorobenzoic acid

A mixture of the compound of Preparation 12(b) (1.8 g, 8.2 mmol), di-t-butyl carbonate (2.1 g, 9.8 mmol) and triethylamine (2.3 mL, 16.4 mmol) in dimethylformamide (15 mL) was stirred for 4 h, concentrated and the residue was distributed between 5% aqueous citric acid and ethyl acetate. The organic phase was washed with 5% aqueous citric acid, dried (magnesium sulfate) and concentrated to give the title compound.

Preparation 13

Preparation of 2-(amino)pyridine-4-ethanamine dihydrochloride a) methyl 2-(acetamido)pyridine4carboxylate To 2-(acetamido)pyridine-4-carboxylic acid (25 g, 139 mmol) was added a saturated solution of anhydrous hydrogen chloride in methanol (600 mL). The cloudy suspension was stirred for 16 h at RT and refluxed for 24 h. The resulting solution was concentrated, dissolved in chloroform, washed with saturated sodium bicarbonate, brine, dried (magnesium sulfate) and concentrated to give the title compound as a white solid (17.86 g, 84%). TLC $R_f$ 0.55 (5% methanol/chloroform); $^1$H NMR (CDCl$_3$) δ3.96 (3H, s), 4.80 (2H, s), 7.12 (1H, J=5 Hz, d), 7.19 (1H, s), 8.10 (1H, d, J=5 Hz).

b) 2-(amino)pyridine-4-methanol

To the compound of Preparation 13(a) (15.14 g, 100 mmol) in dry THF (300 mL) was added dropwise, with stirring at 0° C. under argon, a solution of 1N lithium aluminum hydride in THF (200 mL, 200 mmol) over 1 h. After the addition, the ice bath was removed and the reaction was stirred at RT for 1 h. The reaction was cooled to 0° C. and carefully quenched with ethyl acetate (50 mL) followed by water (8 mL), 15% sodium hydroxide (8 mL) and water (22 mL). After 15 min, the resulting suspension was filtered and the filter was rinsed thoroughly with a solution of 20% methanol/chloroform (200 mL). The filtrate was concentrated and the residue was purified by flash chromatography (silica gel, 10% methanol/chloroform) to obtain the title compound (9.60 g, 77%) as a white solid. TLC $R_f$ 0.17 (5% methanol/chloroform). $^1$H NMR (CD$_3$OD) δ4.55 (2H, s), 4.88 (3H, s), 6.62 (1H, d, J=5 Hz), 6.65 (1H, s), 7.88 (1H, d, J=5 Hz).

c) 2-amino-4-(bromomethyl)pyridine

To the compound of Preparation 13(b) (9.40 g, 76 mmol) was added 48% hydrobromic acid (75 mL). The solution was heated to 100° C. under argon for 16 h, concentrated and dried under vacuum to give the title compound as an off-white solid which was used in the next reaction without purification.

d) methyl 3-[(2-(amino)pyrid-4-yl]-2-(methoxycarbonyl)-propionate

To a stirred solution of dimethyl malonate (20 mL, 175 mmol) and sodium methoxide (25 wt % in methanol, 35 mL, 162 mmol) in dry methanol (100 mL) at 0° C. was added the compound of Preparation 13(c) (18.67 g, 70 mmol) in one portion. After 5 min, the reaction was allowed to warm to RT. The mixture was stirred for 4 h, acidified with acetic acid and concentrated. The residue was dissolved in chloroform, washed with saturated sodium bicarbonate, brine, dried (magnesium sulfate), and concentrated. The residue was purified by flash chromatography (silica gel, 3% methanol/chloroform) to give the title compound (11.00 g, 66%) as an oil which solidified under vacuum. TLC $R_f$ 0.46 (5% methanol:chloroform). $^1$H NMR (CDCl$_3$) δ3.10 (2H, d, J=8 Hz), 3.69 (1H, t), 3.73 (6H, s), 4.51 (2H, br s), 6.38 (1H, s), 6.50 (1H, d, J=5 Hz), 8.01 (1H, d, J=5 Hz).

e) 2-(amino)pyridine-4-propionic acid hydrochloride

To the compound of Preparation 13(d) (11.0 g, 46 mmol) was added concentrated hydrochloric acid (100 mL). The reaction was heated at 100° C. for 16 h and concentrated to give the title compound (9.36 g, 100%) as a white solid.

f) methyl 2-(amino)pyridine-4-propionate

To the compound of Preparation 13(e) (8.36 g, 41 mmol) was added saturated solution of anhydrous hydrogen chloride in methanol (300 mL). The mixture was stirred for 3 d at RT, concentrated, and dried under vacuum. The remaining solid was dissolved in chloroform, washed with saturated sodium carbonate, brine, dried (magnesium sulfate) and concentrated to give the title compound (7.40 g, 100%). TLC $R_f$ 0.44 (5% methanol/chloroform). $^1$H NMR (CDCl$_3$) δ2.72 (4H, m), 3.70 (3H, s), 4.69 (2H, br s), 6.38 (1H, s), 6.52 (1H, d, J=5 Hz), 8.01 (1H, d, J=5 Hz).

g) methyl 2-(acetamido)pyridine-4-propionate

To a stirred solution of the compound of Preparation 13(f) (7.40 g, 41 mmol) in THF (200 mL) was added sodium bicarbonate (4.5 g, 53.6 mmol) followed by acetic anhydride (5 mL, 53 mmol). After stirring for 16 h, the reaction was diluted with ethyl acetate, washed with saturated sodium carbonate, brine, dried (magnesium sulfate) and concentrated. The residue was purified by flash chromatography (silica gel, 3% methanol/chloroform) to yield the title compound (9.02 g, 98%. TLC $R_f$ 0.27 (60% ethyl acetate/hexane). $^1$H NMR (CDCl$_3$) δ2.22 (3H, s), 2.70 (2H, t), 3.0 (2H, t), 3.72 (3H, s), 6.98 (1H, d, J=5 Hz), 8.20 (1H, s), 8.24 (1H, d, J=5Hz), 9.88 (1H, br s).

h) 2-(acetamido)pyridine-4propionic acid

To a stirred solution of the compound of Preparation 13(g) (9.0 g, 40 mmol) in dioxane (150 mL) was added 1N sodium hydroxide (80 mL) dropwise. After stirring for 5 h, the reaction was made acidified with 1N hydrochloric acid (80 mL) and the resulting solution was concentrated to a small volume to precipitate the product, which was filtered off, rinsed with a small volume of cold water and dried under vacuum to give the title compound (7.83 g, 94%). TLC $R_f$ 0.32 (95:4:1 chloroform:methanol:acetic acid). MS(DCI/NH$_3$) m/e 209.1 [M+H]$^+$; $^1$H NMR (D$_6$-DMSO) δ2.08 (3H, s), 2.56 (2H, t), 3.36 (2H, br s), 6.97 (1H, d, J=5 Hz), 7.97 (1H, s), 8.18 (1H, d, J=5 Hz).

i) 2-[(2-(acetamido)pyrid-4-yl]-N-(methoxycarbonyl)ethanamine

To a stirred solution of the compound of Preparation 13(h) (4,75 g, 23 mmol) and triethylamine (3.8 mL, 27 mmol) in dry toluene (150 mL) was added diphenylphosphorylazide (5.7 mL, 26 mmol). The reaction was stirred at RT for 15 min, then heated to 80° C. with a reflux condenser attached, behind a safety shield. Vigorous gas evolution occurred after ~10 min. The reaction was stirred an additional 30 min, the mixture became clear and gas evolution ceased. Methanol (5 mL, 123 mmol) was added and the reaction was allowed to stir at 80° C. for an additional 4 h. The mixture was concentrated and the residue was purified by flash chromatography (silica gel, 3% methanol/chloroform) to yield the title compound (3.92 g, 72%). TLC Rf 0.42 (5% methanol/ chloroform). MS(DCI/NH$_3$) m/e 238.1 [M+H]$^+$; $^1$H NMR (CDCl$_3$) δ2.23 (3H, s), 2.82 (2H, t), 3.39 (2H, m), 3.68 (3H, s), 4.81 (2H, s), 7.02 (1H, d, J=5 Hz), 8.03 (1H, s), 8.22 (1H, d, J=5 Hz).

j) 2-(amino)pyridine-4-ethanamine

To the compound of Preparation 13(i) (3.80 g, 16 mmol) was added a solution of 6N hydrochloric acid (150 mL). The reaction was heated at 110° C. for 24 h, concentrated and dried under vacuum to give the title compound (3.37 g, 100%) as a white solid. MS(DCI) m/e 138.1 [M+H]$^+$.

Preparation 14

Preparation of 2-(hydroxy)pyridine-4-ethanamine hydrochloride a) 2-[(2-methoxy)pyrid-4-yl]-N-(methoxycarbonyl)ethanamine Using the procedure of Preparation 13(i), except substituting 2-(methoxy)pyridine-4-propionic acid for the compound of Preparation 13(h), gave the title compound. TLC R$_f$ 0.24 (30% ethyl acetate/hexane). MS(DCI/NH$_3$) m/e 211.1 [M+H]$^+$; $^1$H NMR (CDCl$_3$) δ2.80 (2H, t), 3.49 (2H, m), 3.72 (3H, s), 3.96 (3H, s), 4.82 (1H, br s), 6.66 (1H, s), 6.79 (1H, d, J=5 Hz), 8.17 (1H, d, J=5 Hz).

b) 2-(hydroxy)pryridine-4-ethanamine hydrochloride

Using the procedure of Preparation 13(j), except substituting the compound of Preparation 14(a) for the compound of Preparation 13(i), gave the title compound. MS(DCI/NH$_3$) m/e 139.1 [M+H]$^+$.

Preparation 15

Preparation of 4-[(t-butoxycarbonyl)(aminomethyl)]phenol 4-(Aminomethyl)phenol [*J. Med. Chem.*, 26, 808–813, 1983] was dissolved in dichloromethane (5 mL) and treated with 1N sodium hydroxide (4 mL) at 0° C. followed by di-t-butyl dicarbonate (610 mg, 2.8 mmol). The solution was allowed to warm to RT, stirred for 4 h and concentrated. The residue was purified by flash chromatography (silica gel, 2% methanol/chloroform) to give the title compound (440 mg). $^1$H NMR (250 MHz) δ7.06 (d, 2H), 6.78 (d, 2H), 4.95 (bs, 1H), 4.20–4.18 (m, 2H), 1.45 (s, 9H).

Preparation 16

Preparation of 4-[2-[N-(t-butoxycarbonyl)aminoethyl]]piperidine a) 4-[[2-(t-butoxycarbonyl)amino]ethyl]pyridine A solution of pyridine-4-ethanamine (1.54 g, 12.6 mmol) in dichloromethane (15 mL) was treated at 0 C. with di-t-butyl dicarbonate (2.75 g, 12.6 mmol) and triethylamine (1.76 mL, 12.6 mmol), and stirred at RT for 3 d. The mixture was diluted with chloroform, washed with 5% sodium carbonate, dried (magnesium sulfate) and concentrated. The residue was purified by flash chromatography (silica gel, 80% ethyl acetate/hexane) to give the tide compound 1.01 g (36%). $^1$H NMR (90 MHz, CDCl$_3$) δ8.53 (d, 2H, J=4.5 Hz), 7.17 (d, 2H, J=4.5 Hz), 5.77 (br s, 1H), 3.40 (d of t, 2H, J=6.0, 7.5 Hz), 2.83 (t, 2H, J=7.5 Hz), 1.45 (s, 9H).

b) 4-[2-[N-(t-butoxycarbonyl)aminoethyl]]piperdine

A mixture of the compound of Preparation 16(a) (1.01 g, 4.54 mmol) and platinum oxide (150 mg) in ethanol was shaken under hydrogen at RT for 4 h. Additional 1N hydrochloric acid (4 mL) and platinum oxide (100 mg) was added and the reaction mixture shaken with hydrogen at RT for 1 h and then allowed to sit at neutral pH (adjusted with 5% sodium carbonate) under argon for 18 h. The catalyst was removed by filtration through Celite® and the filtrate was concentrated. The residue was concentrated twice from methanol:toluene, taken into chloroform, filtered and concentrated to give the tide compound which was used without purification.

Preparation 17

Preparation of N-methyl-2-(1-methyl-1,2,5,6-tetrahydropyrid-4-yl)ethanamine, dihydrochloride a) N-(t-butoxycarbonyl)-N-methyl-2-(1-methyl-pyrid-4-yl)ethanamine A mixture of N-methyl-2-(pyrid-4-yl)ethanamine (4.1 g, 30 mmol), di-t-butyl dicarbonate (26.2 g, 120 mmol) and triethylamine (15.2 g, 150 mmol) in dichloromethane (100 mL) was stirred for 16 h, concentrated, and the residue was diluted with water and extracted with dichloromethane. The organic phase was washed, dried (magnesium sulfate) and concentrated. The residue was chromatographed (silica gel, 5% methanol:dichloromethane) to give the title compound (4 g, 56%).

b) N-(t-butoxycarbonyl)-N-methyl-2-(1-methyl-4-pyridinium)ethanamine iodide

A mixture of the compound of Preparation 17(a) (2 g, 10 mmol) and iodomethane (21.2 g, 150 mmol) in acetonitrile (30 mL) was heated to reflux for 2 h. The mixture was concentrated and the residue was dissolved in dichloromethane, decolorized with charcoal, filtered and the filtrate was concentrated. The residue was treated with ether to give the title compound (3.0 g, 79%) as a yellow solid. MS(ES) m/e 251 [M−I]$^+$.

c) N-(t-butoxycarbonyl)-N-methyl-2-(1-methyl-1,2,5,6-tetrahydropyrid-4-yl)ethanamine, dihydrochloride The compound of Preparation 17(b), 0.95 g, 25 mmol) was dissolved in methanol (30 mL), treated with sodium borohydride (0.38 g, 10 mmol) and stirred for 2 h. The mixture was concentrated, dissolved in water and extracted with dichloromethane. The organic phase was dried (magnesium sulfate), concentrated and the residue was treated with 4N hydrogen chloride in dioxane (5 mL) overnight. The mixture was concentrated and the residue was azeotroped with toluene. The resulting solid was triturated with ether to give the tide compound (0.5 g, 89%).

Preparation 18

Preparation of 3-[N-(t-butoxycarbonyl)piperidin-4-yl]propionaldehyde

To a stirred solution of oxalyl chloride (2 mL, 22 mmol) in dry dichloromethane (50 mL) at −78° C. under argon, was added dropwise a solution of dimethylsulfoxide (3.4 mL, 44 mmol) in dichloromethane (10 mL). After 2 min, a solution of 3-[N-(t-butoxycarbonyl)piperidin-4-yl]propanol (4.86 g, 20 mmol) in dichloromethane (10 mL) was added dropwise over 5 min. After stirring an additional 15 min at −78° C., triethylamine (14 mL) was added dropwise. After 5 min, the reaction became a thick white slurry and was allowed to warm to RT and stirred for 16 h. The reaction mixture was washed with cold 1N hydrochloric acid and with brine, dried (magnesium sulfate) and concentrated. The residue was purified by flash chromatography (silica gel, 30% ethyl acetate/hexane) to yield the title compound (4.18 g, 87%). TLC $R_f$ 0.40 (30% ethyl acetate/hexane); $^1$H NMR (CDCl$_3$) δ0.95–1.80 (7H, m), 1.48 (9H, s), 2.40–2.90 (4H, m), 4.14 (2H, br dt), 9.88 (1H, t).

Preparation 19

Preparation of 4-[N-(t-butoxycarbonyl) aminomethyl]benzaldehyde a) 4-[N-(t-butoxycarbonyl)aminomethyl]benzyl alcohol To a stirred solution of 4-[N-(t-butoxycarbonyl)-aminomethyl]benzoic acid (16.5 g, 65 mmol) and triethylamine (10 mL, 71 mmol) in dry THF (500 mL) at 0° C. was added ethyl chloroformate (7.5 mL, 78 mmol) dropwise. After stirring for 15 min, sodium borohydride (6 g, 159 mmol) was added in one portion and the reaction was allowed to warm to RT and stirred for 16 h. The reaction was cooled in an ice bath and carefully quenched with 1N hydrochloric acid, extracted with ethyl acetate, and the organic phase was washed with brine, dried (magnesium sulfate), and concentrated. The residue was purified by flash chromatography (silica gel, 20% ethyl acetate:chloroform) to give the title compound (10.07 g, 65%) as a white solid. TLC $R_f$ 0.31 (20% ethyl acetate:chloroform); $^1$H NMR (CDCl$_3$) δ1.46 (9H, s), 3.28 (1H, br s), 4.27 (2H, d, J=6 Hz), 4.65 (2H, s), 5.04 (1H, br s), 7.30 (4H, dd).

b) 4-[N-(t-butoxycarbonyl)aminomethyl] benzaldehyde

To a solution of the compound of Example 19(a) (4.0 g, 16.9 mmol) in dry dichloromethane (50 mL) was added manganese dioxide (10 g, 115 mmol). The mixture was stirred and refluxed for 16 h and filtered hot through a pad of Celite® which was rinsed with dichloromethane. The filtrate was concentrated to give the title compound (3.55 g, 89%) as a white solid. TLC $R_f$ 0.45 (5% methanol/ chloroform); $^1$H NMR (CDCl$_3$) δ1.49 (9H, s), 4.43 (2H, d, J=6 Hz), 5.15 (1H, br s), 7.51 (2H, d, J=8 Hz), 7.92 (2H, d, J=8 Hz), 10.10 (1H, s).

Preparation 20

Preparation of 2-[2-(amino)pyrid-4-yl]-N-methyl-ethanamine a) 2-[2-(amino)pyrid-4-yl]-N-formyl-N-methyl-ethanamine To a stirred solution of the compound of Preparation 13(j) (1.5 g, 7.1 mmol) in 1N sodium hydroxide (14.3 mL), water (15 mL) and THF (30 mL) was added dropwise a solution of 4-nitrophenyl formate (1.3 g, 7.8 mmol) in THF (15 mL). After stirring for 16 h, the reaction was concentrated and the residue was purified by flash chromatography (silica gel, 15:85:0.1 methanol/chloroform:ammonium hydroxide) to give the tide compound (1.14 g, 96%) as a slightly yellowish solid. TLC $R_f$ 0.32 (90:10:0.1, chloroform:methanol:ammo-nium hydroxide); $^1$H NMR (CDCl$_3$) δ2.77 (2H, t), 3.57 (2H, dt), 4.84 (2H, br s), 6.47 (1H, s), 6.57 (1H, d, J=6 Hz), 6.94 (1H, br s), 8.0 (1H, d, J=6 Hz), 8.21 (1H, s).

b) 2-[2-(amino)pyrid-4-yl]-N-methyl-ethanamine

To a stirred solution of the compound of Preparation 20(a) (0.5 g, 3 mmol) in dry THF (30 mL) was added dropwise, at 0° C. under argon, a solution of 1N lithium aluminum hydride in THF (20 mL, 20 mmol). The reaction was allowed to warm to RT and was heated to reflux for 16 h. After cooling to 0° C., the reaction was carefully quenched with ethyl acetate (2 mL), water (0.8 mL), 15% sodium hydroxide (0.8 mL) and water (2.3 mL). The resulting suspension was stirred for 15 min, filtered through Celite®, and the filtrate was concentrated. The residue was purified by flash chromatography (silica gel, 75:25:0.1 chloroform-:methanol:ammonium hydroxide) to afford the tide compound (0.30 g, 66%). TLC $R_f$ 0.16 (80:20:0.1, chloroform-:methanol:ammonium hydroxide); $^1$H NMR (CDCl$_3$) δ2.45 (3H, s), 2.82 (4H, dt), 4.95 (3H, br s), 6.53 (1H, s), 6.57 (1H, d, J=6 Hz), 7.87 (1H, d, J=6 Hz).

Preparation 21

Preparation of 4-[N-(t-butoxycarbonyl)piperazin-1-yl]but-1-yne

A mixture of butyn-1-yl-4-tosylate (0.4 g, 1.7 mmol), N-(t-butoxycarbonyl)piperazine (0.28 g, 1.5 mmol) and sodium bicarbonate (0.15 g, 1.7 mmol) in dimethylforma-mide (7 mL) was stirred and heated to 80° C. The mixture was concentrated and the residue was partitioned between dichloromethane and water. The organic phase was washed with brine, dried (magnesium sulfate) and concentrated to give the title compound (0.38 g) as an oil: $^1$H NMR (400 MHz, CDCl$_3$) δ3.45 (m, 4H), 2.60 (t, 2H), 2.42 (m, 4H), 2.38 (t, 2H), 1.99 (s, 1H), 1.98 (s, 9H).

Preparation 22

Preparation of N-(t-butoxycarbonyl)-4,4'-bipiperdine 4,4'-Bipiperidine dihydrochloride (2.5 g, 10 mmol) was dissolved in water (10 mL) and treated with 5N sodium hydroxide to pH 8–9, diluted to 120 mL with ethanol and stirred at RT. The resulting mixture was treated with di-t-butyl dicarbonate (2.4 g, 11 mmol) in ethanol (80 mL) in one portion and the mixture stirred at RT, with periodic additions of 5N sodium hydroxide to maintain a pH of 8–9. After 5 h, the mixture was concentrated and the residue was dissolved in a mixture of 1:1 ether water (100 mL) and the pH adjusted to 12 with 5N sodium hydroxide. The aqueous phase was extracted with ether and the organic phase was washed sequentially with brine, dilute citric acid, and water. The aqueous phase was adjusted to pH 12–13 with 5N sodium hydroxide and extracted with ether. The organic phase was washed with brine, dried (sodium sulfate), concentrated to a clear oil and dried in vacuo to give the title compound (1.7 g, 63%) as a solid. TLC $R_f$ 0.4 (Kieselgel 60 $F_{254}$, 15:3:2 2-butanol:formic acid:water); MS (ES) m/e 268.3 [M+H]$^+$.

Preparation 23

Preparation of (RS)-7-[[[4-(aminoiminomethyl) phenyl]-carbonyl]-amino]-1-methyl-3-oxo-4-(2-phenylethyl)-1,3,4,5-tetrahydro-2H-1,4-benzodiazepine-2-acetic acid a) β-benzyl (RS)-N-methyl-aspartate The title compound was prepared according to the procedure of Benoiton, L., *Can. J. Chem.*, 40, 570 (1962).

Sulphuric acid (3.5 mL) was added to anhydrous diethyl ether (35 mL), followed by benzyl alcohol (35 mL). The ether was removed under vacuum and finely ground (RS)-N-methyl-aspartic acid (5 g, 34 mmol) was added, in portions, while the mixture was magnetically stirred. After 24 h, ethanol (70 mL) was added, followed by dropwise addition of pyridine (17 mL). The mixture was cooled overnight, and filtered to give the title compound (6.6 g, 82%). Mp 219–220° C.

b) (RS)-β-benzyl N-Boc-N-methyl-aspartate

β-benzyl (RS)-N-methyl-aspartate (6.6 g, 27.8 mmol), triethylamine (3.9 mL), and di-t-butyl-dicarbonate (6.1 g, 27.8 mmol) were suspended in DMF (45 mL). Upon dissolution the reaction mixture was treated with cold $KHSO_4$ solution, extracted with EtOAc, dried over $MgSO_4$, and evaporated to give the tide compound (6.8 g, 72%). MS m/e 338 $[M+H]^+$.

c) 2-fluoro-5-nitro-[N-(2-phenylethyl)]-benzylamine

2-Fluoro-5-nitro-benzaldehyde (11.9 g, 70 mmol) and 2-phenylethylamine (13 mL, 0.1 mol) were dissolved in methanol (150 mL) and glacial acetic acid (15 mL). The solution was cooled to 0° C., and sodium cyanoborohydride (6.6 g, 0.1 mol) was added portionwise. The reaction was adjusted to pH 6 with acetic acid and stirred at room temperature for 24 h. The reaction mixture was quenched with ice and diluted with water. The pH was adjusted to 11 with sodium hydroxide and the mixture was extracted with EtOAc. The organic extracts were washed with cold dilute HCl solution and a solid precipitated. Filtration yielded the title compound (15.6 g, 82%). Mp 235–6° C.; MS m/e 275 $[M+H]^+$.

d) (RS)-N-[(1,1-dimethylethoxy)carbonyl]-N-methyl-O-benzyl-aspartyl[(N'-(2-flouro-5-nitro-benzyl),N'-(2-phenylethyl)]amide A solution of the compound of Preparation 23(c) (4.0 g, 11.9 mmol) in $CH_2Cl_2$ (45 mL) was stirred at room temperature under an argon atmosphere. Triethylamine (3.0 mL) and BOP reagent (3.3 g, 11.9 mmol) were added, followed by the compound from Preparation 23(b) (6.0 g, 17.8 mmol). The reaction mixture was stirred overnight at room temperature, and poured into ice water (350 mL). The mixture was extracted with ethyl acetate. The combined organic extracts were washed with 1 M $KHSO_4$, water, 5% $NaHCO_3$ and brine, and dried over $MgSO_4$. Filtration of the mixture, evaporation of the filtrate, and flash chromatography yielded the title compound (2.0 g, 29%). MS m/e 594.2 $[M+H]^+$.

e) (RS)-N-methyl-O-benzyl-aspartyl[(N'-(2-flouro-5-nitro-benzyl),N'-(2-phenylethyl)]amide The compound of Preparation 23(d) (2.0 g, 3.4 mmol) was stirred with 4M HCl/dioxane (9 mL) for 18 h. Evaporation of the solvents in vacuo yielded the title compound.

f) benzyl 1-methyl-7-nitro-3-oxo-4-(2-phenylethyl)-1,3,4,5-tetrahydro-2H-1,4-benzodiazepine-2-acetate To a solution of the compound of Preparation 23(e) (2.0 g, 3.4 mmol) in DMSO (50 mL), triethylamine (2.4 mL) was added. The reaction mixture was stirred overnight, poured into water and extracted with ethyl acetate. The combined organic phases were washed with brine and dried over sodium sulfate. Filtration and concentration of the organic extracts in vacuo yielded the title compound (1.6 g, 98%). MS m/e 474.2 $[M+H]^+$.

g) benzyl 7-amino-1-methyl-3-oxo-4-(2-phenylethyl)-1,3,4,5-tetrahydro-2H-1,4-benzodiazepine-2-acetate A solution of the compound of Preparation 23(f) (1.6 g, 3.38 mmol) in ethyl acetate (100 mL) and platinum oxide catalyst (0.6 g) was shaken on a Parr shaker under hydrogen (40 psi) for 24 h. The catalyst was filtered from the solution and the solvent was evaporated in vacuo to yield the tide compound (1.5 g, 98%). MS m/e 444.2 $[M+H]^+$.

h) benzyl 7-[[[4-(benzyloxycarbonyl-aminoiminomethyl)phenyl]-carbonyl]amino]-1-methyl-3-oxo-4-(2-phenylethyl)-1,3,4,5-tetrahydro-2H-1,4-benzodiazepine-2-acetate A mixture of the compound of Preparation 23(g) (1.5 g, 3.4 mmol), p-(benzyloxycarbonylamidino)benzoic acid (1.01 g, 3.4 mmol), BOP reagent (1.5 g, 3.4 mmol), and triethylamine (1.0 mL) in DMF (12 mL) was stirred overnight under an argon atmosphere. The solution was poured into a mixture of ice water (160 mL) and 5% $NaHCO_3$ (14 mL), and the resulting precipitate was filtered. The filtered solid was dissolved in $CH_2Cl_2$, dried over sodium sulfate, filtered, and the filtrate was concentrated in vacuo to a solid (3.2 g). This material was chromatographed (silica gel, 65% EtOAc/hexane) to yield the title compound (1.5 g, 61%). MS m/e 724 $[M+H]^+$.

i) 7-[[[4-(aminoiminomethyl)phenyl]-carbonyl]amino]-1-methyl-3-oxo-4-(2-phenylethyl)-1,3,4,5-tetrahydro-2H-1,4-benzodiazepine-2-acetic acid benzyl ester, and 7-[[[4-(aminoiminomethyl)phenyl]-carbonyl]amino]-1-methyl-3-oxo-4-(2-phenylethyl)-1,3,4,5-tetrahydro-2H-1,4-benzodiazepine-2-acetic acid To a solution of the compound of Preparation 23(h) (1.5 g, 2.1 mmol) in 1:1 glacial acetic acid:ethyl acetate (30 mL) and concentrated hydrochloric acid (0.5 mL), 10% palladium on carbon catalyst (1.3 g, activated) was added. The mixture was hydrogenated in a Parr shaker (45 psi) for 6 h. The reaction mixture was filtered, the filtrate was evaporated and a portion (0.36 g) of the resulting residue was purified on HPLC (silica gel-ODS, 32% $CH_3CN/H_2O$-0.1% TFA) to yield the tide benzyl ester and acid. For benzyl ester: Anal. ($C_{35}H_{35}N_5O_4 \cdot TFA \cdot H_2O$) calcd: C, 61.58; H, 5.31; N, 9.70. found: C, 61.52; H, 5.00; N, 9.45. For the acid: ESMS m/e 590 $[M+H]^+$.

Preparation 24

Preparation of (R,S)-8-[[[4-(aminoiminomethyl)phenyl]amino]-carbonyl]-1,2,4,5-tetrahydro-3-oxo-4-(2N-phenylethyl)-3H-1,4-benzodiazepine-2-acetic acid, dihydrochloride a) t-butyl 3-nitro-4-[N-(2-phenylethyl)aminomethyl]benzoate, and t-butyl 3-nitro-4-[N-(t-butoxycarbonyl)-N-(2-phenylethyl)aminomethyl]benzoate A solution of t-butyl 4-bromomethyl-3-nitrobenzoate [prepared by the method in *Int. J. Peptide Res.*, 36, 31 (1990)] (1.6 g, 0.005 mol) in $CH_2Cl_2$ (10 mL) was added dropwise, over 15 min, to a solution of phenethylamine (1.89 g, 0.015 mol) in CH$_2$Cl$_2$ (50 mL). The mixture was stirred at room temperature under argon for 24 h and concentrated in vacuo. The residue was dissolved in THF (50 mL) and treated with a solution of triethylamine (2.5 g, 0.025 mol) and di-t-butyl dicarbonate (4.4 g, 0.02 mol) in THF (50 mL). The resulting mixture was stirred overnight at room temperature under argon and concentrated in vacuo. The residue was dissolved in ethyl acetate, washed with water and dried with sodium sulfate. The organic phase was concentrated in vacuo and the residue was triturated with ethyl acetate:hexane (15:85) to yield the title compound (0.87 g, 37%). Mp 110–113° C.

The filtrate was chromatographed (silica gel, ethyl acetate:hexane 15:85) to yield additional compound (0.5 g, 21%). Mp 113–115° C.

b) t-butyl 3-amino-4-[N-(t-butoxycarbonyl)-N-(2-phenylethyl)aminomethyl]benzoate A mixture of the compound of Preparation 24(a) (1.3 g, 0.0028 mol), ethanol (125 mL) and 10% Pd/C (0.32 g) was shaken under a hydrogen atmosphere (40 psi) for 50 min. The mixture was filtered and the filtrate was concentrated in vacuo to give the tide compound. Mp 105–106° C.

c) t-butyl (E/Z)-3-[2-(1,4-dimethoxy-1,4-dioxo-2-butenyl)amino]-4-[N-(t-butoxycarbonyl)-N-(2-phenylethyl)aminomethyl]benzoate A solution of the compound of Preparation 24(b) (1.15 g, 0.0027 mol) in methanol (50 mL) was treated with dimethyl acetylenedicarboxylate (0.45 g, 0.0032 mol) and the resulting solution was heated to reflux under argon for 1 h. The mixture was concentrated in vacuo and the residue was chromatographed (silica gel, ethyl acetate:hexane 20:80) to give the title compound (1.3 g, 85%).

d) t-butyl (R,S)-3-[2-(1,4-dimethoxy-1,4-dioxo-2-butyl)-amino]-4-[N-(t-butoxycarbonyl)-N-(2-phenylethyl)aminomethyl]-benzoate A solution of the compound of Preparation 24(c) (1.3 g, 0.0023 mol) in methanol (100 mL) containing 10% Pd/C (0.38 g) was shaken in a hydrogen atmosphere (40 psi) for 4.5 h. The mixture was filtered and the filtrate concentrated in vacuo to yield the title compound.

e) methyl (R,S)-8-carboxy-1,2,4,5-tetrahydro-3-oxo-4-(2-phenylethyl)-3H-1,4-benzodiazepine-2-acetate A solution of the compound of Preparation 24(d) (1.3 g, 0.003 mol) in CH$_2$Cl$_2$ (50 mL) and TFA (50 mL) was kept at room temperature under argon overnight. The mixture was concentrated in vacuo to give a residue containing crude (R,S)-3-[2-(1,4-dimethoxy-1,4-dioxo-2-butyl)amino]-4-[N-(2-phenylethyl)aminomethyl]benzoic acid. The residue was dissolved in anhydrous methanol (70 mL), treated with methanolic sodium methoxide (1.6 mL, 0.007 mol) and heated to reflux for 8 h. The mixture was kept at room temperature for 14 h, treated with 1N HCl in diethyl ether (7.5 mL), concentrated in vacuo, treated with methanol (3×20 mL) and concentrated in vacuo. The residue was dissolved in methanol:CH$_2$Cl$_2$:acetic acid (10:90:0.4, 15 mL), filtered and chromatographed (silica gel, methanol:CH$_2$Cl$_2$:acetic acid 10:90:0.4) to give the title compound (0.66 g, 70%).

The solid was dissolved in CH$_2$Cl$_2$ (30 mL) and treated with 1N HCl in diethyl ether (3 mL) to give methyl (R,S)-8-carboxy-1,2,4,5-tetrahydro-3-oxo-4-(2-phenylethyl)-3H-1,4-benzodiazepine-2-acetate hydrochloride.

f) methyl (R,S)-8-chlorocarbonyl-1,2,4,5-tetrahydro-3-oxo-4-(2-phenylethyl)-3H-1,4-benzodiazepine-2-acetate, hydrochloride A mixture of the hydrochloride salt of the compound of Preparation 24(e) (0.2 g, 0.5 mmol) and thionyl chloride (6 mL) was heated to reflux under argon for 15 min. The mixture was concentrated in vacuo, treated with CH$_2$Cl$_2$ (3×20 mL) and concentrated in vacuo to give methyl (R,S)-8-chlorocarbonyl-1,2,4,5-tetrahydro-3oxo-4-(2-phenylethyl)-3H-1,4-benzodiazepine-2-acetate hydrochloride as a yellow solid.

g) methyl (R,S)-8-[[[4-[N-(benzyloxycarbonyl)-aminoiminomethyl]phenyl]amino]carbonyl]-1,2,4,5-tetrahydro-3-oxo-4-(2-phenylethyl)-3H-1,4-benzodiazepine-2-acetate A solution of 4-[N-(benzyloxycarbonyl)-aminoiminomethyl]aniline (0.13 g, 0.5 mmol) and diisopropylethylamine (0.062 g, 0.5 mmol) in CH$_2$Cl$_2$ (25 mL) was added a solution of the compound of Preparation 24(f) in CH$_2$Cl$_2$ (5 mL). The mixture was kept at room temperature for 20 h, treated with diisopropylethylamine (0.15 g) and washed with water. The organic phase was dried with sodium sulfate and concentrated in vacuo. The residue was purified by preparative TLC (silica gel, methanol:CH$_2$Cl$_2$ 5:95) and eluted with methanol-CH$_2$Cl$_2$-diisopropylethylamine to the title compound (0.14 g, 46%). MS(ES) m/e 634 [M+H]$^+$. Anal.(C$_{36}$H$_{35}$N$_5$O$_6$.HCl.2.5H$_2$O) clacd: C, 60.45; H, 5.78; N, 9.79. found C, 60.51; H, 5.58; N, 9.84.

h) methyl (R,S)-8-[[[4-(aminoiminomethyl)phenyl]amino]-carbonyl]-1,2,4,5-tetrahydro-3-oxo-4-(2-phenylethyl)-3H-1,4-benzodiazepine-2-acetate A solution of the compound of Preparation 24(g) (0.13 g, 0.2 mmol) and 10% Pd/C (0.1 g) in methanol (50 mL) and 1N HCl in diethyl ether (1.0 mL) was shaken under a hydrogen atmosphere (30 psi) at room temperature for 30 min. The mixture was filtered and the filtrate concentrated in vacuo to yield the title compound. 1H NMR (CD$_3$OD, 400 MHz) d 8.0 (d, 2H), 7,8 (d, 2H), 7.0–7.25 (m, 8H), 5.5 (d, 1H), 5.15 (m, 1H), 3.9 (d, 1H), 3.75 (m, 1H), 3.7 (s, 3H), 3.65 (m, 1H), 2.95 (dd, 1H), 2.75 (t, 2H), 2.65 (dd, 1H); MS(ES) m/e 500.2 [M+H]$^+$.

i) (R,S)-8-[[[4-(aminoiminomethyl)phenyl]amino] carbonyl]-1,2,4,5-tetrahydro-3-oxo-4-(2-phenylethyl)-3H-1,4-benzodiazepine-2-acetate, dihydrochloride A solution of the compound of Preparation 24(h) (0.1 g, 0.175 mmol) in a mixture of methanol (20 mL), water (2 mL) and 1N NaOH (1 mL) was stirred at room temperature for 19 h. The mixture was acidified to pH 1 with 3N HCl, concentrated in vacuo and purified by HPLC-RT 21.19 min (YMC ODS-AQ®, 50×250 mm, 1.5 mL/min, 33% AN/W-TFA, UV detection at 220 nm). Fractions containing product were pooled and lypophylized, redissolved in water (70 mL), 6N HCl (2 mL) and acetonitrile, and lyophylized to yield the title compound (0.37 g, 40%). MS(EI) m/e 486 [M+H]$^+$.

Preparation 25

Preparation of (R,S)-8-[[[4-(aminoiminomethyl) phenyl]-methylamino]carbonyl]-1,2,4,5-tetrahydro-3-oxo-4-(2-phenylethyl)-1H-1,4-benzodiazepine-2-acetic acid a) 4-(aminomethyl)benzonitrile A solution of 4-aminobenzonitrile (5.91 g, 50 mmol) and THF (0.19 mL, 2.5 mmol) in dry, distilled triethylorthoformate (100 mL) was heated to reflux under argon. After 0.5 h at reflux, the yellow solution was concentrated to dryness in vacuo to leave a yellow oil which crystallized on drying in high vacuum. The solid was dissolved in absolute EtOH (100 mL), cooled to 0° C. under argon, and $NaBH_4$ (5.86 g, 150 mmol) was added. The mixture was allowed to warm to room temperature over 0.5 h and heated to reflux. After 1 h, the thick mixture was concentrated vacuo, and the residue was partitioned between $H_2O$ (100 mL) and $Et_2O$ (100 mL). The layers were separated, and the aqueous layer was extracted with $Et_2O$. The combined organic layers were dried ($MgSO_4$) and concentrated to a yellow solid. The solid was purified by chromatography (silica gel, 30% EtOAc/hexane) to yield the tide compound as a faintly yellow solid (6.10 g, 92%). TLC $R_f$ 0.45 (silica gel, 30% EtOAc/hexane); $^1$H NMR (250 MHz, $CDCl_3$) δ7.43 (d, 2H), 6.55 (d, 2H), 4.39 (br s, 1H), 2.88 (s, 3H); IR ($CHCl_3$) 3460, 2220, 1610, 1528, 1337, 1176, 823 $cm^{-1}$; MS(ES) m/e 133.0 $[M+H]^+$.

b) 4-aminomethyl-(N-t-benzyloxycarbonyl) benzamidine

A solution of trimethylaluminum in toluene (2.0M, 51 mL, 102 mmol) was added over 4 to a suspension of powdered $NH_4Cl$ (5.46 g, 102 mmol) in dry toluene (51 mL) in a flame-dried flask at 0° C. under argon. The ice bath was then removed and the reaction was allowed to stir at room temperature until gas evolution ceased (1 h). The compound of Preparation 25(a) (4.49 g, 34 mmol) was added, and the reaction was warmed to 80° C. (oil bath). Gas evolution occured on warming. After 23 h at 80° C., the reaction was cooled to room temperature and poured into a stirred slurry of silica gel (170 g) in $CHCl_3$ (500 mL), causing a significantly exothermic reaction. The resulting mixture was stirred for 0.5 h, then was filtered, and the filter pad was washed with MeOH (1 L). The filtrate was concentrated to a yellow solid which was dried under high vacuum at 50–60° C. for 0.5 h. The resulting material was used without further purification.

The material was dissolved in THF (136 mL) and $H_2O$ (34 mL), and the solution was cooled to 0° C. 5N NaOH (20 mL, 100 mmol) was added dropwise, and the resulting two-phase mixture was cooled for an additional 5 min. Benzyl chloroformate (4.85 mL, 34 mmol) was added dropwise, and the reaction was stirred at 0° C. for 0.5 h. The THF was removed in vacuo and the residue was extracted with $CH_2Cl_2$, followed by EtOAc. The combined organic extracts were dried ($Na_2SO_4$) and concentrated to an off-white solid. Chromatography (silica gel, 3:2 EtOAc:hexane) gave the title compound as an off-white solid (6.50 g, 67%). For characterization purposes, a small sample was recrystallized from EtOAc/hexane. Mp 141–143° C.; TLC $R_f$ 0.49 (silica gel, 3:2 EtOAc:hexane); $^1$H NMR (400 MHz, $CDCl_3$) δ7.77 (d, 2H), 7.45 (m, 2H), 7.27–7.38 (m, 3H), 6.56 (d, 2H), 5.20 (s, 2H), 4.28 (br s, 1H), 2.88 (s, 3H); IR ($CHCl_3$) 3500, 3450, 3310, 1648, 1608, 1575, 1493, 1263, 1141 $cm^{-1}$; MS(ES) m/e 284.2 $[M+H]^+$.

c) methyl (R,S)-8-[[[4-[N-(benzyloxycarbonyl)-aminoiminomethyl]phenyl]methylamino]carbonyl]-1,2,4,5-tetrahydro-3-oxo-4-(2-phenylethyl)-3H-1,4-benzodiazepine-2-acetate The compound of Preparation 24(e) (382.4 mg, 1.0 mmol) was refluxed with $SOCl_2$ (10 mL) for 15 min, and the solution was concentrated to dryness in vacuo. The residue was dissolved in dry toluene (5 mL), reconcentrated in vacuo to remove residual $SOCl_2$, and dissolved in dry $CH_2Cl_2$ (2.5 mL). This solution was added dropwise over 5 min to a well-stirred solution of the compound of Preparation 25(b) (0.85 g, 3.0 mmol) and dry pyridine (0.40 mL, 5 mmol) in dry $CH_2Cl_2$ (30 mL) at 0° C. under argon. The resulting orangish-yellow mixture was warmed to room temperature, stirred for 1 h, diluted with EtOAc (100 mL) and washed with 5% aq. $NaHCO_3$. The solution was dried ($Na_2SO_4$), concentrated, and purified by chromatography (silica gel, 9:1 EtOAc/toluene) to yield the title compound (441.6 mg, 68%). TLC $R_f$ 0.38 (silica gel, 9:1 EtOAc:toluene); $^1$H NMR (400 MHz, $CDCl_3$) δ7.71 (d, J=8.5 Hz, 2H), 7.02–7.46 (m, 12H), 6.62 (d, J=1.4 Hz, 1H), 6.56 (d, J=7.8 Hz, 1H), 6.38 (dd, J=7.8, 1.4 Hz, 1H), 5.19 (s, 2H), 5.18 (d, J=16.8 Hz, 1H), 4.85–4.93 (m, 1H), 4.17 (d, J=5.3 Hz, 1H), 3.71 (s, 3H), 3.57–3.70 (m, 2H), 3.53 (d, J=16.8 Hz, 1H), 3.44 (s, 3H), 2.90 (dd, J=16.1, 6.9 Hz, 1H), 2.63–2.79 (m, 2H), 2.58 (dd, J=16.1, 6.3 Hz, 1H); IR ($CHCl_3$) 3160–3540 (br), 3490, 3300, 1733, 1655, 1616, 1577, 1500, 1443, 1380, 1271, 1149, 1110 $cm^{-1}$; MS(ES) m/e 648.4 $[M+H]^+$.

d) (R,S)-8-[[[4-(aminoiminomethyl)phenyl]-methylamino]-carbonyl]-1,2,4,5-tetrahydro-3-oxo-4-(2-phenylethyl)-1H-1,4-benzodiazepine-2-acetic acid A mixture containing the compound of Preparation 25(c) (556.2 mg, 0.86 mmol), 10% Pd/C (0.18 g, 0.17 mmol), TFA (0.07 mL, 0.86 mmol), ETOAc (15 mL) and MeOh (15 mL) was shaken at room temperature under $H_2$ (30 psi). After 1.5 h, the catalyst was filtered and the filtrate was concentrated to dryness. The residue was resubmitted to the hydrogenation conditions described above using fresh catalyst. After another 1.5 h, the reaction was filtered, the filter pad was washed thoroughly with EtOAc and with MeOH, and the filtrate was concentrated to dryness. The residue was dissolved in MeOH (30 mL), and 1N NaOH (3.4 mL, 3.4 mmol) was added. The yellow solution was stirred at room temperature overnight, and concentrated in vacuo. The residue was dissolved in $CH_3CN:H_2O$ (1:1, 8.6 mL) and cooled to 0° C. TFA (0.66 mL, 8.6 mmol) was added, and the resulting solution was concentrated to dryness in vacuo ($CH_3CN$ azeotrope). The residue was purified by reversed-phase flash chromatography (ODS-silica gel, 25% $CH_3CN$/$H_2O$-0.1% TFA), and lyophilized to yield the title compound as a faintly yellow powder (403.4 mg, 68%). HPLC k' 9.1 (PRP-1® column; 25% $CH_3CN-H_2O$ 0.1% TFA); $^1$H NMR (400 MHz, $CD_3OD$) δ7.67 (m, 2H) 7.37 (m, 2H), 7.06–7.25 (m, 5H), 6.74 (d, J=7.8 Hz, 1H), 6.64 (d, J=1.6 Hz, 1H), 6.40 (dd, J=7.8, 1.6 Hz, 1H), 5.33 (d, J=16.9 Hz, 1H), 5.01 (dd, J=9.0, 5.1 Hz, 1H), 3.77 (d, J=16.9 Hz, 1H), 3.53–371 (m, 2H), 3.46 (s, 3H), 2.88 (dd, J=16.7, 9.0 Hz, 1H), 2.60–2.75 (m, 2H), 2.58 (dd, J=16.7, 5.1 Hz, 1H); MS(ES) m/e 500.2 $[M+H]^+$; Anal. calcd ($C_{28}H_{29}N_5O_4$.1.5 $TFA.H_2O$): C, 54.07; H, 4.76; N, 10.17. found: C, 53.73; H, 4.94; N, 9.84.

Preparation 26

Preparation of (R,S)-8-[[[4-(aminoiminomethyl)phenyl]-carbonyl]amino]-1,2,4,5-tetrahydro-3-oxo-4-(2-phenylethyl)-3H-1,4-benzodiazepine-2-acetic acid, trifluoroacetate a) methyl (R,S)-8-azidocarbonyl-1,2,4,5-tetrahydro-3-oxo-4-(2-phenylethyl)-3H-1,4-benzodiazepine-2-acetate The compound of Preparation 24(f) (0.6 g, 1.3 mmol) was dissolved in dry acetone (6 mL) and added dropwise to a solution of sodium azide (120 mg, 1.8 mmol) in water (3 mL) stirred in an ice bath. The mixture was stirred for 1 h, diluted with water (15 mL) and extracted with ethyl acetate. The organic phase was dried over MgSO$_4$ and concentrated in vacuo to yield the title compound (0.55 g, 90%).

b) methyl (R,S)-8-amino-1,2,4,5-tetrahydro-3-oxo-4-(2-phenylethyl)-3H-1,4-benzodiazepine-2-acetate A solution of the compound of Preparation 26(a) (0.55 g, 1.1 mmol) in dry toluene (12 mL) was heated to 80° C. in an argon atmosphere for 2 h. The mixture was concentrated in vacuo to yield methyl (R,S)-8-isocyanato-1,2,4,5-tetrahydro-3-oxo-4-(2-phenylethyl)-3H-1,4-benzodiazepine-2-acetate.

The residue was stirred in 3N HCl (6 mL) and THF (10 mL) for 1 h. The mixture was concentrated in vacuo and solid sodium bicarbonate was added to pH 8. The mixture was extracted with ethyl acetate and the organic phase was dried with MgSO$_4$ and concentrated in vacuo to give methyl (R,S)-8-amino-1,2,4,5-tetrahydro3-oxo-4-(2-phenylethyl)-3H-1,4-benzodiazepine-2-acetate (0.3 g, 67%).

c) methyl (R,S)-8-[[[4-[N-(benzyloxycarbonyl)-aminoiminomethyl]phenyl]carbonyl]amino]-1,2,4,5-tetrahydro-3-oxo-4-(2-phenylethyl)-3H-1,4-benzodiazepine-2-acetate A mixture of 4-[N-(benzyloxycarbonyl)-(aminoiminomethyl)]benzoic acid (0.23 g, 1.0 mmol) and thionyl chloride (3 mL) in CH$_2$Cl$_2$ (3 mL) was heated to reflux for 10 min, concentrated in vacuo, treated with toluene and concentrated in vacuo several times to give 4-[N-(benzyloxycarbonyl)-(aminoiminomethyl)]benzoyl chloride. A solution of this acid chloride in CH$_2$Cl$_2$ (3 mL) was added dropwise to a solution of the compound of Preparation 26(b) (0.3 g, 0.9 mmol) and diisopropylethylamine (130 mg, 1.0 mmol) in dry CH$_2$Cl$_2$ (5 mL). The mixture was stirred at room temperature under argon for 5 h, diluted with CH$_2$Cl$_2$ (20 mL) and extracted with water, 3N HCl, 5% sodium bicarbonate and brine. The organic phase was dried with MgSO$_4$ and concentrated in vacuo. The residue was chromatographed (silica gel, methanol:CH$_2$Cl$_2$ 2:98) to yield the title compound (0.17 g, 32%).

d) methyl (R,S)-8-[[[4-(aminoimmomethyl)phenyl] carbonyl]-amino]-1,2,4,5-tetrahydro-3-oxo-4-(2-phenylethyl)-3H-1,4-benzodiazepine-2-acetate A solution of the compound of Preparation 26(c) (0.1 g, 0.15 mmol) and 10% Pd/C (20 mg) in methanol (40 mL) and 3N HCl (8 drops) was shaken in a hydrogen atmosphere (45 psi) for 30 min. The mixture was filtered and the filtrate concentrated in vacuo to yield the title compound (65 mg, 87%).

e) (R,S)-8-[[[4-(aminoiminomethyl)phenyl] carbonyl]amino]-1,2,4,5-tetrahydro-3-oxo-4-(2-phenylethyl)-3H-1,4-benzodiazepine-2-acetic acid A solution of the compound of Preparation 26(d) (65 mg, 0.12 mmol) in methanol (15 mL), water (2 mL) and 1N NaOH (1 mL), was stirred at room temperature under argon overnight. The mixture was treated with 3N HCI (1 mL) and concentrated in vacuo. The residue was dissolved in acetonitrile:water (33:67) and purified by HPLC RT 11.2 min (YMC ODS-AQ®, 50×250 mm, 85 mL/min, 33% AN/W-TFA, UV detection at 220 nm) to yield the title compound (26 mg, 33%). MS (EI) m/e 486 [M+H]$^+$.

The following Examples illustrate the manner of making the pharmacologically active compounds and compositions of this invention.

Example 1

Preparation of (R,S)-7-[[[4-(aminoiminomethyl) phenyl]-methylamino]carbonyl]-2,3,4,5-tetrahydro-3-oxo-2-(2-phenylethyl)-1H-2-benzazepine-4-acetic acid a) t-butyl 3-bromo-4-methylbenzoate Dimethylformamide dimethyl acetal (48 mL, 200 mmol) was added dropwise over 15 min to a suspension of 3-bromo-4-methylbenzoic acid (85%; 10.75 g, 42.5 mmol) in toluene (100 mL) at 70° C. The reaction was stirred at 70–80° C. for an additional 0.5 h, then was cooled, washed sequentially with water and 5% sodium bicarbonate, and dried (sodium sulfate). The mixture was filtered through a pad of silica gel, and the filter pad was washed with toluene. The filtrate was concentrated to afford the title compound (8.0 g, 69% ) as a yellow oil. TLC (toluene) R$_f$ 0.68; $^1$H NMR (250 MHz, CDCl$_3$) δ8.13 (d, J=1.7 Hz, 1H), 7.81 (dd, J=7.9, 1.7 Hz, 1H), 7.27 (d, J=7.9 Hz, 1H), 2.44 (3H), 1.59 (s, 9H); IR (CCl$_4$) 1715, 1368, 1297, 1255, 1170, 1123, 1115 cm$^{-1}$; MS(ES) m/e 273.0 [M+H]$^+$, 271.0 [M+H]$^+$, 214.8 (M+H−56)$^+$.

b) t-butyl 3-bromo-4-(bromomethyl)benzoate

A mixture of the compound of Example 1(a) (1.36 g, 5 mmol), N-bromosuccinimide (0.98 g, 5.5 mmol), and benzoyl peroxide (61 mg, 0.25 mmol) in carbon tetrachloride (25 mL) was heated at reflux. After 4 h, the mixture was cooled and filtered, and the filtrate was concentrated. The resulting material was used without purification. TLC R$_f$ 0.39 (5:95 ethyl acetate:hexane).

c) t-butyl 3-bromo-4-[[(2-phenylethyl)amino] methyl]-benzoate

The compound of Example 1(b) was dissolved in dry ether (25 mL), and phenethylamine (1.9 mL, 15 mmol) was added. The addition was slightly exothermic, and the reaction became cloudy. The reaction was stirred at RT overnight, then was diluted with ether (75 mL) and was washed sequentially with 5% sodium bicarbonate and brine (25 mL). Drying (magnesium sulfate), concentration, and silica gel chromatography (33% ethyl acetate/hexane) gave the title compound (1.26 g, 65%) as a pale yellow oil. TLC R$_f$ 0.42 (30:70 ethyl acetate:hexane); $^1$H NMR (250 MHz, CDCl$_3$) δ8.12 (d, J=1.5 Hz, 1H), 7.87 (dd, J=7.9, 1.5 Hz, 1H), 7.40 (d, J=7.9 Hz, 1H), 7.10–7.40 (m, 5 H), 3.90 (s, 2H), 2.70–3.00 (m, 4H), 1.59 (s, 9H); IR (CCl$_4$) 1717, 1368, 1294, 1253, 1170, 1118 cm$^{-1}$; MS(ES) m/e 390.0 [M+H]$^+$.

d) t-butyl 3-bromo-4-[[[N-(2-phenylethyl)-N-t-butoxycarbonyl]amino]methyl]benzoate Di-t-butyl dicarbonate (845 mg, 3.88 mmol) was added all at once to a solution of the compound of Example 1(c) (1.26 g, 3.23 mmol) in chloroform (16 mL) at RT. The reaction was stirred at RT for 1.5 h, then at reflux for 0.5 h. Concentration and chromatography (silica gel, 10% ethyl acetate/hexane) gave the title compound (1.57 g, 99%) as a colorless oil which solidified in vacuo. TLC R$_f$ 0.49 (10:90 ethyl acetate:hexane); $^1$H NMR (250 MHz, CDCl$_3$) Rotameric mixture, ratio ca. 1.5:1; δ8.13 (d, J=1.5 Hz, 1H), 7.88 (dd, J=8.1, 1.5 Hz, 1H), 7.05–7.40 (m, 6H), 4.30–4.60 (m, 2H), 3.30–3.55 (m, 2H), 2.74–2.93 (m, 2H), 1.20–1.80 (m, 18 H); IR (CCl$_4$) 1717, 1698, 1367, 1295, 1251, 1165, 1120 cm$^{-1}$; MS(ES) m/e 490.2 [M+H]$^+$, 436.0.

e) methyl 3-methoxycarbonyl-4-[[5-(t-butoxycarbonyl)-2-[[N-(2-phenylethyl)-N-t-(butoxycarbonyl)]amino]methyl]-phenyl]-2-butenoate and methyl 3-methoxycarbonyl-4-[[5-(t-butoxycarbonyl)-2-[[N-(2-phenylethyl)-N-t-butoxycarbonyl)]amino]methyl]phenyl]-3-butenoate A mixture of the compound of Example 1(d) (1.34 g, 2.73 mmol), dimethyl itaconate (648 mg, 4.10 mmol), palladium (II) acetate (30.7 mg, 0.14 mmol), tri-o-tolylphosphine (83.2 mg, 0.27 mmol), dry triethylamine (0.76 mL, 5.46 mmol), and dry acetonitrile (27 mL) was deoxygenated through a single evacuation/argon purge cycle, then was heated at reflux under argon. After 6 h, the reaction was cooled, and more palladium (II) acetate (30.7 mg, 0.14 mmol) and tri-o-tolylphosphine (83.2 mg, 0.27 mmol) were added. The mixture was deoxygenated through three evacuation/argon purge cycles, then was heated at reflux under argon overnight (16.5 h). The reaction was concentrated, and the residue was dissolved in ether and washed with water and brine. Drying (magnesium sulfate), concentration, and chromatography (silica gel, 15% ethyl acetate/hexane; then 40% ethyl acetate/hexane) gave the crude title compound as a yellow oil. The residue was rechromatographed (silica gel, 25% ethyl acetate/hexane)to yield the title compound (1.36 g, 88%) as a light yellow oil. This material was used without separation of the isomeric reaction products.

f) methyl 3-methoxycarbonyl-4-[5-(t-butoxycarbonyl)-2-[[[N-(2-phenylethyl)-N-t-butoxycarbonyl]amino]methyl]-phenyl]butanoate The compound of Example 1(e) (1.18 g, 2.08 mmol) was dissolved in anhydrous methanol (21 mL), and palladium (II) hydroxide on carbon (0.21 g) was added. The resulting mixture was shaken at RT under H$_2$ (47 psi) for 2 h, then was filtered through Celite®. The filtrate was concentrated and resubmitted to the same reaction conditions. After another 5.5 h, the mixture was filtered as before, and the filtrate was concentrated to afford the title compound (1.13 g, 95%) as a colorless oil.

g) methyl (R,S)-7-carboxy-2,3,4,5-tetrahydro-3-oxo-2-(2-phenylethyl)-1H-2-benzazepine-4-acetate TFA (11 mL) was added all at once to a cloudy solution of the compound of Example 1(f) (1.30 g, 2.28 mmol) in dry CH$_2$Cl$_2$ (11 mL) at 0° C. under argon. The resulting light yellow solution was warmed to RT, stirred for 2 h, and concentrated. The residue was concentrated once from 1,2-dichloroethane to remove residual TFA and give methyl 3-methoxycarbonyl-4-[5-carboxy-2-[[N-(2-phenylethyl)amino]methyl]phenyl]butanoate as a pale green oil.

The oil was dissolved in anhydrous methanol (11 mL), and the solution was cooled to 0° C. under argon. Freshly prepared 1.0 M sodium methoxide/methanol (11 mL, 11 mmol) was added and the ice bath was removed. The yellow solution was allowed to warm to RT over 5 min and heated to reflux under argon. After 3 h, the reaction was cooled in ice and quenched with glacial acetic acid (1.3 mL, 22.8 mmol). The reaction was diluted with ethyl acetate (100 mL) and washed with water. The combined aqueous layers were back-extracted with ethyl acetate, and the combined ethyl acetate layers were washed with brine, dried (magnesium sulfate), and concentrated to a pale green residue. Chromatography ((silica gel, 10% methanol/chloroform/0.1% acetic acid) gave the title compound as a yellow foam. Crystallization from methanol containing a little chloroform gave the title compound (528.2 mg, 61%) as an off-white solid. mp 214–216° C.; TLC R$_f$ 0.49 (10:90 methanol:chloroform); $^1$H NMR (400 MHz, 10% CD$_3$OD/CDCl$_3$) δ7.72–7.78 (m, 2H), 7.11–7.22 (m, 3H), 7.01–7.08 (m, 3H), 5.21 (d, J=16.8 Hz, 1H), 3.70–3.92 (m, 3H), 3.72 (s, 3H), 3.5–3.66 (m, 1H, partially obscured by water peak), 3.03 (app dd, 1H) 2.97 (dd, J=16.7, 8.7 Hz, 1H), 2.86 (dd, J=17.3, 13.6 Hz, 1H), 2.76 (t, J=7.3 Hz, 2H), 2.43 (dd, J=16.7, 5.3 Hz, 1H); MS(ES) m/e 404.0 (M+Na)$^+$, 382.4 [M+H]$^+$, 350.2 (M+H—CH$_3$OH)$^+$.

h) methyl (R,S)-7-[[[4-[N-(benzyloxycarbonyl)-aminoiminomethyl]phenyl]methylamino]carbonyl]-2,3,4,5-tetrahydro-3-oxo-2-(2-phenylethyl)-1H-2-benzazepine-4-acetate The compound of Example 1(g) (117.9 mg, 0.31 mmol) was refluxed with thionyl chloride (3 mL) for 15 min and the yellow solution was concentrated. The residue was concentrated from dry toluene (3 mL) to remove residual thionyl chloride, and the resulting material was dissolved in dry CH$_2$Cl$_2$ (0.5 mL). This solution was added dropwise over 1–2 min to a solution of 4-(methylamino)-(N-benzyloxycarbonyl)benzamidine (263 mg, 0.93 mmol) and anhydrous pynidine (0.125 mL, 1.55 mmol) in dry CH$_2$Cl$_2$ (10 mL) at 0° C. under argon. The resulting yellow mixture was warmed to RT and stirred for 0.5 h, diluted with ethyl acetate, and washed with 5% sodium bicarbonate. Drying (sodium sulfate), concentration, and chromatography (silica gel, 10% ethyl acetate/toluene) gave the title compound (174.8 mg, 87%) as a faintly yellow oil. TLC R$_f$ 0.45 (9:1 toluene:ethyl acetate). $^1$H NMR (400 MHz, CDCl$_3$) δ7.73 (app d, 2H), 7.00–7.45 (m, 13H), 6.89 (app d, 1H), 6.74 (d, J=7.8 Hz, 1H), 5.19 (s, 2H), 5.05 (d, J=16.6 Hz, 1H), 3.52–3.77 (m, 4H), 3.69 (s, 3H), 3.48 (s, 3H), 2.93 (dd, J=16.8, 8.4 Hz, 1H), 2.83 (dd, J=17.3 3.9 Hz, 1H), 2.60–2.77 (m, 3H), 2.34 (dd, J=16.8, 5.4 Hz, 1H); IR (CHCl$_3$) 3490, 3300, 1731, 1650, 1614, 1495, 1437, 1360, 1284 (shoulder), 1264, 1143 cm$^{-1}$; MS(ES) m/e 647.2 [M+H]$^+$.

i) methyl (R,S)-7-[[[4-(aminoiminomethyl)phenyl]methylamino]-carbonyl]-2,3,4,5-tetrahydro-3-oxo-2-(2-phenylethyl)-1H-2-benzazepine-4-acetate 10% Palladium on carbon (58 mg, 0.054 mmol) was added carefully to a solution of the compound of Example 1(h) (174.8 mg, 0.27 mmol) and TFA (0.021 mL, 0.27 mmol) in ethyl acetate/methanol (1:1, 9 mL), and the mixture was stirred briskly under hydrogen (balloon pressure). After 1.5 h, the mixture was filtered through Celite®, and the filter pad was washed thoroughly with ethyl acetate and methanol. Concentration gave the title compound.

j) (R,S)-7-[[[4-(aminoiminomethyl)phenyl]methylamino]-carbonyl]-2,3,4,5-tetrahydro-3-oxo-2-(2-phenylethyl)-1H-2-benzazepine-4-acetic acid The compound of Example 1(i) was dissolved in methanol (9 mL), and 1.0 N sodium hydroxide (0.81 mL, 0.81 mmol) was added. The solution was stirred at RT overnight, then was concentrated. The residue was dissolved in water/acetonitrile (3 mL), cooled to 0° C., and acidified with TFA (0.21 mL, 2.7 mmol). The faintly yellow solution was concentrated and the residue was purified by reversed-phase flash chromatography (C-18 silica gel, 25% AN/W-TFA).

Concentration and lyophilization gave the title compound (123 mg, 67%) as a colorless powder. HPLC k'=1.84 (PRP-1®, 30% AN/W-TFA); $^1$H NMR (400 MHz, CD$_3$OD) δ7.67 (app d, 2H), 7.40 (app d, 2H), 6.96–7.20 (m, 8H), 5.13 (d, J=16.8 Hz, 1H), 3.96 (d, J=16.8 Hz, 1H), 3.66–3.81 (m, 2H), 3.45–3.58 (m, 1H), 3.49 (s, 3H), 2.92 (app dd, 1H), 2.77 (dd, J=17.0, 9.1 Hz, 1H), 2.54–2.68 (m, 3H), 2.38 (dd, J=17.0, 4.8 Hz, 1H); MS(ES) m/e 499.0 [M+H]$^+$; Anal. (C$_{29}$H$_{30}$N$_4$O$_4$·1.5(CF$_3$CO$_2$H)·0.5 H$_2$O) calcd: C, 56.64; H, 4.83; N, 8.26. found: C, 56.77; H, 5.05; N, 8.35.

Example 2

Preparation of (R,S)-8-[[[4-(aminoiminomethyl) phenyl]-methylamino]carbonyl]-2,3,4,5-tetrahydro-1-methyl-3-oxo-4-(2-phenylethyl)-1H-1,4-benzodiazeopine-2-acetic acid a) t-butyl 4-[N-(t-butoxycarbonyl)-N-(phenylethyl) aminomethyl]-3-(methylamino)benzoate Formic acid (0.166 g, 3.6 mmol) was added slowly to acetic anhydride (0.36 g, 3.5 mmol) at 0°. This solution was stirred at 0° for 10 min, then at 55° C. for two hours, cooled to RT, and diluted with THF (15 mL). To this solution was added dropwise a solution of the compound of Preparation 24(b) (0.5 g, 1.17 mmol) in THF (3 mL). The solution was stirred 3 h and concentrated to give a colorless oil. The residue was redissolved in THF (20 mL), cooled to 0° C. and 2.0M borane-methyl sulfide in THF was added (0.22 g, 2.9 mmol, 1.45 mL). After gas evolution had stopped, the solution was heated at reflux 3 h, cooled to RT and methanol (5.0 mL) was added. The resulting solution was refluxed 1 h and concentrated to give the title compound (0.5 g, 98%) as a colorless oil. $^1$H NMR (400 MHz, CDCl$_3$) δ7.1–7.3 (m, 5H), 7.05 (d, 2H), 7.0 (d, 1H), 5.5 (b, 1H), 4.3 (s, 2H), 3.3 (t, 2H), 2.9 (s, 3H), 2.65 (t, 2H), 1.6 (s, 9H), 1.45 (s, 9H); TLC R$_f$0.75 (1:4 ethyl acetate:hexane).

b) t-butyl (E/Z)-4-[N-(t-butoxycarbonyl)-N-(2-phenylethyl)aminomethyl]-3-[N-[2-(1,4-dimethoxy-1,4-dioxo-2-butenyl)]-N-(methyl)amino]benzoate Dimethyl acetylenedicarboxylate (0.34 g, 2.4 mmol) was added to a solution of the compound of Example 2(a) (1.0 g, 2.7 mmol) in methanol (50 mL). The solution was heated to reflux for 1 h, treated with dimethyl acetylenedicarboxylate (0.17 g, 1.2 mmol) and heated at reflux for an additional 1 h. The mixture was cooled, filtered, concentrated and the residual yellow oil was chromatographed (silica gel, 25% ethyl acetate/hexane) to give the title compound (0.5 g, 80%). (1:1;E:Z) $^1$H NMR (400 MHz, CDCl$_3$) δ7.9 (d, 2H), 7.7 (s, 2H), 7.3–7.1 (m, 12H), 6.2 (s, 1H), 5.2 (s, 1H), 4.7 (d, 2H), 4.3 (m, 2H), 3.9 (s, 3H), 3.85 (s, 3H), 3.8 (s, 3H), 3.7 (s, 3H), 3.6–3.2 (m, 8H), 3.0 (b, 3H), 2.9 (b, 3H), 1.6 (s, 18H), 1.4 (d, 1.8H).

c) t-butyl 4-[N-(t-butoxycarbonyl)-N-(2-phenylethyl)-aminomethyl]-3-[N-[2-(1,4-dimethoxy-1,4-dioxo-2-butyl)]-N-(methyl)amino]benzoate A solution of the compound of Example 2(b) in methanol (50 mL) containing 10% Pd/carbon (0.5 g) was hydrogenated (45 psi) at RT. After 4 h, the suspension was filtered and concentrated to give a pale yellow oil. The residue was purified by chromatography (silica gel, 1:4 ethyl acetate:hexane) to give the title compound as a pale yellow oil (0.17 g, 40%) $^1$H NMR (400 MHz, CDCl$_3$) δ7.8 (s, 1H), 7.7 (d, 1H), 7.0–7.3 (m, 6H), 4.4–4.6 (m, 2H), 4.05 (m, 1H), 3.7 (s, 3H), 3.6 (s, 3H), 3.2–3.5 (m, 2H), 3.0 (dd, 1H), 2.7–2.9 (m, 3H), 2.65 (s, 3H), 1.6 (s, 9H), 1.4 (m, 9H).

d) methyl (R,S)-8-carboxy-1-methyl-2,3,4,5-tetrahydro-3-oxo-4-(phenylethyl)-1H-1,4-benzodiazepine-2-acetate TFA (50 mL) was added to a solution of the compound of Example 2(c) (0.17 g, 0.3 mmol) in CH$_2$Cl$_2$ (10 mL). The mixture was stirred for 4 h and concentrated to yield 4-[N-(2-phenylethyl)aminomethyl]-3-[N-[2-(1,4-dimethoxy-1,4-dioxo-2-butyl)]-N-(methyl)amino]-benzoate as a yellow solid.

The yellow solid was dissolved in methanol (20 mL) and treated with 25% sodium methoxide in methanol (0.2 mL, 0.87 mmol). The mixture was heated to 50° C. for 2 h, cooled and treated with 1M hydrogen chloride in ether (2 mL). The mixture was concentrated to give the title compound as a yellow solid (0.12 g, 94%). $^1$H NMR (400 MHz, CD$_3$OD) δ7.55 (s, 1H), 7.5 (d, 1H), 7.1 (m, 4H), 7.0 (m, 2H), 5.2 (d, 1H), 4,8 (m, 1H), 4.1(m, 2H), 3.7 (s, 3H), 3.5 (m, 1H), 3.0 (dd, 1H), 2.8 (t, 2H), 2.7 (dd, 1H), 2.6 (s, 3H).

e) methyl (R,S)-8-[[[4-[N-(benzyloxycarbonyl)-aminoiminomethyl]phenyl]methylamino]carbonyl]-2,3,4,5-tetrahydro-1-methyl-3-oxo-4-(2-phenylethyl)-1H-1,4-benzodiazepine-2-acetate Using the procedure of Example 1(h), except substituting the compound of Example 2(d) for the compound of Example 1(g), the title compound was prepared (0.040 g, 35%). $^1$H NMR (400 MHz, CDC$_3$) δ7.75 (d, 2H), 7.25–7.45 (m, 6H), 7.0–7.2 (m, 6H), 6.95 (s, 1H), 6.7 (m, 2H), 5.2 (s, 2H), 5.0 (d, 1H), 4.6 (m, 1H), 3.9 (m, 1H), 3.65 (m, 4H), 3.6 (m, 1H), 3.5 (s, 3H), 2.9 (dd, 1H), 2.75 (t, 2H), 2.55 (dd, 1H), 2.5 (s, 3H).

f) methyl (R,S)-8-[[[4-(aminoiminomethyl)phenyl] methylamino]-carbonyl]-2,3,4,5-tetrahydro-1-methyl-3-oxo-4-(2-phenylethyl)-1H-1,4-benzodiazepine-2-acetate A solution of the compound of Example 2(e) (0.04 g, 0.06 mmol) in methanol (25 mL) containing 1.0M hydrogen chloride in ether (0.6 mL) was treated with 10% palladium on carbon (0.06 g) and the mixture was shaken in a hydrogen atmosphere (40 psi) for 1 h. The mixture was filtered and concentrated to yield the title compound.

g) (R,S)-8-[[[4-(aminoiminomethyl)phenyl] methylamino]-carbonyl]-2,3,4,5-tetrahydro-1-methyl-3-oxo-4-(2-phenylethyl)-1H-1,4-benzodiazepine-2-acetic Acid Using the procedure of Example 1(j), except substituting the compound of Example 2(f) for the compound of Example 1(i), gave a residue which was purified by HPLC (YMC-ODS AQ, 33% AN/W-TFA) to yield the title compound (0.012 g, 35%). $^1$H NMR (400 MHz, CD$_3$OD) δ7.7 (d, 2H), 7.45 (d, 2H), 7.05–7.15 (m, 3H), 7.0 (d, 2H), 6.9 (m, 2H), 6.8 (d, 1H), 5.1 (dd, 1H), 4.7 (m, 1H), 4.0 (d, 1H), 3.9 (m, 1H), 3.55 (m, 1H), 3.5 (s, 3H), 2.85 (dd, 1H), 2.7 (t, 2H), 2.5 (dd, 1H), 2.4 (s, 3H); MS(ES) m/e 514.2 [M+H]$^+$.

Example 3

Preparation of (R,S)-8-[[[4-(aminoiminomethyl) phenyl]amino]-carbonyl]-2,3,4,5-tetrahydro-4-(2-phenylethyl)-1H-1,4-benzodiazepine-2-acetic acid a) methyl N-[2-Nitro-4-(t-butoxycarbonyl)benzyl]-N-phenylethyl-4-aminocrotonate To a solution of 2-nitro-4-(t-butoxycarbonyl)-benzylbromide (4.06 g, 12.8 mmol) in THF (50 mL), methyl 4-(phenylethylamino)-crotonate (3.4 g, 15.5 mmol) was added with stirring at RT. Triethylamine (2.2 mL, 15.7 mmol) was then added. After stirring for 16 h, the reaction was diluted with ethyl acetate and washed with 1N sodium carbonate, brine, dried (sodium sulfate) and concentrated. Flash chromatography (silica gel, 15% ethyl acetate/n-hexane) gave the title compound as an oil (5.16 g, 88%). $^1$H-NMR (CDCl$_3$) δ1.60(9H, s), 2.74(4H, br s), 3.30(2H, dd), 3.74(3H, s), 4.00(2H, s), 6.00(1H, d, J=15 Hz), 7.02(1H, dt), 7.25(5H, m), 7.67(1H, d, J=8 Hz), 8.15(1H, dd), 8.45 (1H, d, J=2 Hz).

b) methyl N-[2-amino-4-(t-butoxycarbonyl)benzyl]-N-phenylethyl-4-aminocrotonate

Iron powder (0.8 g) was added to a stirred solution of the compound of Example 3(a) (1.03 g, 2.26 mmol) in acetic acid (25 mL) and ethanol (25 mL). After stirring for 16 h the reaction was concentrated and dissolved in ethyl acetate, washed with 1N sodium carbonate, brine, dried (sodium sulfate) and concentrated to give the title compound (0.96 g) as an oil. $^1$H-NMR (CDCl$_3$) δ1.57(9H, s), 2.80(4H, br s), 3.25(2H, d, J=5.2 Hz), 3.70(2H, s), 3.74(3H, s), 4.52(2H, br s), 5.92(1H, d, J=15.7 Hz), 6.94(1H, dt), 7.0–7.3(8H, m).

c) methyl (R,S)-8-(t-butoxycarbonyl)-2,3,4,5-tetrahydro-4-(2-phenylethyl)-1H-1,4-benzodiazepine-2-acetate The compound of Example 3(b) (0.96 g, 2.25 mmol) was dissolved in anhydrous methanol (50 mL) and refluxed under Ar for 72 h. The mixture was cooled, concentrated and the residue was purified by flash chromatography (silica gel, 60% ethyl acetate/n-hexane) to yield the title compound (0.87 g, 91%). $^1$H-NMR (CDCl$_3$) δ1.59(9H, s), 2.39(1H, dd), 2.51(1H, dd), 2.68–3.50(6H, m), 3.56(1H, br s), 3.73 (3H, s), 3.95(2H, br s), 4.47(1H, br s), 7.15–7.27(6H, m), 7.42(1H, s), 7.51(1H, d, J=7.4 Hz); MS(ES) m/e 425.0 [M+H]$^+$.

d) methyl (R,S)-8-carboxy-2,3,4,5-tetrahydro-4-(2-phenylethyl)-1H-1,4-benzodiazepine-2-acetate To the compound of Example 3(c)(0.87 g, 2.05 mmol)) was added 90% TFA in CH$_2$Cl$_2$ (30 mL). After stirring at RT for 45 min, the reaction was concentrated and then re-concentrated twice from anhydrous toluene to yield the title compound (0.87 g, 88%).

e) methyl (R,S)-8-[[[4-[N-(t-butoxycarbonyl)aminoiminomethyl]phenyl]amino]carbonyl]-2,3,4,5-tetrahydro-4-(2-phenylethyl)-1H-1,4-benzodiazepine-2-acetate To the compound of Example 3(d) (0.87 g, 2 mmol) was added thionyl chloride (5 mL). After refluxing for 15 min under Ar, the reaction was concentrated and then re-concentrated twice from anhydrous toluene. The resulting acid chloride in CH$_2$Cl$_2$ (15 mL) was added dropwise with stirring under Ar to a cooled (0° C.) solution of pyridine (0.65 mL) and 4-(Boc-amidino)aniline (0.57 g, 2.4 mmol) in CH$_2$Cl$_2$ (15 mL). The reaction was stirred for 4 h at RT, diluted with chloroform, washed with 1N sodium bicarbonate, dried (sodium sulfate) and concentrated. Purification by flash chromatography (silica gel, 2% methanol/chloroform) gave the title compound as a solid (936 mg, 80%). $^1$H-NMR (CDCl$_3$) δ1.54(9H, s), 2.39(1H, dd), 2.52 (1H, dd), 2.75–2.90(5H, m), 3.00(1H, d), 3.56(1H, br s), 3.70(3H, s), 3.89(2H, dd), 4.62(1H, s), 7.15(4H, m), 7.27 (2H, m), 7.36(2H, m), 7.71(2H, d, J=8.5 Hz), 7.81(2H, d, J=8.5 Hz).

f) (R,S)-8-[[[4-(aminoiminomethyl)phenyl]amino] carbonyl]-2,3,4,5-tetrahydro-4-(2-phenylethyl)-1H-1,4-benzodiazepine-2-acetic Acid To the compound of Example 3(e) (936 mg, 1.6 mmol), 90% TFA in CH$_2$Cl$_2$ (30 mL) was added. After stirring for 45 min, the reaction was concentrated and the residue was triturated with ether, filtered and dried at reduced pressure to give methyl (R,S)-8-[[[4-(aninoiminomethyl)phenyl]amino] carbonyl]-2,3,4,5-tetrahydro-4-(2-phenylethyl)-1H-1,4-benzodiazepine-2-acetate.

The methyl ester was taken up in 20% acetic acid and refluxed under Ar for 48 h. The mixture was concentrated and the residue was purified by HPLC (PRP-1®, 25% AN/W-TFA) to give the title compound as a white solid. HPLC k' 5.7 (PRP-1®, 20% AN/W-TFA, UV detection at 220 nm); TLC R$_f$ 0.40 (4:1:1 n-butanol:acetic acid:water); R$_f$ 0.45 (15:3:12:10 n-butanol:acetic acid:water:pyridine); MS(ES) m/e 472.2 [M+H]$^+$; Anal. (C$_{27}$H$_{29}$N$_5$O$_3$.2.5 CF$_3$CO$_2$H.1.0 H$_2$O) calcd: C, 49.62; H, 4.36; N, 9.04. found: C, 49.37; H, 4.437; N, 9.18.

Example 4

Preparation of (R,S)-8-[[[(4-aminoiminomethyl) phenyl]-methylamino]carbonyl]-2,3,4,5-tetrahydro-3-oxo-1H-1,4-benzodiazepine-2-acetic acid a) t-butyl [N-(t-butoxycarbonyl)-N-(methoxycarbonyl)aminomethyl]-3-nitrobenzoate To a solution of t-butyl 4-bromomethyl-3-nitrobenzoate (2.27 g, 7.2 mmol) (*Int. J. Peptide Res.*, 36, 31 (1990)) in DMF (25 mL) was added a suspension of potassium t-butyl methyl iminodicarboxylate (*J.C.S. Perkin I*, 1088, (1977)) (1.56 g, 7.3 mmol) in DMF (20 mL). The dark brown solution was stirred 1 h and poured into water and extracted with ethyl acetate. The combined organic layers were washed with water, dried (sodium sulfate) and concentrated to give a pale orange oil which was purified by flash chromatography (silica gel, 20% ethyl acetate/hexane) to give the title compound (2.15 g, 73%). $^1$H NMR (400 MHz, CDCl$_3$) δ8.65 (s, 1H), 8.2 (d, 1H), 7.45 (d, 1H), 5.3 (s, 2H), 3.8 (s, 3H), 1.6 (s, 9H), 1.45 (s, 9H).

b) t-butyl 4-[N-(t-butoxycarbonyl)aminomethyl]-3-nitrobenzoate

The compound of Example 4(a) (2.15 g, 5.24 mmol) was dissolved in a mixture of methanol (120 mL) and 0.95 N sodium hydroxide (15 mL). After 15 min, acetic acid (3.0 mL) was added and mixture was concentrated. The residue was dissolved in ethyl acetate and extracted with water. The organic layer was washed with brine, dried (sodium sulfate) and concentrated to give a yellow oil which was purified by chromatography (silica gel, 20% ethyl acetate/hexane) to give the title compound (1.0 g, 54%). $^1$H NMR (400 MHz, CDCl$_3$) δ8.6 (s, 1H), 8.2 (d, 1H), 7.7 (d, 1H), 5.35 (m, 1H), 4.6 (d, 2H), 1.65 (s, 9H), 1.4 (s, 9H).

c) t-butyl 3-amino-4-[N-(tert butoxycarbonyl)-aminomethyl]benzoate

A solution of the compound of Example 4(b) (0.80 g, 2.27 mmol) in ethanol (100 mL) containing 10% palladium on carbon (0.5 g) was hydrogenated (40 psi). After 30 min, the mixture was filtered and concentrated to give the title compound (0.72 g, 100%). $^1$H NMR (400 MHz, CDCl$_3$) δ7.25 (m, 2H), 7.1 (d, 1H), 4.9 (b, 1H), 4.25 (d, 2H), 1.6 (s, 9H), 1.45 (s, 9H).

d) t-butyl (E,Z)-4-[N-(t-butoxycarbonyl) aminomethyl]-3-[2-(1,4-dimethoxy-1,4-dioxo-2-butenyl)amino]benzoate Using the procedure of Example 2(b), except substituting the compound of Example 4(c) for the compound of Example 2(a), the title compound was prepared (0.7 g, 70%). $^1$H NMR (400 MHz, CDCl$_3$) δ9.6 (s, 1H), 7.7 (d, 1H), 7.35 (m, 2H), 5.5 (s, 1H), 5.0 (b, 1H), 4.4 (d, 2H), 3.75 (s, 3H), 3.7 (s, 3H), 1.6 (s, 9H), 1.45 (s, 9H).

e) t-butyl 4-[N-(t-butoxycarbonyl)aminomethyl]-3-[2-(1,4-dimethoxy-1,4-dioxo-2-butyl)amino]benzoate Using the procedure of Example 2(c), except substituting the compound of Example 4(d) for the compound of Example 2(b), the title compound was prepared (0.66 g, 95%). $^1$H NMR (400 MHz, CDCl$_3$) δ7.8 (d, 1H), 7.75 (s, 1H), 7.1 (d, 1H), 5.4 (b, 1H), 4.9 (b, 1H), 4.6 (m, 1H), 4.3 (m, 2H), 3.7 (s, 3H), 3.65 (s, 3H), 2.9 (m, 2H), 1.6 (s, 9H), 1.45 (s, 9H).

f) methyl (R,S)-8-carboxy-2,3,4,5-tetrahydro-3-oxo-1H-1,4-benzodiazepine-2-acetate Using the procedure of Example 2(d), except substituting the compound of Example 4(e) for the compound of Example 2(c), the title compound was prepared (0.44 g, 98%). $^1$H NMR (400 MHz, DMSO-d$_6$) δ8.15 (t, 1H), 7.2 (s, 1H), 7.1 (d, 1H), 7.05 (d, 1H), 5.0 (dd, 1H), 4.9 (m, 1H), 3.75 (dd, 1H), 3.6 (s, 3H), 2.8 (dd, 1H), 2.6 (dd, 1H).

g) methyl (R,S)-8-[[[4-[N-(benzyloxycarbonyl)-aminoiminomethyl]phenyl]methylamino]carbonyl]-2,3,4,5-tetrahydro-3-oxo-1H-1,4-benzodiazepine-2-aceate Using the procedure of Example 1(h), except substituting the compound of Example 4(f) for the compound of Example 1(g), the title compound was prepared (0.30, 45%). $^1$H NMR (400 MHz, CD$_3$OD) δ7.75 (d, 2H), 7.25–7.45 (m, 5H), 7.2 (d, 2H), 6.7 (d, 1H), 6.65 (s, 1H), 6.45 (d, 1H), 5.5 (s, 1H), 5.2 (s, 2H), 4.95 (d, 1H), 4.9 (m, 1H), 3.75 (d, 1H), 3.65 (s, 3H), 3.45 (s, 3H), 2.9 (dd, 1H), 2.6 (dd, 1H).

h) methyl (R,S)-8-[[[(4-aminoiminomethyl)phenyl]-methylamino]carbonyl]-2,3,4,5-tetrahydro-3-oxo-1H-1,4-benzodiazepine-2-acetate Using the procedure of Example 2(f), except substituting the compound of Example 4(g) for the compound of Example 2(e), gave the title compound.

i) (R,S)-8-[[[4-aminoiminomethyl)phenyl]methylamino]-carbonyl]-2,3,4,5-tetrahydro-3-oxo-1H-1,4-benzodiazepine-2-acetic acid Using the procedure of Example 1(j), except substituting the compound of Example 4(h) for the compound of Example 1(i), the title compound was prepared. It was purified by HPLC (YMC ODS-AQ, 15% AN/W-TFA, UV detection at 220 nm) to give a purified product (0.125 g, 57%). $^1$H NMR (400 MHz, DMSO-d$_6$) δ9.75 (s, 2H), 8.95 (s, 2H), 8.1 (d, 1H), 7.75 (d, 2H), 7.4 (d, 2H), 6.75 (s, 1H), 6.7 (d, 1H), 6.25 (d, 1H), 5.9 (d, 1H), 4.9 (dd, 1H), 4.8 (m, 1H), 3.65 (dd, 1H), 3.4 (s, 3H), 2.75 (dd, 1H), 2.5 (dd, 1H); MS(ES) m/e 396.0 [M+H]$^+$.

Example 5

Preparation of (R,S)-8-[[[4-(aminoiminomethyl) phenyl]methylamino]carbonyl]-2,3,4,5-tetrahydro-4-methyl-3-oxo-1H-1,4-benzodiazepine-2-acetic acid a) t-butyl 4-(methylamino)methyl-3-nitrobenzoate

Anhydrous methylamine was bubbled into anhydrous DMF (200 mL) at 0° C. for 15 min. A solution of t-butyl 4-bromomethyl-3-nitrobenzoate (5.0 g, 15.8 mmol) (*Int. J. Peptide. Res.*, 36, 31 (1990)) in DMF (10 mL) was added dropwise to the cold amine solution. The solution was stirred at 0° for 30 min and poured into water. The mixture was extracted with ethyl acetate and the combined organic layers were washed with water, dried (sodium sulfate) and concentrated to give a yellow-brown oil. The oil was purified by chromatography (silica gel, 3% isopropanol/CH$_2$Cl$_2$) to give the title compound (1.5 g, 36%). $^1$H NMR (400 MHz, CDCl$_3$) δ8.5 (s, 1H), 8.2 (d, 1H), 7.7 (d, 1H), 4.05 (s, 2H), 2.5 (s, 3H), 1.6 (s, 9H).

b) t-butyl 4-[N-(t-butoxycarbonyl)-N-(methyl) amino-methyl]-3-nitrobenzoate

A solution of the compound of Example 5(a) (1.4 g, 5.3 mmol), triethylamine (2.1 g, 21 mmol) and di-t-butyl dicarbonate (3.44 g, 15.8 mmol) in THF (50 mL) was stirred 24 h. The mixture was concentrated and the residue dissolved in ethyl acetate (200 mL). The solution was extracted with water, dried (sodium sulfate) and concentrated to give a yellow oil which was purified by chromatography (silica gel, 15:85 ethyl acetate:hexane) to give the title compound (1.85 g, 85%): $^1$H NMR (400 MHz, CDCl$_3$) δ8.6 (s, 1H), 8.25 (d, 1H), 7.4 (d, 1H), 4.85 (d, 2H), 2.9 (d, 3H), 1.6 (s, 9H), 1.45 (d, 9H).

c) t-butyl 3-amino-4-[N-(t-butoxycarbonyl)-N-(methyl)-aminomethyl]benzoate

Using the procedure of Example 4(c), except substituting the compound of give the title compound (1.85 g, 85%): $^1$H NMR (400 MHz, CDCl$_3$) δ8.6 (s, 1H), 8.25 (d, 1H), 7.4 (d, 1H), 4.85 (d, 2H), 2.9 (d, 3H), 1.6 (s, 9H), 1.45 (d, 9H).

c) t-butyl 3-amino-4-[N-(t-butoxycarbonyl)-N-(methyl)-aminomethyl]benzoate

Using the procedure of Example 4(c), except substituting the compound of Example 5(b) for the compound of Example 4(b), the title compound was prepared (1.6 g, 100%). $^1$H NMR (400 MHz, CDCl$_3$) δ7.25 (d, 2H), 7.05 (d, 1H), 4.35 (d, 2H), 2.75 (s, 3H), 1.6 (s, 9H), 1.4 (d, 9H).

d) t-butyl (E,Z)-4-[N-(t-butoxycarbonyl)-N-(methyl)-aminomethyl]-3-[2-(1,4-dimethoxy-1,4-dioxo-2-butenyl)amino]-benzoate Using the procedure of Example 2(b), except substituting the compound of Example 5(c) for the compound of Example 2(a), the title compound was prepared (1.55 g, 68%). $^1$H NMR (400 MHz, CDCl$_3$) δ9.5 (s, 1H), 7.7 (d, 1H), 7.4 (s, 1H), 7.3 (d, 1H), 5.5 (s, 1H), 4.55 (s, 2H), 3.75 (s, 3H), 3.7 (s, 3H), 2.85 (s, 3H), 1.6 (s, 9H), 1.45 (s, 9H).

e) t-butyl 4-[N-(t-butoxycarbonyl)-N-(methyl) amino-methyl]-3-[2-(1,4-dimethoxy-1,4-dioxo-2-butyl)amino]benzoate Using the procedure of Example 2(c), except substituting the compound of Example 5(d) for the compound of Example 2(b), the title compound was prepared (1.55 g, 100%). $^1$H NMR (400 MHz, CDCl$_3$) δ7.45 (d, 2H), 7.05 (d, 1H), 4.65 (q, 1H), 4.45 (d, 1H), 4.35 (d, 1H), 3.7 (s, 6H), 2.95 (dd, 1H), 2.85 (dd, 1H), 2.75 (s, 3H), 1.6 (s, 9H), 1.45 (s, 9H).

f) methyl (R,S)-8-carboxy-2,3,4,5-tetrahydro-4-methyl-3-oxo-1H-1,4-benzodiazepine-2-acetate Using the procedure of Example 2(d), except substituting the compound of Example 5(e) for the compound of Example 2(c), the title compound was prepared (0.72 g, 72%). $^1$H NMR (400 MHz, DMSO-$d_6$) δ 7.2 (s, 1H), 7.1 (s, 2H), 6.1 (s, 1H), 5.5 (d, 1H), 5.1 (m, 1H), 3.9 (s, 1H), 3.6 (s, 3H), 2.9 (s, 3H), 2.8 (dd, 1H), 2.65 (dd, 1H).

g) methyl (R,S)-8-[[[4-[N-(benzyloxycarbonyl) aminoimino-methyl]phenyl]methylamino]carbonyl]-2,3,4,5-tetrahydro-4-methyl-3-oxo-1H-1,4-benzodiazepine-2-acetate Using the procedure of Example 1(h), except substituting the compound of Example 5(f) for the compound of Example 1(g), the title compound was prepared (0.29 g, 40%). $^1$H NMR (400 MHz, CDCl$_3$) δ 7.75 (d, 2H), 7.45 (d, 2H), 7.25–7.4 (m, 3H), 7.1 (d, 2H), 6.7 (d, 1H), 6.65 (s, 1H), 6.45 (d, 1H), 5.3 (d, 1H), 5.2 (s, 2H), 4.95 (m, 1H), 4.2 (d, 1H), 3.75 (s, 3H), 3.65 (d, 1H), 3.45 (s, 3H), 3.0 (s, 3H), 2.9 (dd, 1H), 2.55 (dd, 1H).

h) methyl (R,S)-8-[[[4-(aminoiminomethyl)phenyl] methyl-amino]carbonyl]-2,3,4,5-tetrahydro-4-methyl-3-oxo-1H-1,4-benzodiazepine-2-acetic acid Using the procedure of Example 2(f), except substituting the compound of Example 5(g) for the compound of Example 2(e), gave the title compound. $^1$H NMR (400 MHz, CD$_3$OD) δ 9.25 (s, 2H), 8.8 (s, 2H), 7.7 (d, 2H), 7.4 (s, 2H), 6.85 (d, 1H), 6.7 (s, 1H), 6.45 (d, 2H), 5.45 (d, 1H), 5.1 (m, 1H), 3.85 (d, 1H), 3.7 (s, 3H), 3.5 (s, 3H), 3.35 (s, 3H), 2.9 (dd, 1H), 2.65 (dd, 1H).

i) (R,S)-8-[[[4-(aminoiminomethyl)phenyl] methylamino]-carbonyl]-2,3,4,5-tetrahydro-4-methyl-3-oxo-1H-1,4-benzodiazepine-acetic acid Using the procedure of Example 1(j), except substituting the compound of Example 5(h) for the compound of Example 1(i), and the product purified by HPLC (YMC ODS-AQ, 50×250 mm, 90 mL/min, 15% AN/W-TFA) to give the title compound (0.115 g, 57%). $^1$H NMR (400 MHz, DMSO-$d_6$) δ 9.3 (s, 2H), 9.1 (s, 2H), 7.75 (d, 2H), 7.4 (d, 2H), 6.75 (m, 2H), 6.25 (d, 1H), 6.0 (m, 1H), 5.35 (d, 1H), 4.95 (m, 1H), 3.75 (d, 1H), 3.4 (s, 3H), 2.9 (s, 3H), 2.75 (dd, 1H), 2.5 (dd, 1H); MS(ES) m/e 410.0 [M+H]$^+$.

Example 6

Preparation of (R,S)-7-[[4-(aminoiminomethyl) benzoyl]-methylamino]-2,3,4,5-tetrahydro-1-methyl-3-oxo-4-(2-phenylethyl)-1H-1,4-benzodiazepine-2 acetic acid a) ethyl 7-methylamino-1-methyl-3-oxo-4-(2-phenylethyl)-2,3,4,5-tetrahydro-1H-1,4-benzodiazepine-2-acetate The compound of Preparation 23(g) (700 mg, 1.5 mmol) was dissolved in anhydrous triethyl orthoformate (1 mL). TFA (2 drops) was added and the mixture was refluxed for 4 h. The solution was concentrated to a film (toluene azeotrope), dissolved in ethanol (15 mL), chilled to 5° C., and sodium borohydride (167 mg, 4.4 mmol) was added. The mixture stirred 10 min at RT and was heated to reflux for 2 h. The resulting solution was concentrated, poured into water and extracted with ethyl acetate. The combined extracts were dried (magnesium sulfate) and concentrated. Chromatography (silica gel, 30% ethyl acetate/hexanes) yielded the title compound (350 mg, 60%). MS(ES) m/e 396 [M+H]$^+$; $^1$H NMR (400 MHz, CDCl$_3$) δ 1.2 (3H, t), 2.50 (3H, s), 2.55 (1H, d), 2.70–2.85 (5H, s+t), 2.95 (1H, dd), 3.54 (1H, dt), 3.68 (1H, d), 3.88 (1H, dt), 4.09 (2H, q), 4.58 (1H, m), 5.04 (1H, d), 6.07 (1H, s, 6.45 (1H, d), 6.79 (1H, d), 7.00–7.20 (5H, m).

b) ethyl 7-[[4-[N-(benzyloxycarbonyl) aminoiminomethyl]-benzoyl]methylamino]-1-methyl-3-oxo-4-(2-phenylethyl)-2,3,4,5-tetrahydro-1H-1,4-benzodiazepine-2-acetate

[N-(benzyloxycarbonyl)amidino]benzoic acid (500 mg, 1.7 mmol) was dissolved in thionyl chloride (6.5 mL), heated to reflux for 5 min and concentrated (CH$_2$Cl$_2$ azeotrope) to give 4-[N-(benzyloxy-carbonyl)amidino] benzoyl chloride.

The acid chloride (158 mg, 0.5 mmol) was dissolved CH$_2$Cl$_2$ (3 mL) and added dropwise to a cooled solution of the compound of Example 6(a) (200 mg, 0.5 mmol) and diisopropylethylamine (174 uL, 1.0 mmol). The mixture was stirred for 1 h, concentrated and the residue was chromatographed (silica gel, 25% ethyl acetate/hexanes) to yield the title compound (200 mg, 54%). MS(ES) m/e 676.4 [M+H]$^+$; NMR (400 MHz, CDCl$_3$) δ 1.23 (3H, t), 2.43–2.70 (6H, m), 2.95 (1H, dd), 3.41 (3H, s), 3.60 (1H, d), 3.92 (2H, dt), 4.10 (2H, q), 4.62 (1H, m), 5.00 (1H, d), 5.15 (2H, s), 6.44–7.68 (17H, m).

c) (R,S)-7-[[4-aminoiminomethyl)benzoyl] methylamino]-2,3,4,5-tetrahydro-1-methyl-3-oxo-4-(2-phenylethyl)-1H-1,4-benzodiazepine-2-acetic Acid The compound of Example 6(b) (200 mg, 0.3 mmol) was dissolved in ethyl acetate (20 mL), and added to palladium hydroxide (100 mg) and 3N hydrochloric acid (1 mL). The mixture was hydrogenated (40 psi) for 6 h. The reaction mixture was filtered, the catalyst washed with acetonitrile and the filtrate concentrated to yield ethyl (R,S)-7-[[4-(aminoiminomethyl)benzoyl]methylamino]-2,3,4,5-tetrahydro-1-methyl-3-oxo-4-(2-phenylethyl)-1H-1,4-benzodiazepine-2 acetate (200 mg) as a reddish-brown solid. MS(ES) m/e 542.0 [M+H]$^+$.

The ethyl ester (200 mg, 0.3 mmol) was dissolved in methanol (4 mL) and 1N sodium hydroxide (0.5 mL), stirred, concentrated, diluted with water, acidified with 3N hydrochloric acid and concentrated. The residue was chromatographed by HPLC (YMC ODS-AQ, 25% AN/W-TFA) to yield the title compound as white solid (78 mg, 51%). MS(ES) m/e 514.2 [M+H]$^+$; $^1$H NMR (400 MHz, DMSO) δ 2.35 (3H, s), 2.45 (1H, dd), 2.62 (2H, m), 2.78 (1H, dd), 3.39 (s), 3.95 (1H, dt), 4.05 (1H, d), 4.68 (1H, bt), 5.05 (1H, d), 6.75–7.21 (8H, m), 7.47–7.70 (4H, m), 9.10 (1H, bs), 9.20 (1H, bs). Anal. (C$_{29}$H$_{31}$N$_5$O$_4$.1.8 C$_2$HO$_2$F$_3$) calcd: C, 54.47; H, 4.60; N, 9.74.

found: C, 54.44; H, 4.85; N, 9.36.

Example 7

Preparation of (R,S)-2,3,4,5-tetrahydro-3-oxo-4-(2-phenylethyl)-8-[[[2-(2-pyrazinyl)ethyl]carbonyl] amino]-1H-1,4-benzodiazepine-2-acetic Acid a) methyl (R,S)-8-amino-2,3,4,5-tetrahydro-3-oxo-4-(2-phenylethyl)-1H-1,4-benzodiazepine-2-acetate A mixture of the compound of Preparation 24(e) (1.02 g, 2.67 mmol), triethylamine (0.42 mL, 5.87 mmol) and diphenyl phosphorylazide (0.62 mL, 2.80 mmol) in toluene (20 mL) was heated at 105° C. for 0.5 h. After the temperature was lowered to 80° C., the mixture was treated with benzyl alcohol (0.60 mL, 0.42 mmol), stirred for 14 h and concentrated. The residue was purified by flash chromatography (silica gel, 60% ethyl acetate/hexane) to give methyl (R,S)-8-(carbobenzyloxy)amino-2,3,4,5-tetrahydro-3-oxo-1H-1,4benzodiazepine-2-acetate (0.79 g, 52%) as a light yellow oil. MS(ES) m/e 488 [M+H]$^+$; $^1$H NMR (250 MHz) δ7.12–7.44 (m, 10H), 6.52–6.81 (m, 3H), 5.24 (d, 1H), 5.18 (s, 2H), 4.96 (t, 1H), 3.62–3.79 (m, 6H), 2.95 (dd, 1H), 2.70–2.85 (m, 2H), 2.60 (dd, 1H).

The Cbz compound (0.68 g, 1.38 mmol) was dissolved in methanol(10 mL) and palladium on carbon (5%, 50 mg) was added. The mixture was hydrogenated for 1 h, filtered through Celite® and concentrated to yield the tide compound as a light yellow oil (0.39 g, yield 81%). MS(ES) m/e 354 [M+H]$^+$; $^1$H NMR (250 MHz) δ7.10–7.33 (m, 5H), 6.62 (d, 2H), 6.01 (dd, 1H), 5.89 (d, 1H), 5.19 (d, 1H), 4.93 (q, 1H), 3.50–3.75 (m, 6H), 2.94 (dd, 1H), 2.75–2.85 (m, 2H), 2.63 (dd, 1H).

b) (R,S)-2,3,4,5-tetrahydro-3-oxo-4-(2-phenylethyl)-8-[[[2-(2pyrazinyl)ethyl]carbonyl]amino]-1H-1,4benzodiazepine-2-acetic acid A solution of the compound of 43(a)(0.36 g, 1.02 mmol) and the compound of Preparation 1(b) (0.17 g, 1.12 mmol) in DMF (5 mL) was treated with diisopropylethylamine (0.39 mL, 1.23 mmol) and 1-(3-dimethylaminopropyl)-3-ethylcarbodiimide hydrochloride (0.23 g, 1.23 mmol), and stirred at RT for 24 h. The mixture was concentrated and cold water (3 mL) was added. The white solid that formed was filtered and dissolved in chloroform. The organic solution was washed with 5% sodium bicarbonate, dried (sodium sulfate) and concentrated to yield methyl (R,S)-2,3,4,5-tetrahydro-3-oxo-4-(2-phenylethyl)-8-[[[2-(2-pyrazinyl)ethyl]carbonyl]amino]-1H-1,4-benzodiazepine-2-acetate as a white solid (0.29 g, 60%). MS(ES) m/e 488 [M+H]$^+$; $^1$H NMR (250 MHz) δ840–8.55 (m, 3H), 7.10–7.28 (m, 5H), 6.81–6.99 (m, 3H), 5.46 (d, 1H), 5.14 (m, 1H), 3.56–3.80 (m, 6H), 3.27 (t, 2H), 2.90 (dd, 1H), 2.72–2.85 (m, 4H), 2.61 (dd, 1H).

Using the procedure of Example 1(j), except substituting the methyl ester above for the compound of Example 1(i), and purifying the product by HPLC (PRP column, 21.5×250 mm, 14 mL/min, 30% AN/W-TFA, UV detection at 254 mm) yielded the title compound as an off-white powder (171 mg, 92%). MS(ES) m/e 474 [M+H]$^+$; $^1$H NMR (400 MHz) δ8.40–8.70 (m, 3H), 7.10–7.31 (m, 5H), 6.88 (d, 1H), 6.70 (d, 1H), 6.63 (m, 1H), 5.37 (d, 1H), 5.06 (m, 3H), 3.57–3.81 (m, 3H), 327 (t, 2H), 2.74–2.97 (m, 5H), 2.61 (dd, 1H).

Examples 8–10 a) Using the procedure of Preparation 25(c), except substituting 2-(4-pyridyl)ethylamine, 2-(2-pyridyl) ethylamine and the compound of Preparation 2(b) for 4-(methylamino)-(N-benzyloxycarbonyl) benzamidine, gave the following title compounds 8(a) methyl (R,S)-2,3,4,5-tetrahydro-3-oxo-4-(2-phenylethyl)-8-[[[2-(4-pyridyl)ethyl]amino]carbonyl]-1H-1,4-benzodiazepine-2-acetate. HPLC RT 17.8 min (YMC ODS-AQ, 6×250 mm, 1.5 mL/min, gradient, A:acetonitrile B:water-0.1% trifluoracetic acid, 10–80% A during 20 min, UV detections at 220 nm); $^1$H NMR (250 MHz, CDCl$_3$) δ8.5 (d, 2H), 7.1–7.3 (m, 7H), 6.95 (s, 1H), 6.8 (s, 2H), 6.05 (m, 1H), 5.25 (d, 1H), 4.5 (m, 1H), 4.25 (m, 1H), 3.75 (s, 3H), 3.69–3.7 (m, 2H), 2.95–3.0 (m, 2H), 2.8 (m, 2H), 2.65 (d, 2H).

9(a) methyl (R,S)-2,3,4,5-tetrahydro-3-oxo-4-(2-phenylethyl)-8-[[[2-(2-pyridyl)ethyl]amino]carbonyl]-1H-1,4-benzodiazepine-2-acetate. HPLC RT 18.3 min (YMC ODS-AQ, 6×250 mm, 1.5 mL/min, gradient, A:acetonitrile B:water-0.1% tridfluoracetic acid, 10–80% A during 20 min, UV detections at 220 nm).

10(a) methyl (R,S)-2,3,4,5-tetrahydro-3-oxo-4-(2-phenylethyl)-8-[[[3-(4-pyridyl)propyl]amino]carbonyl]-1H-1,4-benzodiazepine-2-acetate. This compound was purified by flash chromatography (silica gel, chloroform, 5:95 methanol:chloroform). $^1$H NMR (250 MHz, CDCl$_3$/CD$_3$OD) δ8.48 (d, 2H), 7.46–6.68 (m, 12H), 6.17 (m, 1H), 5.28 (d, 1H), 4.98 (q, 1H), 4.32 (d, 1H), 3.90–3.55 (m), 3.72 (s, 3H), 2.98 (dd, 1H), 2.88–2.50 (m), 1.95 (m).

b) Using the procedure of Example 1(j), except substituting the compounds of Examples 8–10(a) for the compound of Example 1(i), gave the following title compounds 8(b) (R,S)-2,3,4,5-tetrahydro-3-oxo-4-(2-phenylethyl)-8-[[[2-(4-pyridyl)ethyl]amino]carbonyl]-1H-1,4-benzodiazepine-2-acetic acid. $^1$H NMR(DMSO d$_6$/TA, 360 MHz) δ8.8 (d, 2H), 8.35 (m, 1H), 7.95 (d, 2H), 7.2 (m, 2H), 7.1 (m, 2H), 7.0 (m, 2H), 6.84 (d, 1H), 5.35 (d, 1H), 4.95 (d, 1H), 3.95 (d, 1H), 3.6 (m, 4H), 3.12 (m, 2H), 2.73 (m, 2H), 2.62 (m, 2H); MS(ES) m/e 473 [M+H]$^+$.

9(b) (R,S)-2,3,4,5-tetrahydro-3-oxo-4-(2-phenylethyl)-8-[[[2-(2-pyridyl)ethyl]amino]carbonyl]-1H-1,4-benzodiazepine-2-acetic acid. MS(ES) m/e 473 [M+H]$^+$.

10(b) (R,S)-2,3,4,5-tetrahydro-3-oxo-4-(2-phenylethyl)-8-[[[3-(4-pyridyl)propyl]amino]carbonyl]-1H-1,4-benzodiazepine-2-acetic acid. This compound was purified by chromatography (Sephadex LH20, water). MS(ES) m/e 487 [M+H]$_+$; HPLC RT 10.10 min (PRP-1®, 4.6×250 mm, 1.5 mL/min, gradient, A:acetonitrile B:water/0.1% TFA, 20–50% A during 20 min, UV detection at 220 and 250 nm); TLC R$_f$ 0.47 (silica, 3:1:1 n-BuOH:HOAc:H$_2$O); Anal. (C$_{28}$H$_{30}$N$_4$O$_4$·3H$_2$O) calcd: C, 62.21; H, 6.71; N, 10.36. found: C, 62.21; H, 6.00; N, 10.36.

Examples 11–12 a) Using the procedure of Preparation 25(c) and 1 (i), except substituting the compound of Preparation 3 and 4-nitrobenzylamine for 4-(methylamino)-(N-benzyloxycarbonyl)benzamidine, gave the following title compounds 11(a) methyl (R,S)-8-[[[5-aminopentyl]amino]carbonyl]-2,3,4,5-tetrahydro-3-oxo-4-(2-phenylethyl)-1H-1,4-benzodiazepine-2-acetate. TLC R$_f$ 0.45 (silica, 1:20 CH$_2$Cl$_2$:methanol); $^1$H NMR (400 MHz, CD$_3$OD) δ6.9–7.4 (m, 13H), 5.4 (d, 1H), 5.1 (m, 1H), 5.05 (s, 2H), 3.87 (d, 1H), 3.7 (s, 3H), 3.6.–3.8 (m, 2H), 3.1 (t, 2H), 2.95 (dd, 1H), 2.75 (t, 2H), 2.65 (dd, 1H), 1.45–1.65 (m, 4H), 1.3–1.4 (m, 2H).

12(a) methyl (R,S)-[8-[[(4-aminophenyl)methyl]amino]-carbonyl]-2,3,4,5-tetrahydro-3-oxo-4-(2-phenylethyl)-1H-1,4-benzodiazepine-2-acetate. $^1$H NMR (400 MHz, CDCl$_3$) δ8.15 (d, 2H), 7.45 (d, 2H), 7.15 (m, 3H), 7.0–7.1(m, 4H), 6.85 (d, 1H), 5.3 (d, 1H), 4.95 (t, 1H), 4.65 (d, 2H), 4.4 (b, 1H), 3.7 (s, 3H), 3.5–3.65 (m, 3H), 2.95 (dd, 1H), 2.75 (m, 2H), 2.6 (dd, 1H).

b) Using the procedure of Example 1(j), except substituting the compounds of Examples 47–48(a) for the compound of Example 1(i) gave the following title compounds 11(b) (R,S)-8-[[(5-aminopentyl)amino]carbonyl]-2,3,4,5-tetrahydro-3-oxo-4-(2-phenylethyl)-1H-1,4- benzodiazepine-2-acetic acid. $^1$H NMR (400 MHz, CD$_3$OD) δ7.05–7.25 (m, 5H), 7.0 (s, 1H), 6.95 (s, 2H), 5.45 (d, 1H), 5.1 (m, 1H), 3.9 (d, 1H), 3.8 (m, 1H), 3.7 (m, 1H), 3.4 (t, 2H), 2.95–2.85 (m, 3H), 2.7–2.8 (m, 2H), 2.55–2.65 (dd, 1H); MS(ES) m/e 453.4 [M+H]$^+$.

12(b) (R,S)-[8-[[(4-aminophenyl)methyl]amino]carbonyl]-2,3,4,5-tetrahydro-3-oxo-4-(2-phenylethyl)-1H-1,4-benzodiazepine-2-acetic acid $^1$H NMR (400 MHz, CD$_3$OD) δ7.3 (d, 2H), 7.15–7.25 (m, 6H), 7.1–7.0 (m, 6H), 5.5 (d, 1H), 5.1 (m, 1H), 4.5 (d, 2H), 3.9 (d, 1H), 3.8 (m, 1H), 3.7 (m, 1H), 2.95 (dd, 1H), 2.8 (m, 2H), 2.65 (dd, 1H); MS(ES) m/e 473.2 [M+H]$^+$.

Example 13

Preparation of (R,S)-8-[[[4-(Propyl)aminomethyl) phenyl]-amino]carbonyl]-2,3,4,5-tetrahydro-3-oxo-4-(2-phenylethyl)-1H-1,4-benzodiazepine-2-acetic Acid a) methyl (R,S)-8-[[[N-(t-butoxycarbonyl)-4-(propyl)aminomethyl]phenyl]amino]carbonyl]-2,3,4,5-tetrahydro-3-oxo-4-(2-phenylethyl)-1H-1,4-benzodiazepine-2-acetate Using the procedure of Preparation 25(c), except substituting the compound of Preparation 4(b) for 4-(methylamino)-(N-benzloxycarbonyl)benzamidine gave the title compound. $^1$H NMR (400 MHz, CDCl$_3$) δ7.6 (d, 2H), 7.0–7.3 (m, 9H), 6.9 (d, 1H), 5.3 (d, 1H), 5.0 (m, 1H), 4.4 (m, 2H), 4.35 (d, 1H), 3.7 (s, 3H), 3.6–3.7 (m, 2H), 3.0–3.2 (m, 2H), 2.95 (dd, 1H), 2.75 (m, 2H), 2.65 (dd, 1H), 1.5–1.7 (m, 9H), 0.9 (t, 3H)

b) methyl (R,S)-8-[[[4-(propyl)aminomethyl) phenyl]amino]-carbonyl]-2,3,4,5-tetrahydro-3-oxo-4-(2-phenylethyl)-1H-1,4-benzodiazepine-2-acetate The compound of Example 13(a) (350 mg, 0.56 mmol) was dissolved in a mixture of CH$_2$Cl$_2$ (25 mL) and TFA (5 mL). After 1 h, the mixture was concentrated to give the title compound.

c) (R,S)-8-[[[4-(propyl)aminomethyl)phenyl]amino] carbonyl]-2,3,4,5-tetrahydro-3-oxo-4-(2-phenylethyl)-1H-1,4-benzodiazepine-2-acetic Acid Using the procedure of Example 1(j), except substituting the compound of Example 13(b) for the compound of Example 1(i) gave the tide compound (142 mg, 40%). $^1$H NMR (400 MHz, CD$_3$OD) δ7.8 (d, 2H), 7.45 (d, 2H), 7.0–7.25 (m, 8H), 5.5 (d, 1H), 5.1 (m, 1H), 4.2 (s, 2H), 3.9 (d, 1H), 3.8 (m, 1H), 3.7 (m, 1H), 2.9–3.1(m, 3H), 2.75 (m, 2H), 2.65 (dd, 1H), 1.7 (m, 2H), 1.0 (t, 3H); MS(ES) m/e 515.2 [M+H]$^+$.

Examples 14–16 a) Using the procedure of Example 13(a)–(c), except substituting the compounds of Preparation 5 and 6(c) for the compound of Preparation 4(b), gave 14(a) (R,S)-8-[[[[4-[N-(t-butoxycarbonyl)-aminomethyl] phenyl]methyl]amino]carbonyl]-2,3,4,5-tetrahydro-3-oxo-4-(2-phenylethyl)-1H-1,4-benzodiazepine-2-acetic acid 15(a) (R,S)-8-[[[[3-[N-(t-butoxycarbonyl)-aminomethyl] phenyl]methyl]amino]carbonyl]-2,3,4,5-tetrahydro-3-oxo-4-(2-phenylethyl)-1H-1,4-benzodiazepine-2-acetic acid 16(a) (R,S)-8-[[[3-[4-[N-(t-butoxycarbonyl)-piperidinyl] propyl]amino]carbonyl]-2,3,4,5-tetrahydro-3-oxo-4-(2-phenylethyl)-1H-1,4-benzodiazepine-2-acetic acid b) Using the procedure of Example 13(b), except substituting the compounds Example 14–16(a) for the compound of Example 13(a), and purifying the residue with chromatography (Sephadex LH20) gave 14(b) (R,S)-8-[[[[4-(aminomethyl)phenyl]methyl]amino]-carbonyl]-2,3,4,5-tetrahydro-3-oxo-4-(2-phenylethyl)-1H-1,4-benzodiazepine-2-acetic acid. MS(ES) m/e 487.0 [M+H]$^+$. Anal. (C$_{28}$H$_{30}$N$_4$O$_4$.1.5 TFA) calcd: C, 56.62; H, 4.83; N, 8.52. found: C, 57.63; H, 5.24; N, 8.82.

15(b) (R,S)-8-[[[[3-(aminomethyl)phenyl]methyl]amino]-carbonyl]-2,3,4,5-tetrahydro-3-oxo-4-(2-phenylethyl)-1H-1,4-benzodiazepine-2-acetic acid. MS(ES) m/e 487.0 [M+H]$^+$; HPLC RT 15.9 min (PRP-1®, 4.6×250 mm, 1.5 mL/min, 25% AN/W-TFA, UV detection at 220 and 250 nm). Anal. (C$_{28}$H$_{30}$N$_4$O$_4$.1.5 TFA) calcd: C, 56.62; H, 4.83; N, 8.52. found: C, 57.28; H, 5.18; N, 8.72.

16(b) (R,S)-8-[[[3-[4-piperidinyl]propyl]amino]carbonyl]-2,3,4,5-tetrahydro-3-oxo-4-(2-phenylethyl)-1H-1,4-benzodiazepine-2-acetic acid. $^1$H NMR (250 MHz, DMSO-d6) δ7.40–6.70 (m, 8H), 5.38 (dd, 1H), 4.99 (m, 1H), 4.29 (s, 1H), 4.00 (dd, 1H), 3.70–2.90 (m), 2.90–2.20 (m), 1.72 (d, 2H), 1.48 (m, 3H), 1.17 (m, 4H); TLC R$_f$ 4.90 (silica gel, 3:1:1 n-BuOH:HOAc:water); HPLC RT 9.82 min (PRP-1®, 4.6×250 mm, 20–50% AN/W-TFA, gradient 20 minutes @1.5 mL/min, UV detection at 220 and 250 nm); MS(ES) m/e 493.2 [M+H]$^+$; Anal. (C$_{28}$H$_{36}$N$_4$O$_4$.HOAC.2H$_2$O) calcd: C, 61.21; H, 7.53; N, 9.52. found: C, 61.56; H, 7.17; N, 9.91.

Examples 17–21 a) Using the procedure of Preparation 25(c), except substituting 4-(aminomethyl)pyridine, 4-(2-pyridyl) butanamine, N-methyl-4-(3-pyridyl)butanamine, 2-(1H-imidazol-1-yl)ethanamine (Syn. Comm., 21, 535 (1991)) and 3-(1H-imidazol-1-yl)propanamine for 4-(methylamino)-(N-benzyloxycarbonyl)] benzamidine and substituting triethylamine for pyridine, gave 17(a) methyl (R,S)-2,3,4,5-tetrahydro-3-oxo-4-(2-phenylethyl)-8-[[[4-(pyridyl)methyl]amino]carbonyl]-1H-1,4-benzodiazepine-2-acetate 18(a) methyl (R,S)-2,3,4,5-tetrahydro-3-oxo-4-(2-phenylethyl)-8-[[[4-(2-pyridyl)butyl]amino]carbonyl]-1H-1,4-benzodiazepine-2-acetate 19(a) methyl (R,S)-2,3,4,5-tetrahydro-3-oxo-4-(2-phenylethyl)-8-[[[4-(3-pyridyl)butyl]methylamino] carbonyl]-1H-1,4-benzodiazepine-2-acetate 20(a) methyl (R,S)-2,3,4,5-tetrahydro-8-[[[2-(1H-imidazol-1-yl)ethyl]amino]carbonyl]-3-oxo-4-(2-phenylethyl)-1H-1,4-benzodiazepine-2-acetate. MS(ES) m/e 476.2 [M+H]$^+$, $^1$NMR (400 MHz, MeOD) δ2.66–2.76 (3H, dd+t), 2.93 (1H, dd), 3.58–3.70 (7H, m), 3.92 (1H, d), 4.30 (2H, t), 5.06 (1H, m), 5.37 (1H, d), 6.90–7.25 (10H, m), 7.92(1H, s).

21(a) methyl (R,S)-2,3,4,5-tetrahydro-8-[[[3-(1H-imidazol-1-yl)propyl]amino]carbonyl]-3-oxo-4-(2-phenylethyl)-1H-1,4-benzodiazepine-2-acetate. MS(ES) m/e 490.2 [M+H]$^+$, $^1$NMR (400 MHz, MeOD) δ2.08 (2H, m), 2.62–2.77 (3H, dd+t), 2.93 (1H, dd), 3.34 (2H, t), 3.61 (1H, m), 3.67–3.77 (4H, s+m), 3.86 (1H, d), 4.08 (2H, t), 5.08 (1H, m), 5.39 (1H, d), 6.90–7.23 (11H, m), 7.75 (1H, bs).

b) Using the procedure of Example 1(j), except substituting the compounds of Examples 17–21(a) for the compound of Example 1(i), gave the title compounds 17(b) (R,S)-2,3,4,5-tetrahydro-3-oxo-4-(2-phenylethyl)-8-[[[4-(pyridyl)methyl]amino]carbonyl]-1H-1,4-benzodiazepine-2-acetic acid: HPLC RT 8.2 min (YMC ODS-AQ, 50×250 mm, 80 mL/min, 30% AN/W-TFA, UV detection at 220 nm); MS(ES) m/e 459.2 [M+H]$^+$; $^1$NMR (400 MHz, DMSO) δ2.55 (1H, dd), 2.67 (2H, t), 2.78 (1H, dd, J$_1$=9 Hz, J$_2$=17 Hz), 3.58 (2H, m), 4.00 (1H, d, J=17 Hz), 4.65 (2H, d, J=6 Hz), 5.03 (1H, m), 5.44 (1H, d, J=17 Hz), 7.00–7.29 (10H, m), 7.80 (2H, d, J=5 Hz), 8.78 (1H, bs), 9.10 (1H, t, J$_1$=6 Hz, J$_2$=12 Hz). Anal. (C$_{26}$H$_{26}$N$_4$O$_4$.1.5C$_2$HF$_3$O$_2$.0.5 H$_2$O) calcd: C, 54.55; H, 4.50; N, 8.77. found C, 54.32; H, 4.61; N, 8.89.

18(b) (R,S)-2,3,4,5-tetrahydro-3-oxo-4-(2-phenylethyl)-8-[[[4-(2-pyridyl)butyl]amino]carbonyl]-1H-1,4-benzodiazepine-2-acetic acid. HPLC RT 10.5 min (YMC ODS-AQ, 50×250 mm, 80 mL/min, 25% AN/W-TFA, UV detection at 220 nm); MS(ES) m/e 501.2 [M+H]$^+$; $^1$NMR (400 MHz, DMSO) δ1.53 (2H, t), 1.75 (2H, t), 2.55 (1H, dd), 2.68 (2H, t) 2.78 (1H, dd), 2.99 (2H, t), 3.27 (2H, m), 3.59 (2H, m), 4.01 (1H, d), 5.00 (1H, t), 5.40 (1H, d), 6.90 (1H, d), 7.06 (2H, m), 7.20 (3H, m), 7.28 (2H, m), 7.77 (1H, t), 7.85 (1H, d), 8.28 (1H, t), 8.35 (1H, t), 8.74 (1H, d). Anal. (C$_{29}$H$_{32}$N$_4$O$_4$.1.4C$_2$HO$_2$F$_3$.H$_2$O) calcd: C, 55.73; H, 5.19; N, 8.12. found: C, 55.61; H, 5.08; N, 8.21.

19(b) (R,S)-2,3,4,5-tetrahydro-3-oxo-4-(2-phenylethyl)-8-[[[4-(3-pyridyl)butyl]methylamino]carbonyl]-1H-1,4-benzodiazepine-2-acetic acid. HPLC RT 12.3 min (YMC ODS-AQ, 50×250 mm, 80 mL/min, 30% AN/W-TFA, UV detection at 220 nm); MS(ES) m/e 515.2 [M+H]$^+$; $^1$NMR (400 MHz, DMSO) δ1.31–1.70 (4H, m), 2.40–2.92 (m), 3.21 (1H, m), 3.40 (1H, m), 3.55 (2H, m), 3.98 (1H, d), 5.01 (1H, m), 5.38 (1H, d), 6.40–6.55 (2H, m), 6.92–7.26 (6H, m), 7.77–7.94 (1H, m), 8.10–8.34 (m), 8.54–8.81 (2H, m). Anal. (C$_{30}$H$_{34}$N$_4$O$_4$.C$_4$H$_2$F$_6$O$_4$) calcd: C, 54.99; H, 4.89; N, 7.54. found: C, 54.86; H, 5.24; N, 7.81.

20(b) (R,S)-2,3,4,5-tetrahydro-8-[[[2-(1H-imidazol-1-yl)ethyl]amino]carbonyl]-3-oxo-4-(2-phenylethyl)-1H-1,4-benzodiazepine-2-acetic acid. HPLC RT 6.8 min (YMC ODS-AQ, 50×250 nm, 80 mL/min, 30% AN/W-TFA, UV detection at 220 nm); MS(ES) m/e 462.2 [M+H]$^+$; $^1$NMR (400 MHz, DMSO-d) δ2.55 (1H, dd), 2.66 (2H, t), 2.78 (1H, dd), 3.55 (2H, t), 3.65 (2H, t), 4.00 (1H, d), 4.35 (2H, t), 5.00 (1H, m), 5.38 (1H, d), 6.00 (1H, bs), 6.87 (1H, d), 7.00 (1H, s), 7.07 (1H, d), 7.13–7.28 (5H, m), 7.63 (1H, s), 7.73 (1H, s), 8.45 (1H, t), 9.09 (1H, s). Anal. (C$_{25}$H$_{27}$N$_5$O$_4$.1.5(C$_2$HF$_3$O$_2$)H$_2$O) calcd: C, 51.69; H, 4.73; N, 10.79. found: C, 51.46; H, 4.66; N, 10.70.

21(b) (R,S)-2,3,4,5-tetrahydro-8-[[[3-(1H-imidazol-1-yl)propyl]amino]carbonyl]-3-oxo-4-(2-phenylethyl)-1H-1,4-benzodiazepine-2-acetic acid. HPLC RT 8.6 min (YMC ODS-AQ, 50×250 nm, 80 ml/min, 30% AN/W-TFA, UV detection at 220 nm); MS(ES) m/e 476.2 [M+H]$^+$; $^1$NMR (400 MHz, DMSO-d) δ2.06 (4H, bt), 2.51 (1H, dd), 2.66 (4H, bt), 2.77 (1H, dd), 3.22 (4H, m), 3.58 (4H, bt), 4.00 (1H, d), 4.20 (4H, t), 5.00 (1H, m), 5.40 (1H, d), 6.92 (1H, d), 7.05 (2H, m), 7.15 (2H, m), 7.23 (2H, m), 7.68 (1H, s), 7.80 (1H, s), 8.37 (1H, t), 9.12 (1H, s); Anal. (C$_{26}$H$_{29}$N$_5$O$_4$.1.75C$_2$HF$_3$O$_2$) calcd: C, 52.48; H, 4.59; N, 10.37. found: C, 52.61; H, 4.98; N, 10.38.

Example 22–23 a) Using the procedure of Example 53(a) and 38(f), except substituting the compounds of Preparation 7 (a) and (b) for 4-(aminomethyl)pyridine, and the procedure of Example 2(f), except substituting palladium hydroxide for palladium on carbon, gave 22(a) methyl (R,S)-2,3,4,5-tetrahydro-3-oxo-4-(2-phenylethyl)-8-[[[2-(1-piperazinyl)ethyl]amino]carbonyl]-1H-1,4-benzodiazepine-2-acetate. HPLC RT 5.3 min (YMC ODS-AQ, 6×250 mm, 1.5 mL/min, 30% AN/W-TFA, UV detection at 220 nm).

23(a) methyl (R,S)-2,3,4,5-tetrahydro-3-oxo-4-(2-phenylethyl)-8-[[[2-(1-piperazinyl)ethyl]methylamino]carbonyl]-1H-1,4-benzodiazepine-2-acetate.

b) Using the procedure of Example 1(j), except substituting the compounds of Example 22(a) and 23(a) for the compound of Example 1(i) gave 22(b)(1) (R,S)-2,3,4,5-tetrahydro-3-oxo-4-(2-phenylethyl)-8-[[[2-(1-piperazinyl)ethyl]amino]carbonyl]-1H-1,4-benzodiazepine-2-acetic acid. HPLC RT 7.4 min (YMC ODS-AQ, 50×250 mm, 80 mL/min, 22% AN/W-TFA, UV detection at 220 nm); MS(ES) m/e 480.2 [M+H]$^+$; $^1$NMR (400 MHz, DMSO-d) δ2.48–2.60 (1H, dd), 2.70 (2H, t), 2.82 (1H, dd), 3.20 (2H, bs), 3.89 (8H, bs), 3.58 (4H, m), 4.05 (1H, d), 5.00 (1H, t), 5.40 (1H, d), 6.97 (1H, d), 7.11 (2H, m), 7.18 (3H, m), 7.26 (1H, m), 8.50 (1H, bs). Anal. (C$_{26}$H$_{33}$N$_5$O$_4$.2.5(C$_2$HF$_3$O$_2$).2(H$_2$O)) calcd: C, 46.39; H, 4.96; N, 8.73. found: C, 46.35; H, 4.88; N, 8.90.

23(b) (R,S)-2,3,4,5-tetrahydro-3-oxo-4-(2-phenylethyl)-8-[[[2-(1-piperazinyl)ethyl]methylamino]carbonyl]-1H-1,4-benzodiazepine-2-acetic acid. HPLC RT 9.8 min (YMC ODS-AQ, 50×250 nm, 80 mL/min, 25% AN/W-TFA, UV detection at 220 nm); MS(ES) m/e 494.2 [M+H]$^+$; $^1$NMR (400 MHz, DMSO-d) δ2.52 (1H, dd), 2.68 (2H, m), 2.75 (1H, dd), 2.92 (3H, s), 2.94–3.30 (8H, m), 3.50–4.10 (7H, m), 5.03 (1H, m), 5.40 (1H, d), 6.49 (1H, d), 6.57 (1H, s), 7.02 (1H, d), 7.10–7.25 (5H, m); Anal.(C$_{27}$H$_{35}$N$_5$O$_4$.2.75 C$_2$HF$_3$O$_2$) calcd: C, 48.36; H, 4.75; N, 8.68. found: C, 48.23; H, 4.86; N, 8.61.

Examples 24–25 a) Using the procedure of Preparation 25(c) and the procedure of 13(b), except substituting the compounds of Preparation 8 and 9 for 4-(methylamino)-N-benzyloxycarbonyl)benzamidine and deleting pyridine, gave 24(a) methyl (R,S)-8-[[[6-aminohexyl]amino]carbonyl]-2,3,4,5-tetrahydro-3-oxo-4-(2-phenylethyl)-1H-1,4-benzodiazepine-2-acetate. TLC Rf 0.35 (Kieselgel 60 F$_{254}$, 15:3:2 2-butanol:formic acid:water); MS(ES) m/e 467.

25(a) methyl (R,S)-8-[[[6-aminobutyl]amino]carbonyl]-2,3,4,5-tetrahydro-3-oxo-4-(2-phenylethyl)-1H-1,4-benzodiazepine-2-acetate. MS(ES) m/e 453.2.

b) Using the procedure of Example 1(j), except substituting the compounds of Examples 24(a) and 25(a) for the compound 1(i) and substituting lithium hydroxide for sodium hydroxide, gave 24(b) (R,S)-8-[[[6-aminohexyl]amino]carbonyl]-2,3,4,5-tetrahydro-3-oxo-4-(2-phenylethyl)-1H-1,4-benzodiazepine-2-acetic acid. MS(ES) m/e 467. Anal. (C26H34N4O4.1.4 C$_2$HO$_2$F$_3$) calcd: C, 55.13; H, 5.55; N, 8.8. found: C, 55.24; H, 5.70; N, 8.9.

25(b) (R,S)-8-[[[4-aminobutyl]amino]carbonyl]-2,3,4,5-tetrahydro-3-oxo-4-(2-phenylethyl)-1H-1,4-benzodiazepine-2-acetic acid. MS(ES) m/e 439.2. Anal. (C$_{24}$H$_{30}$N$_4$O$_4$.1.5 H$_2$O.0.1 HCl) calcd: C, 61.03; H, 7.02; N, 11.62; Cl, 1.10. found: C, 61.44; H, 7.11; N, 11.94; Cl, 0.76.

Example 26

Preparation of (R,S)-2,3,4,5-tetrahydro-3-oxo-4-(2-phenylethyl)-8-[[[3-(4-pyrazolyl)propyl]amino]carbonyl]-1H-1,4-benzodiazepine-2-acetic acid a) methyl (R,S)-2,3,4,5-tetrahydro-3-oxo-4-(2-phenylethyl)-8-[[[3-(4-pyrazolyl)propyl]amino]carbonyl]-1H-1,4-benzodiazepine-2-acetate The compound of Preparation 24(e) (776 mg, 2.0 mmol) dissolved in DMF (30 mL) was treated with 3,3-DDC (458 mg, 2.2 mmol), 1-HOBT (285 mg, 2.1 mmol) and adjusted to pH 7 with triethylamine. The mixture was treated with 2-(4-pyrazolyl)ethanamine dihydrochloride (300 mg, 2.4 mmol) (J. Am. Chem. Soc., 75, 4048 (1953)), stirred at RT for 48 h, concentrated and the residue was purified by flash chromatography (silica gel, step gradient, chloroform to 95:5 chloroform:methanol) to yield the title compound (1 g, 90%). MS ES [M+H]$^+$=490; $^1$H NMR (250 MHz) δ7.44 (s, 2H), 7.29–7.19 (m, 5H), 7.18–7.09 (m, 3H), 5.30 (dd, 2H J=7.5 Hz), 4.98–4.95 (m, 1H), 3.73 (s, 3H), 3.70–3.60 (m, 3H), 3.43 (d, 2H, J=7.5 Hz), 3.00 (dd, 2H, J=7.0 Hz) 2.77–2.65 (m, 2H), 2.63 (t, 2H, J=7 Hz),1.88 (p, 2H, J=7.5).

b) (R,S)-2,3,4,5-tetrahydro-3-oxo-4-(2-phenylethyl)-8-[[[3-(4-pyrazolyl)propyl]amino]carbonyl]-1H-1,4-benzodiazepine-2-acetic acid Using the procedure of Example 1(j), except substituting the compound of Example 26(a) for the compound of Example 1(i), gave the title compound. MS(ES) 476 [M+H]$^+$; $^1$H NMR (400 MHz) δ7.66 (s, 2H), 7.21–7.13 (m, 5H), 7.00–6.96 (m, 3H), 5.47 (d, 1H, J=16 Hz), 5.10 (m, 1H), 3.70 (d, 1H, J=16 Hz), 3.80–3.71 (m, 1H), 3.70–3.60 (m, 1H), 3.32 (t, 2H, J=1.6 Hz), 2.95 (dd, 2H, J=8 Hz), 2.75 (m, 2H), 2.66 (t, 2H, J=8 Hz), 1.89 (p, 2H, J=8 Hz).

Examples 27–29 a) Using the procedure of Example 26(a), except substituting histamine, 2-(1-methyl-1H-imidazol-4-yl)ethanamine and 2-(1-methyl-1H-imidazol-5-yl)ethanamine for 2-(4-pyrazolyl)ethanamine dihydrochloride and substituting 1-(3-dimethylaminopropyl)-3-ethylcarbodiimide hydrochloride for 1,3-dicyclohexylcarbodiimide gave 27(a) methyl (R,S)-2,3,4,5-tetrahydro-8-[[[2-(1H-imidazol-4-yl)ethyl]amino]carbonyl]-3-oxo-4-(2-phenylethyl)-1H-1,4-benzodiazepine-2-acetate
28(a) methyl (R,S)-2,3,4,5-tetrahydro-8-[[[2-(1-methyl-1H-imidazol-4-yl)ethyl]amino]carbonyl]-3-oxo-4-(2-phenylethyl)-1H-1,4-benzodiazepine-2-acetate
29(a) methyl (R,S)-2,3,4,5-tetrahydro-8-[[[2-(1-methyl-1H-imidazol-5-yl)ethyl]amino]carbonyl]-3-oxo-4-(2-phenylethyl)-1H-1,4-benzodiazepine-2-acetate b) Using the procedure of Example 1(j), except substituting the compounds of Examples 27–29(a) for the compound of Example 1(i), gave 27(b) (R,S)-2,3,4,5-tetrahydro-8-[[[2-(1H-imidazol-4-yl)ethyl]amino]carbonyl]-3-oxo-4-(2-phenylethyl)-1H-1,4-benzodiazepine-2-acetic acid. MS(ES) m/e 462.2 [M+H]$^+$; HPLC k' 3.2 (YMC ODS AQ, 22% AN/W-TFA, UV detection at 220 nm); TLC R$_f$ 0.85 (silica gel, 15:5:10:10 pyridine:acetic acid:butanol:water). Anal. (C$_{25}$H$_{27}$N$_5$O$_4$·1.25 H$_2$O) calcd: C, 62.03; H, 6,14; N, 14.47. found: C, 61.89; H, 6.37; N, 14.20.

28(b) (R,S)-2,3,4,5-tetrahydro-8-[[[2-(1-methyl-1H-imidazol-4-yl)ethyl]amino]carbonyl]-3-oxo-4-(2-phenylethyl)-1H-1,4-benzodiazepine-2-acetic acid. MS(ES) m/e 476 [M+H]$^+$; HPLC k' 2.03 (YMC ODS AQ, 25% AN/W-TFA, UV detection at 220 nm); TLC Rf 0.90 (silica gel, 15:5:10:10 pyridine:acetic acid:butanol:water); Anal. (C$_{26}$H$_{29}$N$_5$O$_4$·3.5 HCl·0.5 H$_2$O) calcd: C, 51.01; H, 5.51; N, 11.44. found: C, 50.96; H, 5.13; N, 11.72.

29(b) (R,S)-2,3,4,5-tetrahydro-8-[[[2-(1-methyl-1H-imidazol-5-yl)ethyl]amino]carbonyl]-3-oxo-4-(2-phenylethyl)-1H-1,4-benzodiazepine-2-acetic acid. MS(ES) m/e 476 [M+H]$^+$; HPLC k' 2.03 (YMC ODS AQ, 25% AN/W-TFA, UV detection at 220 nm); TLC R$_f$ 0.90 (silica gel, 15:5:10:10 pyridine:acetic acid:butanol:water); Anal. (C$_{26}$H$_{29}$N$_5$O$_4$·.5 HCl·0.5 H$_2$O) calcd: C, 46.83; H, 5.29; N, 10.50. found: C, 47.20; H, 5.70; N, 10.47.

Example 30

Preparation of (R,S)-2,3,4,5-tetrahydro-3-oxo-4-(2-phenylethyl)-8-[[[2-(2-pyrazinyl)ethyl]amino]carbonyl]-1H-1,4-benzodiazepine-2-acetic acid a) methyl (R,S)-2,3,4,5-tetrahydro-3-oxo-4-(2-phenylethyl)-8-[[[2-(2-pyrazinyl)ethyl]amino]carbonyl]-1H-1,4-benzodiazepine-2-acetate Using the procedure of Example 26(a), except substituting the compound of Preparation 10(b) for histamine and substituting diisopropylethylamine for triethylamine gave the title compound. MS(ES) m/e [M+H]$^+$ 488; $^1$H NMR (250 MHz) δ8.40–8.55 (m, 3H), 7.10–7.28 (m, 5H), 6.81–6.99 (m, 3H), 5.46 (d, 1H), 5.14 (m, 1H), 3.56–3.80 (m, 6H), 3.19 (t, 2H), 2.90 (dd, 1H), 2.72–2.85 (m, 4H), 2.61 (dd, 1H).

b) (R,S)-2,3,4,5-tetrahydro-3-oxo-4-(2-phenylethyl)-8-[[[2-(2-pyrazinyl)ethyl]amino]carbonyl]-1H-1,4-benzodiazepine-2-acetic acid Using the procedure of Example 1(j), except substituting the compound of Example 30(a) for the compound of Example 1(i), gave the title compound. MS(ES) m/e [M+H]+ 474; $^1$H NMR (400 MHz) δ8.40–8.70 (m, 3H), 7.10–7.31 (m, 5H), 6.88 (d, 1H), 6.70 (d, 1H), 6.63 (m, 1H), 5.37 (d, 1H), 5.06 (m, 1H), 3.57–3.81 (m, 3H), 3.18 (t, 2H), 2.74–2.97 (m, 5H), 2.61 (dd, 1H).

Example 31

Preparation of (R,S)-7-[[[4-(aminomethyl)phenyl]carbonyl]-amino]-2,3,4,5-tetrahydro-1-methyl-3-oxo-4-(2-phenylethyl)-1H-1,4-benzodiazepine-2-acetic Acid a) benzyl (R,S)-7-[[[4-[N-(t-butoxycarbonyl)aminomethyl]phenyl]carbonyl]amino]-2,3,4,5-tetrahydro-1-methyl-3-oxo-4-(2-phenylethyl)-1H-1,4-benzodiazepine-2-acetate Using the procedure of 30(a), except substituting the compound of Preparation 23(g) for the compound of Preparation 24(e) and substituting 4-[(t-butoxycarbonyl)(aminomethyl)]benzoic acid for the compound of Preparation 10(b) and substituting CH$_2$Cl$_2$ for DMF, yielded the title compound (100 mg, 38%). $^1$H NMR (400 MHz, CDCl$_3$)

δ1.45 (9H, s), 2.54 (3H, s), 2.61 (1H, dd), 2.74 (2H, t), 3.04 (1H, dd), 3.50 (1H, dt), 3.72 (1H, d), 3.88 (1H, dt), 4.28 (2H, d), 4.66 (1H, m), 4.99 (1H, d), 5.08 (2H, ABq), 5.40 (1H, t), 6.72 (1H, d), 7.00 (2H, d), 7.05–7.19 (3H, 2t), 7.20–7.48 (5H, m), 7.80 (1H, d), 8.70 (1H, s).

b) (R,S)-7-[[[(4-aminomethyl)phenyl]carbonyl] amino]-2,3,4,5-tetrahydro-1-methyl-3-oxo-4-(2-phenylethyl)-1H-1,4-benzodiazepine-2-acetic acid A solution of the compound of Example 31(a) (100 mg, 0.2 mmol) in $CH_2Cl_2$ (15 mL) was treated with 4M hydrogen chloride in dioxane (0.5 mL, 2.0 mmol) and stirred at RT for 4.5 h. The mixture was concentrated and the residue was suspended in a mixture of ethyl acetate (15 mL), 3N hydrochloric acid (2 mL) and 4M hydrogen chloride in dioxane (1 mL). The suspension was added to an argon purged Parr bottle containing palladium hydroxide (100 mg) and hydrogenated (50 psi) for 24 h. The mixture was filtered and concentrated to yield the title compound as a white powder (50 mg, 52%). HPLC RT 8.0 min (YMC ODS-AQ, 50×250 mm, 80 mL/min, 27.5% AN/W-TFA, UV detection at 220 nm); MS(ES) m/e 487.2 [M+H]$^+$; $^1$NMR (400 MHz, DMSO-$d_6$) δ2.70 (1H, dd), 2.82 (1H, dd), 3.88 (2H, dt), 4.08 (1H, d), 4.13 (2H, s), 4.68 (1H, m), 5.13 (1H, d), 6.94 (1H, d), 7.02–7.20 (4H, m), 7.48–7.62 (3H, m), 8.01 (2H, d), 8.25 (2H, m); Anal. ($C_{28}H_{30}N_4O_4 \cdot 1.5(C_2HF_3O_2) \cdot 1.4$ ($H_2O$)) calcd: C, 54.57; H, 5.06; N, 8.21. found: C, 54.95; H, 5.11; N, 7.81.

Example 32

Preparation of (R,S)-8-[[[2-(4-pyridyl)ethyl]methylamino]carbonyl]-2,3,4,5-tetrahydro-3-oxo-4-(2-phenylethyl)-1H-1,4-benzodiazepine-2-acetic acid a) methyl (R,S)-8-[[[2-(4-pyridyl)ethyl] methylamino]carbonyl]-2,3,4,5-tetrahydro-3-oxo-4-(2-phenylethyl)-1H-1,4-benzodiazepine-2-acetic acid Using the procedure of Example 27(a), except substituting N-methyl-2-(4-pyridyl)ethanamine for histamine and deleting the diisopropylethylamine, gave the title compound. HPLC RT 16.6 min (YMC ODS-AQ, 6×250 mm, 1.5 mL/min, gradient, A:acetonitrile B:water-0.1% trifluoroacetic acid, 10–80% A during 20 min, UV detection at 220 nm; MS(ES) m/e 487 [M+H]$^+$.

b) (R,S)-8-[[[2-(4-pyridyl)ethyl]methylamino] carbonyl]-2,3,4,5-tetrahydro-3-oxo-4-(2-phenylethyl)-1H-1,4-benzodiazepine-2-acetic Acid Using the procedure of Example 1(j), except substituting the compound of Example 32(a) for the compound of Example 1(i), gave the title compound. $^1$H NMR(DMSO $d_6$/TFA, 360 MHz) δ8.8 (br, 2H), 8.0 (br, 1H), 7.7 (br, 1H), 7.15 (m, 5H), 6.0 (br, 1H), 6.3 (br, 2H), 5.35 (d, 1H), 5.0 (m, 1H), 3.95 (d, 1H), 3.75 (br, 2H), 3.6 (m, 3H), 3.15 (br, 2H), 2.9 (br, 3H), 2.75 (m, 1H), 2.65 (m, 2H); MS(ES) m/e 487 [M+H]$^+$.

Example 33

Preparation of (R,S)-8-[[[4-(Dimethylamino)butyl] amino]-carbonyl]-2,3,4,5-tetrahydro-3-oxo-4-(2-phenylethyl)-1H-1,4-benzodiazepine-2-acetic acid a) methyl (R,S)-8-[[[4-(Dimethylamino)butyl] amino]carbonyl]-2,3,4,5-tetrahydro-3-oxo-4-(2-phenylethyl)-1H-1,4-benzodiazepine-2-acetate Using the procedure of Example 32(a), except substituting 4-(dimethylamino)butanamine for N-methyl-2-(4-pyridyl)ethanamine and except substituting dimethylaminopyridine for 1-hydroxybenzotriazole, gave the title compound. MS(ES) m/e 481 [M+H]$^+$; $^1$H NMR (250 MHz) δ7.44–7.50 (m, 1H), 6.98–7.28 (m, 7H), 6.81 (d, 1H), 5.27 (d, 1H), 5.00 (m, 1H), 3.56–3.80 (m, 6H), 3.44 (q, 2H), 3.00 (dd, 1H), 2.63–2.85 (m, 3H), 2.69 (dd, 1H), 2.48–2.52 (m, 2H), 2.32 (s, 6H), 1.66–1.77 (m, 4H).

b) (R,S)-8-[[[4-(Dimethylamino)butyl]amino] carbonyl]-2,3,4,5-tetrahydro-3-oxo-4-(2-phenylethyl)-1H-1,4-benzodiazepine-2-acetic acid Using the procedure of Example 1(j), except substituting the compound of Example 33(a) for the compound of Example 1(i), gave the title compound. MS(ES) m/e 467 [M+H]$^+$; $^1$H NMR (400 MHz) δ7.00–7.31 (m, 6H), 6.98 (d, 1H), 6.84 (d, 1H), 5.34 (d, 1H), 5.00 (m, 1H), 3.57–3.81 (m, 3H), 3.42 (q, 2H), 2.96 (dd, 1H), 2.62–2.80 (m, 3H), 2.50 (q, 2H), 2.34 (s, 6H), 1.65–1.74 (m, 4H).

Example 34

Preparation (R,S)-2,3,4,5-tetrahydro-3-oxo-4-(2-phenylethyl)-8-[[[2-(4-piperidinyl)ethyl]amino] carbonyl]-1H-1,4-benzodiazepine-2-acetic acid a) methyl (R,S)-2,3,4,5-tetrahydro-3-oxo-4-(2-phenylethyl)-8-[[[2-(4-piperidinyl)ethyl]amino] carbonyl]-1H-1,4-benzodiazepine-2-acetate A solution of the compound of Example 9(a) (0.45 g, 1 mmol) and 0.6N hydrochloric acid (3.1 mL) in methanol was treated with platinum oxide (90 mg) and hydrogenated (45 psi) for 5 h. The mixture was degassed and platinum oxide (74 mg) was added and the mixture was hydrogenated (45 psi) for 16 h, filtered and concentrated to yield the title compound. MS(ES) m/e 479.2 [M+H]$^+$.

b) (R,S)-2,3,4,5-tetrahydro-3-oxo-4-(2-phenylethyl)-8-[[[2-(4-piperidinyl)ethyl]amino]carbonyl]-1H-1,4-benzodiazepine-2-acetic acid bis(trifluoroacetate)

Using the procedure of Example 1(j), except substituting the compound of Example 34(a) for the compound 1(i), gave the title compound. HPLC RT 16.1 min (YMC ODS-AQ, 6×250 mm, 1.5 mL/min, gradient, A:acetonitrile B:water-0.1% trifluoracetic acid, 10–80% A during 20 min, UV detection at 220 nm); $^1$H NMR(DMSO $d_6$/TFA, 360 MHz) δ8.5 (br, 1H), 8.3 (m, 2H), 7.3 (m, 2H), 7.15 (m, 2H), 7.05 (m, 2H), 6.9 (d, 1H, 5.39 (d, 1H), 5.0 (m, 1H), 4.0 (d, 1H), 3.55 (m, 2H), 3.25 (d, 3H), 2.55–2.8 (m, 3H), 1.2–1.8 (m, 9H); MS(ES) m/e 479 [M+H]$^+$.

Example 35

Preparation (R,S)-2,3,4,5-tetrahydro-3-oxo-4-(2-phenylethyl)-8-[[[2-(4-piperidinyl)ethyl] methylamino]carbonyl]-1H-1,4-benzodiazepine-2-acetic acid a) methyl (R,S)-2,3,4,5-tetrahydro-3-oxo-4-(2-phenylethyl)-8-[[[2-(4-piperidinyl)ethyl] methylamino]carbonyl]-1H-1,4-benzodiazepine-2-acetate A solution of the compound of Example 32(a) (0.1 g, 0.2 mmol) and 0.6N hydrochloric acid (0.6 mL) in methanol (30 mL) was treated with platinum oxide (5 mg) and hydrogenated (45 psi) overnight. The mixture was filtered and concentrated to give the title compound. MS(ES) m/e 493 [M+H]$^+$.

b) (R,S)-2,3,4,5-tetrahydro-3-oxo-4-(2-phenylethyl)-8-[[[2-(4-piperidinyl)ethyl]methylamino]carbonyl]-1H-1,4-benzodiazepine-2-acetic Acid Bis (trifluoroacetate)

Using the procedure of Example 1(j), except substituting the compound of Example 35(a) for the compound 1(i), gave the title compound (130 mg, 92%). HPLC RT 16.6 min (YMC ODS-AQ, 6×250 mm, 1.5 mL/min, gradient, A:acetonitrile B:water-0.1% TFA, 10–80% A during 20 min, UV detections at 220 nm); $^1$H NMR(DMSO d$_6$/TFA, 360 MHz) δ8.5 (br, 1H), 8.1 (br, 1H), 7.2 (m, 5H), 70 (d, 1H), 6.5 (s, 1H), 6.45 (d, 1H), 5.4 (d, 1H), 4,95 (m, 1H), 3.95 (d, 1H), 3.6 (br, 2H), 3.44 (br, 1H), 3.09–3.25 (br, 4H), 2.69–2.85 (m, 6H), 1.85 (br, 1H), 1.1–1.86 (m, 8H); MS(ES) m/e 493 [M+H]$^+$.

Example 36

Preparation (R,S)-2,3,4,5-tetrahydro-3-oxo-4-[2-(cyclohexyl)-ethyl]-8-[[[2-(4-piperidinyl)ethyl]methylamino]carbonyl]-1H-1,4-benzodiazeine-2-acetic acid a) methyl (R,S)-2,3,4,5-tetrahydro-3-oxo-4-[2-(cyclohexyl)-ethyl]-8-[[[2-(4-pyridyl)ethyl]methylamino]carbonyl]-1H-1,4-benzodiazepine-2-acetate A solution of the compound of Example 32(a) (0.6 g, 1.2 mmol) and 0.6N hydrochloric acid (4.0 mL) in methanol (50 mL) was treated with platinum oxide (120 mg) and hydrogenated (45 psi) and the mixture was filtered and concentrated to give the title compound. HPLC RT 22 min (YMC ODS-AQ, 6×250 mm, 1.5 mL/min, gradient, A:acetonitrile B:water-0.1% TFA, 10–80% A during 20 min, UV detections at 220 nm; MS(ES) m/e 512 [M+H]$^+$.

b) (R,S)-2,3,4,5-tetrahydro-3-oxo-4-[2-(cyclohexyl)ethyl]-8-[[[2-(4-pyridyl)ethyl]methylamino]carbonyl]-1H-1,4-benzodiazepine-2-acetic acid bis (trifluoroacetate)

Using the procedure of Example 1(j), except substituting the compound of Example 36(a) for the compound 1(i), gave the title compound (35 mg, 4%). HPLC RT 19.8 min (YMC ODS-AQ, 6×250 mm, 1.5 mL/min, gradient, A:acetonitrile B:water-0.1% trifluoroacetic acid, 10–80% A during 20 min, UV detection at 220 nm); $^1$H NMR(DMSO d$_6$/TFA, 360 MHz) δ8.5 (br, 1H), 8.15 (br, 1H), 7.0 (d, 1H), 6.5 (s, 1H), 6.4 (d, 1H), 5.4 (d, 1H), 4.95 (m, 1H), 3.89 (d, 1H), 3.2–3.5 (br, 7H), 2.8 (br, 7H), 0.75–1.85 (m, 23H); MS(ES) m/e 499 [M+H]$^+$.

Example 37

Preparation of methyl (R,S)-8-[[2-[4-[1-(methyl)pyridinium]-ethyl]methylamino]carbonyl]-2,3,4,5-tetrahydro-3-oxo-4-(2-phenylethyl)-1H-1,4-benzodiazepine-2-acetate Iodide The compound of Example 32(a) (0.11 g, 2.2 mmol) dissolved in acetonitrile (10 mL) was treated with iodomethane (0.2 mL, 3.2 mmol) and heated to reflux for 24 h, concentrated in vacuo (toluene azeotrope) and triturated with ether to yield the title compound as a yellow solid. $^1$H NMR(DMSO d$_6$/TFA, 250 MHz) δ8.8 (br, 2H), 8.05 (br, 1H), 7.15 (m, 6H), 6.99 (br, 1H), 6.4 (br, 2H), 5.35 (d, 1H), 5.05 (m, 1H), 4.25 (s, 3H), 3.95 (d, 1H), 3.75 (br, 3H), 3.55 (s, 3H), 2.6–3.15 (m, 11H); MS(ES) m/e 641 [M–H], 515.2 [M+H]$^+$.

Example 38–39

Preparation (R,S)-2,3,4,5-tetrahydro-3-oxo-4-[2-(cyclohexyl)ethyl]-8-[[[2-(1-methyl-4-piperidinyl)ethyl]methylamino]carbonyl]-1H-1,4-benzodiazepine-2-acetic acid and (R,S)-2,3,4,5-tetrahydro-3-oxo-4-(2-phenylethyl)-8-[[[2-(1-methyl-4-piperidinyl)ethyl]methylamino]carbonyl]-1H-1,4-benzodiazepine-2-acetic acid a) A solution of the compound of Example 37 (0.3 g, 0.47 mmol) in methanol (35 mL) was treated with platinum oxide (27 mg) and hydrogenated for 8 h, filtered and concentrated to yield a mixture of the following compounds 38(a) methyl (R,S)-2,3,4,5-tetrahydro-3-oxo-4-[2-(cyclohexyl)ethyl]-8-[[[2-(1-methyl-4-piperidinyl)ethyl]methylamino]carbonyl]-1H-1,4-benzodiazepine-2-acetic acid 39(a) methyl (R,S)-2,3,4,5-tetrahydro-3-oxo-4-(2-phenylethyl)-8-[[[2-(1-methyl-4-piperidinyl)ethyl]methylamino]carbonyl]-1H-1,4-benzodiazepine-2-acetate b) Using the procedure of the Example 1(j), except substituting the compounds of Examples 38–39(a) for the compound of Example 1(i), and purifying the resultant mixture by HPLC (YMC ODS AQ, 50×250 mm, 90 mL/min, 27% AN/W-TFA, UV detection at 220 nm) yielded 38(b) (R,S)-2,3,4,5-tetrahydro-3-oxo-4-[2-(cyclohexyl)ethyl]-8-[[[2-(1-methyl-4-piperidinyl)ethyl]methylamino]carbonyl]-1H-1,4-benzodiazepine-2-acetic acid: $^1$H NMR(DMSO d$_6$/TFA, 360 MHz) δ9.14 (br, 1H), 7.0 (d, 1H), 6.5 (s, 1H), 6.45 (d, 1H), 5.4 (d, 1H), 5.0 (m, 1H), 3.89 (d, 1H), 2.9–3.5 (br, 6H), 2.25–2.85 (m, 10H), 1.9 (br, 1H), 0.76–1.55 (m, 19H); MS(ES) m/e 513 [M+H]$^+$.

39(b) (R,S)-2,3,4,5-tetrahydro-3-oxo-4-(2-phenylethyl)-8-[[[2-(1-methyl-4-piperidinyl)ethyl]methylamino]carbonyl]-1H-1,4-benzodiazepine-2-acetic acid: $^1$H NMR (DMSO d$_6$/TFA, 360 MHz) δ9.1 (br, 1H), 7.2 (m, 5H), 7.0 (d, 1H), 6.5 (s, 1H), 6.45 (d, 1H), 5.4 (d, 1H), 5.0 (m, 1H), 3.95 (m, 1H), 3.55 (m, 9H), 3.4 (br, 2H), 3.2 (br, 2H), 2.85 (s, 3H), 2.65–2.75 (m, 7H), 1.95 (br, 1H), 1.0–1.49(br, 8H); MS(ES) m/e 507 [M+H]$^+$.

Example 40

Preparation of [S-(R,S)]-8-[[[4-[N-(alanyl)aminomethyl]phenyl]amino]carbonyl]-2,3,4,5-tetrahydro-3-oxo-4-(2-phenylethyl)-1H-1,4-benzodiazepine-2-acetic acid a) methyl [S-(R,S)]-8-[[[4-[N-[N-(t-butoxycarbonyl)-alanyl]aminomethyl]phenyl]amino]carbonyl]-2,3,4,5-tetrahydro-3-oxo-4-(2-phenylethyl)-1H-1,4-benzodiazepine-2-acetate Using the procedure of Example 17, except substituting the compound of Preparation 11(b) for 4-(aminomethyl)pyridine, gave the title compound (427 mg, 65%): TLC R$_f$ 0.52 (ethyl acetate); HPLC RT 84.0 min (Ultrasphere ODS 4.6 mm×15 cm, 30% AN/W-TFA, 1.5 mL/min, UV detection at 240 nm); $^1$H NMR (CDCl$_3$) δ1.34 (d, J=7.16 Hz, 3H), 1.39 (s, 9H), 2.61 (m, 1H), 2.75 (m, 2H), 2.92 (m, 1H), 3.62–3.72 (m, 3H), 3.70 (s, 3H), 4.18 (m, 1H), 4.34 (m, 2H), 4.96 (dd, J=6.6, 6.6 Hz, 1H), 5.12 (br s, 1H), 5.27 (d, J=16.6 Hz, 1H), 6.71 (br s, 1H), 6.84 (d, J=8.3 Hz, 1H), 7.04–7.23 (m, 9H), 7.51 (d, J=7.9 Hz, 2H), 8.13 (br s, 1H).

b) [S-(R,S)]-8-[[[4-[N-[N-(t-butoxycarbonyl)-alanyl]aminomethyl]phenyl]amino]carbonyl]-2,3,4,5-tetrahydro-3-oxo-4-(2-phenylethyl)-1H-1,4-benzodiazepine-2-acetic acid Using the procedure of Example 1(j), except substituting the compound of Example 40(a) for the compound of Example 1(i), gave the title compound (360 mg, 88%): HPLC RT 33.8 min (Ultrasphere ODS, 4.6 mm×15 cm, 30% AN/W-TFA, 1.5 mL/min, UV detection at 240 nm); $^1$H NMR (CD$_3$OD) δ1.32 (d, J=7.2 Hz, 3H), 1.44 (s, 9H), 2.65 (dd, J=5.2, 16.7 Hz, 1H), 2.78 (m, 2H), 2.95 (dd, J=8.9, 16.7 Hz, 1H), 3.67 (m, 1H), 3.76 (m, 1H), 3.92 (d, J=17.0 Hz, 1H), 4.09 (m, 1H), 4.33 (m, 1H), 4.42 (m, 1H), 5.12 (dd, J=5.2, 8.9 Hz, 1H), 5.48 (d, J=16.8 Hz, 1H), 7.01–7.23 (m, 8H), 7.28 (d, J=8.3 Hz, 2H), 7.61 (d, J=8.3 Hz, 2H).

c) [S-(R,S)]-8-[[[4-[N-(alanyl)aminomethyl]phenyl]-amino]carbonyl]-2,3,4,5-tetrahydro-3-oxo-4-(2-phenylethyl)-1H-1,4-benzodiazepine-2-acetic acid hydrochloride Using the procedure of Example 31(b), except substituting the compound of Example 40(b) for the compound of Example 31(a) gave the title compound (160 mg, 51%) as a pale yellow powder: HPLC RT 3.1 min (Ultrasphere ODS 4.6 mm×15 cm, 30% AN/W-TFA, 1.5 mL/min, UV detection at 240 nm); $^1$H NMR (CD$_3$OD) δ1.52 (d, J=7.1 Hz, 3H), 2.67 (dd, J=5.1, 16.7 Hz, 1H), 2.77 (m, 2H), 2.96 (dd, J=8.9, 16.7 Hz, 1H), 3.59–3.77 (m, 2H), 3.84–3.98 (m, 2H), 4.40 (s, 2H), 5.11 (dd, J=5.1, 8.9 Hz, 1H), 5.45 (d, J=16.7 Hz, 1H), 7.02–7.22 (m, 8H), 7.29 (d, J=8.5 Hz, 2H), 7.64 (d, J=8.5 Hz, 2H); MS(ES) m/e 544.2 (M+H)$^+$. Anal. calcd (C$_{30}$H$_{33}$N$_5$O$_5$.HCl.3H$_2$O): C, 56.82; H, 6.36; N, 11.04. found: C, 56.89; H, 6.11; N, 10.90.

Example 41

Preparation of 8-[[4-(aminoiminomethyl)benzoyl]amino]-4,5-dihydro-2-methyl-3-oxo-4-(2-phenylethyl)-3H-1,4-benzodiazepine Using the procedure of Preparation 26(e), except substituting TFA for hydrochloric acid, yielded a mixture of 8-[[4-(aminoiminomethyl)benzoyl]-amino]-2,3,4,5-tetrahydro-3-oxo-4-(2-phenylethyl)-1H-1,4-benzodiazepine-2-acetic acid and the title compound (80 mg) which were separated by HPLC RT 24.8 min (YMC ODS AQ, 50×250 mm, 85 mL/min, 30% AN/W-TFA, UV detection at 220 nm); $^1$H NMR (400 MHz, MeOD$_4$) δ8.1(d, 2H), 7.9(d, 2H), 7.75(s, 1H), 7.60(d, 1H), 7.35(d, 1H), 7.22–7.12(m, 5H), 4.20(m, 2H), 3.70(m, 2H), 2.85(m, 2H), 2.42(s, 3H); MS(ES) m/e 440 [M+H]$^+$.

Example 42

Preparation of (R,S)-8-[[[4-(aminoiminomethyl)phenyl]-methylamino]carbonyl]-2,3,4,5-tetrahydro-2-methyl-3-oxo-4-(2-phenylethyl)-1H-1,4-benzodiazepine a) t-butyl (R,S)-3-[2-(1-methoxy-1-oxo-2-propyl)-amino]-4-[N-(t-butoxycarbonyl]-N-(2-phenylethyl)-aminomethyl]benzoate The compound of Preparation 24(b) (850 mg, 2 mmol), diisopropylethylamine (400 mg, 3 mmol), D,L-methyl-α-bromopropionate (600 mg, >3 mmol), and a catalytic amount of tetrabutylammonium iodide (12 mg) were dissolved in DMF (10 mL) and heated to 90° C. for 20 h with stirring. The mixture was concentrated and the residue was dissolved in ethyl acetate and washed sequentially with dilute hydrochloric acid, 5% sodium bicarbonate and brine, dried (magnesium sulfate) and concentrated. The residue was dissolved in ethyl acetate and chromatographed (silica gel, 4% ethyl acetate:hexane) to give the title compound (800 mg, 70%): MS(ES) m/e 513 [M+H]$^+$.

b) methyl (R,S)-8-carboxy-2,3,4,5-tetrahydro-2-methyl-3-oxo-4-(2-phenylethyl)-1H-1,4-benzodiazepine Using the procedure of Example 1(g), except substituting the compound of Example 42(a) for the compound of Example 1(f), gave the title compound (290 mg, 54%): MS(ES) m/e 325 [M+H]$^+$. Anal. (C$_{19}$H$_{20}$N$_2$O$_3$.0.5 H$_2$O) calcd: C, 68.45; H, 6.35; N, 8.40. found: C, 68.24; H, 6.23; N, 7.92.

c) (R,S)-8-[[[4-[N-(benzyloxycarbonyl)-aminoiminomethyl]phenyl]methylamino]carbonyl]-2,3,4,5-tetrahydro-2methyl-3-oxo-4-(2-phenylethyl)-1H-1,4-benzodiazepine Using the procedure of Example 1(h), except substituting the compound of Example 42(b) for the compound of Example 1(g), gave the title compound (120 mg, 39%): MS(ES) m/e 590 [M+H]$^+$.

d) (R,S)-8-[[[4-(aminoiminomethyl)phenyl]methylamino]-carbonyl]-2,3,4,5-tetrahydro-2-methyl-3-oxo-4-(2-phenylethyl)-1H,-1,4-benzodiazepine dihydrochloride Using the procedure of Example 2(f), except substituting the compound of Example 42(c) for the compound of Example 2(e), gave the title compound (70 mg, 54%): MS(ES) m/e 456.2 [M+H]$^+$; $^1$H NMR (400 MHz, MeOD$_4$) δ9.2 (s, 1H), 8.7 (s, 1H), 7.65 (d, 2H), 7.36 (d, 2H), 7.2–7.06 (m, 5H), 6.77 (d, 1H), 6.75 (s, 1H), 6.47 (d, 1H), 5.3 (d, 1H), 4.77 (m, 1H), 3.85 (d, 1H), 3.75–3.6 (m, 2H), 3.45 (s, 3H), 2.67 (m, 2H), 1.25 (d, 3H); Anal. (C$_{27}$H$_{29}$N$_5$O$_2$.2HCl.1.5 H$_2$O) calcd: C, 58.38; H, 6.07; N, 12.60. found: C, 58.59; H, 5.89; N, 12.65.

Example 43

Preparation of ethyl (R,S)-8-[[[[4-(aminoiminomethyl)phenyl]-methylamino]carbonyl]-2,3,4,5-tetrahydro-3-oxo-4-(2-phenylethyl)-1H-1,4-benzodiazepine-2-acetate a) ethyl (R,S)-8-carboxy-2,3,4,5-tetrahydro-3-oxo-4-(2-phenylethyl)-1H-1,4-benzodiazepine-2-acetate The compound of Preparation 24(e) (2.0 g, 4.77 mmol) was dissolved in a solution prepared by dissolving sodium metal (1.15 g) in absolute ethanol (75 mL). The reaction mixture was stirred 2 h, acidified with 1.0 M hydrogen chloride in ether, concentrated and the residue was dissolved in ethanol and 5% sodium carbonate was added until all material dissolved. The solution was then acidified with acetic acid and the resulting precipitate filtered, dried and recrystallized from ethanol to give the title compound (0.6 g., 42%): $^1$H NMR (400 MHz, DMSO-d$_6$) δ7.1–7.3 (m, 6H), 7.05 (s, 2H), 6.1 (d, 1H), 5.4 (d, 1H), 5.05 (m, 1H), 4.0–4.15 (m, 3H), 3.6 (t, 2H), 2.8 (dd, 1H), 2.7 (m, 2H), 2.6 (dd, 1H), 1.7 (t, 3H).

b) ethyl (R,S)-8-[[[4-(aminoiminomethyl)phenyl]methyl-amino]carbonyl]-2,3,4,5-tetrahydro-3-oxo-4-(2-phenylethyl)-1H-1,4-benzodiazepine-2-acetate Using the procedure of Examples 1(h) and 2(f), except substituting the compound of Example 43(a) for the compound of Example 1(g), gave the title compound (0.07 g, 50%): $^1$H NMR (400 MHz, DMSO-d$_6$) δ9.2 (s, 2H), 9.0 (s, 2H), 7.7 (d, 2H), 7.4 (d, 2H), 7.1–7.25 (m, 6H), 6.8 (d, 1H), 6.75 (s, 1H), 6.25 (d, 1H), 6.0 (d, 1H), 5.3 (d, 1H), 5.0 (m, 1H), 4.1 (q, 2H), 3.9 (d, 1H), 3.55 (m, 2H), 3.4 (s, 3H), 2.8 (dd, 1H), 2.55–2.7 (m, 3H), 1.2 (t, 3H); MS(ES) m/e 528.4 [M+H]$^+$.

Example 44

Preparation of (R,S)-[[8-[4-(aminoiminomethyl)phenyl]-methylamino]carbonyl]-2,3,4,5-tetrahydro-3-oxo-4-(2-phenylethyl)-1H-1,4-benzodiazepine-2-acetamide a) 8-[[[4-[N-(benzyloxycarbonyl)-aminoiminomethyl]-phenyl]methylamino]carbonyl]-2,3,4,5-tetrahydro-3-oxo-4-(2-phenylethyl)-1H-1,4-benzodiazepine-2-acetamide The compound of Preparation 25(c) (400 mg, 0.61 mmol) was dissolved in methanol (50 mL), cooled in an ice bath and saturated with ammonia. The flask was stoppered securely and put in the refrigerator for 5 d. The solution was concentrated and the residue was purified by flash chromatography (silica gel, 5% methanol/water) to give the title compound (190 mg, 48%): MS(ES) m/e 633.2 [M+H]$^+$; $^1$H NMR (400 MHz, CDCl$_3$) δ7.7 (d, J=8.5 Hz, 2H), 7.45–7.05 (m, 12H), 6.6 (d, J=1.4 Hz, 1H), 6.56 (d, J=8.0 Hz, 1H), 6.38 (d,d, J=8.0, 1.4 Hz, 1H), 5.19 (s, 2H), 5.18 (d, J=16.8 Hz, 1H), 4.88 (m, 1H), 4.17 (d, J=5.3 Hz, 1H), 3.7 (s, 3H), 3.65 (m, 2H), 3.55 (d, J=16.8 Hz, 1H) 3.45 (s, 3H), 2.9 (d,d, J=16, 6.9 Hz, 1H), 2.7 (m, 2H), 2.6 (d,d, J=16, 6.3 Hz, 1H).

b) 8-[[[4-(aminoiminomethyl)phenyl]methylamino]-carbonyl]-2,3,4,5-tetrahydro-3-oxo-4-(2-phenylethyl)-1H-1,4-benzodiazepine-2-acetamide trifluoroacetate Using the procedure of Example 2(f), except substituting the compound of Example 44(a) for the compound of Example 2(e), gave the title compound (45 mg, 25%): MS(ES) m/e 499 (M+H)$^+$, 497 (M–H)$^-$; $^1$H NMR (400 MHz, MeOD$_4$) δ7.75 (d, J=8.5 Hz, 2H), 7.36 (d, J=8.5 Hz, 2H), 7.22–7.10 (m, 5H), 6.77 (d, J=7.8, 1H) 6.71 (s, 1H), 6.48 (d, J=7.8 Hz, 1H),5.31 (d, J=16.8 Hz, 1H), 5.04 (m, 1H), 3.84 (d, J=16.8 Hz), 3.68–3.5 (m, 2H), 3.47 (s, 3H), 2.88 (d,d, J=16, 6.9 Hz, 1H), 2.68 (m, 2H), 2.49 (d,d, J=16, 6.3 Hz, 1H); Anal. (C$_{28}$H$_{30}$N$_6$O$_3$ 1.5 TFA) calcd: C, 55.60; H, 4.74; N, 12.55. found: C, 55.52; H, 4.90; N=12.47.

Example 45

Preparation of (R,S)-8-[[[4-(aminoiminomethyl)phenyl]-methylamino]carbonyl]-2,3,4,5-tetrahydro-3-oxo-4-(2-phenylethyl)-1H-1,4-benzodiazepine-2-ethanol a) (R,S)-8-[[[4-[N-(benzyloxycarbonyl)-(aminoiminomethyl]phenyl]methylamino]carbonyl]-2,3,4,5-tetrahydro-3-oxo-4-(2-phenylethyl)-1H-1,4-benzodiazepine-2-ethanol The compound of Preparation 25(c) (0.5 g, 0.77 mmol) in THF (25 mL) was treated with sodium borohydride (300 mg, 8 mmol), lithium chloride (255 mg, 6 mmol) and absolute ethanol (40 mL). The reaction stirred 4.5 h, neutralized with 3N hydrochloric acid, concentrated and the residue was treated with water and ethyl acetate. The organic phase was washed with brine, dried (magnesium sulfate), concentrated, and chromatographed (silica gel, 3% methanol/dichloromethane) to yield the title compound (95 mg, 20%): MS(ES) m/e 620.2 [M+H]$^+$, 618.2 [M–H]$^-$; $^1$H NMR (400 MHz, CDCl$_3$) δ7.65(d, 2H; J=8.45), 7.44–7.27(m, 5H), 7.20(d, 2H; J=8.45), 7.18–7.08(m, 5H), 6.60 (m, 2H), 6.25 (s, 1H), 5.21(d, 2H), 5.16(d, 2H; J=16.8), 4.50(m, 1H), 3.68–3.64 (m, 4H), 3.55(d, 2H; J=16.8), 3.47(s, 3H), 2.72 (m, 2H), 1.96(m, 1H), 1.85(m, 1H)

b) (R,S)-8-[[[4-(aminoiminomethyl)phenyl]methylamino]-carbonyl]-2,3,4,5-tetrahydro-3-oxo-4-(2-phenylethyl)-1H-1,4-benzodiazepine-2-ethanol dihydrochloride A solution of the compound of Example 45(a) (80 mg, 0.12 mmol) in methanol (10 mL) was treated with 10% palladium on carbon (60 mg) and concentrated hydrochloric acid (0.1 mL) and hydrogenated (40 psi) for 2 h. The mixture was filtered and concentrated. The residue was triturated with ethyl acetate and filtered to give the title compound (58 mg, 86%). MS(ES) m/e 486.2 [M+H]$^+$; $^1$H NMR (400 MHz, MeOD$_4$) δ9.20(s, 1H), 8.66(s, 1H), 7.66(d, 2H), 7.36(d, 2H), 7.30–7.08(m, 5H), 6.75(d, 1H), 6.67(s, 1H), 6.40(d, 1H), 5.30(d, 1H), 4.78(m, 1H), 3.80(d, 1H), 3.76–3.60(m, 4H), 3.45(s, 3H), 2.70(m, 2H), 2.08(m, 1H), 1.80(m, 1H). Anal. (C$_{28}$H$_{31}$N$_5$O$_3$.2HCl.1.5H$_2$O) calcd: C, 57.44; H, 5.76; N, 11.96. found: C, 57.52; H, 5.89; N, 11.87.

Example 46

Preparation of (R,S)-8-[[2-[4-(pyridyl)ethyl]methylamino]-carbonyl]-2,3,4,5-tetrahydro-3-oxo-4-(2-phenylethyl)-1H-1,4-benzodiazepine-2-ethanol The compound of Example 32(a) (0.2 g, 0.4 mmol) and sodium borohydride (200 mg, 5.3 mmol) was stirred in methanol (40 mL) at RT for 2 h. Additional sodium borohydride (200 mg, 5.3 mmol) was added and the mixture was stirred overnight, concentrated, diluted with water and extracted with CH$_2$Cl$_2$. The organic phase was concentrated and the residue was purified by flash chromatography (silica gel, CH$_2$Cl$_2$/methanol) to yield the title compound as a white solid (37 mg, 20%): MS(ES) m/e 473.2 [M+H]$^+$.

Example 47

Preparation of (R,S)-8-[2-[4-(aminomethyl)phenyl]ethyl]-2,3,4,5-tetrahydro-3-oxo-4-(2-phenylethyl)-1H-1,4-benzodiazepine-2-acetic acid a) methyl 2,3,4,5-tetrahydro-8-hydroxymethyl-3-oxo-4-(2-phenylethyl)-1H-1,4-benzodiazepine-2-acetic Thionyl chloride (50 mL) was added to the compound of Preparation 24(e) (3.8 g, 10 mmol) was added. The resulting suspension was stirred and heated to reflux for 15 min, cooled to RT, and concentrated. The residue was dissolved in toluene and concentrated. The residue was dissolved in THF (50 mL), stirred at RT, treated with sodium borohydride (2.0 g, 53 mmol) and stirred for 16 h. The mixture was quenched at 0° C. with 1N hydrochloric acid, extracted with ethyl acetate, washed with brine, dried (magnesium sulfate) and concentrated. The residue was purified by flash chromatography (silica gel, 1% methanol/chloroform) to yield the title compound (1.71 g, 47%). TLC $R_f$ 0.49 (silica gel, 5% methanol/chloroform); $^1$H NMR (CDCl$_3$) δ2.62 (dd, 1H), 2.77 (m, 2H), 2.97 (dd, 1H), 3.27 (br s, 2H), 3.68 (m, 3H), 3.72 (s, 3H), 4.51 (s, 2H), 4.94 (t, 1H), 5.24 (d, J=16.5 Hz, 1H), 6.56 (s, 1H), 6.62 (d, J=7.4, 1H), 6.80 (d, J=7.7 Hz, 1H), 7.20 (m, 5H).

b) methyl 8-formyl-2,3,4,5-tetrahydro-3-oxo-4-(2-phenylethyl)-1H-1,4-benzodiazepine-2-acetate To the compound of Example 47(a) (1.60 g, 4.3 mmol) in CH$_2$Cl$_2$ (50 mL) was added manganese dioxide (2.8 g, 32 mmol). The resulting suspension was stirred at reflux for 16 h, filtered through a pad of Celite®. The pad was rinsed with CH$_2$Cl$_2$ and the filtrate was concentrated. The residue was purified by flash chromatography (silica gel, 50% ethyl acetate/n-hexane) to give the title compound (0.71 g, 44%): TLC $R_f$ 0.67 (silica gel, 5% methanol/chloroform); $^1$H NMR (CDCl$_3$) δ2.68 (dd, 1H), 2.81 (dt, 2H), 3.0 (dd, 1H), 3.72 (m, 3H), 3.75 (s, 3H), 5.0 (t, 1H), 5.31 (d, J=16.7 Hz, 1H), 6.93 (d, J=7.6 Hz, 1H), 7.03 (s, 1H), 7.11 (d, 7.8 Hz, 1H), 7.19 (m, 5H), 9.85 (s, 1H).

c) E/Z methyl 8-[2-[4-(Cyano)phenyl]ethenyl]-2,3,4,5-tetrahydro-3-oxo-4-(2-phenylethyl)-1H-1,4-benzodiazepine-2-acetate A solution of the compound of Example 47(b)(0.67 g, 1.8 mmol) and (4-cyanobenzyl)triphenylphosphonium chloride (0.80 g, 1.9 mmol) in anhydrous DMF (50 mL) was treated with sodium hydride (74 mg, 60% dispersion in oil, 1.8 mmol) and stirred for 5 h. The mixture was concentrated and the residue was taken up in ethyl acetate, washed with brine, dried (magnesium sulfate) and concentrated. The residue was purified by flash chromatography (silica gel, 5% ethyl acetate/chloroform) to yield the title compound as a (2:3) mixture of E/Z olefin isomers (693 mg, 81%). Further chromatography (silica gel, 40% ethyl acetate/n-hexane) yielded the pure E and Z isomers. E isomer TLC $R_f$ 0.39 (silica gel, 40% ethyl acetate/n-hexane); $^1$H NMR (CDCl$_3$) δ2.65 (dd, 1H), 2.82 (dt, 2H), 2.97 (dd, 1H), 3.71 (m, 3H), 3.74 (s, 3H), 4.94 (t, 1H), 5.23 (d, J=16.5, 1H), 6.46 (m, 2H), 6.52 (d, J=12.3 Hz, 1H), 6.61 (d, J=12.3 Hz, 1H), 6.71 (d, J=8.1 Hz, 1H), 7.21 (m, 5H), 7.32 (d, J=8.3, 2H), 7.5 (d, J=8.3, 2H); MS(ES) m/e 466.2 [M+H]$^+$. Z isomer: TLC $R_f$ 0.33 (silica gel, 40% ethyl acetate/n-hexane); $^1$H NMR (CDCl$_3$) δ2.71 (dd, 1H), 2.82 (dt, 2H), 3.03 (dd, 1H), 3.70 (m, 3H), 3.75 (s, 3H), 4.97 (t, 1H), 5.27 (d, J=16.6 Hz, 1H), 6.76 (s, 1H), 6.85 (s, 2H), 7.02 (d, J=4.2, 2H), 7.18 (m, 5H), 7.54 (d, J=8.4, 2H), 7.63 (d, J=8.4, 2H); MS(ES) m/e 466.2 [M+H]$^+$.

d) methyl 8-[2-[4-(aminomethyl)phenyl]ethyl]-2,3,4,5-tetrahydro-3-oxo-4-(2-phenylethyl)-1H-1,4-benzodiazepine-2-acetate A mixture of the compounds of Example 47(c) (693 mg, 1.5 mmol), 10% palladium on carbon (1 g) and acetic acid (100 mL) was hydrogenated (50 psi) for 5 h. The mixture was filtered, the filtrate was concentrated and to yield the title compound: TLC $R_f$ 0.77 (silica, 4:1:1 n-butanol:acetic acid:water), HPLC k' 2.5 (PRP-1, 50% AN/W-TFA, UV detection at 220 nm).

e) 8-[2-[4-(aminomethyl)phenyl]ethyl]-2,3,4,5-tetrahydro-3-oxo-4-(2-phenylethyl)-1H-1,4-benzodiazepine-2-acetic acid The compound of Example 47(d) was dissolved in 20% acetic acid and refluxed for 72 h. The mixture was concentrated and purified by HPLC (PRP-1, 35% AN/W-TFA) to give the title compound: TLC $R_f$ 0.55 (silica, 4:1:1 n-butanol:HOAc:water), $R_f$ 0.59 (silica, 15:3:12:10 n-butanol, acetic acid, water, pyridine); MS(ES) 458.2 (M+H)$^+$; HPLC k' 3.7 (PRP-1®, 35% AN/W-TFA; Anal. (C$_{28}$H$_{31}$N$_3$O$_3$.CF$_3$CO$_2$H.H$_2$O) calcd: C, 46.98; H, 4.14; N, 4.63. found: C, 46.84; H, 3.96;N, 4.80.

Examples 48

Preparation of 7-[3-(4-pyridyl)propyloxy]-2-(2-phenylethyl)-3-oxo-2,3,4,5-tetrahydro-1H-2-benzazepine-4-acetic acid a) N-(2-phenylethyl)-4-nitrophthalimide A mixture of 4-nitrophthalic anhydride (18 g, 93.3 mmol) and phenethylamine (11.5 g, 95 mmol) in toluene (250 mL) was heated to reflux using a Dean-Stark trap to remove water. After 2.5 h, the mixture was concentrated to solid residue, which was triturated and filtered to give the titled compound (24.5 g, 89%): mp 142–3° C.).

b) N-(2-phenylethyl)-4-methoxyphthalimide

A stirred solution of the compound of Example 48(a) (18 g, 0.06 mol) in DMF (85 mL) at 0° C. was treated with sodium methoxide (3.6 g, 0.066 mol) portionwise. The dark brown mixture was stirred at RT for 3.5 h, quenched with ice-water, extracted with ethyl acetate, dried (magnesium sulfate) and concentrated. Trituration with ether afforded the title compound (10.9 g, 64%): mp 112–4° C.; MS(ES) m/e 282 [M+H]$^+$; $^1$H NMR (400 MHz, CDCl$_3$) δ7.72 (d, J=8.25 Hz, 1H), 7.25–7.30 (m, 6H), 7.14 (dd, J=2.30, 8.25 Hz, 1H), 3.9 (s, 3H), 3.89 (t, J=7.87 Hz, 2H), 2.99 (t, J=7.87 Hz, 2H).

c) 2-hydroxymethyl-4-methoxy-N-(2-phenylethyl)-1-benzamide

A solution of the compound of Example 48(b) (15 g, 0.05 mol) in isopropanol (300 mL) and water (60 mL) was treated with sodium borohydride (12 g, 0.3 mmol) portionwise. After 3.5 h, the mixture was concentrated to half of the original volume, quenched with 5% sodium bicarbonate solution, extracted with ethyl acetate, dried (sodium sulfate), concentrated to a small volume, and filtered to yield the title compound (10 g, 67%): mp 154–6° C.; MS m/e 286 [M+H]$^+$; $^1$H NMR (400 MHz, CDCl$_3$) δ7.39 (d, J=8.25 Hz, 1H), 7.12–7.28 (m, 5H), 6.81 (d, J=2.3 Hz, 1H), 7.35 (dd, J=2.30, 8.25 Hz, 1H), 4.46 (s, 2H), 3.76 (s, 3H), 3.61 (q, J=7.87 Hz, 2H), 2.89 (t, J=7.87 Hz, 2H).

d) 2-hydroxymethyl-4-methoxy-[N-(2-phenylethyl)]benzylamine

To a solution of borane (800 mL, 1M in THF, 0.8 mol) at RT, a suspension of the compound of Example 48(c) (25 g, 0.088 mol) in THF (250 mL) was added over 0.5 h. The mixture was heated to reflux for 12 h, cooled and treated with 1N hydrochloric acid (150 mL). The mixture was heated for 1.5 h until evolution of hydrogen gas ceased, basified in the cold and extracted with ethyl acetate. The organic phase was dried (sodium sulfate) and concentrated to yield the title compound (24 g, 100%): MS m/e 272.2 [M+H]$^+$; $^1$H NMR (400 MHz, CDCl$_3$) δ7.08–7.29 (m, 5H), 6.90 (d, J=2.62 Hz, 1H), 6.73 (dd, J=2.62, 8.29 Hz, 1H), 4.58 (s, 2H), 3.83 (s, 2H), 3.77 (s, 3H), 3.10 (t, J=6.78 Hz, 2H), 2.89 (t, J=6.78 Hz, 2H).

e) 2-hydroxymethyl-4-methoxy-[N-(2-phenylethyl)-N-(t-butyloxycarbonyl)]benzylamine A mixture of Example 48(d) (23 g, 0.085 mol), di-t-butyldicarbonate (19.3 g, 0.089 mmol) and triethylamine (12.3 mL, 0.089 mmol) in CH$_2$Cl$_2$ (250 mL) was stirred at RT for 18 h, concentrated and azeotroped twice with CH$_2$Cl$_2$. MS(ES) m/e 372.2 [M+H]; $^1$H NMR (400 MHz, CDCl$_3$) δ7.13–7.28 (m, 5H), 6.90 (d, J=2.53 Hz, 1H), 6.79 (dd, J=2.53, 8.29 Hz, 1H), 4.60 (bs, 2H), 4.43 (bs, 2H), 3.43 (s, 3H), 3.36 (t, J=7.90 Hz, 2H), 2.72 (t, J=7.90 Hz, 2H).

f) 5-methoxy-2-[N-(2-phenylethyl)-N-(t-butyloxycarbonyl)aminomethyl]benzaldehyde A suspension of the compound of Example 48(e) and MnO$_2$ (75 g, 0.86 mol) in CH$_2$Cl$_2$ (275 mL) was stirred at RT for 18 h. The reaction mixture was filtered and concentrated to give the titled compound (20 g, 70%): MS m/e 370.2 [M+H]$^+$; $^1$H NMR (400 MHz, CDCl$_3$) δ10.16 (s, 1H), 7.34 (d, J=2.14 Hz, 1H), 7.07–7.27 (m, 7H), 4.79 (bs, 2H), 3.81 (s, 3H), 3.32 (bt, 2H), 2.75 (bt, 2H), 1.46 (s, 9H).

g) 2-[5-methoxy-2-[N-(2-phenylethyl)-N-(t-butoxycarbonyl)aminomethyl]phenyl]-5-oxo-tetrahydro-3-furancarboxylic acid To a suspension of zinc chloride (27 g, 0.2 mol; flame-dried at reduced pressure), succinic anhydride (20 g, 0.2 mol), and the compound of Example 48(f) (20 g, 0.05 mol) in CH$_2$Cl$_2$ (150 mL), triethylamine (28 mL, 0.2 mol) was added dropwise at 0° C. The mixture was stirred for 18 h, diluted with CH$_2$Cl$_2$ (100 mL), washed with cold 1N hydrochloric acid, dried (sodium sulfate) and concentrated. The residue was triturated with ether/CH$_2$Cl$_2$ (75 mL, 2:1) and filtered The filtrate was concentrated to give the title compound (23 g, 87%).

h) trans-3a,5,6,10b-tetrahydro-9-methoxy-5-(2-phenylethyl)-2H-furo[3,2-d][2]benzazepin-2,4(3H)-dione A mixture of the compound of Example 48(g) (23 g, 0.05 mol) and hydrogen chloride (200 mL, 4M in dioxane 0.8 mol) in CH$_2$Cl$_2$ (150 mL) was stirred at RT for 18 h and concentrated to give 2-[5-methoxy-2-[N-(2-phenylethyl) aminomethyl]phenyl]-5-oxo-tetrahydro-3-furancarboxylic acid as grayish solid (18 g, 97%): MS(ES) m/e 370.2 [M+H]$^+$.

This solid, triethylamine (14 mL, 0.1 mol), and benzotriazol-1-yloxy-tris(dimethylamino)phosphonium hexafluorophosphate (22 g, 0.05 mol) were dissolved in CH$_2$Cl$_2$ (400 mL) and allowed to stir at RT overnight The mixture was concentrated and the residue was purified by flash column chromatography (silica gel, 0.2% methanol/CH$_2$Cl$_2$) to yield the title compound (9.5 g, 55%): MS(ES) m/e 352.2 [M+H]$^+$; $^1$H NMR (400 MHz, CDCl$_3$) δ7.12–7.16 (m, 3H), 6.97–7.00 (m, 3H), 6.91–6.94 (d, J=8.47 Hz, 1H), 6.79 (dd, J=2.75,8.47 Hz, 1H), 5.01 (d, J=17.26 Hz, 1H), 4.92 (d, J=11.48 Hz, 1H), 4.07 (dt, J=7.82 Hz, J=13.57 Hz, 1H), 3.92 (d, J=17.26 Hz, 1H), 3.85 (m, 1H), 3.79 (s, 3H), 3.52 (m, 1H), 3.25 (dd, J=17.61 Hz, J=11.76, 1H), 2.78 (m, 2H), 2.65 (dd, J=17.26 Hz, J=7.26 Hz, 1H).

i) ethyl 7-methoxy-2-(2-phenylethyl)-3-oxo-2,3,4,5-tetrahydro-1H-2-benzazepine-4-acetate A solution of the compound of Example 48(h) (0.123 g, 0.35 mmol) in 3N hydrochloric acid (15 mL) in ethanol (50 mL) was treated with palladium hydroxide (120 mg) and hydrogenated (50 psi) for 4 h. The mixture was filtered and the filtrate was concentrated. The residue was azeotroped with ethanol and toluene. The residue was dissolved in ethanol (75 mL) and heated to reflux in the presence of 4 M hydrogen chloride/dioxane (2 mL) for 2 h. The solution was concentrated to give the title compound (0.11 g, 83%): MS(ES) m/e 382 [M+H]$^+$; $^1$H NMR (400 MHz, CDCl$_3$) δ7.08–7.26 (m, 5H), 6.90 (d J=8.31 Hz, 1H), 6.63 (dd, J=2.41, 8.28 Hz, 1H), 6.60 (d, J=2.41 Hz, 1H), 5.11 (d, J=16.47 Hz, 1H), 4.16 (q, J=7.10 Hz, 2H), 3.76 (s, 3H), 3.72 (d, J=16.47 Hz, 1H), 3.63 (m, 3H), 2.97 (m, 2H), 2.82 (m, 1H), 2.75 (t, J=7.30 Hz, 2H), 1.27 (t, J=7.10 Hz, 3H).

j) ethyl 7-hydroxy-2-(2-phenylethyl)-3-oxo-2,3,4,5-tetrahydro-1H-2-benzazepine-4-acetate To a solution of the compound of Example 48(i) (0.11 g, 0.29 mmol) and ethanethiol (1 mL, 13.5 mmol) in CH$_2$Cl$_2$ (20 mL) at 0° C. was added aluminum chloride (0.2 g, 1.5 mmol). The mixture was warmed to RT over 1 h, diluted with CH$_2$Cl$_2$, washed with cold 3N hydrochloric acid, dried (sodium sulfate), and concentrated to give the title compound (0.08 g, 74%): MS(ES) m/e 368.2 [M+H]$^+$.

k) ethyl 7-[3-(4-pyridyl)propyloxy]-2-(2-phenylethyl)-3-oxo-2,3,4,5-tetrahydro-1H-2-benzazepine-4-acetate A mixture of the compound of Example 48(j) (20 mg, 0.05 mmol), 3-(4-pyridyl)propyl chloride hydrochloride (50 mg, 0.2 mmol), sodium iodide (3 mg), and sodium hydride (12 mg, 0.5 mmol) was heated at 90° C. for 18 h. The mixture was quenched with ice water, extracted with ethyl acetate, dried (sodium sulfate) and concentrated to give the title compound (0.01 g, 42%): MS(ES) m/e 486 [M+H]$^+$.

l) 7-[3-(4-pyridyl)propyloxy]-2-(2-phenylethyl)-3-oxo-2,3,4,5-tetrahydro-1H-2-benzazepine-4-acetic acid A mixture the compound of Example 48(k) and 1N sodium hydroxide solution in methanol is stirred at RT for 5 h and acidified with 1N hydrochloric acid to give the title compound.

Example 49

Preparation of 7-[3-(4-piperidinyl)propyloxy]-2-(2-phenylethyl)-3-oxo-2,3,4,5-tetrahydro-1H-2-benzazepine-4-acetic acid Using the procedure of Example 34, except substituting the compound of Example 48(l) for the compound of Example 9(a) gives the title compound.

Example 50

Preparation of (R,S)-8-[[[3-(aminomethyl)phenyl]amino]-carbonyl]-2,3,4,5-tetrahydro-3-oxo-4-(2-phenylethyl)-1H-1,4-benzodiazepine-2-acetic acid a) methyl (R,S)-8-[[[3-(aminomethyl)phenyl]amino]carbonyl]-2,3,4,5-tetrahydro-3-oxo-4-(2-phenylethyl)-1H-1,4-benzodiazepine-2-acetic acid Using the procedure of Example 13(a) and (b), except substituting 3-[N-(t-butoxycarbonyl)aminomethyl]aniline for the compound of Preparation 4(b), gave the title compound: $^1$H NMR (CD$_3$OD, 250 MHz) δ2.60–2.73 (m, 3H), 2.95 (d of d, 1H, J=9, 16 Hz), 3.50–3.83 (m, 2H), 3.70(s, 3H), 3.91 (d, 1H, J=17 Hz), 4.90–5.20 (m, 3H), 5.43 (d, 1H, J=17 Hz), 6.93–7.93 (m, 12H).

b) (R,S)-8-[[[3-(aminomethyl)phenyl]amino]carbonyl]-2,3,4,5-tetrahydro-3-oxo-4(2-phenylethyl)-1H-1,4-benzodiazepine-2-acetic acid Using the procedure of Example 1(j), except substituting the compound of Example 50(a) for the compound of Example 1(i), gave the title compound (85 mg): MS(ES) m/e 473 [M+H]$^+$; $^1$H NMR (CD$_3$OD, 250 MHz) δ2.60–3.10 (m, 4H), 3.58–3.88 (m, 2H), 3.95 (d, J=17 Hz, 1Hx), 4.67–5.04 (m, 2H), 5.10–5.20 (m, 1H), 5.50 (d, J=17 Hz, 1H), 6.93–8.05 (m, 12H); HPLC k'=2.61 (PRP-1®, 30% AN/W-TFA, UV detection at 220 nm).

Example 51

Preparation of 8-[1-[4-(4-pyridyl)piperazinyl] carbonyl]-2,3,4,5-tetrahydro-3-oxo-4-(2-phenylethyl)-1H-1,4-benzodiazepine-2-acetic acid Using the procedure of Example 32, except substituting 1-(4-pyridyl)piperazine for N-methyl-2-(4-pyridyl) ethanamine, gave the title compound: HPLC RT 16.6 min (YMC ODS-AQ, 6×250 mm, 1.5 mL/min, gradient, A:acetonitrile B:water-0.1% TFA, 10–80% A in 20 min, UV detection at 220 nm).

Example 52

Preparation of (R,S)-8-[[[4-(aminomethyl)-3-chlorophenyl]carbonyl]amino]-2,3,4,5-tetrahydro-3-oxo-4-(2-phenylethyl)-1H-1,4-benzodiazepine-2-acetic acid Using the procedure of Examples 7(b), 13(b) and 13(c), except substituting the compound of Preparation 12(c) for the compound of Preparation 1(b) in Example 7(b), yielded the title compound: MS(ES) m/e 507 [M+H]$^+$; Anal [C$_{27}$H$_{27}$ClN$_4$O$_4$.1.5(C$_2$HF$_3$O$_2$).H$_2$O] calcd: C,51.43; H,4.39; N,7.99; found: C,51.36; H,4.29; N,7.90. $^1$H NMR (DMSO-d$_6$, 250 MHz) δ2.51–2.60(m, 2H), 2.65–2.70(m, 2H), 3.45–3.55(m, 2H), 3.85(d, J=17 Hz, 1H), 4.15(s, 2H), 4.95–5.00(m, 1H), 5.30(d, J=17 Hz, 1H), 5.85(s, 1H), 6.70–8.05(m, 13H), 8.20–8.30(m, 2H).

Example 53

Preparation of 2-[3-(4-piperidinyl)propyloxy]-7-oxo-6,7,8,9-tetrahydro-5H-benzocycloheptene-6-acetic acid; and 3-[3-(4-piperidinyl)propyloxy]-7-oxo-6,7,8,9-tetrahydro-5H-benzocycloheptene-6-acetic acid a) methyl 2-methoxy-7-oxo-6,7,8,9-tetrahydro-5H-benzocycloheptene-6-acetate, and methyl 3-methoxy-7-oxo-6,7,8,9-tetrahydro-5H-benzocycloheptene-6-acetate Using the general method of *J. Org. Chem.*, 57, 1429 (1992), except substituting 2-methoxy-benzosuberone (*J. Org. Chem.* 47, 5201 (1982)) for benzosuberone, and separating the resulting mixture of isomers by chromatography, gives the title compounds.

b) 2-[3-(4-piperidinyl)propyloxy]-7-oxo-6,7,8,9-tetrahydro-5H-benzocycloheptene-6-acetic acid, and 3-[3-(4-piperidinyl)propyloxy]-7-oxo-6,7,8,9-tetrahydro-5H-benzocycloheptene-6-acetic acid Using the procedures of Examples 48, and 49 except substituting each of the compounds of Example 53(a) for the compound of Examples 48(i), gives the title compounds.

Example 54

Preparation of (R,S)-8-[[[2-[4-(2-aminopyridyl)] ethyl]-amino]carbonyl]-2,3,4,5-tetrahydro-3-oxo-4-(2-phenylethyl)-1H-1,4-benzodiazepine-2-acetic acid Using the procedures of Example 27(a) and Example 24(b), except substituting the compound of Preparation 13(j) for histamine and benzotriazol-1-yloxy-tris (dimethylamino)-phosphonium hexafluorophosphate for 1-(3-dimethylamino-propyl)-3-ethylcarbodiimide hydrochloride, gave the title compound. MS(ES) m/e 488.2 [M+H]$^+$; Anal. (C$_{27}$H$_{29}$N$_5$O$_4$.1.5 CF$_3$CO$_2$H.H$_2$O) calcd: C, 53.35; H, 4.56; N, 10.35. found: C, 53.25; H, 4.84; N,10.35; HPLC k' 3.88 (PRP-1®, 25% AN/W-TFA).

Example 55

Preparation of (R,S)-2,3,4,5-tetrahydro-8-[[[2-[2-(hydroxy)pyrid-4-yl]ethyl]amino]carbonyl]-3-oxo-4-(2-phenylethyl)-1H-1,4-benzodiazepine-2-acetic acid Using the procedure of Example 54, except substituting the compound of Preparation 14(b) for the compound of Preparation 13(j), gave the title compound. MS(ES) m/e 489.4 [M+H]$^+$; Anal. (C$_{27}$H$_{28}$N$_4$O$_5$.1.125 H$_2$O) calcd: C, 63.74; H, 5.74; N, 10.71. found: C, 63.74; H, 5.99; N,11.01; HPLC k' 3.70 (PRP-1®, 25% AN/W-TFA).

Example 56

Preparation of (R,S)-2,3,4,5-tetrahydro-3-oxo-4-(2-phenylethyl)-8-[[[4-(trimethylammonium)butyl] amino]carbonyl]-1H-1,4-benzodiazepine-2-acetic acid, hydrochloride)

The compound of Example 33(a) (92 mg, 0.19 mmol) in THF (5 mL) was treated with iodomethane (14.3 mL, 2.0 mmol) and the reaction mixture was heated to reflux for 16 h. The white solid that formed was collected by filtration and washed with cold ether. The solid was treated with 1N hydrochloric acid and lyophilized to yield the title compound (39 mg, 41%). MS(ES) m/e 481 [M+H]$^+$; $^1$H NMR (400 MHz, CD$_3$OD) δ8.06 (d, 1H), 6.90–7.25 (m, 8H), 5.44 (d, 1H), 5.09 (t, 1H), 3.54–3.90 (m, 4H), 3.20–3.45 (m, 8H), 3.13 (s, 9H), 2.93 (dd, 1H), 2.68–2.79 (m, 2H), 2.53–2.65 (m, 1H), 1.78–1.90 (m, 2H), 1.66 (t, 2H).

Example 57

Preparation of (R,S)-8-[4-(aminomethyl) phenoxymethyl]-2,3,4,5-tetrahydro-3-oxo-4-(2-phenylethyl)-1H-1,4-benzodiazepine-2-acetic acid a) methyl (R,S)-2,3,4,5-tetrahydro-8-hydroxymethyl-3-oxo-4-(2-phenylethyl)-1H-1,4-benzodiazepine-2-acetate Methyl (R,S)-8-carboxy-2,3,4,5-tetrahydro-3-oxo-4-(2-phenylethyl)-1H-1,4-benzodiazepine-2-acetate (3 g, 7.8 mmol) was dissolved in dry THF (20 mL) and treated at −5° C. with triethylamine (1.14 mL, 8.19 mmol) and ethyl chloroformate (775 mL, 8.11 mmol). The reaction was stirred for 1 h and filtered. The filtrate was cooled to 0° C. and treated with sodium borohydride (651 mg, 17.23 mmol) in water (7.5 mL). The reaction was allowed to warm to RT and stirred for 4 h. The mixture was acidified with 3N hydrochloric acid and extracted with ethyl acetate. The organic phase was washed twice with 0.5N sodium hydroxide and with brine, dried (magnesium sulfate) and concentrated to give the title compound (2.31 g). $^1$H NMR (250 MHz) δ7.25–7.10 (m, 5H), 7.09–6.78 (m, 1H), 6.75–6.51 (m, 2H), 5.26–5.25 (m, 1H), 4.94–4.91 (m, 1H), 4.46 (s, 2H), 3.69 (s, 3H), 3.66–3.61 (m, 3H), 3.10–2.62 (m, 6H).

b) methyl (R,S)-8-[4-(N-t-butoxycarbonyl)-(aminomethyl)phenoxymethyl]-2,3,4,5-tetrahydro-3-oxo-4-(2-phenylethyl)-1H-1,4-benzodiazepine-2-acetate The compound of Example 57(a) (100 mg, 0.24 mmol) was dissolved in dry THF (10 mL) and treated at 0° C. with the compound of Preparation 15 (122 mg, 0.546 mmol) followed by triphenylphosphine (143 mg, 0.546 mmol) and diethyl azodicarboxylate (86 mL, 0.546 mmol). The mixture was stirred at RT for 48 h, concentrated and the residue was purified by flash chromatography (silica gel, 40% ethyl acetate/hexane) to give the title compound (150 mg). MS(ES) m/e 474 [M+H]$^+$.

c) methyl (R,S)-8-[4-(aminomethyl) phenoxymethyl]-2,3,4,5-tetrahydro-3-oxo-4-(2-phenylethyl)-1H-1,4-benzodiazepine-2-acetate Using the procedure of Example 13(b), except substituting the compound of Example 57(b) for the compound of Example 13(a), gave the title compound (65 mg). MS(ES) m/e 574 [M+H]$^+$.

d) (R,S)-8-[4-(aminomethyl)phenoxymethyl]-2,3,4,5-tetrahydro-3-oxo-4-(2-phenylethyl)-1H-1,4-benzodiazepine-2-acetic acid The compound of Example 57(c) (65 mg, 0.137 mmol) was dissolved in THF (1 mL), cooled to 0° C. and treated with 1N lithium hydroxide (137 mL). The reaction was allowed to warm to RT and stirred for 15 h. The reaction was acidified to pH 5 with acetic acid and the crystals that formed were filtered off to yield the title compound (70 mg); 95% purity by HPLC. MS(ES) mle 460 [M+H]$^+$.

Example 58

Preparation of (R,S)-8-[[4-(2-aminoethyl)piperidin-1-yl]carbonyl]-2,3,4,5-tetrahydro-3-oxo-4-(2-phenylethyl)-1H-1,4-benzodiazepine-2-acetic acid a) methyl (R,S)-8-[[4-[(N-t-butoxycarbonyl)-(2-aminoethyl)]piperidin-1-yl]carbonyl]-2,3,4,5-tetrahydro-3-oxo-4-(2-phenylethyl)-1H-1,4-benzodiazepine-2-acetate Using the procedure of Preparation 25(c), except substituting the compound of Preparation 16(b) for the compound of Example 1(g), gave the title compound (657 mg, 37%). $^1$H NMR (90 MHz, CDCl$_3$) δ7.40–7.08 (m, 5H), 6.95–6.50 (m, 3H), 5.50–4.40 (m, 5H), 4.00–2.43 (m, 14H), 3.73 (s, 3H), 1.90–1.00 (m, 5H), 1.43 (s, 9H).

b) (R,S)-8-[[4-(2-aminoethyl)piperidin-1-yl]carbonyl]-2,3,4,5-tetrahydro-3-oxo-4-(2-phenylethyl)-1H-1,4-benzodiazepine-2-acetic acid Using the procedures of Examples 13(b) and 13(c), except substituting the compound of Example 58(a) for the compound of Example 13(a), gave the title compound (160 mg). MS(ES) m/e 479 [M+H]$^+$; $^1$H NMR (CD$_3$OD, 250 MHz) δ7.30–7.08 (m, 5H), 6.98 (d, 1H, J=7.6 Hz), 6.60–6.50 (m, 2H), 5.47 (d, 1H, J=17 Hz), 5.15–5.08 (m, 1H), 3.90–3.58 (m, 3H), 3.89 (d, 1H, J=17 Hz), 3.18–2.55 (m, 9H), 1.95–1.52 (m, 5H), 1.35–1.08 (m, 2H); HPLC k' 2.43 (PRP-1®, 25% AN/W-TFA, UV detection at 220 nm); Anal. (C$_{27}$H$_{34}$N$_4$O$_4$·1.5 TFA) calcd: C, 55.46; H, 5.51; N, 8.62, found C, 55.19; H, 5.68; N, 8.58.

Example 59

Preparation of (R,S)-8-[[[4-(aminomethyl)phenyl] methylamino]-carbonyl]-2,3,4,5-tetrahydro-3-oxo-4-(2-phenylethyl)-1H-1,4-benzodiazepine-2-acetic acid a) methyl (R,S)-8-[[[4-(cyano)phenyl]methylamino] carbonyl]-2,3,4,5-tetrahydro-3-oxo-4-(2-phenylethyl)-1H-1,4-benzodiazepine-2-acetate Using the procedure of Preparation 25(c), except substituting 4-cyano-N-methylaniline for the compound of Example 1(g), gave the title compound. $^1$H NMR (400 MHz, CDCl$_3$) δ7.52 (d, J=8.6 Hz, 2H), 7.05–7.30 (m, 7H), 6.66 (d, J=1.5 Hz, 1H), 6.59 (d, J=7.8 Hz, 1H), 6.33 (dd, J=7.8, 1.5 Hz, 1H), 5.19 (d, J=16.7 Hz, 1H), 4.93 (t, J=6.5 Hz, 1H), 4.13 (br s, 1H), 3.68–3.79 (m, 1 H), 3.75 (s, 3H), 3.58–3.67 (m, 1H), 3.54 (d, J=16.7 Hz, 1H), 3.48 (s, 3H), 2.95 (dd, J=16.0, 6.6 Hz, 1H), 2.67–2.82 (m, 2H), 2.62 (dd, J=16.0, 6.5 Hz, 1H); IR (CHCl$_3$) 3230–3580 (br), 2230, 1731, 1656, 1603, 1437, 1375 cm$^{-1}$; MS(ES) m/e 497.2 [M+H]$^+$, 993.4 [2M+H]$^+$.

b) methyl (R,S)-8-[[[4-(aminomethyl)phenyl] methylamino]-carbonyl]-2,3,4,5-tetrahydro-3-oxo-4-(2-phenylethyl)-1H-1,4-benzodiazepine-2-acetate A mixture of the compound of Example 59(a) (0.125 g, 0.25 mmol) and 10% palladium on carbon (0.25 g) in glacial acetic acid (50 mL) was shaken under hydrogen (47 psi) for 5 h. The reaction mixture was filtered through Celite®, and the filtrate was concentrated to give the title compound (0.153 g, 99%) as a bis(acetate) which was used without further purification.

c) (R,S)-8-[[[4-(aminomethyl)phenyl]methylamino] carbonyl]-2,3,4,5-tetrahydro-3-oxo-4-(2-phenylethyl)-1H-1,4-benzodiazepine-2-acetic acid The compound of Example 59(b) (0.15 g, 0.25 mmol) was stirred in 10% aqueous acetic acid (25 mL) at 110° C. overnight. 1N Hydrochloric acid (4 mL) was added and heating was continued for an additional 3 h. The reaction was cooled, lyophilized and the residue was purified on reverse phase prep HPLC (ODS, AN/W-TFA) to give the title compound. MS(ES) m/e 487.2 [M+H]$^+$. Anal. (C$_{28}$H$_{30}$N$_4$O$_4$·2C$_2$HF$_3$O$_2$) calcd: C, 53.78; H, 4.51; N, 7.84. found: C, 53.69; H, 4.79; N, 7.76.

Example 60

Preparation of (R,S)-2,3,4,5-tetrahydro-8-[[[2-[1-methyl-1,2,5,6-tetrahydropyrid-4-yl]ethyl] methylamino]carbonyl]-3-oxo-4-(2-phenylethyl)-1H-1,4-benzodiazepine-2-acetic acid a) methyl (R,S)-2,3,4,5-tetrahydro-8-[[[2-[1-methyl-1,2,5,6-tetrahydropyrid-4-yl]ethyl]methylamino] carbonyl]-3-oxo-4-(2-phenylethyl)-1H-1,4-benzodiazepine-2-acetate Using the procedure of Example 27(a), except substituting the compound of Preparation 17(c) for histamine, gave the title compound. MS(ES) m/e 519 [M+H]$^+$.

b) (R,S)-2,3,4,5-tetrahydro-8-[[[2-[1-methyl-1,2,5,6-tetrahydropyrid-4-yl]ethyl]-methylamino]carbonyl]-3-oxo-4-(2-phenylethyl)-1H-1,4-benzodiazepine-2-acetic acid Using the procedure of Example 1(j), except substituting the compound of Example 60(a) for the compound of Example 1(i), gave the title compound. HPLC RT 15.7 min (YMC ODS-AQ, 6×250 mm, 1.5 mL/min, gradient, A:acetonitrile B:water-0.1% TFA, 10–80% A during 20 min, UV detection at 220 nm); $^1$H NMR (DMSO-d$_6$/TFA, 400 MHz) δ9.6 (br d, 1H), 7.25–7.15 (m, 5H), 7.0 (d, 1H), 6.49 (s, 1H), 6.45 (s, 1H), 5.5 (s, 1H), 5.4 (d, 1H), 5.0 (m, 1H), 4.0 (d, 1H), 3.75–3.05 (br m, 6H), 2.9–2.16 (br m, 16H); MS(ES) m/e 505 [M+H]$^+$.

Example 61

Preparation of (R,S)-2,3,4,5-tetrahydro-3-oxo-4-(2-phenylethyl)-8-[4-(piperidin-4-yl)-1(E)-butenyl]-1H-1,4-benzodiazepine-2-acetic acid a) methyl (R,S)-2,3,4,5-tetrahydro-8-hydroxymethyl-3-oxo-4-(2-phenylethyl)-1H-1,4-benzodiazepine-2-acetate Methyl (R,S)-8-carboxy-1,2,3,4-tetrahydro-3-oxo-4-(phenylethyl)-1H-1,4-benzodiazepine-2-acetate (3.8 g, 10 mmol) was treated with thionyl chloride (50 mL) and the resulting suspension was heated at reflux under argon with stirring for 15 min, cooled to RT and concentrated. The residual oil was re-dissolved in toluene (25 mL), concentrated and the residue was dissolved in dry THF (50 mL). The solution was stirred at RT and sodium borohydride (2.0 g, 53 mmol) as added in one portion. After stirring for 16 h, the reaction was carefully quenched at 0°0 C. with 1N hydrochloric acid, basified with 1N sodium carbonate, extracted with ethyl acetate (150 mL), washed with brine, dried (magnesium sulfate) and concentrated. Purification by flash chromatography (silica gel, 1% methanol/chloroform) gave the title compound (1.71 g, 47%) as a solid foam. TLC $R_f$=0.49 (silica gel, 5% methanol/chloroform); $^1$H NMR (CDCl$_3$) δ2.62 (dd, 1H), 2.77 (m, 2H), 2.97 (dd, 1H), 3.27 (br s, 2H), 3.68 (m, 3H), 3.72 (s, 3H), 4.51 (s, 2H), 4.94 (t, 1H), 5.24 (d, J=16.5 Hz, 1H), 6.56 (s, 1H), 6.62 (d, J=7.4, 1H), 6.80 (d, J=7.7 Hz, 1H), 7.20 (m, 5H).

b) methyl (R,S)-8-bromomethyl-2,3,4,5-tetrahydro-3-oxo-4-(2-phenylethyl)-1H-1,4-benzodiazepine-2-acetate To a solution of the compound of Example 61(a) (1.20 g, 3.3 mmol) and carbon tetrabromide (1.4 g, 4.2 mmol) in dry THF (40 mL), stirred at 0° C. under argon, was added triphenylphosphine (1.1 g, 4.2 mmol) in one portion. After 10 min, the reaction was allowed to warm to RT and stirred for 3 h. The mixture was concentrated and the residue was purified by flash chromatography (silica gel, 50% ethyl acetate/hexane) to yield the title compound (1.17 g, 83%). TLC $R_f$ 0.38 (silica gel, 40% ethyl acetate/hexane); $^1$H NMR (CDCl$_3$) δ1.26 (1H, s), 2.82(3H, m), 3.11 (1H, dd), 3.71 (2H, m), 3.74 (3H, s), 3.83 (1H, d, J=16.5 Hz), 4.37 (2H, s), 4.90 (1H, t), 5.13 (1H, d, J=16.5 Hz), 6.82 (2H, s), 6.89 (1H, d), 7.1–7.28 (6H, m).

c) (R,S)-[2-methoxycarbonylmethyl-3-oxo-4-(2-phenylethyl)-2,3,4,5-tetrahydro-1H-1,4-benzodiazepin-8-yl]methyltriphenyl-phosphonium bromide To a solution of Example 61(b) (1.15 g, 2.67 mmol) in dry THF (30 mL) was added triphenylphosphine (0.71 g, 2.7 mmol). The reaction was refluxed for 4 h, cooled to RT, concentrated and triturated with ether, filtered and dried under vacuum to give the title compound (1.89 g, 100%). $^1$H NMR (CDCl$_3$) δ2.01 (1H, s), 2.73 (2H, m), 2.90 (1H, dd), 3.08 (1H, dd), 3.54 (1H, m), 3.65 (1H, m), 3.70 (3H, s), 3.74 (1H, d, J=16.7 Hz), 4.49 (2H, dt), 5.08 (1H, d, J=15.5 Hz), 5.17 (1H, t), 6.40 (1H, d), 6.58 (1H, d, J=11.4 Hz), 6.87 (1H, s), 7.18 (5H, m), 7.58–7.80 (15H, m).

d) methyl (R,S)-8-[4-[N-(t-butoxycarbonyl)-piperidin-4-yl]-1-(E and Z)butenyl]-2,3,4,5-tetrahydro-3-oxo-4-(2-phenylethyl)-1H-1,4-benzodiazepine-2-acetate To a solution of compound of Example 61(c) (1 g, 1.44 mmol) and the compound of Preparation 18 (1.75 mmol) in dry THF (30 mL) was added, with stirring under argon, a 60% dispersion of sodium hydride in mineral oil (58 mg, 1.44 mmol) in one portion. After sting for 16 h, the reaction was concentrated. The residue was purified by flash chromatography (silica gel, 5% ethyl acetate:chloroform) to give a mixture of the title compounds (0.717 g, 86%). Pure olefin isomers in the ratio of approximately (1:2) (Z:E) were obtained by HPLC chromatography (silica gel, 40% ethyl acetate/hexane). E-isomer: $^1$H NMR (CDCl$_3$) δ1.11 (2H, m), 1.43 (4H, m), 1.45 (9H, s), 1.68 (2H, d, J=12.5 Hz), 2.20 (2H, dd), 2.67 (2H, dt), 2.72 (1H, dd), 2.81 (1H, dd), 3.72 (2H, dd), 2.67 (2H, dt), 2.72 (1H, dd), 2.81 (1H, dd), 3.72 (3H, m), 3.74 (3H, s), 4.08 (2H, d, J=13.7 Hz), 4.90 (1H, t), 5.18 (1H, d, J=16.5 Hz), 6.14 (1H, dt, J$_{trans}$=15.8 Hz), 6.24 (1H, d, J$_{trans}$=15.8 Hz), 6.67 (1H, s), 6.72 (1H, dd, J=7.8 Hz), 6.80 (1H, d, J=7.8 Hz), 7.20 (5H, m); MS(ES) m/e 576.2 (M+H)$^+$.

e) (R,S)-2,3,4,5-tetrahydro-3-oxo-4-(2-phenylethyl)-8-[4-(piperidin-4-yl)-1(E)-butenyl]-1H-1,4-benzodiazepine-2-acetic acid Using the procedures of Example 13(b) and 13(c), except substituting the compounds of Example 61(d) for the compound of Example 13(a) gave the title compound. MS(ES) m/e 462.2 [M+H]$^+$; Anal. (C$_{28}$H$_{35}$N$_3$O$_3$.1.5 CF$_3$CO$_2$H) calcd: C, 58.86; H, 5.82; N, 6.64. found: C, 58.68; H, 5.84; N, 6.32; HPLC k' 4.07 (PRP-1®, 35% AN/W-TFA); $^1$H NMR (CD$_3$OD) δ1.38 (2H, m), 1.45 (2H, m), 1.61 (1H, br s), 1.95 (2H, d, J=13.6 Hz), 2.22 (2H, dd), 2.61 (1H, m), 2.77 (2H, m), 2.91 (3H, m), 3.35 (2H, m), 3.67 (2H, m), 3.79 (1H, d, J=16.8 Hz), 5.02 (1H, dd), 5.37 (1H, d, J=16.5 Hz), 6.15 (1H, dt), 6.26 (1H, d, J=15.9 Hz), 6.58 (1H, s), 6.60 (1H, d, J=7.8 Hz), 6.81 (1H, d, J=7.8 Hz), 7.17 (5H, m).

Example 62

(R,S)-2,3,4,5-tetrahydro-3-oxo-4-(2-phenylethyl)-8-[4-(piperidin-4-yl)-1(Z)-butenyl]-1H-1,4-benzodiazepine-2-acetic acid a) methyl (R,S)-8-[4-[N-(t-butoxycarbonyl)-piperidin-4-yl]-1-(Z)butenyl]-2,3,4,5-tetrahydro-3-oxo-4-(2-phenylethyl)-1H-1,4-benzodiazepine-2-acetate The title compound was prepared by chromatography of the mixture of Example 61(d). Z-isomer: MS(ES) m/e 462.2 [M+H]$^+$; Anal. (C$_{28}$H$_{35}$N$_3$O$_3$.1.5 CF$_3$CO$_2$H.0.5 H$_2$O) calcd: C, 57.83; H, 5.73; N, 6.27. found: C, 58.03; H, 5.89; N, 6.55; HPLC k' 4.98 (PRP-1®, 35% CH$_3$CN/water/0.1% TFA); $^1$H NMR (CD$_3$OD) δ1.30 (2H, m), 1.41 (2H, dd), 1.58 (1H, br s), 1.82 (2H, d, J=13.1 Hz), 2.34 (2H, m), 2.60 (1H, m), 2.76 (2H, m), 2.88 (3H, m), 3.29 (3H, m), 3.69 (2H, m), 3.81 (1H, d, J=16.9 Hz), 5.04 (1H, m), 5.40 (1H, d, J=16.6 Hz), 5.58 (1H, dt), 6.31 (1H, d, J=11.6 Hz), 6.48 (1H, d, J=7.9 Hz), 6.50 (1H, s), 6.85 (1H, d, J=7.6 Hz), 7.18 (5H, m).

b) (R,S)-2,3,4,5-tetrahydro-3-oxo-4-(2-phenylethyl)-8-[4-(piperidin-4-yl)-1(Z)-butenyl]-1H-1,4-benzodiazepine-2-acetic acid The title compound was prepared in the same manner as in Example 61(e), except substituting the compound of Example 62(a). $^1$H NMR (CDCl$_3$) δ1.08 (2H, m), 1.41 (4H, m), 1.45 (9H, s), 1.62 (2H, d, J=12.9 Hz), 2.31 (2H, dd), 2.64 (2H, dt), 2.72 (1H, dd), 2.82 (2H, dt), 3.03 (1H, dd), 3.73 (3H, m), 3.75 (3H, s), 4.06 (2H, d, J=13.2 Hz), 4.93 (1H, t), 5.22 (1H, d, J=16.5 Hz), 5.59 (1H, dt, J$_{cis}$=11.6 Hz), 6.27 (1H, d, J$_{cis}$=11.7 Hz), 6.55 (1H, s), 6.63 (1H, d, J=7.7 Hz), 6.82 (1H, d, J=7.7 Hz), 7.20 (5H, m); MS(ES) m/e 576.2 (M+H)$^+$.

Example 63

Preparation of (R,S)-8-[2(E)-[4-(aminomethyl)phenyl]ethenyl]-2,3,4,5-tetrahydro-3-oxo-4-(2-phenylethyl)-1H-1,4-benzodiazepine-2-acetic acid a) methyl (R,S)-8-[2(E and Z)-[4-(N-t-butoxycarbonyl)(amino-methyl)phenyl]ethenyl]-2,3,4,5-tetrahydro-3-oxo-4-(2-phenylethyl)-1H-1,4-benzodiazepine-2-acetate Using the procedure of Examples 61(d), except substituting the compound of Preparation 19 for the compound of Preparation 18, gave the title compounds in the ratio of approximately (2:3) (Z:E). E-isomer: $^1$H NMR (CDCl$_3$) δ1.47 (9H, s), 2.72 (1H, dd), 2.83 (2H, dt), 3.04 (1H, dd), 3.73 (3H, m), 3.75 (3H, s), 4.32 (2H, br s), 4.85 (1H, br s), 4.95 (1H, t), 5.24 (1H, d, J=16.5 Hz), 6.77 (1H, s), 6.83 (2H, 2d), 6.92 (1H, d, J$_{trans}$=16.5 Hz), 7.01 (1H, d, J$_{trans}$=16.5 Hz), 7.2 (7H, m), 7.43 (2H, d, J=8.2 Hz); MS(DCI) m/e 570.5 (M+H)$^+$. Z isomer: $^1$H NMR (CDCl$_3$) δ1.46 (9H, s), 2.66 (1H, dd), 2.82 (2H, m), 2.98 (1H, dd), 3.70 (3H, m), 3.74 (3H, s), 4.28 (2H, br s), 4.87 (1H, br s), 4.90 (1H, t), 5.20 (1H, d, J=16.5 Hz), 6.43 (1H, d, J$_{cis}$=12.2 Hz), 6.49 (1H, s), 6.53 (1H, d, J$_{cis}$=11.8 Hz), 6.55 (1H, d, J=6.2 Hz), 6.69 (1H, d, J=7.8 Hz), 7.20 (9H, m); MS(DCI) m/e 570.5 (M+H)$^+$.

b) (R,S)-8-[2(E)-[4-(aminomethyl)phenyl]ethenyl]-2,3,4,5-tetrahydro-3-oxo-4-(2-phenylethyl)-1H-1,4-benzodiazepine-2-acetic acid Using the procedure of Example 61(e), except substituting the E isomer of Example 63(a) for the compound of Example 61(d), yielded the title compound. MS(ES) m/e 456.2 [M+H]$^+$; Anal. (C$_{28}$H$_{35}$N$_3$O$_3$·1.5 CF$_3$CO$_2$H) calcd: C, 59.36; H, 5.03; N, 6.64. found: C, 59.42; H, 4.91; N, 6.71; HPLC k' 3.34 (PRP-1®, 35% CH$_3$CN/water/0.1% TFA); $^1$H NMR (CD$_3$OD) δ2.64 (1H, dd), 2.78 (2H, m), 2.93 (1H, dd), 3.70 (2H, m), 3.84 (1H, d, J=16.8 Hz), 4.91 (2H, s), 5.07 (1H, m), 5.42 (1H, d, J=16.4 Hz), 6.77 (1H, s), 6.81 (1H, d, J=7.5 Hz), 6.91 (1H, d, J=7.5 Hz), 7.08 (2H, s), 7.18 (5H, m), 7.42 (2H, d, J=7.7 Hz), 7.59 (2H, d, J=7.9 Hz).

Example 64

(R,S)-8-[2(Z)-[4-(aminomethyl)phenyl]ethenyl]-2,3,4,5-tetrahydro-3-oxo-4-(2-phenylethyl)-1H-1,4-benzodiazepine-2-acetic acid Using the procedure of Example 61(e), except substituting the Z isomer of Example 63(a) for the compound of Example 61(d), yielded the title compound. MS(ES) m/e 462.2 [M+H]$^+$; Anal. (C$_{28}$H$_{35}$N$_3$O$_3$·1.75 CF$_3$CO$_2$H) calcd: C, 57.53; H, 4.67; N, 6.38. found: C, 57.75; H, 4.73; N, 6.41.; HPLC k' 4.33 (PRP-1®, 35% CH$_3$CN/water/0.1% TFA); $^1$H NMR (CD$_3$OD) δ2.59 (1H, dd), 2.76 (2H, m), 2.88 (1H, dd), 3.69 (2H, m), 3.78 (1H, d, J=16.8 Hz), 4.02 (2H, s), 5.00 (1H, dd), 5.35 (1H, d, J=16.6 Hz), 6.39 (1H, dd), 6.47 (1H, s), 6.54 (2H, s), 6.73 (1H, d, J=7.8 Hz), 7.17 (5H, m), 7.27 (4H, 2d).

Example 65

Preparation of (R,S)-2,3,4,5-tetrahydro-3-oxo-4-(2-phenylethyl)-7-[[4-(pyrid-4-yl)piperazin-1-yl]carbonyl]-1H-1,4-benzodiazepine-2-acetic acid a) methyl (R,S)-2,3,4,5-tetrahydro-3-oxo-4-(2-phenylethyl)-7-[[4-(pyrid-4-yl)piperazin-1-yl]carbonyl]-1H-1,4-benzodiazepine-2-acetate Using the procedure of Example 32(a), except substituting 1-(pyrid-4-yl)piperazine for N-methyl-2-(4-pyridyl) ethanamine, gave the title compound. HPLC RT 16.3 min (YMC ODS-AQ, 6×250 mm, 1.5 mL/min, gradient, A:acetonitrile B:water-0.1% TFA, 10–80% A during 20 min, UV detection at 220 nm); MS(ES) m/e 528 [M+H]$^+$.

b) (R,S)-2,3,4,5-tetrahydro-3-oxo-4-(2-phenylethyl)-7-[[4-(pyrid-4-yl)piperazin-1-yl]carbonyl]-1H-1,4-benzodiazepine-2-acetic acid Using the procedure of Example 1(j), except substituting the compound of Example 65(a) for the compound of Example 1(i), gave the title compound. HPLC RT 14.6 min (YMC ODS-AQ, 6×250 mm, 1.5 mL/min, gradient, A:acetonitrile B:water-0.1% TFA, 10–80% A during 20 min, UV detection at 220 nm); $^1$H NMR (DMSO-d$_6$:TFA, 250 MHz) δ8.3 (m, 2H), 7.19 (m, 9H), 6.55 (d, 1H), 5.4 (d, 1H), 5.09 (m, 1H), 4.0 (d, 1H), 3.7 (m, 8H), 2.8–2.4 (br m, 6H); MS(ES) m/e 514 [M+H]$^+$.

Example 66

Preparation of (R,S)-2,3,4,5-tetrahydro-3-oxo-7-[[[2-(piperidin-4-yl)ethyl]methylamino]carbonyl]-1H-2-benzazepine-4-acetic acid a) t-butyl 3-bromo-4-methylbenzoate A mixture of 3-bromo-4-methylbenzoic acid (10.75 g, 50 mmol) in dry ether (50 mL) in a glass bomb was cooled to −30° C. and isobutylene gas was bubbled in to give a total reaction volume of approximately 150 mL. Trifluoromethanesulfonic acid (0.22 g, 2.5 mmol) was added dropwise to the stirred mixture, and the bomb was sealed. The reaction was allowed to warm to RT and was stirred for 6 d. The bomb was opened carefully, and 5% sodium bicarbonate (50 mL) was added slowly. The mixture was allowed to stir for 15 min and ether (250 mL) was added. The layers were separated and the organic layer was washed with 5% sodium bicarbonate (2×50 mL) and then with brine (50 mL). Drying (magnesium sulfate) and concentration gave the title compound (12.88 g, 95%) as a yellow oil. TLC R$_f$ 0.68 (toluene); $^1$H NMR (250 MHz, CDCl$_3$) δ8.13 (d, J=1.7 Hz, 1 H), 7.81 (dd, J=7.9, 1.7 Hz, 1 H), 7.27 (d, J=7.9 Hz, 1 H), 2.44 (s, 3H), 1.59 (s,9 H); IR (CCl$_4$) 1715, 1368, 1297, 1255, 1170, 1123, 1115 cm$^{-1}$; MS(ES) m/e 273.0 [M+H]$^+$, 271.0 [M+H]$^+$, 214.8 [M+H−C$_4$H$_8$]$^+$.

b) t-butyl 3-bromo-4-(bromomethyl)benzoate

A mixture of the compound of Example 66(a)(5.25 g, 19.36 mmol), N-bromosuccinimide (3.79 g, 21.3 mmol), and benzoyl peroxide (0.23 g, 0.97 mmol) in carbon tetrachloride (100 mL) was heated to reflux. After 15 h, the mixture was cooled, filtered, and the filtrate was concentrated. The resulting material was used without purification. TLC R$_f$ 0.57 (10% ethyl acetate/hexane).

c) t-butyl 3-bromo-4-[[N-t-butoxycarbonyl-N-methoxycarbonyl]amino]methylbenzoate The compound of Example 66(b) and methyl t-butyl iminodicarboxylate potassium salt (prepared according to *J. Chem. Soc. Perkin Trans. I*, 1088, (1988)) (3.10 g, 14.52 mmol) were combined in dry dimethylformamide (20 mL), and the mixture was warmed in an oil bath at 60° C. More methyl t-butyl iminodicarboxylate potassium salt (0.83 g, 3.89 mmol) was added after 20 min and the mixture which was stirred an additional 5 min and concentrated. The residue was partitioned between water (100 mL) and ether (100 mL), and the layers were separated. The aqueous layer was extracted with ether, and the combined organic layers were dried (magnesium sulfate) and concentrated to a brown oil. Chromatography (silica gel, 20% ethyl acetate/hexane) gave the title compound (5.21 g, 61%) as a yellow oil which solidified in vacuum. TLC R$_f$ 0.49 (20% ethyl acetate/hexane); $^1$H NMR (250 MHz, CDCl$_3$) δ8.15 (d, J=1.6 Hz, 1 H), 7.89 (dd, J=8.1, 1.6 Hz, 1 H), 7.16 (d, J=8.1 Hz, 1 H), 4.95 (s, 2 H), 3.84 (s, 3 H), 1.59 (s, 9 H), 1.41 (s, 9 H); IR (carbon tetrachloride) 1756, 1719, 1369, 1352, 1297, 1255, 1222, 1155, 1113 cm$^{-1}$; MS(ES) m/e 446 [M+H]$^+$, 444

[M+H]$^+$, 390 [M+H−C$_4$H$_8$]$^+$, 388 [M+H−C$_4$H$_8$]$^+$, 334 [M+H−2×C$_4$H$_8$]$^+$, 332 [M+H−2×C$_4$H$_8$]$^+$.

d) t-butyl 3-bromo-4-[(t-butoxycarbonyl)amino] methylbenzoate

A solution of the compound of Example 66(c) (5.21 g, 11.73 mmol) and 1N sodium hydroxide (11.7 mL, 11.7 mmol) in methanol (105 mL) was stirred at RT. After 20 min, the reaction was diluted with water (250 mL) and extracted with ether. The combined organic layers were washed with brine (100 mL), dried (magnesium sulfate), and concentrated. Chromatography (silica gel, 15% ethyl acetate/hexane) gave the title compound (4.29 g, 95%) as a light yellow oil which slowly, partially solidified. TLC R$_f$ 0.41 (15% ethyl acetate/hexane); $^1$H NMR (400 MHz, CDCl$_3$) δ8.13 (d, J=1.5 Hz, 1 H), 7.90 (dd, J=8.0, 1.5 Hz, 1 H), 7.42 (d, J=8.0 Hz, 1 H), 5.07 (m, 1 H), 4.41 (d, J=6.3 Hz, 2 H), 1.59 (s, 9 H), 1.45 (s, 9 H); IR (carbon tetrachloride) 3450, 1719, 1496, 1394, 1371, 1300, 1255, 1172, 1120 cm$^{-1}$; MS(ES) m/e 410.0 [M+Na]$^+$, 408.2 [M+Na]$^+$, 386.2 [M+H]$^+$, 388 [M+H]$^+$, 330.0 [M+H−C$_4$H$_8$]$^+$, 332 [M+H−C$_4$H$_8$]$^+$, 274 [M+H−2×C$_4$H$_8$]$^+$, 276 [M+H−2×C$_4$H$_8$]$^+$.

e) methyl 3-methoxycarbonyl-4-[5-(t-butoxycarbonyl)-2-[[(t-butoxycarbonyl)amino] methyl]phenyl]-3-butenoate Dimethyl itaconate (607 mg, 3.84 mmol) was added to a solution of the compound of Example 66(d) (1.14 g, 2.95 mmol), palladium(II) acetate (33 mg, 0.15 mmol), tri-ortho-tolylphosphine (90 mg, 0.30 mmol), and diisopropylethylamine (1.03 mL, 5.90 mmol) in propionitrile (15 mL). The solution was deoxygenated through three evacuation/argon purge cycles, and was heated to reflux under argon. After 55 min, the reaction was cooled in ice/water and poured into cold ether (150 mL). After standing for 10 min, the mixture was filtered, and the filter pad was washed with ether. The filtrate was concentrated to a yellow oil, which was concentrated from toluene to remove residual propionitrile. The residue was chromatographed (silica gel, step gradient, 15–30% ethyl acetate/hexane). All products with R$_f$ 0.26 (major product) to R$_f$ 0.65 (25% ethyl acetate/hexane) were isolated together as a cloudy, yellow oil. TLC Rf 0.26 (major product), 0.37, 0.49, 0.56, 0.65 (minor products) (25% ethyl acetate/hexane).

f) methyl (R,S)-3-methoxycarbonyl-4-[5-(t-butoxycarbonyl)-2-[[(t-butoxycarbonyl)amino] methyl]phenyl]butanoate 10% Palladium on carbon (0.94 g) was added carefully to a well-stirred solution of the compound of Example 66(e) (1.36 g, 2.93 mmol) in ethyl acetate-methanol (1:1) (29 mL) at 0° C. The stirring bar was removed, and the mixture was shaken at RT under H$_2$ (50 psi). After 2 h, the mixture was filtered through Celite®, and the filtrate was concentrated to a pale yellow residue. The residue was dissolved in methanol (29 mL), and palladium(II) hydroxide on carbon (moist, Pearlman's catalyst, 0.59 g) was added. The mixture was shaken at RT under H$_2$ (50 psi) for 3 h, then was filtered through Celite®. The filtrate was concentrated to a cloudy, colorless oil, which was reconcentrated from toluene to remove residual methanol. Chromatography (silica gel, 30% ethyl acetate/hexane) gave the title compound (1.03 g, 76%) as a colorless oil. TLC R$_f$ 0.35 (25% ethyl acetate/hexane); $^1$H NMR (250 MHz, CDCl$_3$) δ7.83 (dd, J=8.0, 1.6 Hz, 1 H), 7.73 (d, J=1.6 Hz, 1 H), 7.36 (d, J=8.0 Hz, 1 H), 4.90–5.05 (m, 1 H), 4.25–4.50 (m, 2 H), 3.66 (s, 3 H), 3.64 (s, 3 H), 3.03–3.20 (m, 2 H), 2.67–2.93 (m, 2 H), 2.48 (dd, J=16.8, 5.1 Hz, 1 H), 1.59 (s, 9 H), 1.45 (s, 9 H); IR (CCl$_4$) 3300–3480 (br), 1740, 1715, 1368, 1157 cm$^{-1}$; MS(ES) m/e 953.4 [2M+Na]$^+$, 931.4 [2M+H]$^+$, 488.0 [M+Na]$^+$, 466.0 [M+H]$^+$, 410.0 [M+H−C$_4$H$_8$]$^+$, 354 [M+H−2×C$_4$H$_8$]$^+$, 310 [M+H−2×C$_4$H$_8$−CO$_2$]$^+$.

g) methyl (R,S)-3-methoxycarbonyl-4-[5-carboxy-2-(aminomethyl)phenyl]butanoate TFA (3.2 mL) was added all at once to a cloudy solution of the compound of Example 66(f) (296.5 mg, 0.64 mmol) in dry dichloromethane (3.2 mL) at 0° C. under argon. The solution was warmed to RT, stirred for 2 h and concentrated. The residue was concentrated once from 2:1 1,2-dichloroethane:toluene (10 mL) to remove residual TFA. The resulting material was used without purification.

h) methyl (R,S)-7-carboxy-2,3,4,5-tetrahydro-3-oxo-1H-2-benzazepine-4-acetate The compound of Example 66(g) was dissolved in anhydrous methanol (3.2 mL) and the solution was cooled to 0° C. under argon. Freshly prepared 1.0 M sodium methoxide/methanol (3.2 mL, 3.2 mmol) was added rapidly, and the ice bath was removed. The reaction was allowed to warm to RT over 10 min and heated to reflux under argon. After 2 h, the reaction was cooled in ice, and cold 1N hydrochloric acid (3.4 mL, 3.4 mmol) was added rapidly. The mixture was filtered after 1 h at 0° C., and the filter pad was washed with water and then with cold methanol, to afford the title compound (149.2 mg, 84%) as a colorless powder. TLC R$_f$ 0.38 (10% methanolchloroform); $^1$H NMR (400 MHz, DMSO-d$_6$) δ8.08 (app t, 1 H), 7.65–7.72 (m, 2 H), 7.27 (d, J=7.8 Hz, 1 H), 4.79 (dd, J=16.4, 4.9 Hz, 1 H), 4.01 (dd, J=16.4, 6.7 Hz, 1 H), 3.59 (s, 3 H), 3.50–3.61 (m, 1 H), 3.07 (dd, J=17.2, 3.6 Hz, 1 H), 2.87 (dd, J=17.2, 13.0 Hz, 1 H), 2.70 (dd, J=16.7, 8.7 Hz, 1 H), 2.45 (dd, J=16.7, 5.2 Hz, 1 H); MS(ES) m/e 278.0 [M+H]$^+$.

i) methyl (R,S)-2,3,4,5-tetrahydro-3-oxo-7-[[[2-(pyrid-4-yl)ethyl]methylamino]carbonyl]-1H-2-benzazepine-4-acetate 1-(3-dimethylaminopropyl)-3-ethylcarbodiimide hydrochloride (90 mg, 0.47 mmol) was added to a solution of the compound of Example 66(h) (107.6 mg, 0.39 mmol), N-methyl-2-(pyrid-4-yl)ethanamine (64 mg, 0.47 mmol), 1-hydroxybenzotriazole (63 mg, 0.47 mmol), and diisopropylethylamine (0.14 mL, 0.78 mmol) in dry dimethylformamide (2 mL) at RT under argon. The reaction was stirred for 23 h and concentrated. The residue was partitioned between ethyl acetate and water. The layers were separated, and the organic phase was washed with water. The combined aqueous layers were back-extracted with ethyl acetate. The combined organic layers were dried (sodium sulfate) and concentrated to leave a yellow oil. The combined aqueous layers were concentrated and sodium chloride was added. The resulting mixture was exhaustively extracted with chloroform. The combined organic phase was dried (sodium sulfate) and concentrated to give a yellow oil, which was combined with the material from the ethyl acetate phase. Chromatography (silica gel, 10% methanol/chloroform) gave the title compound (139.7 mg, 91%) as a colorless oil. TLC R$_f$ 0.45 (10% methanol/chloroform); $^1$H NMR (400 MHz, CDCl$_3$) Rotameric mixture; δ8.41–8.63 (m, 2 H), 6.72–7.28 (m, 5 H), 6.53 (t, J=6.0 Hz, 1 H), 4.83 (dd, J=16.3, 4.8 Hz, 1 H), 4.09 (dd, J=16.3, 6.5 Hz, 1 H), 3.45–3.88 (m, 3 H), 3.72 (s, 3 H), 2.70–3.25 (m, 8 H), 2.50 (dd, J=16.9, 6.1

Hz, 1 H); IR (chloroform) 3400, 1727, 1660, 1623 cm$^{-1}$; MS(ES) m/e 396.2 [M+H]$^+$.

j) methyl (R,S)-2,3,4,5-tetrahydro-3-oxo-7-[[[2-(piperidin-4-yl)ethyl]methylamino]carbonyl]-1H-2-benzazepine-4-acetate Platinum oxide (4 mg) was added to a solution of the compound of Example 66(i) (139.7 mg, 0.35 mmol) and 1N hydrochloric acid (0.35 mL, 0.35 mmol) in methanol (3.5 mL), and the mixture was stirred briskly under H$_2$ (balloon pressure). After 7 h, the reaction was filtered through Celite® and concentrated, and the residue was dissolved in methanol (3.5 mL). Platinum oxide (4 mg) was added, and the mixture was stirred briskly under H$_2$ (balloon pressure) for 16.5 h. Filtration through Celite® and concentration left a colorless oil. This was used without purification. HPLC k' 3.2 (PRP-1®, 15% AN/W-TFA).

k) (R,S)-2,3,4,5-tetrahydro-3-oxo-7-[[[2-(piperidin-4-yl)ethyl]methylamino]carbonyl]-1H-2-benzazepine-4-acetic acid The compound of Example 66(j) was dissolved in methanol (12 mL) and cooled to 0° C. 1N Sodium hydroxide (1.05 mL, 1.05 mmol) was added dropwise, and the solution was allowed to warm to RT. The reaction was stirred at RT for 24 h and concentrated. The residue was concentrated from 1:1-acetonitrile:water (4 mL) to remove methanol, the residue dissolved in 1:1-acetonitrile:water (4 mL), and cooled in ice. TFA (0.27 mL, 3.5 mmol) was added and the reaction was concentrated. The residue was purified by reversed-phase flash chromatography (ODS, 10–12.5% AN/W-TFA). Concentration and lyophilization gave the title compound (97.5 mg, 47%) as a colorless powder. HPLC k' 5.19 (PRP-1®, 10% AN/W-TFA); $^1$H NMR (400 MHz, DMSO-d$_6$) Rotameric mixture; δ8.52–8.72 (m, 1 H), 8.15–8.43 (m, 1 H), 8.07 (t, J=5.8 Hz, 1 H), 7.20 (d, J=8.3 Hz, 1 H), 7.08–7.15 (m, 2 H), 4.77 (dd, J=16.3, 4.7 Hz, 1 H), 3.96 (dd, J=16.3, 6.7 Hz, 1 H), 2.70–3.55 (m, 12 H), 2.65 (dd, J=16.8, 8.4 Hz, 1 H), 2.34 (dd, J=16.8, 5.2 Hz, 1 H), 1.82–1.95 (m, 1 H), 1.02–1.62 (m, 6 H); MS(ES) m/e 388.2 [M+H]$^+$; Anal. (C$_{21}$H$_{29}$N$_3$O$_4$.1.75 (CF$_3$CO$_2$H)) calcd: C, 50.13; H, 5.28; N, 7.16. found: C, 50.20; H, 5.21; N, 7.21.

Example 67

Preparation of (R,S)-2,3,4,5-tetrahydro-3-oxo-2-(2-phenylethyl)-7-[[[2-(piperidin-4-yl)ethyl]methylamino]-carbonyl]-1H-2-benzazepine-4-acetic acid a) methyl (R,S)-2,3,4,5-tetrahydro-3-oxo-2-(2-phenylethyl)-7-[[[2-(pyrid-4-yl)ethyl]methylamino]carbonyl]-1H-2-benzazepine-4-acetate Using the procedure of Example 32(a), except substituting the compound of Example 1(g) for methyl (R,S)-8-carboxy-1,2,4,5-tetrahydro-3-oxo-4-(2-phenylethyl)-3H-1,4-benzodiazepine-2-acetate, gave the title compound. HPLC RT 16.2 min (YMC ODS-AQ, 6×250 mm, 1.5 mL/min, gradient, A:acetonitrile B:water-0.1% TFA, 10–80% A during 20 min, UV detection at 220 nm).

b) methyl (R,S)-2,3,4,5-tetrahydro-3-oxo-2-(2-phenylethyl)-7-[[[2-(piperidin-4-yl)ethyl]methylamino]carbonyl]-1H-2-benzazepine-4-acetate; and methyl (R,S)-2,3,4,5-tetrahydro-3-oxo-2-(cyclohexylethyl)-7-[[[2-(piperidin4-yl)ethyl]methylamino]carbonyl]-1H-2-benzazepine-4-acetate Using the procedure of Example 36(a), except substituting the compound of Example 67(a) for the compound of Example 32(a), gave a mixture of the title compounds. 2-(2-phenylethyl) compound: MS(ES) n/e 506 [M+H]$^+$; HPLC RT 16.47 min (YMC ODS-AQ, 6×250 mm, 1.5 mL/min, gradient, A:acetonitrile B:water-0.1% TFA, 10–80% A during 20 min, UV detection at 220 nm). 2-(2-cyclohexylethyl) compound: MS(ES) m/e 511 [M+H]$^+$; HPLC RT 19.14 min (YMC ODS-AQ, 6×250 mm, 1.5 mL/min, gradient, A:acetonitrile B:water-0.1% TFA, 10–80% A during 20 min, UV detection at 220 nm).

c) (R,S)-2,3,4,5-tetrahydro-3-oxo-2-(2-phenylethyl)-7-[[[2-(piperidin-4-yl)ethyl]methylamino]carbonyl]-1H-2-benzazepine-4-acetic acid; and Using the procedure of Example 1(j), except substituting the compounds of Example 67(b) for the compound of Example 1(i), yielded the title compound which was separated from the 2-ethylcyclhexyl compound by HPLC. HPLC RT 14.59 min (YMC ODS-AQ, 6×250 mm, 1.5 mL/min, gradient, A:acetonitrile B:water-0.1% TFA, 10–80% A during 20 min, UV detection at 220 nm); MS(ES) m/e 492 [M+H]$^+$.

Example 68

(R,S)-2,3,4,5-tetrahydro-3-oxo-2-(cyclohexylethyl)-7-[[[2-(piperidin-4-yl)ethyl]methylamino]carbonyl]-1H-2-benzazepine-4-acetic acid The title compound was isolated from the reaction mixture of Example 67(c) by HPLC. HPLC RT 17.61 min (YMC ODS-AQ, 6×250 mm, 1.5 mL/min, gradient, A:acetonitrile B:water-0.1% TFA, 10–80% A during 20 min, UV detection at 220 nm); MS(ES) m/e 498 [M+H]$^+$.

Example 69

Preparation of (R,S)-2,3,4,5-tetrahydro-3-oxo-4-(2-phenylethyl)-8-[4-(piperidin-4-yl)butyl]-1H-1,4-benzodiazepine-2-acetic acid a) methyl (R,S)-8-[4-[(N-t-butoxycarbonyl)-piperidin-4-yl]butyl]-2,3,4,5-tetrahydro-3-oxo-4-(2-phenylethyl)-1H-1,4-benzodiazepine-2-acetate A mixture of the E/Z isomers of Example 61(d) and 10% palladium on carbon in acetic acid was shaken under hydrogen (50 psi) for 4 h to give the title compound.

b) (R,S)-2,3,4,5-tetrahydro-3-oxo-4-(2-phenylethyl)-8-(piperidin-4-yl)butyl]-1H-1,4-benzodiazepine-2-acetic acid Using the procedure of Example 13(b) and 13(c), except substituting the compound of Example 69(a) for the compound of Example 13(a), gave the title compound. MS(ES) m/e 464.2 [M+H]$^+$; Anal. (C$_{28}$H$_{37}$N$_3$O$_3$.CF$_3$CO$_2$H.1.25 H$_2$O) calcd: C, 59.91; H, 6.51; N, 6.73. found: C, 60.04; H, 6.80; N, 7.00; HPLC k' 4.73 (PRP-1®, 35% AN/W-TFA); $^1$H NMR (CD$_3$OD) δ1.32 (6H, m), 1.57 (3H, m), 1.87 (2H, d, J=14.0 Hz), 2.49 (2H, t), 2.61 (1H, dd), 2.75 (2H, m), 2.90 (3H, m), 3.30 (2H, m), 3.68 (2H, m), 3.80 (1H, d, J=16.7 Hz), 5.02 (1H, dd), 5.37 (1H, d, J=16.5 Hz), 6.41 (1H, d, J=8.0 Hz), 6.42 (1H, s), 6.80 (1H, d, J=8.0 Hz), 7.17 (5H, m).

Example 70

Preparation of 8-[[4-(aminoiminomethyl)benzoyl]amino]-2,3,4,5-tetrahydro-3-oxo-1H-2,4-benzodiazepine-2-acetic acid a) α,α'-diphthalimidoyl-o-xylene

A mixture of α,α'-dibromo-o-xylene (26 g, 98 mmol) and potassium phthalimide (54.7 g, 294 mmol) in dimethylformamide (500 mL) was refluxed for 18 h. The solution was cooled to RT, poured into water, filtered and the filter cake was dried at reduced pressure to give the title compound (35 g, 90%).

b) 4-nitro-α,α'-diphthalimidoyl-o-xylene

To a cold solution of potassium nitrate (6.2 g, 61.2 mmol) in concentrated sulfuric acid (350 mL) was added portion wise the compound of Example 70(a) (22 g, 55.6 mmol). The resulting solution was warmed to RT and stirred for 18 h. The mixture was carefully poured into ice water and the mixture was filtered. The filter cake was washed with water and dried at reduced pressure to give the title compound (23.58 g, 96%).

c) 1,2-bis(aminomethyl)-4-nitro-benzene

To a solution of hydrazine (26 mL, 535 mmol) in ethanol (1000 mL) was added portion wise the compound of Example 70(b) (23.58 g, 53.5 mmol). The solution was refluxed for 1 h. Additional hydrazine (26 mL, 535 mmol) was added followed by ethanol (500 mL). The solution was stirred at RT for 18 h, filtered and the filtrate was concentrated. The residue was triturated with chloroform (600 mL) for 1 h. Filtration and concentration gave the title compound (9.42 g, 97%).

d) 2,3,4,5-tetrahydro-7-nitro-3-oxo-1H-2,4-benzodiazepine

To a solution of the compound of Example 70(c) (9.42 g, 51.9 mmol) in THF (500 mL) was added dropwise 1,1'-carbonyldiimidazole (9.2 g, 56.8 mmol) dissolved in THF (250 mL). The resulting mixture was stirred at RT for 6 d, filtered and concentrated to yield the title compound (7.7 g, 71%).

e) 2,3,4,5-tetrahydro-7-nitro-3-thioxo-1H-2,4-benzodiazepine

A heterogeneous solution consisting of the compound of Example 70(d) (5.5 g, 26.6 mmol) and Lawesson's Reagent (7.0 g, 17.3 mmol) in toluene (100 mL) was heated to 80° C. under an argon atmosphere for 1.5 h. The solution was cooled and filtered. The solid was triturated with (7:3) dichloromethane:methanol for 1 h, filtered, and concentrated to give the title compound (4.3 g, 73%).

f) methyl 2,5-dihydro-3-methylthio-7-nitro-1H-2,4-benzodiazepine-2-acetate; and methyl 2,5-dihydro-3-methylthio-8-nitro-1H-2,4-benzodiazepine-2-acetate To a solution of the compound of Example 70(e) (2.2 g, 9.9 mmol) in dimethylformamide (50 mL) was added dropwise iodomethane (0.614 mL, 9.9 mmol) dissolved in dimethylformamide (5 mL). The solution was stirred for 1 h and potassium carbonate (3.0 g, 21.8 mmol) was added followed by methyl bromoacetate (0.934 mL, 9.9 mmol). The solution was stirred for 18 h, filtered and concentrated to give a residue which was partitioned between ethyl acetate and water. The organic layer was concentrated to give a mixture of the title compounds (2.26 g, 74%).

g) methyl 2,3,4,5-tetrahydro-7-nitro-3-oxo-1H-2,4-benzodiazepine-2-acetate; and methyl 2,3,4,5-tetrahydro-8-nitro-3-oxo-1H-2,4-benzodiazepine-2-acetate The mixture of the compounds of Example 70(f) (2.26 g, 7.3 mmol) was dissolved in water/dioxane (1:1) (50 mL) and refluxed for 18 h. The solution was concentrated and the residue was triturated with water (30 mL), filtered and dried at reduced pressure to give a mixture of the title compounds (1.38 g, 68%).

h) methyl 8-amino-2,3,4,5-tetrahydro-3-oxo-1H-2,4-benzodiazepine-2-acetate

The mixture of the compound of Example 70(g) (470 mg, 1.7 mmol) was dissolved in (1:1) methanol:dimethylformamide (20 mL). Argon was bubbled through the system and 10% palladium on carbon (80 mg) was added and the mixture was shaken under hydrogen (40 psi) for 1.5 h. The solution was filtered through Celite® and concentrated. The residue was chromatographed (silica gel, 4% methanol/dichloromethane) to yield the title compound (110 mg, 42%). $^1$H NMR (360 MHz, DMSOd$_{d6}$) δ3.6–3.65 (s, 3H), 4.0–4.1 (m, 4H), 4.25–4.3 (s, 2H), 5.7 (s, 2H), 6.35–6.45 (dd, 1H), 6.45–6.5 (d, 1H), 6.6–6.65 (t, 1H), 6.85–6.9 (d, 1H); MS(ES) m/e 250.2 [M+H]$^+$; TLC R$_f$ 0.60 (9:1 dichloromethane:methanol).

i) methyl 8-[[4-(N-benzyloxycarbonyl)(aminoiminomethyl)-benzoyl]amino]-2,3,4,5-tetrahydro-3-oxo-1H-2,4-benzodiazepine-2-acetate Using the procedure of Example 32, except substituting the compound of example 70(h) for methyl (R,S)-8-carboxy-2,3,4,5-tetrahydro-3-oxo-4-(2-phenylethyl)-1H-1,4-benzodiazepine-2-acetate, and substituting 4-(benzyloxycarbonyl-amidino)benzoic acid for N-methyl-2-(4-pyridyl)ethanamine, and substituting dicyclohexylcarbodiimide for 1-(3-dimethylaminopropyl)-3-ethylcarbodiimide hydrochloride, gave the title compound.

j) 8-[[4-(aminoiminomethyl)benzoyl]amino]-2,3,4,5-tetrahydro-3-oxo-1H-2,4-benzodiazepine-2-acetic acid Using the procedures of Example 1(i) and 1(j), except substituting the compound of Example 70(i) for the compound of Example 1(h) gave the title compound. Anal. ($C_{21}H_{26}N_5O_{7.5}$) calcd: C, 53.84; H, 5.59; N, 14.95. found: C, 54.04; H, 5.92; N, 14.81; MS(ES) m/e 382.0 [M+H]$^+$. $^1$H NMR (DMSO-d$_6$, 360 MHz) δ2.5 (s, 3H), 3.9–4.0 (d, 2H), 4.2–4.3 (d, 2H), 4.4–4.5 (d, 2H), 6.5–6.6 (m, 1H), 7.2–7.3 (d, 1H), 7.6–8.1 (m, 10 H).

Example 71

Preparation of (R,S)-8-[[[2-[(2-amino)pyrid-4-yl]ethyl]methylamino]carbonyl]-2,3,4,5-tetrahydro-3-oxo-4-(2-phenylethyl)-1H-1,4-benzodiazepine-2-acetic acid Using the procedure of Example 54, except substituting the compound of Preparation 20(b) for the compound of Preparation 13(j), and purifying the product by flash chromatography (YMC ODS-AQ S-50, 20–25% AN/W-TFA) gave the title compound. MS(ES) m/e 502.2 [M+H]$^+$; HPLC k' 4.92 (PRP-1®, 25% AN/W-TFA); $^1$H NMR (400 MHz, CD$_3$OD) δ2.65 (1H, m), 2.75 (2H, m), 2.84 (1H, t), 2.92 (1H, m), 2.99 (3H, s), 3.10 (1H, s), 3.63 (2H, m), 3.72 (1H, m), 3.79 (1H, t), 3.87 (1H, d, J=16.8 Hz), 5.11 (1H, 2t), 5.43 (1H, d, J=15.6 Hz), 6.35, 6.53 (1H, 2s), 6.40, 6.49 (1H, 2d, J=7.5 Hz), 6.46, 6.88 (1H, 2d), 6.61, 6.89 (1H, 2s), 6.94, 6.97 (1H, 2d), 7.17 (5H, m), 7.57, 7.74 (1H, 2d, J=6.5 Hz).

Example 72

Preparation of (R,S)-7-[[[2-[(2-amino)pyrid-4-yl]ethyl]methylamino]carbonyl]-2,3,4,5-tetrahydro-3-oxo-2-(2-phenylethyl)-1H-2-benzazepine-4-acetic acid Using the procedure of Example 71, except substituting the compound of Example 1(g) for methyl (R,S)-8-carboxy- 2,3,4,5-tetrahydro-3-oxo-4-(2-phenylethyl)-1H-1,4-benzodiazepine-2-acetate, gave the title compound: MS(ES) m/e 501.2 [M+H]$^+$; Anal. ($C_{29}H_{32}N_4O_4$·1.25 $CF_3CO_2H$·0.5 $H_2O$) calcd: C, 57.97; H, 5.22; N, 8.60. found: C, 58.01; H, 5.29; N,8.59.; HPLC k' 3.42 (PRP-1®, 25% AN/W-TFA); $^1$H NMR (400 MHz, $CD_3OD$) δ2.46 (1H. m), 2.70 (3H, m), 2.83 (2H, m), 2.98 (3H, s), 3.02 (1H, m), 3.13 (1H, s), 3.57 (1H, m), 3.64 (1H, m), 3.81 (3H, m), 4.03 (1H, d, J=16.7 Hz), 5.21 (1H, d, J=16.7 Hz), 6.47–7.01 (3H, m), 7.01–7.22 (7H, m), 7.57, 7.76 (1H, 2d).

Example 73

Preparation of 8-[[[4-(aminoiminomethyl)phenyl] methylamino]carbonyl]-2,3,4,5-tetrahydro-3-oxo-2-benzazepine-2-propionic acid a) 7-methoxy-2-tetralone oxime A mixture of 7-methoxy-2-tetralone (0.50 g, 2.8 mmol), hydroxyl amine hydrochloride (0.38 g, 5.6 mmol) and sodium bicarbonate (0.47 g, 5.6 mmol) in methanol (20 mL) was heated to reflux for 3 h. The mixture was poured into water (15 mL) and extracted with chloroform. The organic phases were combined, washed with brine, and concentrated to give a white solid. Precipitation from ethyl acetate/hexane gave the title compound (420 mg, 79%) as a granular solid. MS(ES) m/e 191 [M+H]$^+$.

b) 8-methoxy-2,3,4,5-tetrahydro-3-oxo-1H-2-benzazepine

A stirred suspension of the compound of Example 73(a) (3.0 g, 15.5 mmol) in polyphosphoric acid (30 g) was heated to 110° C. for 10 min. The dark solution was cooled to ambient temperature, quenched with crushed ice (300 mL) and extracted with ethyl acetate. The organic extracts were combined, washed with brine, dried (magnesium sulfate) and concentrated to afford a mixture of the title compound and 8-methoxy-2,3,4,5-tetrahydro-2-oxo-1H-3-benzazepine (2.63 g, 88%). MS(ES) m/e 191 [M+H]$^+$.

c) 8-hydroxy-2,3,4,5-tetrahydro-3-oxo-1H-2-benzazepine

A solution of the compound of Example 73(b)(3.79 g, 19.8 mmol) in dichloromethane (40 mL) was added in one portion to a 0° C. suspension of aluminum chloride (8 g, 60 mmol) in ethanethiol (20 mL) under argon. The mixture was allowed to come to RT and stirring was continued for 18 h. The mixture was quenched with ice (500 mL), acidified with 1N hydrochloric acid and extracted with ethyl acetate. The organic phases were combined, washed with brine, dried (magnesium sulfate), and concentrated. The residue was chromatographed (silica gel, 0–4% methanol/chloroform) to yield 8-hydroxy-2,3,4,5-tetrahydro-2-oxo-1H-3-benzazepine and the title compound (1.43 g, 42%). MS(ES) m/e 177 [M+H]$^+$.

d) 8-(trifluoromethylsulfonyl)oxy-2,3,4,5-tetrahydro-3-oxo-1H-2-benzazepine

The compound of Example 73(c)(310 mg, 1.8 mmol) in dichloromethane (50 mL) was stirred at −30° C. and treated with 2,6-lutidine (0.32 mL, 2.7 mmol), 4-(dimethylamino) pyridine (44 mg, 0.36 mmol), and triflic anhydride (0.45 mL, 2.7 mmol) under a stream of argon. The reaction was allowed to come to RT and stirred for 4 h. The mixture was concentrated and the residue was triturated with ether, filtered, and the filtrate was washed with 1N hydrochloric acid and with brine, and concentrated to give the title compound (220 mg, 40%). MS(ES) m/e 309 [M+H]$^+$.

e) 8-benzyloxycarbonyl-2,3,4,5-tetrahydro-3-oxo-1H-2-benzazepine

A flame dried three neck flask was charged with the compound of Example 73(d) (440 mg, 1.5 mmol), palladium (II) acetate (90 mg, 0.4 mmol), 1,1'-bis(diphenylphosphino)-ferrocene (443 mg, 0.8 mmol), and dry triethylamine (0.42 mL, 3.0 mmol) in dimethylformamide (10 mL). Carbon monoxide was bubbled through the solution for 15 min, and benzyl alcohol (1.55 mL, 15 mmol) was added. The resulting solution was then heated to 70° C. under a carbon monoxide balloon for 4 h. The reaction was cooled to RT, diluted with ethyl acetate, extracted with 1N hydrochloric acid, water, and brine, dried (magnesium sulfate), and concentrated. The resulting solid was chromatographed (silica gel, 2% methanol/chloroform) to afford the title compound (290 mg, 91%). MS(ES) m/e 295 [M+H]$^+$.

f) methyl 8-benzyloxycarbonyl-2,3,4,5-tetrahydro-3-oxo-1H-2-benzazepine-2-propionate To a solution of the compound of Example 73(e) (290 mg, 0.98 mmol), methyl acrylate (0.9 mL, 9.8 mmol) and methanol (5 mL) was added sodium hydride (24 mg, 0.98 mmol). The resulting solution was refluxed overnight and the mixture was concentrated. The residue was chromatographed (silica gel, 30% ethyl acetate/hexane) to give title compound (260 mg, 70%). MS(ES) m/e 381 [M+H]$^+$.

g) methyl 8-carboxy-2,3,4,5-tetrahydro-3-oxo-2-benzazepine-2-propionate

A suspension of the compound of Example 73(f) (260 mg, 0.7 mmol), 5% palladium on barium sulfate (50 mg) in ethanol (10 mL) was shaken under hydrogen (50 psi) for 4 h. The resulting suspension was filtered through Celite® and the filtrate was concentrated. Precipitation of the residue from ethyl acetate/hexane afforded the title compound (180 mg, 90%) as a white wax. MS(ES) m/e 291 [M+H]$^+$.

h) 8-[[[4-(aminoiminomethyl)phenyl]methylamino] carbonyl]-2,3,4,5-tetrahydro-3-oxo-2-benzazepine-2-propionic Acid Using the procedure of Examples 1(h) through 1(j), except substituting the compound of Example 73(g) for the compound of Example 1(g), gives the title compound.

Example 74

Preparation of 7-[[4-(aminoiminomethyl)phenyl] ethynyl]-2,3,4,5-tetrahydro-3-oxo-2-(2-phenylethyl)-1H-2-benzazepine-4-acetic acid a) ethyl 7-[[(trifluoromethyl)sulfonyl]oxy]-2-(2-phenyl-ethyl)-3-oxo-2,3,4,5-tetrahydro-1H-2-benzazepine-4-acetate A solution of the compound of Example 48(j) (360 mg, 1 mmol) and N,N-diisopropylethylamine (1 mL) in dichloromethane (8 mL) was stirred in an ice bath and treated with triflic anhydride (0.25 mL, 1.2 mmol). The mixture was stirred for 30 min, and allowed to warm to RT and stirred for 4 h. The mixture was diluted with dichloromethane, washed sequentially with 3N hydrochloric acid, 5% sodium bicarbonate and brine, dried (magnesium sulfate) and concentrated. The residue was chromatographed (silica gel, 1% methanol/dichloromethane) to give the title compound (0.35 g, 70%) as an amber oil. MS (ES) m/e 500 [M+H]+, $^1$H NMR (400 MHz, CDCl$_3$) δ7.2–7.1 (m, 3H), 7.0–7.1 (m, 2H), 6.96 (s, 3H), 5.16–5.0 (d, J=17 Hz, 1H), 4.15 (q, 2H), 3.9 (m, 1H), 3.78–3.70 (d, J=17 Hz, 1H), 3.6 (m, 1H), 3.0–2.9 (m, 2H), 2.8–2.7 (m, 3H), 2.4–2.3 (q, 1H), 1.3 (t, 3H).

b) ethyl 7-[(4-cyanophenyl)ethynyl]-2-(2-phenylethyl)-3-oxo-2,3,4,5-tetrahydro-1H-2-benzazepine-4-acetate The compound of Example 74(a) is treated with 4-cyanophenylacetylene [prepared as in *Synthesis,* 627 (1980)], bis(triphenylphosphine)palladium chloride, cuprous iodide and triethylamine in dimethylformamide and the mixture is heated and stirred. The mixture is cooled, diluted and extracted with ethyl acetate. The organic phase is washed with dilute hydrochloride acid and with water, dried and concentrated to give the title compound.

c) ethyl 7-[4-(thiocarbamoyl)phenyl)ethynyl]-2-(2-phenylethyl)-3-oxo-2,3,4,5-tetrahydro-1H-2-benzazepine-4-acetate Using the general procedure of European Patent Application 0 502 536 A1, the compound of Example 74(b) in pyridine:triethylamine is treated with a stream of hydrogen sulfide and let stand. The mixture is concentrated to give the title compound.

d) ethyl 7-[4-(methylthioimino)phenyl)ethynyl]-2-(2-phenylethyl)-3-oxo-2,3,4,5-tetrahydro-1H-2-benzazepine-4-acetate Using the general procedure of EP 502 536, the compound of Example 74(c) is treated with iodomethane in acetone. The mixture is concentrated to give the title compound.

e) ethyl 7-[4-(aminoiminomethyl)phenyl)ethynyl]-2-(2-phenylethyl)-3-oxo-2,3,4,5-tetrahydro-1H-2-benzazepine-4-acetate Using the general procedure of EP 502 536, the compound of Example 74(d) is treated with ammonium acetate in methanol and the mixture is heated to reflux. The mixture is cooled and concentrated to give the title compound.

f) 7-[[4-(aminoiminomethyl)phenyl]ethynyl]-2-(2-phenylethyl)-3-oxo-2,3,4,5-tetrahydro-1H-2-benzazepine-4-acetic acid The compound of Example 74(e) is treated with dilute sodium hydroxide in methanol and then with dilute hydrochloric acid to give the title compound.

Example 75

Preparation of 7-[1-[4-(piperazin-1-yl)but-1-ynyl]]-2-(2-phenylethyl)-3-oxo-2,3,4,5-tetrahydro-1H-2-benzazepine-4-acetic acid a) ethyl 7-[1-[4-[N-(t-butoxycarbonyl)piperazin-1-yl]-but-1-ynyl]]-2-(2-phenylethyl)-3-oxo-2,3,4,5-tetrahydro-1H-2-benzazepine-4-acetate A mixture of the compound of Example 74(a) (0.3 g, 0.7 mmol), the compound of Preparation 21 (190 mg, 0.8 mmol), triethylamine (3 mL), bis(triphenylphosphine)-palladium chloride (10 mg, 0.14 mmol) and cuprous iodide (2.5 mg, 0.14 mmol) in acetonitrile (10 mL) was heated to reflux for 20 h. The mixture was diluted with water and extracted with ethyl acetate. The organic phase was dried (magnesium sulfate), concentrated and the residue was purified by flash chromatography (silica gel, 2% methanol/ dichloromethane) to yield the title compound (90 mg, 25%). $^1$H NMR (400 MHz, CDCl$_3$) δ7.15–7.26 (m, 5H), 7.10 (s, 1H), 7.06 (d, J=8 Hz, 1H), 6.8 (d, J=8 Hz, 1H), 5.1 (d, J=17 Hz, 1H), 4.15 (q, 2H), 3.8 (m, 2H), 3.7 (d, J=17 Hz, 1H), 3.6 (m, 1H), 3.5 (s, 4H), 3.0 (m, 2H), 2.8 (m, 1H), 2.7 (t, 2H), 2.6 (m, 2H), 2.5 (s, 4H), 2.4 (q, 1H), 1.4 (s, 9H), 1.3 (t, 3H).

b) ethyl 7-[1-[4-(piperazin-1-yl)but-1-ynyl]]-2-(2-phenylethyl)-3-oxo-2,3,4,5-tetrahydro-1H-2-benzazepine-4-acetate The compound of Example 75(a) is stirred with TFA in dichloromethane. The mixture is washed with water, dried and concentrated to give the title compound.

c) 7-[1-[4-(piperazin-1-yl)but-1-ynyl]]-2-(2-phenylethyl)-3-oxo-2,3,4,5-tetrahydro-1H-2-benzazepine-4-acetic acid The compound of Example 75(b) is stirred with dilute aqueous sodium hydroxide in methanol and then treated with dilute hydrochloric acid to give the title compound.

Example 76

Preparation of (E)-2,5-dioxo-2,3,4,5-tetrahydro-7-[[4-(piperidin-4-yl)but-1-enyl]-1H-1,4-benzodiazepine-4-acetic acid a) ethyl 7-bromo-2,5-dioxo-2,3,4,5-tetrahydro-1H-1,4-benzodiazepine-4-acetate Using the general procedures of U.S. Pat. No. 3,415,814 (Examples 1N and 20 therein), except substituting 5-bromo-2-nitrobenzoyl chloride [prepared as in *Monatshefte fur Chemie,* 100, 469 (1969)] for 3,4-dichloro-2-nitro-benzoyl chloride and substituting ethyl N-(2-ethoxy-2-oxoethyl) glycinate [prepared as in *Synthetic Communications,* 22, 1249 (1992)] for ethyl N-(5-ethoxy-5-oxopentyl)glycinate, gives the title compound.

b) ethyl 7-hydroxymethyl-2,5-dioxo-2,3,4,5-tetrahydro-1H-1,4-benzodiazepine-4-acetate Using the general procedure of *Chemistry Letters,* 997 (1985), the compound of Example 76(a) is treated with [(trimethylsilyloxy)methyl]tributyltin to give the title compound.

c) (E)-2,5-dioxo-2,3,4,5-tetrahydro-7-[1-[4-(piperidin-4-yl)but-1-enyl]-1H-1,4-benzodiazepine-4-acetic acid Using the procedures of Example 61(b)–61(e), except substituting the compound of Example 76(b) for the compound of Example 61(a), gives the title compound.

Example 77

Preparation of 2,5-dioxo-2,3,4,5-tetrahydro-7-[[[2-(piperidin-4-yl)ethyl]methylamino]carbonyl]-1H-1,4-benzodiazepine-4-propanoic acid a) ethyl 7-bromo-2,5-dioxo-2,3,4,5-tetrahydro-1H-1,4-benzodiazepine-4-propionate Using the general procedures of U.S. Pat. No. 3,415,814 (Examples 1N and 20 therein), which is incorporated herein by reference, except substituting 5-bromo-2-nitrobenzoyl chloride [prepared as in *Monatshefte fur Chemie*, 100, 469 (1969)] for 3,4-dichloro-2-nitro-benzoyl chloride and substituting ethyl N-(3-ethoxy-3-oxopropyl)glycinate [prepared as in *Synthetic Communications*, 22, 1249 (1992)] for ethyl N-(5-ethoxy-5-oxopentyl)glycinate, gives the title compound.

b) ethyl 2,5-dioxo-2,3,4,5-tetrahydro-7-[[[2-(pyrid-4-yl)ethyl]methylamino]carbonyl]-1H-1,4-benzodiazepine-4-propionate The compound of Example 77(a) is treated with N-methyl-2-(pyrid-4-yl)ethanamine, carbon monoxide and dibromobistriphenylphosphinepalladium according to the general procedure of *J. Org. Chem.*, 39, 3327, (1974) to give the title compound.

c) ethyl 2,5-dioxo-2,3,4,5-tetrahydro-7-[[[2-(piperidin-4-yl)ethyl]methylamino]carbonyl]-1H-1,4-benzodiazepine-4-propionate The compound of Example 77(b) is dissolved in dilute hydrochloric acid and methanol containing platinum oxide and the mixture is shaken in a hydrogen atmosphere. The mixture is filtered and concentrated to give the title compound.

d) 2,5-dioxo-2,3,4,5-tetrahydro-7-[[[2-(piperidin-4-yl)ethyl]methylamino]carbonyl]-1H-1,4-benzodiazepine-4-propanoic acid The compound of Example 77(c) is treated with dilute sodium hydroxide in methanol and then with dilute hydrochloric acid to give the title compound.

Example 78

Preparation of (R,S)-7-[[[2-(piperidin-4-yl)ethyl]methylamino]carbonyl]-2,3,4,5-tetrahydro-2-methyl-3-oxo-1H-2-benzazepine-4-acetic acid a) methyl (R,S)-7-benzyloxycarbonyl-2,3,4,5-tetrahydro-3-oxo-1H-2-benzazepine-4-acetate 1-(3-Dimethylaminopropyl)-3-ethylcarbodiimide hydrochloride (1.19 g, 6.23 mmol) was added all at once to a solution of the compound of Example 66(h) (1.44 g, 5.19 mmol), benzyl alcohol (2.7 mL, 25.95 mmol), diisopropylethylamine (1.8 mL, 10.38 mmol), and 4-(dimethylamino) pyridine (761 mg, 6.23 mmol) in anhydrous dimethylformamide (26 mL) at RT. The reaction was stirred for 24 h and concentrated to leave a pale yellow oil. The oil was diluted with ethyl acetate (200 mL), and the cloudy mixture was washed sequentially with 1N hydrochloric acid (2×20 mL) and water (20 mL). The combined aqueous layers were extracted with ethyl acetate (50 mL), and the combined organic layers were dried (magnesium sulfate) and concentrated. Chromatography (silica gel, 5% methanol in 1:1 ethyl acetate:chloroform) gave the title compound (1.59 g, 83%) as a colorless, very viscous oil which could be induced to solidify on scratching and treatment with a little ethyl acetate. TLC $R_f$ 0.52 (5% methanol in 1:1 ethyl acetate:chloroform); $^1$H NMR (250, CDCl$_3$) δ7.72–7.92 (m, 2H), 7.28–7.55 (m, 5H), 7.14 (d, J=8.3 Hz, 1H), 6.76 (br t, 1H), 5.35 (s, 2H), 4.85 (dd, J=16.5, 5.2 Hz, 1H), 4.12 (dd, J=16.5, 6.7 Hz, 1H), 3.71 (s, 3H), 3.50–3.70 (m, 1H), 3.00–3.17 (m, 2H), 2.96 (dd, J=16.9, 7.4 Hz, 1H), 2.50 (dd, J=16.9, 6.1 Hz, 1H); IR (CHCl$_3$) 3410, 1718, 1677, 1274 cm$^{-1}$; MS(ES) m/e 390.2 [M+Na]$^+$, 268.2 [M+H]$^+$.

b) methyl (R,S)-7-benzyloxycarbonyl-2,3,4,5-tetrahydro-2-methyl-3-oxo-1H-2-benzazepine-4-acetate The compound of Example 78(a) (220.4 mg, 0.60 mmol) was suspended in toluene (5–10 mL), and the mixture was carefully concentrated to remove water and residual solvents. The resulting solid was dissolved in dry 1:1 THF:DMF (12 mL), and iodomethane (0.19 mL, 3.0 mmol) was added. Sodium hydride (60% in mineral oil, 29 mg, 0.72 mmol) was added, causing gas evolution and slight warming. After 15 min, the reaction was cooled to 0° C. and quenched with saturated aqueous ammonium chloride (2 mL). The mixture was diluted with ether (50 mL) and washed with water. The combined aqueous layers were extracted with ether, and the combined organic layers were dried (magnesium sulfate) and concentrated. Chromatography (silica gel, 1:1 ethyl acetate:toluene) gave the title compound (229.2 mg, 100%) as a colorless oil. TLC $R_f$ 0.66 (silica gel, ethyl acetate); $^1$H NMR (400, CDCl$_3$) δ7.77–7.87 (m, 2H), 7.31–7.47 (m, 5H), 7.16 (d, J=8.4 Hz, 1H), 5.27–5.38 (m, 3H), 3.90 (d, J=16.7 Hz, 1H), 3.77–3.90 (m, 1H), 3.71 (s, 3H), 3.11 (dd, J=17.4, 4.2 Hz, 1H), 3.04 (s, 3H), 2.91–3.07 (m, 2H), 2.43 (dd, J=16.7, 5.4 Hz, 1H); IR (CCl$_4$) 1724, 1666, 1273 cm$^{-1}$; MS(ES) m/e 382.0 [M+H]$^+$.

c) methyl (R,S)-7-carboxy-2,3,4,5-tetrahydro-2-methyl-3-oxo-1H-2-benzazepine-4-acetate 10% Palladium-on-carbon (64 mg, 0.06 mmol) was added carefully to a solution of the compound of Example 78(b) (229.2 mg, 0.60 mmol) in methanol (12 mL). The mixture was purged with hydrogen and stirred briskly at RT under hydrogen (balloon pressure). After 15 h, the mixture was filtered through Celite®, and the filtrate was concentrated to afford the title compound (162.7 mg, 93%) as a colorless solid which was used without further purification: $^1$H NMR (250, CD$_3$OD) δ7.65–7.85 (m, 2H), 7.28 (d, J=7.7 Hz, 1H), 5.38 (d, J=16.6 Hz, 2H), 4.11 (d, J=16.6 Hz, 1H), 3.85–4.01 (m, 1H), 3.68 (s, 3H), 3.17 (dd, J=17.1, 4.3 Hz, 1H), 3.01 (s, 3H), 2.75–2.95 (m, 2H), 2.51 (dd, J=16.9, 4.7 Hz, 1H); MS(ES) m/e 605.2 [2M+Na]$^+$, 314.0 [M+Na]$^+$, 292.0 [M+H]$^+$.

d) Methyl (R,S)-7-[[[2-(pyrid-4-yl)ethyl]methylamino]carbonyl]-2,3,4,5-tetrahydro-2-methyl-3-oxo-1H-2-benzazepine-4-acetate Using the procedure of Example 66(i), except substituting the compound of Example 78(c) for the compound of Example 66(h), gave the title compound (221.3 mg, 97%) as a faintly yellow, very viscous oil: TLC $R_f$ 0.37 (10% methanol in 1:1 ethyl acetate:chloroform); $^1$H NMR (400 MHz, CDCl$_3$) rotameric mixture; δ8.42–8.62 (m, 2H), 6.70–7.40 (m, 5H), 5.30 (d, J=16.7 Hz, 1H), 3.46–3.92 (m, 4H), 3.72 (s, 3H), 2.73–3.22 (m, 8H), 3.04 (s, 3H), 2.43 (dd, J=16.7, 5.5 Hz, 1H); IR (CHCl$_3$) 1730, 1643 cm$^{-1}$; MS(ES) m/e 410.0 [M+H]$^+$.

e) Methyl (R,S)-7-[[[2-(piperidin-4-yl)ethyl]methylamino]carbonyl]-2,3,4,5-tetrahydro-2-methyl-3-oxo-1H-2-benzazepine-4-acetate Using the procedure of Example 66(j), except substituting the compound of Example 78(d) for the compound of Example 66(i) gave the title compound: NMR (250 MHz, CD$_3$OD) δ7.05–7.45 (m, 3H), 5.36 (d, J=16.6 Hz, 1H), 4.10 (d, J=16.6 Hz, 1H), 3.84–4.03 (m, 1H), 3.67 (s, 3H), 2.65–3.77 (m, 12H), 3.00 (s, 3H), 2.42–2.60 (m, 1H), 1.89–2.18 (m, 1H), 1.15–1.80 (m, 6H).

f) (R,S)-7-[[[2-(Piperidin-4-yl)ethyl]methylamino]carbonyl]-2,3,4,5-tetrahydro-2-methyl-3-oxo-1H-2-benzazepine-4-acetic acid Using the procedure of Example 66(k), except substituting the compound of Example 78(e) for the compound of Example 66(j) gave the title compound. HPLC k'=2.11 (PRP-1®; 15% AN/W-TFA); $^1$H NMR (400 MHz, DMSO-$d_6$) rotameric mixture δ8.44–8.63 (m, 1H), 8.11–8.37 (m, 1H), 7.27 (d, J=7.6 Hz, 1H), 7.07–7.17 (m, 2H), 5.26 (d, J=16.5 Hz, 1H), 4.04 (d, J=16.5 Hz, 1H), 3.71–3.82 (m, 1H), 3.00–3.52 (m, 5H), 2.60–2.99 (m, 10H), 2.35 (dd, J=16.8, 4.6 Hz, 1H), 1.80–1.93 (m, 1H), 1.01–1.63 (m, 6H); MS(ES) m/e 402.2 [M+H]$^+$; Anal. [$C_{22}H_{31}N_3O_4 \cdot 1.75$ ($CF_3CO_2H$)] calcd: C, 50.96; H, 5.49; N, 6.99; found: C, 51.14; H, 5.54; N, 7.00.

Example 79

Preparation of (R,S)-7-[[[4-aminomethylphenyl]methylamino]carbonyl]-2,3,4,5-tetrahydro-3-oxo-2-(2-phenylethyl)-1H-2-benzazepine-4-acetic acid a) methyl (R,S)-7-[[[4-cyanophenyl]methylamino]carbonyl]-2,3,4,5-tetrahydro-3-oxo-2-(2-phenylethyl)-1H-2-benzazepine-4-acetate Using the procedure of Example 59(a), except substituting the compound of Example 1(h) for methyl (R,S)-8-carboxy-2,3,4,5-tetrahydro-3-oxo-4-(2-phenylethyl)-1H-1,4-benzodiazepine-2-acetate gave the title compound (0.44 g, 89%) as a white solid.

b) methyl (R,S)-7-[[[4-aminomethylphenyl]methylamino]carbonyl]-2,3,4,5-tetrahydro-3-oxo-2-(2-phenylethyl)-1H-2-benzazepine-4-acetate Using the procedure of Example 59(b), except substituting the compound of Example 79(a) for the compound of Example 59(a), gave the crude compound (0.29 g) which was used without further purification.

c) (R,S)-7-[[[4-aminomethylphenyl]methylamino]carbonyl]-2,3,4,5-tetrahydro-3-oxo-2-(2-phenylethyl)-1H-2-benzazepine-4-acetic acid Using the procedure of Example 57(d), except substituting the compound of Example 79(b) for the compound of Example 57(c), gave the title compound. MS(ES) m/e 484.0 [M−H]$^+$, 486.2 [M+H]$^+$; Anal. ($C_{29}H_{31}N_3O_4 \cdot 1.5C_2HF_3O_2 \cdot 0.5H_2O$) calcd: C, 57.74; H, 5.07; N, 6.31. found: C, 57.67; H, 5.21; N, 6.59.

Example 80

Preparation of (R,S)-8-[[[4-(N,N-dimethylaminomethyl)phenyl]amino]carbonyl]-2,3,4,5-tetrahydro-3-oxo-4-(2-phenylethyl)-1H-1,4-benzodiazepine-2-acetic acid a) methyl (R,S)-8-[[[4-(N,N-dimethylaminomethyl)phenyl]amino]carbonyl]-2,3,4,5-tetrahydro-3-oxo-4-(2-phenylethyl)-1H-1,4-benzodiazepine-2-acetate Using the procedure of Example 1(h), except substituting methyl (R,S)-8-carboxy-2,3,4,5-tetrahydro-3-oxo-4-(2-phenylethyl)-1H-1,4-benzodiazepine-2-acetate for the compound of Example 1(g) and substituting the compound of Preparation 21(b) for 4-(methylamino)-(N-benzyloxycarbonyl)-benzamidine gave the title compound.

b) (R,S)-8-[[[4-(N,N-dimethylaminomethyl)phenyl]-amino]carbonyl]-2,3,4,5-tetrahydro-3-oxo-4-(2-phenylethyl)-1H-1,4-benzodiazepine-2-acetic acid Using the procedure of Example 1(j), except substituting the compound of Example 80(a) for the compound of Example 1(i), gave the title compound (154 mg, 25%) as a pale yellow solid. $^1$H NMR (400 MHz, DMSO-$d_6$) δ7.85 (d, 2H), 7.4 (2H), 7.35 (d, 2H), 7.2–7.0 (m, 6H), 6.1 (m, 1H), 5.45 (d, 1H), 5.05 (m, 1H), 4.25 (s, 2H), 4.05 (d, 1H), 3.6 (m, 2H), 2.8 (dd, 1H), 2.75 (s, 6H), 2.7 (m, 2H), 2.6 (dd, 1H).

Example 81

Preparation of (R,S)-7-[(4,4'-bipiperidin-1-yl)carbonyl]-2,3,4,5-tetrahydro-3-oxo-4-(phenylethyl)-1H-1,4-benzodiazepine-2-acetic acid a) methyl (R,S)-7-[1'-(t-butoxycarbonyl)-4,4'-bipiperidin-1-yl]carbonyl]-2,3,4,5-tetrahydro-3-oxo-4-(phenylethyl)-1H-1,4-benzodiazepine-2-acetate Using the procedure of Example 32(a), except substituting (R,S)-7-carboxy-2,3,4,5-tetrahydro-3-oxo-4-(phenylethyl)-1H-1,4-benzodiazepine-2-acetate for (R,S)-8-carboxy-2,3,4,5-tetrahydro-3-oxo-4-(phenylethyl)-1H-1,4-benzodiazepine-2-acetate and substituting the compound of Preparation 22 for N-methyl-2-(4-pyridyl)-ethanamine and deleting triethylamine gave the title compound (0.43 g, 68%): MS(ES) m/e 633.2 [M+H]$^+$.

b) methyl (R,S)-7-[(4,4'-bipiperidin-1-yl]carbonyl]-2,3,4,5-tetrahydro-3-oxo-4-(phenylethyl)-1H-1,4-benzodiazepine-2-acetate Using the procedure of Example 13(b), except substituting the compound of Example 81(a) for the compound of Example 13(a), gave the title compound (0.27 g, 75%): MS(ES) m/e 533.2 [M+H]$^+$; HPLC k'=9.4 (Vydac C18, 4.6×250 mm, 1.5 mL/min, gradient A:acetonitrile B:water-0.1% TFA, 5–50% acetonitrile during 20 min, UV detection at 254 nm).

c) (R,S)-7-[(4,4'-bipiperidin-1-yl)carbonyl]-2,3,4,5-tetrahydro-3-oxo-4-(phenylethyl)-1H-1,4-benzodiazepine-2-acetic acid The compound of Example 81(b) (0.2 g, 0.3 mmol) was suspended in acetone (2 mL) and treated lithium hydroxide hydrate (25 mg) in water (2 mL). The mixture was stirred overnight, treated with methanol and additional lithium hydroxide hydrate (5.5 mg) was added in two portions over 9 h. The mixture was concentrated and the aqueous residue was neutralized with N hydrochloric acid and concentrated. The residue was placed in the refrigerator overnight and filtered. The filter cake was washed with cold water, acetone and ether to yield the title compound (0.07 g). MS(ES) m/e 519.2 [M+H]$^+$; HPLC k'=7.9 (Vydac ODS, 4.6×250 mm, 1.5 mL/min, gradient A:acetonitrile B:water-0.1% TFA, 5–50% A during 20 min, UV detection at 254 nm); $^1$H NMR (400 MHz, $CD_3OD$) δ7.2 (t, 2H), 7.14 (d, 3H), 7.10 (d, 1H), 7.08 (d, 1H), 7.04 (s, 1H), 6.59 (d, 1H), 5.46 (d, 1H), 5.15 (q, 1H), 3.87 (d, 1H), 3.76 (m, 1H), 3.63 (m, 1H), 3.38 (d, 2H), 2.93 (dd, 4 H), 2.77 (t, 2H), 2.63 (dd, 1H), 1.93 (m, 2H) 1.45(bs, 2H), 1.23 (m, 4H), 1.23 (m, 2H).

Example 82

Preparation of 7-[3-(piperazin-1-yl)propyloxy]-2-(2-phenylethyl)-3-oxo-2,3-dihydro-1H-2-benzazepine-4-acetic acid a) ethyl 7-methoxy-3-oxo-2,3-dihydro-2-(2-phenylethyl)-1H-2-benzazepine-4-acetate A solution of the compound of Example 48(h) (2.6 g, 6.8 mmol) in methanol (120 mL) was treated with 25% sodium methoxide/methanol solution (14.1 mL, 68 mmol) and heated to reflux for 2.5 h. The mixture was quenched with ice-water (300 mL), acidified with 3N hydrochloric acid, extracted with ethyl acetate, dried and concentrated to give the acid. MS(ES) m/e 352 [M+H]⁺. The residue was dissolved in ethanol (75 mL) and heated to reflux in the presence of 4M hydrogen chloride/dioxane (2 mL) for 2 h and concentrated to give the title compound (2.5 g, 97%). $^1$H NMR (400 MHz, CDCl$_3$) δ7.18–7.26 (m, 5H), 7.08 (d J=7.95 Hz, 1H), 6.89 (s 1H), 6.82 (m, 2H), 4.18 (m, 4H), 3.81 (s, 3H), 3.80 (t, J=5.57, 2H), 3.71 (t, J=5.57 Hz, 3H), 2.85 (t, J=7.62 Hz, 2H), 1.28 (t, J=6.5 Hz, 3H).

b) ethyl 7-hydroxy-2-3-oxo-(2-phenylethyl)-2,3-dihydro-1H-2-benzazepine-4-acetate To a solution of the compound of Example 82(a) (2.67 g, 7.0 mmol) and ethanethiol (2.6 mL, 35 mmol) in dichloromethane (50 mL) at 0° C. was added aluminum chloride (4.6 g, 35 mmol). The mixture was warmed to RT over 1 h, diluted with dichloromethane (100 mL), washed with cold 3N hydrochloric acid, dried (sodium sulfate), and concentrated to give the title compound (2.4 g, 93%). MS(ES) m/e 366.0 [M+H]⁺; $^1$H NMR (400 MHz, CDCl$_3$) δ7.17–7.26 (m, 5H), 7.02 (d J=8.16 Hz, 1H), 6.78 (s 1H), 6.75 (m, 1H), 6.67 (d, J=2.4, 1H), 4.18 (q, J=7.16, 2H), 3.71 (t, J=5.57 Hz, 4H), 2.85 (t, J=7.58 Hz, 4H), 1.26 (t, J=7.16 Hz, 3H).

c) ethyl 7-[3-[(4-t-butyloxycarbonyl)piperazin-1-yl]propyloxy]-3-oxo-2-(2-phenylethyl)-2,3-dihydro-1H-2-benzazepine-4-acetate A mixture of the compound of Example 82b) (1.28 g, 3.5 mmol) and 3-[(4-t-butyloxycarbonyl)piperazin-1-yl]propyl chloride (1.3 g, 5 mmol), potassium carbonate (0.58 g, 4.2 mmol),and tetraethylammonium iodide (20 mg) in dimethylformamide (15 mL) was heated at 90° C. for 2 h. The reaction mixture was quenched with ice-water, extracted with ethyl acetate, dried (sodium sulfate), filtered and concentrated to give the title compound (1.5 g, 75%). MS(ES) m/e 592.0 [M+H]⁺; $^1$H NMR (400 MHz, CDCl$_3$) δ7.2–7.26 (m, 5H), 7.02 (d J=8.16 Hz, 1H), 6.83 (s, 1H), 6.81 (d, J=2.4, 1H), 4.19 (m, 4H), 4.0 (m, 2H), 3.70 (m, 4H), 3.46 (bs, 4H), 2.84 (t, J=7.56 Hz, 2H), 2.52 (t, J=7.1 Hz, 2H), 1.96 (m, 2H), 1.45 (s, 9H), 1.28 (t, J=7.23 Hz, 3H).

d) 7-[3-(1-piperazinyl)propyloxy]-2-(2-phenylethyl)-3-oxo-2,3-dihydro-1H-2-benzazepine-4-acetic acid A mixture of the compound of Example 82(c) (0.7 g, 1.2 mmol) was dissolved in 1N sodium hydroxide solution (12 mL) and methanol (35 mL). After stirring at RT for 4 h, the reaction mixture was quenched with ice-water, acidified with 1N hydrochloric acid, extracted with ethyl acetate, dried (sodium sulfate), filtered and concentrated to give the N-Boc acid (0.42 g, 63%; MS(ES) m/e 564.2 [M+H]⁺), which was stirred in 4N hydrogen chloride/dioxane solution (4 mL) and methylene chloride (30 mL) for 18 h. The mixture was evaporated to give the title compound (0.39 g, 97%). MS (ES) m/e 464.2 [M+H]⁺; $^1$H NMR (400 MHz, CDCl$_3$) δ7.16–7.83 (m, 6H), 7.06 (s, 1H) 6.94 (m, 2H), 4.15 (m, 2H), 3.65 (m, 14H), 3.47 (m, 2H), 2.82 (m, 2H), 2.32 (m, 2H).

Example 83

Preparation of 7-[3-(piperazin-1-yl)propyloxy]-2-(2-phenylethyl)-3-oxo-2,3,4,5-tetrahydro-1H-2-benzazepine-4-acetic acid A solution of the compound of Example 82(d) (0.01 g, 0.02 mmol) in methanol (15 mL) is treated with palladium hydroxide (0.05 mg) and hydrogenated (50 psi) for 4 h to give the title compound.

Examples 84–88

Using routine variations of the procedures disclosed above for preparing 2,3,4,5-tetrahydro-3-oxo-1H-1,4-benzazepines, the following compounds were prepared.

84. 8-[[[2-(pyridin-4-yl)-ethenyl]carbonyl]amino]-2,3,4,5-tetrahydro-3-oxo-4-(2-phenylethyl)-1H-1,4-benzodiazepine-2-acetic acid;
85. 8-[[[2-(2-amino-pyridin-4-yl)-ethyl]methylamino]carbonyl]-2,3,4,5-tetrahydro-3-oxo-4-(2-phenylethyl)-1H-1,4benzodiazepine-2-acetic acid;
86. 8-[[(quinuclidin-3-yl)amino]carbonyl]-2,3,4,5-tetrahydro-3-oxo-4-(2-phenylethyl)-1H-1,4benzodiazepine-2-acetic acid; and
87. 8-[2-[4-(aminomethyl)phenyl]ethyl]-2,3,4,5-tetrahydro-3-oxo-4-(2-phenylethyl)-1H-1,4-benzodiazepine-2-acetic acid.
88. 8-[[[[3-(2-methyl)pyrid-2-yl]propyl]methylamino]carbonyl]-2,3,4,5-tetrahydro-3-oxo-4-(2-phenylethyl)-1H-1,4-benzodiazepine-2-acetic acid.

Example 89
Parenteral Dosage Unit Composition

A preparation which contains 20 mg of the compound of Example 10 as a sterile dry powder is prepared as follows: 20 mg of the compound is dissolved in 15 mL of distilled water. The solution is filtered under sterile conditions into a 25 mL multi-dose ampoule and lyophilized. The powder is reconstituted by addition of 20 mL of 5% dextrose in water (D5W) for intravenous or intramuscular injection. The dosage is thereby determined by the injection volume. Subsequent dilution may be made by addition of a metered volume of this dosage unit to another volume of D5W for injection, or a metered dose may be added to another mechanism for dispensing the drug, as in a bottle or bag for IV drip infusion or other injection-infusion system.

Example 90
Oral Dosage Unit Composition

A capsule for oral administration is prepared by mixing and milling 50 mg of the compound of Example 34 with 75 mg of lactose and 5 mg of magnesium stearate. The resulting powder is screened and filled into a hard gelatin capsule.

Example 91
Oral Dosage Unit Composition

A tablet for oral administration is prepared by mixing and granulating 20 mg of sucrose, 150 mg of calcium sulfate dihydrate and 50 mg of the compound of Example 34 with a 10% gelatin solution. The wet granules are screened, dried, mixed with 10 mg starch, 5 mg talc and 3 mg stearic acid; and compressed into a tablet.

The foregoing is illustrative of the making and using of this invention. This invention, however, is not limited to the precise embodiments described herein, but encompasses all modifications within the scope of the claims which follow.

What is claimed is:
1. A compound of the formula (I):

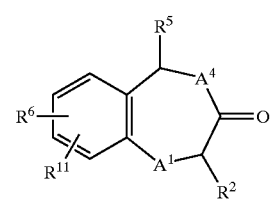

(I)

wherein $A^1$ is N—$R^1$;

$A^4$ is N—$R^4$;

$R^2$ is $R^7$ or Q—$C_{1-4}$alkyl, Q—$C_{2-4}$alkenyl or Q—$C_{2-4}$alkynyl substituted by $R^7$;

$R^1$, $R^4$ and $R^5$ are H, Q—$C_{1-6}$alkyl, Q—$C_{1-6}$oxoalkyl, Q—$C_{2-6}$alkenyl, Q—$C_{3-4}$oxoalkenyl, Q—$C_{3-4}$oxoalkynyl, Q—$C_{2-4}$alkynyl, $C_{3-6}$cycloalkyl, Ar or Het, optionally substituted by one or more of $R^{11}$;

Q is H, $C_{3-6}$cycloalkyl, Het or Ar;

$R^6$ is W—$(CR'_2)_q$—Z—U—$(CR'_2)_s$ or W—$(CR'_2)_q$—Z—$(CR'R^{10})_r$—U—, where U is CO, CONR' or NR'CO;

$R^7$ is —$COR^8$, —$COCR'_2R^9$, —C(S)$R^8$, —S(O)$_m$OR', —S(O)$_m$NR'R", —PO(OR'), —PO(OR')$_2$, —B(OR')$_2$, —NO$_2$ and Tet;

$R^8$ is —OR', —NR'R", —NR'SO$_2$R', —NR'OR', —OCR'$_2$C(O)OR', —OCR'$_2$OC(O)—R', —OCR'$_2$C(O)NR'$_2$, CF$_3$ or AA1;

$R^9$ is —OR', —CN, —S(O)$_r$R', S(O)$_m$NR'$_2$, —C(O)R'C(O)NR'$_2$ or —CO$_2$R';

$R^{10}$ is H, $C_{1-4}$alkyl or —NR'R";

$R^{11}$ is H, halo, —OR$^{12}$, —CN, —NR'R$^{12}$, —NO$_2$, —CF$_3$, CF$_3$S(O)$_r$-, —CO$_2$R', —CONR'$_2$, Q—$C_{0-6}$alkyl-, Q—$C_{1-6}$oxoalkyl-, Q—$C_{2-6}$alkenyl-, Q—$C_{2-6}$alkynyl-, Q—$C_{0-6}$alkyloxy-, Q—$C_{0-6}$alkylamino- or Q—$C_{0-6}$alkyl-S(O)$_r$-;

$R^{12}$ is R', —C(O)R', —C(O)NR'$_2$, —C(O)OR$^{15}$, —S(O)$_m$R' or S(O)$_m$NR'$_2$;

$R^{15}$ is H, $C_{1-6}$alkyl or Ar—$C_{0-4}$alkyl;

R' is H, $C_{1-6}$alkyl, $C_{3-7}$cycloalkyl-$C_{0-4}$alkyl or Ar—$C_{0-4}$alkyl;

R" is R', —C(O)R' or —C(O)OR$^{15}$;

R'" is R" or AA2;

AA1 is an amino acid attached through its amino group and having its carboxyl group optionally protected, and AA2 is an amino acid attached through its carboxyl group, and having its amino group optionally protected;

W is R'R'"N— or Ⓝ;

Z is piperidinyl;

m is 1 or 2;

n is 0 to 3;

q is 0 to 3;

r is 0 to 2;

s is 0 to 2; and t is 0 to 2; or pharmaceutically acceptable salts thereof.

2. A compound according to claim 1 wherein $R^6$ is:

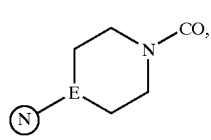

wherein E is CH.

3. A compound according to claim 1 wherein $R^6$ is:

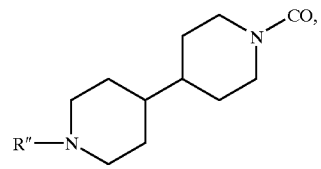

wherein R" is H or $C_{1-4}$alkyl.

4. A pharmaceutical composition comprising a compound according to claim 1 and a pharmaceutically acceptable carrier.

5. A method of inhibiting platelet aggregation which comprises administering to a mammal in need thereof an effective amount of a compound according claim 1.

6. A compound according to claim 3 wherein $R^1$ is H or methyl and $R^4$ is H, methyl, cyclohexylethyl or phenylethyl.

7. A compound according to claim 6 wherein $R^2$ is CH$_2$CO$_2$R'.

8. A compound according to claim 7 wherein $R^5$, $R^{10}$ and $R^{11}$ are H.

9. A method for inhibiting or treating acute myocardial infarction, transient ischemia attack, stroke, or unstable angina comprising administering a compound according to claim 1.

10. A method for inhibiting or treating pulmonary embolism or dissecting anurysm comprising administering a compound according to claim 1.

11. A method for inhibiting reocclusion of an artery or vein following fibrinolytic therapy comprising administering a compound according to claim 1 and a fibrinolytic agent.

12. A compound according to claim 1 wherein $R^6$ is

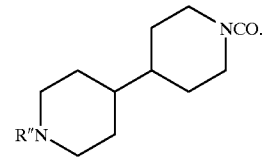

13. A compound according to claim 1 wherein the compound is:

(R,S)-7-[(4,4'-bipiperidin-1-yl)carbonyl]-2,3,4,5-tetrahydro-3-oxo-4-(phenylethyl)-1H-1,4-benzodiazepine-2-acetic acid.

14. A method for inhibiting platelet aggregation comprising administering a compound according to claim 8.

15. A method for inhibiting or treating myocardial infarction, transient ischemia attack, stroke, or unstable angina comprising administering a compound according to claim 8.

16. A method for inhibiting or treating pulmonary embolism or dissecting annurysm comprising administering a compound according to claim 8.

17. A method for inhibiting reocclusion of an artery or vein following fibrinolytic therapy comprising administering a compound according to claim 8 and a fibrinolytic agent.

18. A pharmaceutical composition comprising a compound according to claim 8 and a pharmaceutically acceptable carrier.

* * * * *